United States Patent
Merchant

(10) Patent No.: US 12,404,497 B2
(45) Date of Patent: Sep. 2, 2025

(54) USES AND METHODS FOR ONCOLYTIC VIRUS TARGETING OF IL-4/IL-13 AND FUSIONS THEREOF

(71) Applicant: Medicenna Therapeutics, Inc., Toronto (CA)

(72) Inventor: Fahar Merchant, Vancouver (CA)

(73) Assignee: Medicenna Therapeutics Inc., Toronto (CA)

( * ) Notice: Subject to any disclaimer, the term of this patent is extended or adjusted under 35 U.S.C. 154(b) by 827 days.

(21) Appl. No.: 15/733,815

(22) PCT Filed: Jun. 3, 2019

(86) PCT No.: PCT/IB2019/000759
§ 371 (c)(1),
(2) Date: Nov. 30, 2020

(87) PCT Pub. No.: WO2019/239213
PCT Pub. Date: Dec. 19, 2019

(65) Prior Publication Data
US 2021/0238558 A1    Aug. 5, 2021

Related U.S. Application Data

(60) Provisional application No. 62/687,228, filed on Jun. 19, 2018, provisional application No. 62/679,689, filed on Jun. 1, 2018.

(51) Int. Cl.
| | |
|---|---|
| *C12N 15/861* | (2006.01) |
| *A61K 35/766* | (2015.01) |
| *A61K 48/00* | (2006.01) |
| *A61P 35/00* | (2006.01) |
| *C07K 14/54* | (2006.01) |
| *C07K 14/55* | (2006.01) |
| *C12N 7/00* | (2006.01) |
| *C12N 7/01* | (2006.01) |
| *C12N 15/86* | (2006.01) |

(52) U.S. Cl.
CPC ............. *C12N 7/00* (2013.01); *A61K 35/766* (2013.01); *C07K 14/544* (2013.01); *C07K 14/55* (2013.01); *C12N 15/86* (2013.01); *C12N 2760/20232* (2013.01); *C12N 2760/20243* (2013.01)

(58) Field of Classification Search
None
See application file for complete search history.

(56) References Cited

U.S. PATENT DOCUMENTS

| | | |
|---|---|---|
| 6,011,002 A | 1/2000 | Pastan et al. |
| 6,028,176 A | 2/2000 | Greve et al. |
| 6,130,318 A | 10/2000 | Wild et al. |
| 6,335,426 B1 | 1/2002 | Shanafelt et al. |
| 6,673,602 B1 | 1/2004 | Spear et al. |
| 6,737,511 B1 | 5/2004 | Youle et al. |
| 9,512,194 B2 | 12/2016 | Garcia et al. |
| 9,629,899 B2 * | 4/2017 | Puri ............... A61P 35/00 |
| 10,093,708 B2 | 10/2018 | Merchant |
| 10,106,592 B2 | 10/2018 | Merchant |
| 2003/0013851 A1 | 1/2003 | Powers et al. |
| 2004/0248260 A1 | 12/2004 | Heavner et al. |
| 2005/0106148 A1 | 5/2005 | Kay et al. |
| 2006/0035856 A1 | 2/2006 | Caput et al. |
| 2007/0160658 A1 | 7/2007 | Connor et al. |
| 2010/0183545 A1 | 7/2010 | Puri |
| 2010/0317577 A1 | 12/2010 | Youle |
| 2011/0023680 A1 | 2/2011 | Wang |
| 2011/0319336 A1 * | 12/2011 | Kawakami ........... C07K 14/485 435/254.2 |
| 2012/0294931 A1 | 11/2012 | Kim et al. |
| 2014/0050709 A1 | 2/2014 | Leen et al. |
| 2016/0151490 A1 | 6/2016 | Sampath et al. |
| 2016/0271231 A1 | 9/2016 | Merchant |
| 2016/0340649 A1 | 11/2016 | Brown et al. |
| 2019/0016797 A1 * | 1/2019 | Arenas-Ramirez ..... A61P 35/00 |

FOREIGN PATENT DOCUMENTS

| | | |
|---|---|---|
| CN | 102792358 | * 10/2012 |
| WO | WO1994004680 A1 | 3/1994 |
| WO | WO2001018051 A2 | 9/2000 |
| WO | WO2001025282 A1 | 4/2001 |
| WO | WO2001034645 A2 | 5/2001 |
| WO | WO2001062933 A3 | 8/2001 |
| WO | WO2002018422 A1 | 3/2002 |
| WO | WO2006074451 A2 | 7/2006 |
| WO | WO2007146046 A2 | 12/2007 |
| WO | WO2008101671 A2 | 8/2008 |
| WO | WO2009029601 A2 | 3/2009 |
| WO | WO2009140598 A1 | 5/2009 |

(Continued)

OTHER PUBLICATIONS

Suzuki et al, Targeting of IL-4 and IL-13 receptors for cancer therapy, Cytokine, 2015, pp. 79-88.*
Post et al, Local delivery of the anti-tumorigenic interleukin-4(IL-4) cytokine to tumors using an oncolytic adenovirus, 2005, abstract.*
CN 102792358 translation, 2012, pp. 1-40.*
Sosman et al, A phase I trial of continuous infusion interleukin-4 (IL-4) alone and following interleukin-2 (IL-2) in cancer patients, Annals of Oncology 5: 447-452, 1994.*
Hallett, M.A et al., Cancer Res., (Dec. 7, 2012), vol. 72, No. 24, pp. OF1-OF6, Cytokine Stimulation of Epithelial Cancer cells.
Kawakami, M et al., J. Neurooncol., (2003), vol. 65, pp. 15-25, Interleukin-4-Pseudomonas exotoxin chimeric fusion protein for malignant glioma therapy.

(Continued)

*Primary Examiner* — Maria Marvich
(74) *Attorney, Agent, or Firm* — Sara E. Sims; Christina A. MacDougall; Morgan Lewis & Bockius, LLP

(57) ABSTRACT

The present invention provides an oncolytic virus vector containing a sequence encoding IL-4 receptor targeted cargo protein, including IL-4 muteins and/or IL-13 muteins, the oncolytic virus encoded therefrom, the uses of the oncolytic virus for treating cancer.

11 Claims, 2 Drawing Sheets
Specification includes a Sequence Listing.

(56) References Cited

FOREIGN PATENT DOCUMENTS

| WO | WO2010031185 A1 | 3/2010 |
|---|---|---|
| WO | WO2011106779 A1 | 9/2011 |
| WO | WO2012054929 A2 | 4/2012 |
| WO | WO2012088446 A1 | 6/2012 |
| WO | WO2012139112 A1 | 10/2012 |
| WO | WO2015042705 A1 | 9/2014 |
| WO | WO2015042707 A1 | 4/2015 |
| WO | WO2015070210 A1 | 5/2015 |
| WO | WO2018112266 A1 | 6/2018 |
| WO | WO2020160639 A1 | 8/2020 |
| WO | WO2021258213 A1 | 12/2021 |

OTHER PUBLICATIONS

Agholme et al. "An in vitro model for neuroscience: differentiation of SH-SY5Y cells into cells with morphological and biochemical characteristics of mature neurons." J Alzheimer's Disease 20: 1069-1082, 2010.
Allen et al. "Interleukin-13 Displaying Retargeted Oncolytic Measles Virus Strains Have Significant Activity Against Gliomas With Improved Specificity". Molecular Therapy, Sep. 2008 (Sep. 2008), vol. 16, No. 9, pp. 1556-1564, ISSN 1525-0016 See whole document.
"Alzheimer's Disease", ninds.nih.gov/disorders/alzheimersdisease/alzheimersdisease.htm; Jan. 4, 2012; 3 total pages.
Bachran et al. "Anthrax Toxin-Mediated Delivery of the Pseudomonas Exotoxin A Enzymatic Domain to the Cytosol of Tumor Cells via Cleavable Ubiquitin Fusions" mBio vol. 4, pp. 201-213 (2013).
Bates, D.L., et al., "3QB7: Interleukin-4 mutant RGA bound to cytokine receptor common gamma," <<RCSB PDB>> Protein Data Bank, pp. 1-2 (Apr. 25, 2012).
Baeurle Patrick A. et al. "Bispecific T-cell engaging antibodies for cancer therapy", Cancer Research, AACR, US Philadephia, PA, vol. 69, No. 12, Jun. 15, 2009 (Jun. 15, 2009), pp. 4941-4944, XP002665118, ISSN: 1538-7445, CAN-09-0547 [retrieved on Jun. 9, 2009] the whole document.
Bhatia et al., Innovative approaches for enhancing cancer gene therapy. Discovery Medicine 15(84): 309-317, 2013.
Boise et al. "bcl-x, a bcl-2-Related Gene That Functions as a Dominant Regulator of Apoptotic Cell Death" Cell, vol. 74, pp. 597-608 (1993).
Burt, B.M. et al. "Expression of Interleukin-4 Receptor Alpha in Human Pleural Mesothelioma Is Associated with Poor Survival and Promotion of Tumor Inflammation". Clinical Cancer Research, Mar. 15, 2012 (Mar. 15, 2012), vol. 18, No. 6, pp. 1568-1577 See entire document.
Cao et al., In vivo delivery of a Bcl-xl fusion protein containing the TAT protein transduction domain protects against ischemic brain injury and neuronal apoptosis. J Neurosci 22(13): 5423-5431, 2002.
Candolfi et al. "Gene therapy-mediated delivery of targeted cytotoxin for glioma therapeutics". Proceedings of the National Academy of Sciences of the United States of America, Nov. 16, 2010 (Nov. 16, 2010), vol. 107, No. 46, pp. 20021-20026, ISSN 1091-6490.
Castro et al. "Therapy and Targeted Toxins for Glioma". Current Gene Therapy, Jun. 1, 2011 (Jun. 1, 2011), vol. 11, No. 3, pp. 155-180, ISSN 1875-5631.
C.E. Brown et al.: "Bioactivity and Safety of IL13Rα2-Redirected Chimeric Antigen Receptor CD8+ T Cells in Patients with Recurrent Glioblastoma", Clinical Cancer Research, vol. 21, No. 18, Jun. 9, 2015 (Jun. 9, 2015), pp. 4062-4072, XP055362974, US ISSN: 1078-0432, DOI: 10.1158/1072-0432.CCR-15-0428 The whole document.
Cleary et al "Cloning and structural analysis of cDNAs for bcl-2 and a hybrid bcl-2/immunoglobulin transcript resulting from the t(14;18) translocation" Cell Press, vol. 47, No. 1, pp. 19-28 (1986).
Corren et al. "Lebrikizumab treatment in adults with asthma.", N Eng I J Med., Sep. 22, 2011, pp. 1088-1098, 365(1), Massachusetts Medical Society, Waltham, MA.
Creusot, et al., "Engineering cell-type selective immune responses using mechanism-based designer IL-4 cytokines," The Journal of Immunology, 186:57.8 (2011).
Cuny, G.D. Neurodegenerative diseases: challenges and opportunities. Future Med Chem 4(13): 1647-1649, 2012.
Diehn et al. "Cancer Stem Cells and Radiotherapy: New Insights Into Tumor Radioresistance" Journal of National Cancer Institute, vol. 98, pp. 1755-1757 (2006).
Eisenmesser et al., "Solution structure of interleukin-13 and insights into receptor engagement." J Mol. Biol., Jun. 2001, pp. 231-241, 310(1), Elsevier, Amsterdam, Netherlands.
Elgert, K. Immunology, understanding the immune system. New York: Wiley-Liss, Inc., 1996; pp. 323-326.
Feigin et al. Recent advances in Huntington's disease: implications for experimental therapeutics. Curr Opin Neurol 15: 483-489, 2002.
Fernandez et al. "Genetically Engineered Vesicular Stomatitis Virus in Gene Therapy; Application for Treatment of Malignant Disease". Journal of Virology, Jan. 2002 (2002), vol. 76, No. 2, pp. 895-904, ISSN 0022-538X See whole document.
Fernando, R. et al. "Breast cancer cell proliferation is inhibited by bAD: regulation of cyclin D1." The Journal of biological chemistry vol. 282,39 (2007): 28864-73.
Forster et al. Characterization of differentiated SH-SY5Y as neuronal screening model reveals increased oxidative vulnerability. J Biomlecul Screen 21(5): 496-509, 2016.
Fueller, J. et al. "C-RAF activation promotes BAD polyubiquitylation and turn-over by the proteasome." Biochemical and biophysical research communications vol. 370,4 (2008): 552-6.
Garland, L. et al. "Phase I trial of intravenous IL-4 Pseudomonas Exotoxin protein (NBI-3001) in patients with advanced solid tumors that express the IL-4 receptor". Journal of Immunotherapy, 2005, vol. 28; No. 4, pp. 376-381.
GenBank Accession No. Z23115, bcl XL gene [*Homo sapiens*] Oct. 7, 2008.
GenBank Accession No. 3QB7_A, chain A, Interleukin 4 [*Homo sapiens*] Apr. 25, 2012.
GenBank Accession No. Q07817, bcl gene apotosis [*Homo sapiens*] Feb. 28, 2018.
Halliday et al. Alzheimer's disease and inflammation: a review of cellular and therapeutic mechanisms. Clin Exp Pharmacol Physiol 27: 1-8, 2000.
Han, J. et al. "Analysis of the cancer genome atlas (TCGA) database identifies an inverse relationship between interleukin-13 receptor α1 and α2 gene expression and poor prognosis and drug resistance in subjects with glioblastoma multiforme". Journal of Neuro-Oncology, Nov. 22, 2017 (Nov. 22, 2017), vol. 136, No. 3, pp. 463-474 See entire document.
Harvey, A. "Overview of Cell Signaling Pathways in Cancer." Predictive Biomarkers in Oncology, edited by Sunil Badve and George Louis Kumar. 2019, pp. 167-182.
Hotchkiss et al., TAT-BH4 and TAT-Bcl-xl peptides protect against sepsis-induced lymphocyte apoptosis in vivo. J Immunol 176: 5471-5477, 2006.
Ichinose, M. et al. "Extracellular Bad fused to toxin transport domains induces apoptosis." Cancer research vol. 62,5 (2002): 1433-8.
Ito, et al., "Distinct structural requirements for interleukin-4 (IL-4) and IL-13 binding to the shared IL-13 receptor facilitate cellular tuning of cytokine responsiveness." J. Biol. Chem., Sep. 4, 2009, pp. 24289-24296, 284(36), ASBMB, Rockville, MD.
Joshi et al. "In Situ Expression of Interleukin-4 (IL-4) Receptors in Human Brain Tumors and Cytotoxicity of a Recombinant IL-4 Cytotoxin in Primary Glioblastoma Cell Cultures", Cancer Research, Nov. 15, 2001, pp. 8058-8061, vol. 61.
Juengst, E.T. What next for human gene therapy? BMJ 326: 1410-1411, 2003.
Junttila et al "Redirecting cell-type specific cytokine responses with engineered interleukin-4 superkines" Nat Chem Biol., vol. 8, No. 12, pp. 990-998 (2012).
Kahlon, et al., "Specific Recognition and Killing of Glioblastoma Multiforme by Interleukin 13-Zetakine Redirected Cytolytic T Cells", Cancer Research, 64:9160-9166 (2004).

(56) References Cited

OTHER PUBLICATIONS

Kreitman et al. "Recombinant Toxins Containing Human Granulocyte-Macrophage Colony-Stimulating Factor and Either Pseudomonas Exotoxin or Diphtheria Toxin Kill Gastrointestinal Cancer and Leukemia Cells" Blood vol. 90, pp. 252-259 (1997).
Laske et al. "Tumor regression with regional distribution of the targeted toxin TF-CRM107 in patients with malignant brain tumors" Nature, vol. 3, pp. 1362-1368 (1997).
Levin, et al., "Exploiting a natural conformational switch to engineer an interleukin-2 "superkine"," Nature 484:529-533 (A & B) (2012).
Lomonosova and Chinnadurai "BH3-only proteins in apoptosis and beyond: an overview" Oncogene, vol. 27, pp. S2-S19 (2009).
Madhankumar et al., "interleukin 13 mutants of enhanced avidity toward the glioma-associated receptor, IL 13Ralpha2." Neoplasia, Jan./Feb. 2004, pp. 15-22, 6(1), Neoplasia Press, Ann Arbor, MI.
Mardor, Y. et al. "Convection-Enhanced Drug Delivery of Interleukin-4 Pseudomonas Exotoxin (PRX321): Increased Distribution and Magnetic Resonance Marketing". J Pharmacol Exp Ther., Aug. 2009 (Aug. 2009). vol. 330(2), pp. 520-525, ISSN 0022-3565 (Print), 1521-0103 (Electronic), 0022-3565 (Linking) [online] [retrieved on Feb. 12, 2019 (Feb. 12, 2019)].
McCormick et al. Commentary: IL-4 and IL-13 receptors and signaling. Cytokine 75: 38-50, 2015.
Munitz et al, Distinct roles for IL-13 and IL-4 via IL-13 receptor a1 and the type II IL-4 receptor in asthma pathogenesis, 2008, PNAS:105:7240-7245.
Murray, E.J. "Cloning Genes in Mammalian Cell-lines" in Molecular Biology and Biotechnology. Great Britain: The Royal Society of Chemistry, 2000, pp. 177-201.
Natoli, A. et al. "Targeting the IL-4/IL-13 signaling pathway sensitizes Hodgkin lymphoma cells to chemotherapeutic drugs." International journal of cancer vol. 133,8 (2013): 1945-54.
Oshima et al., "Conversion of interleukin-13 into a high affinity agonist by a single amino acid substitution." J. Biol. Chem., May 12, 2000, pp. 14375-14380, 275(19), ASBMB, Rockville, MD.
Oshima et al., "Characterization of a powerful high affinity antagonist that inhibits biological activities of human interleukin-13." J. Biol. Chem., May 4, 2001, pp. 15185-15191, 276(18), ASBMB, Rockville, MD.
Pahlman et al. Differentiation and survival influences of growth factors in human neuroblastoma. Eur J Cancer 31A(4): 453-458, 1995.
Partaledis et al., "In vitro selection and characterization of human immunodeficiency virus type 1 (HIV-1) isolates with reduced sensitivity to hydroxyethylamino sulfonamide inhibitors of HIV-1 aspartyl protease." J. Viral, Sep. 1995, pp. 5228-5235, 69(9), American Society for Microbiology, Washington DC.
Phillips, A.J. The challenge of gene therapy and DNA delivery. J Pharmacy and Pharmacol 53: 1169-1174, 2001.
Polzein, L. et al. "Identification of novel in vivo phosphorylation sites of the human proapoptotic protein BAD: pore-forming activity of BAD is regulated by phosphorylation." The Journal of biological chemistry vol. 284,41 (2009): 28004-20.
Post et al. "Targeted Cancer Gene Therapy Using a Hypoxia Inducible Factor-Dependent Oncolytic Andenovirus Armed with Interleukin-4". Cancer Research, Jul. 15, 2007 (Jul. 15, 2007), vol. 67, No. 14, pp. 6872-6881, ISSN 1538-7445 See whole document.
Puri et al. "Human Neurological Cancer Cells Express Interleukin-4 (IL-4) Receptors Which Are Targets for the Toxic Effects of IL4-Pseudomonas Exotoxin Chimeric Protein". The International Journal of Cancer, 1994, vol. 58, pp. 574-581, ISSN 1097-0215.
Reynolds et al., "Genetic Instability Induced by the Tumor Microenvironment", Cancer Research, vol. 56, pp. 5754-5757 (1996), New insights into the regulation of T cells by g3 family cytokines. Rochman et al., 2009. 9(7) p. 1-23 (Year: 2009).
Rubanyi, G.M., The future of human gene therapy. Molecular Aspects Med 22: 113-142, 2001.
Rubin "Neuronal cell death: when, why and how" British Medical Bulletin, vol. 53, Issue 3, pp. 617-631 (1997).
Sakariassen et al. "Cancer Stem Cells as Mediators of Treatment Resistance in Brain Tumors: Status and Controversies" Neoplasia, vol. 9, No. 11, pp. 882-892 (2007).
Schnare et al., "Specific Antagonism of Type I IL-4 Receptor with a Mutated Form of Murine IL-4," The Journal of Immunology, 161:7, pp. 3484-3492 (1998).
Sharma et al. "Interleukin-4 Mediates Down Regulation of Antiviral Cytokine Expression and Cytotoxic T-Lymphocyte Responses and Exacerbates Vaccinia Virus Infection In Vivo". Journal of Virology, Oct. 1996, vol. 70, No. 10, pp. 7103-7107, ISSN 0022-538X See whole document.
Shimamura et al. "The IL-4 and IL-13 pseudomonas exotoxins: new hope for brain tumor therapy". Neurosurgical FOCUS, 2006, vol. 20, No. 3:E11, ISSN 1092-0684.
Shimamura et al. "Interleukin-4 Cytotoxin Therapy Synergizes with Gemcitabine in a Mouse Model of Pancreatic Ductal Adenocarcinoma" Cancer Research, vol. 67, pp. 9903-9912 (2007).
Steece-Collier et al. Etiology of Parkinson's disease: genetics and environment revisited. Proc Natl Acad Sci USA 99(22): 13972-13974, 2002.
Suga et al. "Transplant Immunosuppression Enhances Efficiency of Adenoviral-Mediated Gene Retransfection: Inhibition of Interferon-y and Immunoglobin G" The Society of Thoracic Surgeons, vol. 73, pp. 1092-1097 (2002).
Thompson, et al., "Mutants of interleukin 13 with altered reactivity toward interleukin 13 receptors." J. Biol. Chem., Oct. 15, 1999, pp. 29944-29950, 274(42), ASBMB, Rockville, MD.
Thorpe et al. "Toxicity of diphtheria toxin for lymphoblastoid cells is increased by conjugation to antilymphocytic globulin" Nature, vol. 271, pp. 752-755 (1978).
Tsujimoto and Croce "Analysis of the structure, transcripts, and protein products of bcl-2, the gene involved in human follicular lymphoma" Proc. Natl. Acad. Sci., vol. 83, pp. 5214-5218 (1986).
UniProtKB database P05112 (Aug. 13, 1987).
Vallera, D.A. et al. "Retroviral immunotoxin gene therapy of leukemia in mice using leukemia-specific T cells transduced with an interleukin-3/Bax fusion protein gene." Human gene therapy vol. 14, 18 (2003): 1787-98.
Van Den Broek, et al. "IL-4 and IL-10 Antagonize IL-12-Mediated Protection Against Acute Vaccinia Virus Infection with a Limited Role of IFN-γ and Nitric Oxide Synthetase 2". Journal of Immunology, Jan. 1, 2000 (Jan. 1, 2000), vol. 164, No. 1, pp. 371-378, ISSN 1550-6606.
White "Life, Death, and the Pursuit of Apoptosis" Genes and Development 10, pp. 1-15 (1996).
Yang et al. "Bad, a heterodimeric partner for Bcl-XL and Bcl-2, displaces Bax and promotes cell death" Cell, vol. 80, pp. 285-291 (1995).
Yang et al. Targeting cancer stern cell pathways for cancer therapy. Signal Transd Targeted Ther 5:8, 2020 (35 total pages).
Yeung et al. Signaling pathways in inflammation and anti-inflammatory therapies. Curr Pharm Design 24: 1449-1484, 2018.
Youle et al. "Receptor-mediated uptake of an extracellular Bcl-xL fusion protein inhibits apoptosis" Proceedings of Nat'l Academy of Sciences, vol. 96, pp. 9563-9567 (1999).
Youle et al. "The Cytokine, Granulocyte-Macrophage Colony-stimulating Factor (GM-CSF), Can Deliver Bcl-XL as an Extracellular Fusion Protein to Protect Cells from Apoptosis and Retain Differentiation Induction" The Journal of Biological Chemistry, vol. 282, No. 15, pp. 11246-11254 (2007).
Youle et al., "The BCL-2 protein family: opposing activities that mediate cell death", Nature Reviews, vol. 9, pp. 47-59 (2008).
ISR/WO issued in PCT/IB2019/000759 on Jan. 20, 2020.
Bhattacharya et al. Impact of genetic variation on three dimensional structure and function of proteins. PLoS ONE 12(3): e0171355, 2017.
Bork, P. Powers and pitfalls in sequence analysis: the 70% hurdle. Genome Res 10: 398-400, 2000.
Brenner. S.E. Errors in genome annotation. Trends in Genetics 15:132-133, 1999.
Chen et al. Fusion protein linkers: property, design, and functionality. Adv Drug Rev 65: 1357-1369, 2013 (online Sep. 29, 2012).

(56) References Cited

OTHER PUBLICATIONS

Doerks et al. Protein annotation: detective work for function prediction. Trends in Genetics 14:248-250, 1998.
Fenton et al. Rheostat positions: a new classification of protein positions relevant to pharmacogenomics. Medicinal Chem Res 29:1133-1146, 2020.
Gardai et al. Phosphorylation of Bax Ser184 by Akt regulates its activity and apoptosis in neutrophils. J Biol Chem 279(20): 21085-21095, 2004.
Guo et al. Protein tolerance to random amino acid change. Proc Natl Acad Sci USA 101 (25): 9205-9210, 2004.
Kazunari et al. Neurosurgery 38(4):p. 733-736, Apr. 1996.
Ngo et al. "Computational complexity, protein structure prediction, and the Levinthal paradox" in The Protein Folding Problem and Tertiary Structure Prediction, pp. 492-495, 1994.
Oka K, Yamamoto M, Nonaka T, Tomonaga M. The significance of artificial cerebrospinal fluid as perfusate and endoneurosurgery. Neurosurgery.Apr. 1996;38(4):733-6. PMID: 8692392.
Skolnick et al. From genes to protein structure and function: novel applications of computational approaches in the genomic era. Trends Biotechnol 18(1) :34-39 2000.
Smith et al. The challenges of genome sequence annotation or "the devil is in the details". Nature Biotechnol 15: 1222-1223, 1997.
Tokuriki et al. Stability effects of mutations and protein evolvability. Curr Opin Structural Biol 19: 596-604, 2009.
Wang et al. Mono- or double-site phosphorylation distinctly regulates the proapoptotic function of Bax. PLoS One 5(10): e13393, 2010 (8 total pages).
Wells, J.A. Additivity of mutational effects in proteins. Biochemistry 29(37): 8509-8517, 1990.
Ding et al., Convection-enhanced Delivery of Free Gadolinium with the Experimental Chemotherapeutic Agent PRX321., Neurol Res. Oct. 2010; 32(8): 810-815.
Weber et al., Safety, tolerability, and tumor response of IL4-Pseudomonas exotoxin (NBI-3001) in patients with recurrent malignant glioma., J Neurooncol. Aug.-Sep. 2003;64(1-2):125-37. doi: 10.1007/BF02700027.

Thaci et al., "Significance of interleukin-13 receptor alpha 2-targeted glioblastoma therapy," Neuro Oncol. Oct. 2014;16(10):1304-12.
Sampson et al., "MDNA55, a Locally Administered IL4 Guided Toxin for Targeted Treatment of Recurrent Glioblastoma Shows Long Term Survival Benefit," European Journal of Cancer (2020). 138. S6. 10.1016/S0959-8049(20)31084-4.
Medicenna, "Convection-Enhanced Delivery (CED) of MDNA55 in Adults With Recurrent or Progressive Glioblastoma," Clinical Trial NCT02858895, First posted Aug. 8, 2016. (https://clinicaltrials.gov/study/NCT02858895).
Bautz, "Medicenna Therapeutics Corp.," Zacks Small-Cap Research, May 14, 2019 (May 14, 2019), acquired from: http://s27.q4cdn.com/906368049/files/News/2019/Zacks_SCR_Research_05142019_T.MDNA_Bautz.pdf.
Yu et al., "Efficacy and safety of bevacizumab for the treatment of glioblastoma," Exp Ther Med. Feb. 2016;11(2):371-380.
Gramatzki et al., "Bevacizumab may improve quality of life, but not overall survival in glioblastoma: an epidemiological study," Ann Oncol. Jun. 1, 2018;29(6):1431-1436.
Anonymous: "Medicenna Reports Compelling Results from Recurrent Glioblastoma Trial When Compared to an Eligibility-Matched Control Arm", Jan. 13, 2020 (Jan. 13, 2020), XP093209969.
Sampson, John H. et al.: MDNA55 survival in recurrent glioblastoma (rGBM) patients expressing the interleukin-4 receptor (IL4R) as compared to a matched synthetic control., Journal of Clinical Oncology, Meeting Abstract: 2020 ASCO Annual Meeting I, May 25, 2020.
Charo et al. Bcl-2 Overexpression Enhances Tumor-Specific T-Cell Survival. Cancer Res 65(5): 2001-2008, Mar. 1, 2005.
Vella et al. Interleukin 4 (IL-4) or IL-7 Prevents the Death of Resting T Cells: Stat Is Probably Not Required for the Effect of IL-4. J Exp Med 186(2): 325-330, 1997.
Wilkie et al. Selective Expansion of Chimeric Antigen Receptor-targeted T-cells with Potent Effector Function using Interleukin-4. J Biol Chem 285(33): 25538-25544, 2010 (and supplementary materials) (17 total pages).

\* cited by examiner

Figure 1A

| Name (serotype) | Adenoviruses used as oncolytic agents | |
|---|---|---|
| | Basis of tumor-selective propagation | Therapeutic traits |
| Ad wild type (various serotypes) | None | Oncolysis |
| Ad5/IFN (Ad5) | None | Oncolysis & immuno-stimulatory gene therapy |
| A1520 or Onyx015 < Ad2/5) | EIbSSkDa-deletion abrogates p53 binding | Oncolysis |
| AdTK$^{RC}$ | EIbSSkDa-deletion abrogates p53 binding | Oncolysis & suicide gene therapy (TK) |
| Ad-5-CD-TKrep or FGR (ad5) | EIbSSkDa-deletion abrogates p53 binding | Oncolysis ft suicide gene therapy (CD + TK) |
| AdvEIAdB-F/K20 (Ad5) | EIbSSkDa-deletion abrogates p53 binding | Oncolysis with enhanced infectivity |
| AxE1AdB (Ad5) & AdCAhIL-2 (Ad5) | EIbSSkDa-deletion abrogates p53 binding | Oncolysis & immuno-stimulatory gene therapy |
| AdD24 (Ad5) | EIa deletion abrogates Rb binding | Oncolysis |
| CN706 (Ad5) | Regulation of EIa under the PSA promoter | Oncolysis |
| CN763 (Ad5) | Regulation of EIa under the kalikrein 2 promoter | Oncolysis |
| CN764 (Ad5) | Regulation of EIa under the PSA promoter and EIb under the kalikrein 2 promoter | Oncolysis |
| CV739 | Regulation of EIa under rat probasin promoter and EIb under human PSA promoter | Oncolysis |
| | Adenoviruses used as oncolytic agents | |
| Name (serotype) | Basis of tumor-selective propagation | Therapeutic traits |
| CV787 | Regulation of EIa under rat probasin promoter and EIb under human PSA promoter | Oncolysis (enhanced compared with CV739 due to the presence of E) |
| AvEIa041 | Regulation of EIa under the AFP promoter | Oncolysis |
| GT5610 (Ad5) + AdHB (Ad5) | Regulation of EIa under the AFP promoter | Oncolysis |
| D1337 (Ad5) | None | Oncolysis (enhanced due to EIb-19 kDa deletion) |
| D1316 (Ad5) | The complete deletion of EIa makes this mutant dependent on Nrinsic or ML-6-induced EIa-like activity | Oncolysis |
| D1118 (Ad5) | The complete deletion of EIb abrogates p53 binding; however EIa-induced apoptosts is not inhibited by EIb-19 kDa | Oncolysis |

Figure 1 B

Replication-Selective Viruses in Clinical Trials

| Parental Strain | Agent | Clinical Phase | Tumor targets in clinical trials | Genetic alterations | Cell phenotype allowing selective replication |
|---|---|---|---|---|---|
| Engineered | | | | | |
| Adenovirus (2/5 chimera) | 1520 | I-III | SCCHN Colorectal Ovarian Pancreatic | E1B-55-kD gene deletion | Prostate cells (malignant, normal) |
| Adenovirus (serotype 5) | CN706 | I | | B3-10.4/14.5 deletion E1A expression driven by PSE element | |
| | CN787 | I | Prostate | E1A driven by rat probasin promoter/ E1B by PSE/promoter/enhancer | Prostate cells (malignant, normal) |
| Adenovirus (2/5 chimera) | Ad5-CD/tk-rep | I | Prostate | E1B-55-kD gene deletion Insertion of HSV-tk/CD fusion gene | Controversial cells lacking p53 function (for example, deletion, mutation,) other? |
| Herpes simplex virus-1 | G207 | I-II | GBM | ribonucleotide reductase disruption (locZ insertion into ICP6 gene) neuropathogenesis gene mutation (γ-34.5 gene)—both copies | Proliferating cells |
| Herpes simplex virus-1 | NV1020 | I-II | Colorectal | neuropathogenesis gene mutation (γ-34.5 gene)-single copy | Proliferating cells |
| Vaccinia virus | Wild-type ± GM-CSF | I | Melanoma | For selectivity: none or deletion Immunostimulatory gene (GM-CSF) insertion | Unknown |
| Non-engineered | | | | | |
| Newcastle Disease virus | 73-T | I | Bladder SCCHN Ovarian | Unknown (serial passage on tumor cells) | Loss of IFN response in tumor cells |
| Autonomous parvovirus | H-I | I | | None | Transformed cells ↑ proliferation ↓ differentiation ras, p53 mutation |
| Reovirus | Reolysin | I | SCCHN | None | Ras-pathway activation (for example, ras mutation, EGFR signalling) |

SEQUENCE LISTING

<160> NUMBER OF SEQ ID NOS: 112

<210> SEQ ID NO 1
<211> LENGTH: 113
<212> TYPE: PRT
<213> ORGANISM: Artificial Sequence
<220> FEATURE:
<223> OTHER INFORMATION: IL-13 Amino Acid

<400> SEQUENCE: 1

Pro Gly Pro Val Pro Pro Ser Thr Ala Leu Arg Glu Leu Ile Glu Glu
1               5                   10                  15

Leu Val Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Arg Asp Thr Lys Ile Glu Val Ala Gln Phe Val
                85                  90                  95

Lys Asp Leu Leu Leu His Leu Lys Lys Leu Phe Arg Glu Gly Gln Phe
            100                 105                 110

Asn

<210> SEQ ID NO 2
<211> LENGTH: 113
<212> TYPE: PRT
<213> ORGANISM: Artificial Sequence
<220> FEATURE:
<223> OTHER INFORMATION: IL-13 Amino Acid

<400> SEQUENCE: 2

Pro Gly Pro Val Pro Pro Ser Thr Ala Val Arg Ala Leu Ile Glu Glu
1               5                   10                  15

Leu Ile Asn Ile Thr Gln Asn Gln Lys Ala Pro Leu Cys Asn Gly Ser
            20                  25                  30

Met Val Trp Ser Ile Asn Arg Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Asp Met Leu Ser Gly Phe Cys Pro His Lys Val Ser Ala Gly Gln Phe
65                  70                  75                  80

Ser Ser Leu His Val Arg Ser Ser Lys Ile Glu Val Ala Gln Phe Val
                85                  90                  95

Lys Asp Leu Leu Phe His Leu Arg Thr Leu Phe Arg Glu Gly Gln Phe
            100                 105                 110

Asn

<210> SEQ ID NO 3
<211> LENGTH: 113
<212> TYPE: PRT
<213> ORGANISM: Artificial Sequence
<220> FEATURE:
<223> OTHER INFORMATION: IL-13 Amino Acid

<400> SEQUENCE: 3

Pro Gly Pro Val Pro Pro Ser Thr Ala Ile Arg Glu Leu Ile Glu Glu

-continued

```
1               5                   10                  15
Leu Ile Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
            35                  40                  45

Glu Ser Leu Ile Asn Val Ser Gly Cys Ser Ala Ile Glu Lys Thr Gln
            50                  55                  60

Arg Met Leu Ser Gly Phe Cys Pro His Lys Val Ser Ala Gly Gln Phe
65                      70                  75                  80

Ser Ser Leu His Val Arg Gly Ser Lys Ile Glu Val Ala Gln Phe Val
                    85                  90                      95

Lys Asp Leu Leu His His Leu Arg Ala Leu Phe Arg Glu Gly Gln Phe
                100                 105                 110

Asn
```

<210> SEQ ID NO 4
<211> LENGTH: 113
<212> TYPE: PRT
<213> ORGANISM: Artificial Sequence
<220> FEATURE:
<223> OTHER INFORMATION: IL-13 Amino Acid

<400> SEQUENCE: 4

```
Pro Gly Pro Val Pro Pro Ser Thr Ala Val Arg Glu Leu Ile Glu Glu
1               5                   10                  15

Leu Ile Asn Ile Thr Gln Asn Gln Lys Ala Pro Leu Cys Asn Gly Ser
            20                  25                  30

Met Val Trp Ser Ile Asn Arg Thr Ala Gly Met Tyr Cys Ala Ala Leu
            35                  40                  45

Glu Ser Leu Ile Asn Val Ser Gly Cys Ser Ala Ile Glu Lys Thr Gln
            50                  55                  60

Arg Met Leu Ser Gly Phe Cys Pro His Lys Val Ser Ala Gly Gln Phe
65                      70                  75                  80

Ser Ser Leu His Val Arg Ser Ser Lys Ile Glu Val Ala Gln Phe Val
                    85                  90                      95

Lys Asp Leu Leu Phe His Leu Arg Thr Leu Phe Arg Glu Gly Gln Phe
                100                 105                 110

Asn
```

<210> SEQ ID NO 5
<211> LENGTH: 113
<212> TYPE: PRT
<213> ORGANISM: Artificial Sequence
<220> FEATURE:
<223> OTHER INFORMATION: IL-13 Amino Acid

<400> SEQUENCE: 5

```
Pro Gly Pro Val Pro Pro Ser Thr Ala Leu Ile Glu Leu Ile Glu Glu
1               5                   10                  15

Leu Ile Asn Ile Thr Gln Asn Gln Lys Ala Pro Leu Cys Asn Gly Ser
            20                  25                  30

Met Val Trp Ser Ile Asn Leu Thr Ala Gly Ile Tyr Cys Ala Ala Leu
            35                  40                  45

Glu Ser Leu Ile Asn Val Ser Gly Cys Ser Ala Ile Glu Lys Thr Gln
            50                  55                  60

Arg Met Leu Ser Gly Phe Cys Pro His Lys Val Ser Ala Gly Gln Phe
65                      70                  75                  80
```

Ser Ser Leu His Val Lys Gly Ser Lys Ile Glu Val Ala Gln Phe Val
                85                  90                  95

Lys Asp Leu Leu His His Leu Arg Ala Leu Met Arg Glu Gly Gln Phe
            100                 105                 110

Asn

<210> SEQ ID NO 6
<211> LENGTH: 113
<212> TYPE: PRT
<213> ORGANISM: Artificial Sequence
<220> FEATURE:
<223> OTHER INFORMATION: IL-13 Amino Acid

<400> SEQUENCE: 6

Pro Gly Pro Val Pro Ser Thr Ala Ile Arg Glu Leu Ile Glu Glu
1               5                   10                  15

Leu Leu Asn Ile Thr Gln Asn Gln Lys Ala Pro Leu Cys Asn Gly Ser
                20                  25                  30

Met Val Trp Ser Ile Asn Leu Thr Ala Gly Met Tyr Cys Ala Ala Leu
            35                  40                  45

Glu Ser Leu Ile Asn Val Ser Gly Cys Ser Ala Ile Glu Lys Thr Gln
50                  55                  60

Arg Met Leu Ser Gly Phe Cys Pro His Lys Val Ser Ala Gly Gln Phe
65                  70                  75                  80

Ser Ser Leu His Val Met Lys Ser Lys Ile Glu Val Ala Gln Phe Val
                85                  90                  95

Lys Asp Leu Leu His His Leu Arg Ala Leu Phe Arg Glu Gly Gln Phe
            100                 105                 110

Asn

<210> SEQ ID NO 7
<211> LENGTH: 113
<212> TYPE: PRT
<213> ORGANISM: Artificial Sequence
<220> FEATURE:
<223> OTHER INFORMATION: IL-13 Amino Acid

<400> SEQUENCE: 7

Pro Gly Pro Val Pro Ser Thr Ala Ile Arg Glu Leu Ile Glu Glu
1               5                   10                  15

Leu Ile Asn Ile Thr Gln Asn Gln Lys Ala Pro Leu Cys Asn Gly Ser
                20                  25                  30

Met Val Trp Ser Ile Asn Leu Thr Ala Gly Met Tyr Cys Ala Ala Leu
            35                  40                  45

Glu Ser Leu Ile Asn Val Ser Gly Cys Ser Ala Ile Glu Lys Thr Gln
50                  55                  60

Arg Met Leu Ser Gly Phe Cys Pro His Lys Val Ser Ala Gly Gln Phe
65                  70                  75                  80

Ser Ser Leu His Val Arg Ser Ser Arg Ile Glu Val Ala Gln Phe Val
                85                  90                  95

Lys Asp Leu Leu His His Leu Arg Thr Leu Phe Arg Glu Gly Gln Phe
            100                 105                 110

Asn

<210> SEQ ID NO 8
<211> LENGTH: 113
<212> TYPE: PRT

<213> ORGANISM: Artificial Sequence
<220> FEATURE:
<223> OTHER INFORMATION: IL-13 Amino Acid

<400> SEQUENCE: 8

```
Pro Gly Pro Val Pro Pro Ser Thr Ala Leu Arg Glu Leu Ile Glu Glu
1               5                   10                  15

Leu Ile Asn Ile Thr Gln Asn Glu Lys Ala Pro Leu Cys Asn Gly Ser
            20                  25                  30

Met Val Trp Ser Ile Asn Leu Thr Ala Gly Ile Tyr Cys Ala Ala Leu
        35                  40                  45

Glu Ser Leu Ile Asn Val Ser Gly Cys Ser Ala Ile Glu Lys Thr Gln
50                  55                  60

Arg Met Leu Ser Gly Phe Cys Pro His Lys Val Ser Ala Gly Gln Phe
65                  70                  75                  80

Ser Ser Leu His Val Thr Gly Ser Lys Ile Glu Val Ala Gln Phe Val
                85                  90                  95

Lys Asp Leu Leu Tyr His Leu Arg Ala Leu Phe Arg Glu Gly Gln Phe
            100                 105                 110

Asn
```

<210> SEQ ID NO 9
<211> LENGTH: 113
<212> TYPE: PRT
<213> ORGANISM: Artificial Sequence
<220> FEATURE:
<223> OTHER INFORMATION: IL-13 Amino Acid

<400> SEQUENCE: 9

```
Pro Gly Pro Val Pro Pro Ser Thr Ala Leu Ser Glu Leu Ile Glu Glu
1               5                   10                  15

Leu Ile Asn Ile Thr Gln Asn Gln Lys Ala Pro Leu Cys Asn Gly Ser
            20                  25                  30

Met Val Trp Ser Ile Asn Pro Thr Ala Gly Met Tyr Cys Ala Ala Leu
        35                  40                  45

Glu Ser Leu Ile Asn Val Ser Gly Cys Ser Ala Ile Glu Lys Thr Gln
50                  55                  60

Arg Met Leu Ser Gly Phe Cys Pro His Lys Val Ala Ala Gly Gln Phe
65                  70                  75                  80

Ser Ser Leu His Asp Lys Gly Ser Met Ile Glu Val Ala Gln Phe Val
                85                  90                  95

Lys Asp Leu Leu Tyr His Leu Arg Thr Leu Phe Arg Glu Gly Gln Phe
            100                 105                 110

Asn
```

<210> SEQ ID NO 10
<211> LENGTH: 113
<212> TYPE: PRT
<213> ORGANISM: Artificial Sequence
<220> FEATURE:
<223> OTHER INFORMATION: IL-13 Amino Acid

<400> SEQUENCE: 10

```
Pro Gly Pro Val Pro Pro Ser Thr Ala Thr Arg Glu Leu Ile Glu Glu
1               5                   10                  15

Leu Ile Asn Ile Thr Gln Asn Gln Lys Ala Pro Leu Cys Asn Gly Ser
            20                  25                  30

Met Val Trp Ser Ile Asn Leu Thr Ala Asp Met Tyr Cys Ala Ala Leu
```

```
                35                  40                  45
Glu Ser Leu Ile Asn Val Ser Gly Cys Ser Ala Ile Glu Lys Thr Gln
 50                  55                  60

Arg Met Leu Ser Gly Phe Cys Pro His Lys Val Ser Val Gly Gln Phe
 65                  70                  75                  80

Ser Ser Leu His Val Arg Gly Ser Lys Ile Glu Val Ala Gln Phe Val
                 85                  90                  95

Lys Asp Leu Leu Tyr His Leu Arg Thr Leu Phe Arg Glu Gly Gln Phe
                100                 105                 110

Asn

<210> SEQ ID NO 11
<211> LENGTH: 113
<212> TYPE: PRT
<213> ORGANISM: Artificial Sequence
<220> FEATURE:
<223> OTHER INFORMATION: IL-13 Amino Acid

<400> SEQUENCE: 11

Pro Gly Pro Val Pro Pro Ser Thr Ala Asp Ile Glu Leu Ile Ala Glu
  1               5                  10                  15

Leu Ile Asn Ile Thr Gln Asn Gln Lys Ala Pro Leu Cys Asn Gly Ser
                 20                  25                  30

Met Val Trp Ser Ile Asn Leu Thr Ala Asp Met Tyr Cys Ala Ala Leu
             35                  40                  45

Glu Ser Leu Ile Asn Val Ser Gly Cys Ser Ala Ile Glu Lys Thr Gln
 50                  55                  60

Arg Met Leu Ser Gly Phe Cys Pro His Lys Val Ser Ala Gly Gln Phe
 65                  70                  75                  80

Ser Ser Leu His Val Lys Lys Thr Arg Ile Glu Val Ala Gln Phe Val
                 85                  90                  95

Lys Asp Leu Leu Leu His Leu Lys Lys Leu Phe Lys Glu Gly Gln Phe
                100                 105                 110

Asn

<210> SEQ ID NO 12
<211> LENGTH: 113
<212> TYPE: PRT
<213> ORGANISM: Artificial Sequence
<220> FEATURE:
<223> OTHER INFORMATION: IL-13 Amino Acid

<400> SEQUENCE: 12

Pro Gly Pro Val Pro Pro Ser Thr Ala Ala Arg Glu Leu Ile Glu Glu
  1               5                  10                  15

Leu Val Asn Ile Thr Gln Asn Gln Lys Ala Pro Leu Cys Asn Gly Ser
                 20                  25                  30

Met Val Trp Ser Ile Asn Leu Thr Ala Gly Met Tyr Cys Ala Ala Leu
             35                  40                  45

Glu Ser Leu Ile Asn Val Ser Gly Cys Ser Ala Ile Glu Lys Thr Gln
 50                  55                  60

Arg Met Leu Ser Gly Phe Cys Pro His Lys Val Ser Ala Gly Gln Leu
 65                  70                  75                  80

Ser Ser Leu His Val Thr Gly Lys Arg Ile Glu Val Ala Gln Phe Val
                 85                  90                  95

Lys Asp Leu Leu Asn His Leu Arg Ala Leu Phe Lys Glu Gly Gln Phe
                100                 105                 110
```

Asn

<210> SEQ ID NO 13
<211> LENGTH: 113
<212> TYPE: PRT
<213> ORGANISM: Artificial Sequence
<220> FEATURE:
<223> OTHER INFORMATION: IL-13 Amino Acid

<400> SEQUENCE: 13

```
Pro Gly Pro Val Pro Pro Ser Thr Ala Val Arg Glu Leu Ile Glu
1               5                   10                  15

Leu Val Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Arg Asp Thr Arg Ile Glu Val Ala Gln Phe Val
                85                  90                  95

Lys Asp Leu Leu Asn His Leu Lys Glu Leu Phe Thr Gly Gly Gln Phe
                100                 105                 110
```

Asn

<210> SEQ ID NO 14
<211> LENGTH: 113
<212> TYPE: PRT
<213> ORGANISM: Artificial Sequence
<220> FEATURE:
<223> OTHER INFORMATION: IL-13 Amino Acid

<400> SEQUENCE: 14

```
Pro Gly Pro Val Pro Pro Ser Thr Ala Leu Ser Glu Leu Met Glu Glu
1               5                   10                  15

Leu Val Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Arg Asp Ser Lys Ile Glu Val Ala Gln Phe Val
                85                  90                  95

Lys Asp Leu Leu Asn His Leu Lys Ala Leu Phe Lys Glu Gly Gln Phe
                100                 105                 110
```

Asn

<210> SEQ ID NO 15
<211> LENGTH: 112
<212> TYPE: PRT
<213> ORGANISM: Artificial Sequence
<220> FEATURE:
<223> OTHER INFORMATION: IL-13 Amino Acid

<400> SEQUENCE: 15

```
Gly Pro Val Pro Pro Ser Thr Ala Phe Arg Glu Leu Ile Glu Glu Leu
1               5                   10                  15

Val Asn Ile Thr Gln Asn Gln Lys Ala Pro Leu Cys Asn Gly Ser Met
            20                  25                  30

Val Trp Ser Ile Asn Leu Thr Ala Gly Met Tyr Cys Ala Ala Leu Glu
            35                  40                  45

Ser Leu Ile Asn Val Ser Gly Cys Ser Ala Ile Glu Lys Thr Gln Arg
    50                  55                  60

Met Leu Ser Gly Phe Cys Pro His Lys Val Ser Pro Gly Gln Phe Ser
65                  70                  75                  80

Ser Leu His Val Thr Asn Ser Arg Ile Glu Val Ala Gln Phe Val Lys
                85                  90                  95

Asp Leu Leu Asn His Leu Lys Ala Leu Phe Lys Glu Gly Gln Tyr Asn
                100                 105                 110
```

<210> SEQ ID NO 16
<211> LENGTH: 112
<212> TYPE: PRT
<213> ORGANISM: Artificial Sequence
<220> FEATURE:
<223> OTHER INFORMATION: IL-13 Amino Acid

<400> SEQUENCE: 16

```
Gly Pro Val Pro Pro Ser Thr Ala His Leu Glu Leu Ile Glu Glu Leu
1               5                   10                  15

Ile Asn Ile Thr Gln Asn Gln Lys Ala Pro Leu Cys Asn Gly Ser Met
            20                  25                  30

Val Trp Ser Ile Asn Leu Thr Ala Gly Met Tyr Cys Ala Ala Leu Glu
            35                  40                  45

Ser Leu Ile Asn Val Ser Gly Cys Ser Ala Ile Glu Lys Thr Gln Arg
    50                  55                  60

Met Leu Ser Gly Phe Cys Pro His Lys Val Ser Ala Gly Gln Phe Ser
65                  70                  75                  80

Ser Leu His Val Lys Glu Thr Arg Ile Glu Val Ala Gln Phe Val Lys
                85                  90                  95

Asp Leu Leu Asn His Leu Lys Thr Leu Phe Lys Glu Gly Gln Phe Asn
                100                 105                 110
```

<210> SEQ ID NO 17
<211> LENGTH: 113
<212> TYPE: PRT
<213> ORGANISM: Artificial Sequence
<220> FEATURE:
<223> OTHER INFORMATION: IL-13 Amino Acid

<400> SEQUENCE: 17

```
Pro Gly Pro Val Pro Pro Ser Thr Ala His Leu Glu Leu Ile Glu Glu
1               5                   10                  15

Leu Ile Asn Ile Thr Gln Asn Gln Lys Ala Pro Leu Cys Asn Gly Ser
            20                  25                  30

Met Val Trp Ser Ile Asn Pro Thr Ala Gly Met Tyr Cys Ala Ala Leu
            35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Met Asp Thr Arg Ile Glu Val Ala Gln Phe Val
                85                  90                  95
```

Lys Asp Leu Leu Leu His Leu Lys Lys Leu Phe Lys Glu Gly Gln Phe
              100                 105                 110

Asn

<210> SEQ ID NO 18
<211> LENGTH: 113
<212> TYPE: PRT
<213> ORGANISM: Artificial Sequence
<220> FEATURE:
<223> OTHER INFORMATION: IL-13 Amino Acid

<400> SEQUENCE: 18

Pro Gly Pro Val Pro Pro Ser Thr Ala His Arg Glu Leu Ile Glu Glu
1               5                   10                  15

Leu Val Asn Ile Thr Gln Asn Gln Lys Ala Pro Leu Cys Asn Gly Ser
              20                  25                  30

Met Val Trp Ser Ile Asn Leu Thr Ala Gly Met Tyr Cys Ala Ala Leu
            35                  40                  45

Glu Ser Leu Ile Asn Val Ser Gly Cys Ser Ala Ile Glu Lys Thr Gln
          50                  55                  60

Arg Met Leu Ser Gly Phe Cys Pro His Lys Val Ser Ala Gly Gln Phe
65                  70                  75                  80

Ser Ser Leu His Val Thr Gly Arg Lys Ile Glu Val Ala Gln Phe Val
                85                  90                  95

Lys Asp Leu Leu Leu His Leu Lys Lys Leu Phe Lys Glu Gly Gln Phe
              100                 105                 110

Asn

<210> SEQ ID NO 19
<211> LENGTH: 113
<212> TYPE: PRT
<213> ORGANISM: Artificial Sequence
<220> FEATURE:
<223> OTHER INFORMATION: IL-13 Amino Acid

<400> SEQUENCE: 19

Pro Gly Pro Val Pro Pro Ser Thr Ala His Arg Glu Leu Ile Glu Glu
1               5                   10                  15

Leu Val Asn Ile Thr Gln Asn Gln Lys Ala Pro Leu Cys Asn Gly Ser
              20                  25                  30

Met Val Trp Arg Ile Asn Arg Thr Ala Gly Met Tyr Cys Ala Ala Leu
            35                  40                  45

Glu Ser Leu Ile Asn Val Ser Gly Cys Ser Ala Ile Glu Lys Thr Gln
          50                  55                  60

Arg Met Leu Ser Gly Phe Cys Pro His Lys Val Ser Ala Gly Gln Phe
65                  70                  75                  80

Ser Ser Leu His Val Met Asp Ser Arg Ile Glu Val Ala Gln Phe Val
                85                  90                  95

Lys Asp Leu Leu Asn His Leu Arg Ala Leu Phe Lys Glu Gly Gln Phe
              100                 105                 110

Asn

<210> SEQ ID NO 20
<211> LENGTH: 113
<212> TYPE: PRT
<213> ORGANISM: Artificial Sequence
<220> FEATURE:
<223> OTHER INFORMATION: IL-13 Amino Acid

<400> SEQUENCE: 20

```
Pro Gly Pro Val Pro Pro Ser Thr Ala Ala Arg Glu Leu Ile Glu Glu
1               5                   10                  15
Leu Phe Asn Ile Thr Gln Asn Gln Lys Ala Pro Leu Cys Asn Gly Ser
            20                  25                  30
Met Val Trp Ser Ile Asn Leu Thr Ala Gly Met Tyr Cys Ala Ala Leu
        35                  40                  45
Glu Ser Leu Ile Asn Val Ser Gly Cys Ser Ala Ile Glu Lys Thr Lys
50                  55                  60
Arg Met Leu Ser Gly Phe Cys Pro His Lys Val Ser Ala Gly Gln Phe
65                  70                  75                  80
Pro Ser Leu His Val Lys Lys Thr Arg Ile Glu Val Ala Gln Phe Val
            85                  90                  95
Lys Asp Leu Leu Ile His Leu Arg Lys Leu Phe Lys Glu Gly Gln Phe
            100                 105                 110
Asn
```

<210> SEQ ID NO 21
<211> LENGTH: 113
<212> TYPE: PRT
<213> ORGANISM: Artificial Sequence
<220> FEATURE:
<223> OTHER INFORMATION: IL-13 Amino Acid

<400> SEQUENCE: 21

```
Pro Gly Pro Val Pro Pro Ser Thr Ala Leu Ile Glu Leu Ile Glu Glu
1               5                   10                  15
Leu Ile Asn Ile Thr Gln Asn Gln Lys Ala Pro Leu Cys Asn Gly Ser
            20                  25                  30
Met Val Trp Ser Ile Asn Leu Thr Ala Gly Met Tyr Cys Ala Ala Leu
        35                  40                  45
Glu Ser Leu Ile Asn Val Ser Gly Cys Ser Ala Ile Glu Lys Thr Gln
50                  55                  60
Arg Met Leu Ser Gly Phe Cys Pro His Lys Val Ser Ala Gly Gln Phe
65                  70                  75                  80
Ser Ser Leu His Val Lys Gly Ser Lys Ile Glu Val Ala Gln Phe Val
            85                  90                  95
Lys Asp Leu Leu His His Leu Arg Ala Leu Met Arg Glu Gly Gln Phe
            100                 105                 110
Asn
```

<210> SEQ ID NO 22
<211> LENGTH: 113
<212> TYPE: PRT
<213> ORGANISM: Artificial Sequence
<220> FEATURE:
<223> OTHER INFORMATION: IL-13 Amino Acid

<400> SEQUENCE: 22

```
Pro Gly Pro Val Pro Pro Ser Thr Ala Ile Arg Glu Leu Ile Glu Glu
1               5                   10                  15
Leu Leu Asn Ile Thr Gln Asn Gln Lys Ala Pro Leu Cys Asn Gly Ser
            20                  25                  30
Met Val Trp Ser Ile Asn Leu Thr Ala Gly Met Tyr Cys Ala Ala Leu
        35                  40                  45
Glu Ser Leu Ile Asn Val Ser Gly Cys Ser Ala Ile Glu Lys Thr Gln
```

```
                    50                  55                  60
Arg Met Leu Ser Gly Phe Cys Pro His Lys Val Ser Ala Gly Gln Phe
 65                  70                  75                  80

Ser Ser Leu His Val Met Lys Ser Lys Ile Glu Val Ala Gln Phe Val
                     85                  90                  95

Lys Asp Leu Leu His His Leu Arg Ala Leu Phe Arg Glu Gly Gln Phe
                    100                 105                 110

Asn
```

<210> SEQ ID NO 23
<211> LENGTH: 113
<212> TYPE: PRT
<213> ORGANISM: Artificial Sequence
<220> FEATURE:
<223> OTHER INFORMATION: IL-13 Amino Acid

<400> SEQUENCE: 23

```
Pro Gly Pro Val Pro Pro Ser Thr Ala Ile Arg Glu Leu Ile Glu Glu
  1               5                  10                  15

Leu Ile Asn Ile Thr Gln Asn Gln Lys Ala Pro Leu Cys Asn Gly Ser
                 20                  25                  30

Met Val Trp Ser Ile Asn Leu Thr Ala Gly Met Tyr Cys Ala Ala Leu
             35                  40                  45

Glu Ser Leu Ile Asn Val Ser Gly Cys Ser Ala Ile Glu Lys Thr Gln
 50                  55                  60

Arg Met Leu Ser Gly Phe Cys Pro His Lys Val Ser Ala Gly Gln Phe
 65                  70                  75                  80

Ser Ser Leu His Val Arg Gly Ser Lys Ile Glu Val Ala Gln Phe Val
                     85                  90                  95

Lys Asp Leu Leu His His Leu Arg Ala Leu Phe Arg Glu Gly Gln Phe
                    100                 105                 110

Asn
```

<210> SEQ ID NO 24
<211> LENGTH: 113
<212> TYPE: PRT
<213> ORGANISM: Artificial Sequence
<220> FEATURE:
<223> OTHER INFORMATION: IL-13 Amino Acid

<400> SEQUENCE: 24

```
Pro Gly Pro Val Pro Pro Ser Thr Ala Ile Arg Glu Leu Ile Glu Glu
  1               5                  10                  15

Leu Ile Asn Ile Thr Gln Asn Gln Lys Ala Pro Leu Cys Asn Gly Ser
                 20                  25                  30

Met Val Trp Ser Ile Asn Leu Thr Ala Gly Met Tyr Cys Ala Ala Leu
             35                  40                  45

Glu Ser Leu Ile Asn Val Ser Gly Cys Ser Ala Ile Glu Lys Thr Gln
 50                  55                  60

Arg Met Leu Ser Gly Phe Cys Pro His Lys Val Ser Ala Gly Gln Phe
 65                  70                  75                  80

Ser Ser Leu His Val Arg Ser Ser Arg Ile Glu Val Ala Gln Phe Val
                     85                  90                  95

Lys Asp Leu Leu His His Leu Arg Thr Leu Phe Arg Glu Gly Gln Phe
                    100                 105                 110

Asn
```

<210> SEQ ID NO 25
<211> LENGTH: 113
<212> TYPE: PRT
<213> ORGANISM: Artificial Sequence
<220> FEATURE:
<223> OTHER INFORMATION: IL-13 Amino Acid

<400> SEQUENCE: 25

```
Pro Gly Pro Val Pro Pro Ser Thr Ala Val Arg Glu Leu Ile Glu Glu
1               5                   10                  15

Leu Ile Asn Ile Thr Gln Asn Gln Lys Ala Pro Leu Cys Asn Gly Ser
                20                  25                  30

Met Val Trp Ser Ile Asn Leu Thr Ala Gly Met Tyr Cys Ala Ala Leu
            35                  40                  45

Glu Ser Leu Ile Asn Val Ser Gly Cys Ser Ala Ile Glu Lys Thr Gln
        50                  55                  60

Arg Met Leu Ser Gly Phe Cys Pro His Lys Val Ser Ala Gly Gln Phe
65                  70                  75                  80

Ser Ser Leu His Val Arg Ser Ser Lys Ile Glu Val Ala Gln Phe Val
                85                  90                  95

Lys Asp Leu Leu Phe His Leu Arg Thr Leu Phe Arg Glu Gly Gln Phe
            100                 105                 110

Asn
```

<210> SEQ ID NO 26
<211> LENGTH: 113
<212> TYPE: PRT
<213> ORGANISM: Artificial Sequence
<220> FEATURE:
<223> OTHER INFORMATION: IL-13 Amino Acid

<400> SEQUENCE: 26

```
Pro Gly Pro Val Pro Pro Ser Thr Ala Leu Arg Glu Leu Ile Glu Glu
1               5                   10                  15

Leu Ile Asn Ile Thr Gln Asn Gln Lys Ala Pro Leu Cys Asn Gly Ser
                20                  25                  30

Met Val Trp Ser Ile Asn Leu Thr Ala Gly Met Tyr Cys Ala Ala Leu
            35                  40                  45

Glu Ser Leu Ile Asn Val Ser Gly Cys Ser Ala Ile Glu Lys Thr Gln
        50                  55                  60

Arg Met Leu Ser Gly Phe Cys Pro His Lys Val Ser Ala Gly Gln Phe
65                  70                  75                  80

Ser Ser Leu His Val Thr Gly Ser Lys Ile Glu Val Ala Gln Phe Val
                85                  90                  95

Lys Asp Leu Leu Tyr His Leu Arg Ala Leu Phe Arg Glu Gly Gln Phe
            100                 105                 110

Asn
```

<210> SEQ ID NO 27
<211> LENGTH: 113
<212> TYPE: PRT
<213> ORGANISM: Artificial Sequence
<220> FEATURE:
<223> OTHER INFORMATION: IL-13 Amino Acid

<400> SEQUENCE: 27

```
Pro Gly Pro Val Pro Pro Ser Thr Ala Leu Ser Glu Leu Ile Glu Glu
1               5                   10                  15
```

-continued

```
Leu Ile Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
 50                  55                  60

Arg Met Leu Ser Gly Phe Cys Pro His Lys Val Ser Ala Gly Gln Phe
65                  70                  75                  80

Ser Ser Leu His Val Lys Gly Ser Met Ile Glu Val Ala Gln Phe Val
                85                  90                  95

Lys Asp Leu Leu Tyr His Leu Arg Thr Leu Phe Arg Glu Gly Gln Phe
            100                 105                 110

Asn

<210> SEQ ID NO 28
<211> LENGTH: 113
<212> TYPE: PRT
<213> ORGANISM: Artificial Sequence
<220> FEATURE:
<223> OTHER INFORMATION: IL-13 Amino Acid

<400> SEQUENCE: 28

Pro Gly Pro Val Pro Pro Ser Thr Ala Thr Arg Glu Leu Ile Glu Glu
1               5                   10                  15

Leu Ile Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
 50                  55                  60

Arg Met Leu Ser Gly Phe Cys Pro His Lys Val Ser Ala Gly Gln Phe
65                  70                  75                  80

Ser Ser Leu His Val Arg Gly Ser Lys Ile Glu Val Ala Gln Phe Val
                85                  90                  95

Lys Asp Leu Leu Tyr His Leu Arg Thr Leu Phe Arg Glu Gly Gln Phe
            100                 105                 110

Asn

<210> SEQ ID NO 29
<211> LENGTH: 113
<212> TYPE: PRT
<213> ORGANISM: Artificial Sequence
<220> FEATURE:
<223> OTHER INFORMATION: IL-13 Amino Acid

<400> SEQUENCE: 29

Pro Gly Pro Val Pro Pro Ser Thr Ala Asp Ile Glu Leu Ile Glu Glu
1               5                   10                  15

Leu Ile Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
 50                  55                  60

Arg Met Leu Ser Gly Phe Cys Pro His Lys Val Ser Ala Gly Gln Phe
65                  70                  75                  80

Ser Ser Leu His Val Lys Lys Thr Arg Ile Glu Val Ala Gln Phe Val
```

85                  90                  95

Lys Asp Leu Leu Leu His Leu Lys Lys Leu Phe Lys Glu Gly Gln Phe
                100                 105                 110

Asn

<210> SEQ ID NO 30
<211> LENGTH: 113
<212> TYPE: PRT
<213> ORGANISM: Artificial Sequence
<220> FEATURE:
<223> OTHER INFORMATION: IL-13 Amino Acid

<400> SEQUENCE: 30

Pro Gly Pro Val Pro Pro Ser Thr Ala Ala Arg Glu Leu Ile Glu Glu
1               5                   10                  15

Leu Val Asn Ile Thr Gln Asn Gln Lys Ala Pro Leu Cys Asn Gly Ser
                20                  25                  30

Met Val Trp Ser Ile Asn Leu Thr Ala Gly Met Tyr Cys Ala Ala Leu
            35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Thr Gly Lys Arg Ile Glu Val Ala Gln Phe Val
                85                  90                  95

Lys Asp Leu Leu Asn His Leu Arg Ala Leu Phe Lys Glu Gly Gln Phe
                100                 105                 110

Asn

<210> SEQ ID NO 31
<211> LENGTH: 113
<212> TYPE: PRT
<213> ORGANISM: Artificial Sequence
<220> FEATURE:
<223> OTHER INFORMATION: IL-13 Amino Acid

<400> SEQUENCE: 31

Pro Gly Pro Val Pro Pro Ser Thr Ala Val Arg Glu Leu Ile Glu Glu
1               5                   10                  15

Leu Val Asn Ile Thr Gln Asn Gln Lys Ala Pro Leu Cys Asn Gly Ser
                20                  25                  30

Met Val Trp Ser Ile Asn Leu Thr Ala Gly Met Tyr Cys Ala Ala Leu
            35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Arg Asp Thr Arg Ile Glu Val Ala Gln Phe Val
                85                  90                  95

Lys Asp Leu Leu Asn His Leu Lys Glu Leu Phe Thr Glu Gly Gln Phe
                100                 105                 110

Asn

<210> SEQ ID NO 32
<211> LENGTH: 113
<212> TYPE: PRT
<213> ORGANISM: Artificial Sequence
<220> FEATURE:

<223> OTHER INFORMATION: IL-13 Amino Acid

<400> SEQUENCE: 32

Pro Gly Pro Val Pro Pro Ser Thr Ala Leu Ser Glu Leu Met Glu Glu
1               5                   10                  15

Leu Val Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Arg Asp Ser Lys Ile Glu Val Ala Gln Phe Val
                85                  90                  95

Lys Asp Leu Leu Asn His Leu Lys Ala Leu Phe Lys Glu Gly Gln Phe
            100                 105                 110

Asn

<210> SEQ ID NO 33
<211> LENGTH: 113
<212> TYPE: PRT
<213> ORGANISM: Artificial Sequence
<220> FEATURE:
<223> OTHER INFORMATION: IL-13 Amino Acid

<400> SEQUENCE: 33

Pro Gly Pro Val Pro Pro Ser Thr Ala His Leu Glu Leu Ile Glu Glu
1               5                   10                  15

Leu Ile Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Lys Glu Thr Arg Ile Glu Val Ala Gln Phe Val
                85                  90                  95

Lys Asp Leu Leu Asn His Leu Lys Thr Leu Phe Lys Glu Gly Gln Phe
            100                 105                 110

Asn

<210> SEQ ID NO 34
<211> LENGTH: 113
<212> TYPE: PRT
<213> ORGANISM: Artificial Sequence
<220> FEATURE:
<223> OTHER INFORMATION: IL-13 Amino Acid

<400> SEQUENCE: 34

Pro Gly Pro Val Pro Pro Ser Thr Ala His Leu Glu Leu Ile Glu Glu
1               5                   10                  15

Leu Ile Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

```
Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Met Asp Thr Arg Ile Glu Val Ala Gln Phe Val
                85                  90                  95

Lys Asp Leu Leu Leu His Leu Lys Lys Leu Phe Lys Glu Gly Gln Phe
                100                 105                 110

Asn

<210> SEQ ID NO 35
<211> LENGTH: 113
<212> TYPE: PRT
<213> ORGANISM: Artificial Sequence
<220> FEATURE:
<223> OTHER INFORMATION: IL-13 Amino Acid

<400> SEQUENCE: 35

Pro Gly Pro Val Pro Pro Ser Thr Ala His Arg Glu Leu Ile Glu Glu
1               5                   10                  15

Leu Val Asn Ile Thr Gln Asn Gln Lys Ala Pro Leu Cys Asn Gly Ser
                20                  25                  30

Met Val Trp Ser Ile Asn Leu Thr Ala Gly Met Tyr Cys Ala Ala Leu
            35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Thr Gly Arg Lys Ile Glu Val Ala Gln Phe Val
                85                  90                  95

Lys Asp Leu Leu Leu His Leu Lys Lys Leu Phe Lys Glu Gly Gln Phe
                100                 105                 110

Asn

<210> SEQ ID NO 36
<211> LENGTH: 113
<212> TYPE: PRT
<213> ORGANISM: Artificial Sequence
<220> FEATURE:
<223> OTHER INFORMATION: IL-13 Amino Acid

<400> SEQUENCE: 36

Pro Gly Pro Val Pro Pro Ser Thr Ala His Arg Glu Leu Ile Glu Glu
1               5                   10                  15

Leu Val Asn Ile Thr Gln Asn Gln Lys Ala Pro Leu Cys Asn Gly Ser
                20                  25                  30

Met Val Trp Ser Ile Asn Leu Thr Ala Gly Met Tyr Cys Ala Ala Leu
            35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Met Asp Ser Arg Ile Glu Val Ala Gln Phe Val
                85                  90                  95

Lys Asp Leu Leu Asn His Leu Arg Ala Leu Phe Lys Glu Gly Gln Phe
                100                 105                 110

Asn
```

<210> SEQ ID NO 37
<211> LENGTH: 113
<212> TYPE: PRT
<213> ORGANISM: Artificial Sequence
<220> FEATURE:
<223> OTHER INFORMATION: IL-13 Amino Acid

<400> SEQUENCE: 37

```
Pro Gly Pro Val Pro Pro Ser Thr Ala Ala Arg Glu Leu Ile Glu Glu
1               5                   10                  15

Leu Phe Asn Ile Thr Gln Asn Gln Lys Ala Pro Leu Cys Asn Gly Ser
                20                  25                  30

Met Val Trp Ser Ile Asn Leu Thr Ala Gly Met Tyr Cys Ala Ala Leu
            35                  40                  45

Glu Ser Leu Ile Asn Val Ser Gly Cys Ser Ala Ile Glu Lys Thr Gln
        50                  55                  60

Arg Met Leu Ser Gly Phe Cys Pro His Lys Val Ser Ala Gly Gln Phe
65                  70                  75                  80

Ser Ser Leu His Val Lys Lys Thr Arg Ile Glu Val Ala Gln Phe Val
                85                  90                  95

Lys Asp Leu Leu Ile His Leu Arg Lys Leu Phe Lys Glu Gly Gln Phe
                100                 105                 110

Asn
```

<210> SEQ ID NO 38
<211> LENGTH: 113
<212> TYPE: PRT
<213> ORGANISM: Artificial Sequence
<220> FEATURE:
<223> OTHER INFORMATION: IL-13 Amino Acid

<400> SEQUENCE: 38

```
Pro Gly Pro Val Pro Pro Ser Thr Ala Val Arg Ala Leu Ile Glu Glu
1               5                   10                  15

Leu Ile Asn Ile Thr Gln Asn Gln Lys Ala Pro Leu Cys Asn Gly Ser
                20                  25                  30

Met Val Trp Ser Ile Asn Leu Thr Ala Gly Met Tyr Cys Ala Ala Leu
            35                  40                  45

Glu Ser Leu Ile Asn Val Ser Gly Cys Ser Ala Ile Glu Lys Thr Gln
        50                  55                  60

Asp Met Leu Ser Gly Phe Cys Pro His Lys Val Ser Ala Gly Gln Phe
65                  70                  75                  80

Ser Ser Leu His Val Arg Ser Ser Lys Ile Glu Val Ala Gln Phe Val
                85                  90                  95

Lys Asp Leu Leu Phe His Leu Arg Thr Leu Phe Arg Glu Gly Gln Phe
                100                 105                 110

Asn
```

<210> SEQ ID NO 39
<211> LENGTH: 146
<212> TYPE: PRT
<213> ORGANISM: Artificial Sequence
<220> FEATURE:
<223> OTHER INFORMATION: IL-13 Amino Acid - signal peptide

<400> SEQUENCE: 39

```
Met His Pro Leu Leu Asn Pro Leu Leu Leu Ala Leu Gly Leu Met Ala
1               5                   10                  15
```

```
Leu Leu Leu Thr Thr Val Ile Ala Leu Thr Cys Leu Gly Gly Phe Ala
            20                  25                  30

Ser Pro Gly Pro Val Pro Pro Ser Thr Ala His Arg Glu Leu Ile Glu
        35                  40                  45

Glu Leu Val Asn Ile Thr Gln Asn Gln Lys Ala Pro Leu Cys Asn Gly
 50                  55                  60

Ser Met Val Trp Ser Ile Asn Leu Thr Ala Gly Met Tyr Cys Ala Ala
 65                  70                  75                  80

Leu Glu Ser Leu Ile Asn Val Ser Gly Cys Ser Ala Ile Glu Lys Thr
                85                  90                  95

Gln Arg Met Leu Ser Gly Phe Cys Pro His Lys Val Ser Ala Gly Gln
            100                 105                 110

Phe Ser Ser Leu His Val Thr Gly Arg Lys Ile Glu Val Ala Gln Phe
        115                 120                 125

Val Lys Asp Leu Leu Leu His Leu Lys Lys Leu Phe Lys Glu Gly Gln
    130                 135                 140

Phe Asn
145
```

<210> SEQ ID NO 40
<211> LENGTH: 113
<212> TYPE: PRT
<213> ORGANISM: Artificial Sequence
<220> FEATURE:
<223> OTHER INFORMATION: IL-13 Amino Acid

<400> SEQUENCE: 40

```
Pro Gly Pro Val Pro Pro Ser Thr Ala Val Arg Ala Leu Ile Glu Glu
 1               5                  10                  15

Leu Ile Asn Ile Thr Gln Asn Gln Lys Ala Pro Leu Cys Asn Gly Ser
            20                  25                  30

Met Val Trp Ser Ile Asn Arg Thr Ala Gly Met Tyr Cys Ala Ala Leu
        35                  40                  45

Glu Ser Leu Ile Asn Val Ser Gly Cys Ser Ala Ile Glu Lys Thr Gln
 50                  55                  60

Asp Met Leu Ser Gly Phe Cys Pro His Lys Val Ser Ala Gly Gln Phe
 65                  70                  75                  80

Ser Ser Leu His Val Arg Ser Ser Lys Ile Glu Val Ala Gln Phe Val
                85                  90                  95

Lys Asp Leu Leu Phe His Leu Arg Thr Leu Phe Arg Glu Gly Gln Phe
            100                 105                 110

Asn
```

<210> SEQ ID NO 41
<211> LENGTH: 113
<212> TYPE: PRT
<213> ORGANISM: Artificial Sequence
<220> FEATURE:
<223> OTHER INFORMATION: IL-13 Amino Acid

<400> SEQUENCE: 41

```
Pro Gly Pro Val Pro Pro Ser Thr Ala Val Arg Ala Leu Ile Glu Glu
 1               5                  10                  15

Leu Ile Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45
```

```
Glu Ser Leu Ile Asn Val Ser Gly Cys Ser Ala Ile Glu Lys Thr Gln
    50                  55                  60

Asp Met Leu Ser Gly Phe Cys Pro His Lys Val Ser Ala Gly Gln Phe
65                  70                  75                  80

Ser Ser Leu His Val Arg Ser Ser Lys Ile Glu Val Ala Gln Phe Val
                85                  90                  95

Lys Asp Leu Leu Phe His Leu Arg Thr Leu Phe Arg Glu Gly Gln Phe
                100                 105                 110

Asn

<210> SEQ ID NO 42
<211> LENGTH: 114
<212> TYPE: PRT
<213> ORGANISM: Artificial Sequence
<220> FEATURE:
<223> OTHER INFORMATION: IL-13 Amino Acid

<400> SEQUENCE: 42

Met Pro Gly Pro Val Pro Pro Ser Thr Ala Leu Arg Glu Leu Ile Glu
1               5                   10                  15

Glu Leu Val Asn Ile Thr Gln Asn Gln Lys Ala Pro Leu Cys Asn Gly
                20                  25                  30

Ser Met Val Trp Ser Ile Asn Leu Thr Ala Gly Met Tyr Cys Ala Ala
            35                  40                  45

Leu Glu Ser Leu Ile Asn Val Ser Gly Cys Ser Ala Ile Glu Lys Thr
        50                  55                  60

Gln Arg Met Leu Ser Gly Phe Cys Pro His Lys Val Ser Ala Gly Gln
65                  70                  75                  80

Phe Ser Ser Leu His Val Arg Asp Thr Lys Ile Glu Val Ala Gln Phe
                85                  90                  95

Val Lys Asp Leu Leu Leu His Leu Lys Lys Leu Phe Arg Glu Gly Gln
                100                 105                 110

Phe Asn

<210> SEQ ID NO 43
<211> LENGTH: 117
<212> TYPE: PRT
<213> ORGANISM: Artificial Sequence
<220> FEATURE:
<223> OTHER INFORMATION: IL-13 Amino Acid

<400> SEQUENCE: 43

Met Tyr Cys Ala Ala Leu Glu Ser Leu Ile Asn Val Ser Gly Cys Ser
1               5                   10                  15

Ala Ile Glu Lys Thr Gln Arg Met Leu Ser Gly Phe Cys Pro His Lys
                20                  25                  30

Val Ser Ala Gly Gln Phe Ser Ser Leu His Val Arg Asp Thr Lys Ile
            35                  40                  45

Glu Val Ala Gln Phe Val Lys Asp Leu Leu Leu His Leu Lys Lys Leu
        50                  55                  60

Phe Arg Glu Gly Gln Phe Asn Gly Gly Ser Gly Pro Gly Pro Val Pro
65                  70                  75                  80

Pro Ser Thr Ala Leu Arg Glu Leu Ile Glu Glu Leu Val Asn Ile Thr
                85                  90                  95

Gln Asn Gln Lys Ala Pro Leu Cys Asn Gly Ser Met Val Trp Ser Ile
                100                 105                 110
```

Asn Leu Thr Ala Gly
        115

<210> SEQ ID NO 44
<211> LENGTH: 118
<212> TYPE: PRT
<213> ORGANISM: Artificial Sequence
<220> FEATURE:
<223> OTHER INFORMATION: IL-13 Amino Acid

<400> SEQUENCE: 44

Met Tyr Cys Ala Ala Leu Glu Ser Leu Ile Asn Val Ser Gly Cys Ser
1               5                   10                  15

Ala Ile Glu Lys Thr Gln Arg Met Leu Ser Gly Phe Cys Pro His Lys
            20                  25                  30

Val Ser Ala Gly Gln Phe Ser Ser Leu His Val Arg Asp Thr Lys Ile
        35                  40                  45

Glu Val Ala Gln Phe Val Lys Asp Leu Leu Leu His Leu Lys Lys Leu
    50                  55                  60

Phe Arg Glu Gly Gln Phe Asn Gly Gly Ser Gly Met Pro Gly Pro Val
65                  70                  75                  80

Pro Pro Ser Thr Ala Leu Arg Glu Leu Ile Glu Glu Leu Val Asn Ile
                85                  90                  95

Thr Gln Asn Gln Lys Ala Pro Leu Cys Asn Gly Ser Met Val Trp Ser
            100                 105                 110

Ile Asn Leu Thr Ala Gly
        115

<210> SEQ ID NO 45
<211> LENGTH: 117
<212> TYPE: PRT
<213> ORGANISM: Artificial Sequence
<220> FEATURE:
<223> OTHER INFORMATION: IL-13 Amino Acid

<400> SEQUENCE: 45

Met Tyr Cys Ala Ala Leu Glu Ser Leu Ile Asn Val Ser Gly Cys Ser
1               5                   10                  15

Ala Ile Glu Lys Thr Gln Arg Met Leu Ser Gly Phe Cys Pro His Lys
            20                  25                  30

Val Ser Ala Gly Gln Phe Ser Ser Leu His Val Arg Ser Ser Lys Ile
        35                  40                  45

Glu Val Ala Gln Phe Val Lys Asp Leu Leu Phe His Leu Arg Thr Leu
    50                  55                  60

Phe Arg Glu Gly Gln Phe Asn Gly Gly Ser Gly Pro Gly Pro Val Pro
65                  70                  75                  80

Pro Ser Thr Ala Val Arg Glu Leu Ile Glu Glu Leu Ile Asn Ile Thr
                85                  90                  95

Gln Asn Gln Lys Ala Pro Leu Cys Asn Gly Ser Met Val Trp Ser Ile
            100                 105                 110

Asn Arg Thr Ala Gly
        115

<210> SEQ ID NO 46
<211> LENGTH: 118
<212> TYPE: PRT
<213> ORGANISM: Artificial Sequence
<220> FEATURE:
<223> OTHER INFORMATION: IL-13 Amino Acid

```
<400> SEQUENCE: 46

Met Tyr Cys Ala Ala Leu Glu Ser Leu Ile Asn Val Ser Gly Cys Ser
1               5                   10                  15

Ala Ile Glu Lys Thr Gln Arg Met Leu Ser Gly Phe Cys Pro His Lys
            20                  25                  30

Val Ser Ala Gly Gln Phe Ser Ser Leu His Val Arg Ser Ser Lys Ile
        35                  40                  45

Glu Val Ala Gln Phe Val Lys Asp Leu Leu Phe His Leu Arg Thr Leu
    50                  55                  60

Phe Arg Glu Gly Gln Phe Asn Gly Gly Ser Gly Met Pro Gly Pro Val
65                  70                  75                  80

Pro Pro Ser Thr Ala Val Arg Glu Leu Ile Glu Glu Leu Ile Asn Ile
                85                  90                  95

Thr Gln Asn Gln Lys Ala Pro Leu Cys Asn Gly Ser Met Val Trp Ser
            100                 105                 110

Ile Asn Arg Thr Ala Gly
            115

<210> SEQ ID NO 47
<211> LENGTH: 117
<212> TYPE: PRT
<213> ORGANISM: Artificial Sequence
<220> FEATURE:
<223> OTHER INFORMATION: IL-13 Amino Acid

<400> SEQUENCE: 47

Met Tyr Cys Ala Ala Leu Glu Ser Leu Ile Asn Val Ser Gly Cys Ser
1               5                   10                  15

Ala Ile Glu Lys Thr Gln Asp Met Leu Ser Gly Phe Cys Pro His Lys
            20                  25                  30

Val Ser Ala Gly Gln Phe Ser Ser Leu His Val Arg Ser Ser Lys Ile
        35                  40                  45

Glu Val Ala Gln Phe Val Lys Asp Leu Leu Phe His Leu Arg Thr Leu
    50                  55                  60

Phe Arg Glu Gly Gln Phe Asn Gly Gly Ser Gly Pro Gly Pro Val Pro
65                  70                  75                  80

Pro Ser Thr Ala Val Arg Ala Leu Ile Glu Glu Leu Ile Asn Ile Thr
                85                  90                  95

Gln Asn Gln Lys Ala Pro Leu Cys Asn Gly Ser Met Val Trp Ser Ile
            100                 105                 110

Asn Leu Thr Ala Gly
        115

<210> SEQ ID NO 48
<211> LENGTH: 118
<212> TYPE: PRT
<213> ORGANISM: Artificial Sequence
<220> FEATURE:
<223> OTHER INFORMATION: IL-13 Amino Acid

<400> SEQUENCE: 48

Met Tyr Cys Ala Ala Leu Glu Ser Leu Ile Asn Val Ser Gly Cys Ser
1               5                   10                  15

Ala Ile Glu Lys Thr Gln Asp Met Leu Ser Gly Phe Cys Pro His Lys
            20                  25                  30

Val Ser Ala Gly Gln Phe Ser Ser Leu His Val Arg Ser Ser Lys Ile
        35                  40                  45
```

-continued

Glu Val Ala Gln Phe Val Lys Asp Leu Leu Phe His Leu Arg Thr Leu
 50                  55                  60

Phe Arg Glu Gly Gln Phe Asn Gly Gly Ser Gly Met Pro Gly Pro Val
 65                  70                  75                  80

Pro Pro Ser Thr Ala Val Arg Ala Leu Ile Glu Glu Leu Ile Asn Ile
                 85                  90                  95

Thr Gln Asn Gln Lys Ala Pro Leu Cys Asn Gly Ser Met Val Trp Ser
            100                 105                 110

Ile Asn Leu Thr Ala Gly
            115

<210> SEQ ID NO 49
<211> LENGTH: 153
<212> TYPE: PRT
<213> ORGANISM: Artificial Sequence
<220> FEATURE:
<223> OTHER INFORMATION: IL-4 wildtype with signal peptide

<400> SEQUENCE: 49

Met Gly Leu Thr Ser Gln Leu Leu Pro Pro Leu Phe Phe Leu Leu Ala
 1               5                  10                  15

Cys Ala Gly Asn Phe Val His Gly His Lys Cys Asp Ile Thr Leu Gln
                 20                  25                  30

Glu Ile Ile Lys Thr Leu Asn Ser Leu Thr Glu Gln Lys Thr Leu Cys
             35                  40                  45

Thr Glu Leu Thr Val Thr Asp Ile Phe Ala Ala Ser Lys Asn Thr Thr
 50                  55                  60

Glu Lys Glu Thr Phe Cys Arg Ala Ala Thr Val Leu Arg Gln Phe Tyr
 65                  70                  75                  80

Ser His His Glu Lys Asp Thr Arg Cys Leu Gly Ala Thr Ala Gln Gln
                 85                  90                  95

Phe His Arg His Lys Gln Leu Ile Arg Phe Leu Lys Arg Leu Asp Arg
            100                 105                 110

Asn Leu Trp Gly Leu Ala Gly Leu Asn Ser Cys Pro Val Lys Glu Ala
            115                 120                 125

Asn Gln Ser Thr Leu Glu Asn Phe Leu Glu Arg Leu Lys Thr Ile Met
        130                 135                 140

Arg Glu Lys Tyr Ser Lys Cys Ser Ser
145                 150

<210> SEQ ID NO 50
<211> LENGTH: 130
<212> TYPE: PRT
<213> ORGANISM: Artificial Sequence
<220> FEATURE:
<223> OTHER INFORMATION: IL-4 Amino Acid

<400> SEQUENCE: 50

Met His Lys Cys Asp Ile Thr Leu Gln Glu Ile Ile Lys Thr Leu Asn
 1               5                  10                  15

Ser Leu Thr Glu Gln Lys Thr Leu Cys Thr Glu Leu Thr Val Thr Asp
                 20                  25                  30

Ile Phe Ala Ala Ser Lys Asp Thr Thr Glu Lys Glu Thr Phe Cys Arg
             35                  40                  45

Ala Ala Thr Val Leu Arg Gln Phe Tyr Ser His His Glu Lys Asp Thr
 50                  55                  60

Arg Cys Leu Gly Ala Thr Ala Gln Gln Phe His Arg His Lys Gln Leu
 65                  70                  75                  80

```
Ile Arg Phe Leu Lys Arg Leu Asp Arg Asn Leu Trp Gly Leu Ala Gly
            85                  90                  95

Leu Asn Ser Cys Pro Val Lys Glu Ala Asn Gln Ser Thr Leu Glu Asn
            100                 105                 110

Phe Leu Glu Arg Leu Lys Thr Ile Met Arg Glu Lys Tyr Ser Lys Cys
            115                 120                 125

Ser Ser
    130
```

<210> SEQ ID NO 51
<211> LENGTH: 128
<212> TYPE: PRT
<213> ORGANISM: Artificial Sequence
<220> FEATURE:
<223> OTHER INFORMATION: IL-4 Amino Acid

<400> SEQUENCE: 51

```
Lys Cys Asp Ile Thr Leu Gln Glu Ile Ile Lys Thr Leu Asn Ser Leu
1               5                   10                  15

Thr Glu Gln Lys Thr Leu Cys Thr Glu Leu Thr Val Thr Asp Ile Phe
            20                  25                  30

Ala Ala Ser Lys Asn Thr Thr Glu Lys Glu Thr Phe Cys Arg Ala Ala
            35                  40                  45

Thr Val Leu Arg Gln Phe Tyr Ser His His Lys Asp Thr Arg Cys
50                  55                  60

Leu Gly Ala Thr Ala Gln Gln Phe His Arg His Lys Gln Leu Ile Arg
65                  70                  75                  80

Phe Leu Lys Arg Leu Asp Arg Asn Leu Trp Gly Leu Ala Gly Leu Asn
            85                  90                  95

Ser Cys Pro Val Lys Glu Ala Asn Gln Ser Thr Leu Glu Asn Phe Leu
            100                 105                 110

Glu Arg Leu Lys Thr Ile Met Lys Glu Lys Phe Arg Lys Cys Ser Ser
            115                 120                 125
```

<210> SEQ ID NO 52
<211> LENGTH: 134
<212> TYPE: PRT
<213> ORGANISM: Artificial Sequence
<220> FEATURE:
<223> OTHER INFORMATION: IL-4 Amino Acid

<400> SEQUENCE: 52

```
Met Asp Thr Thr Glu Lys Glu Thr Phe Cys Arg Ala Ala Thr Val Leu
1               5                   10                  15

Arg Gln Phe Tyr Ser His His Glu Lys Asp Thr Arg Cys Leu Gly Ala
            20                  25                  30

Thr Ala Gln Gln Phe His Arg His Lys Gln Leu Ile Arg Phe Leu Lys
            35                  40                  45

Arg Leu Asp Arg Asn Leu Trp Gly Leu Ala Gly Leu Asn Ser Cys Pro
50                  55                  60

Val Lys Glu Ala Asn Gln Ser Thr Leu Glu Asn Phe Leu Glu Arg Leu
65                  70                  75                  80

Arg Val Ile Met Gln Ser Lys Trp Phe Lys Cys Gly Ala Gly Gly Asn
            85                  90                  95

Gly Gly His Lys Cys Asp Ile Thr Leu Gln Glu Ile Ile Lys Thr Leu
            100                 105                 110

Asn Ser Leu Thr Glu Gln Lys Thr Leu Cys Thr Glu Leu Thr Val Thr
```

115                 120                 125

Asp Ile Phe Ala Ala Ser
    130

<210> SEQ ID NO 53
<211> LENGTH: 134
<212> TYPE: PRT
<213> ORGANISM: Artificial Sequence
<220> FEATURE:
<223> OTHER INFORMATION: IL-4 Amino Acid

<400> SEQUENCE: 53

Met Asp Thr Thr Glu Lys Glu Thr Phe Cys Arg Ala Ala Thr Val Leu
1               5                   10                  15

Arg Gln Phe Tyr Ser His His Glu Lys Asp Thr Arg Cys Leu Gly Ala
            20                  25                  30

Thr Ala Gln Gln Phe His Arg His Lys Gln Leu Ile Arg Phe Leu Lys
        35                  40                  45

Arg Leu Asp Arg Asn Leu Trp Gly Leu Ala Gly Leu Asn Ser Cys Pro
    50                  55                  60

Val Lys Glu Ala Asn Gln Ser Thr Leu Glu Asn Phe Leu Glu Arg Leu
65                  70                  75                  80

Lys Thr Ile Met Arg Glu Lys Tyr Ser Lys Cys Ser Ser Gly Gly Asn
                85                  90                  95

Gly Gly His Lys Cys Asp Ile Thr Leu Gln Glu Ile Ile Lys Thr Leu
            100                 105                 110

Asn Ser Leu Thr Glu Gln Lys Thr Leu Cys Thr Glu Leu Thr Val Thr
        115                 120                 125

Asp Ile Phe Ala Ala Ser
    130

<210> SEQ ID NO 54
<211> LENGTH: 252
<212> TYPE: PRT
<213> ORGANISM: Artificial Sequence
<220> FEATURE:
<223> OTHER INFORMATION: IL-4 Amino Acid

<400> SEQUENCE: 54

Met Asp Thr Thr Glu Lys Glu Thr Phe Cys Arg Ala Ala Thr Val Leu
1               5                   10                  15

Arg Gln Phe Tyr Ser His His Glu Lys Asp Thr Arg Cys Leu Gly Ala
            20                  25                  30

Thr Ala Gln Gln Phe His Arg His Lys Gln Leu Ile Arg Phe Leu Lys
        35                  40                  45

Arg Leu Asp Arg Asn Leu Trp Gly Leu Ala Gly Leu Asn Ser Cys Pro
    50                  55                  60

Val Lys Glu Ala Asn Gln Ser Thr Leu Glu Asn Phe Leu Glu Arg Leu
65                  70                  75                  80

Lys Thr Ile Met Lys Glu Lys Phe Arg Lys Cys Ser Ser Gly Gly Asn
                85                  90                  95

Gly Gly His Lys Cys Asp Ile Thr Leu Gln Glu Ile Ile Lys Thr Leu
            100                 105                 110

Asn Ser Leu Thr Glu Gln Lys Thr Leu Cys Thr Glu Leu Thr Val Thr
        115                 120                 125

Asp Ile Phe Ala Ala Ser Arg Gln Phe Tyr Ser His His Glu Lys Asp
    130                 135                 140

```
Thr Arg Cys Leu Gly Ala Thr Ala Gln Gln Phe His Arg His Lys Gln
145                 150                 155                 160

Leu Ile Arg Phe Leu Lys Arg Leu Asp Arg Asn Leu Trp Gly Leu Ala
                165                 170                 175

Gly Leu Asn Ser Cys Pro Val Lys Glu Ala Asn Gln Ser Thr Leu Glu
            180                 185                 190

Asn Phe Leu Glu Arg Leu Arg Val Ile Met Gln Ser Lys Trp Phe Lys
        195                 200                 205

Cys Gly Ala Gly Gly Asn Gly Gly His Lys Cys Asp Ile Thr Leu Gln
    210                 215                 220

Glu Ile Ile Lys Thr Leu Asn Ser Leu Thr Glu Gln Lys Thr Leu Cys
225                 230                 235                 240

Thr Glu Leu Thr Val Thr Asp Ile Phe Ala Ala Ser
                245                 250

<210> SEQ ID NO 55
<211> LENGTH: 133
<212> TYPE: PRT
<213> ORGANISM: Artificial Sequence
<220> FEATURE:
<223> OTHER INFORMATION: IL-4 Amino Acid

<400> SEQUENCE: 55

Met Asp Thr Thr Glu Lys Glu Thr Phe Cys Arg Ala Ala Thr Val Leu
1               5                   10                  15

Arg Gln Phe Tyr Ser His His Glu Lys Asp Thr Arg Cys Leu Gly Ala
            20                  25                  30

Thr Ala Gln Gln Phe His Arg His Lys Gln Leu Ile Arg Phe Leu Lys
        35                  40                  45

Arg Leu Asp Arg Asn Leu Trp Gly Leu Ala Gly Leu Asn Ser Cys Pro
    50                  55                  60

Val Lys Glu Ala Asn Gln Ser Thr Leu Glu Asn Phe Leu Glu Arg Leu
65                  70                  75                  80

Lys Thr Ile Met Lys Glu Lys Phe Lys Cys Ser Ser Gly Gly Asn Gly
                85                  90                  95

Gly His Lys Cys Asp Ile Thr Leu Gln Glu Ile Ile Lys Thr Leu Asn
            100                 105                 110

Ser Leu Thr Glu Gln Lys Thr Leu Cys Thr Glu Leu Thr Val Thr Asp
        115                 120                 125

Ile Phe Ala Ala Ser
    130

<210> SEQ ID NO 56
<211> LENGTH: 286
<212> TYPE: PRT
<213> ORGANISM: Artificial Sequence
<220> FEATURE:
<223> OTHER INFORMATION: Cytokine Fusion containing either IL-4 or IL-13

<400> SEQUENCE: 56

Pro Gly Pro Val Pro Pro Ser Thr Ala His Arg Glu Leu Ile Glu Glu
1               5                   10                  15

Leu Val Asn Ile Thr Gln Asn Gln Lys Ala Pro Leu Cys Asn Gly Ser
            20                  25                  30

Met Val Trp Ser Ile Asn Leu Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60
```

Arg Met Leu Ser Gly Phe Cys Pro His Lys Val Ser Ala Gly Gln Phe
65                  70                  75                  80

Ser Ser Leu His Val Thr Gly Arg Lys Ile Glu Val Ala Gln Phe Val
                85                  90                  95

Lys Asp Leu Leu Leu His Leu Lys Lys Leu Phe Lys Glu Gly Gln Phe
            100                 105                 110

Asn Gly Gly Gly Gly Ser Met Phe Gln Ile Pro Glu Phe Glu Pro Ser
        115                 120                 125

Glu Gln Glu Asp Ser Ser Ala Glu Arg Gly Leu Gly Pro Ser Pro
    130                 135                 140

Ala Gly Asp Gly Pro Ser Gly Ser Gly Lys His His Arg Gln Ala Pro
145                 150                 155                 160

Gly Leu Leu Trp Asp Ala Ser His Gln Gln Glu Gln Pro Thr Ser Ser
                165                 170                 175

Ser His His Gly Gly Ala Gly Ala Val Glu Ile Arg Ser Arg His Ser
            180                 185                 190

Ala Tyr Pro Ala Gly Thr Glu Asp Asp Glu Gly Met Gly Glu Glu Pro
        195                 200                 205

Ser Pro Phe Arg Gly Arg Ser Arg Ala Ala Pro Pro Asn Leu Trp Ala
    210                 215                 220

Ala Gln Arg Tyr Gly Arg Glu Leu Arg Arg Met Ser Asp Glu Phe Val
225                 230                 235                 240

Asp Ser Phe Lys Lys Gly Leu Pro Arg Pro Lys Ser Ala Gly Thr Ala
                245                 250                 255

Thr Gln Met Arg Gln Ser Ser Ser Trp Thr Arg Val Phe Gln Ser Trp
            260                 265                 270

Trp Asp Arg Asn Leu Gly Arg Gly Ser Ser Ala Pro Ser Gln
        275                 280                 285

<210> SEQ ID NO 57
<211> LENGTH: 286
<212> TYPE: PRT
<213> ORGANISM: Artificial Sequence
<220> FEATURE:
<223> OTHER INFORMATION: Cytokine Fusion containing either IL-4 or IL-13

<400> SEQUENCE: 57

Pro Gly Pro Val Pro Pro Ser Thr Ala Val Arg Glu Leu Ile Glu Glu
1               5                   10                  15

Leu Ile Asn Ile Thr Gln Asn Gln Lys Ala Pro Leu Cys Asn Gly Ser
            20                  25                  30

Met Val Trp Ser Ile Asn Arg Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Arg Met Leu Ser Gly Phe Cys Pro His Lys Val Ser Ala Gly Gln Phe
65                  70                  75                  80

Ser Ser Leu His Val Arg Ser Lys Ile Glu Val Ala Gln Phe Val
                85                  90                  95

Lys Asp Leu Leu Phe His Leu Arg Thr Leu Phe Arg Glu Gly Gln Phe
            100                 105                 110

Asn Gly Gly Gly Gly Ser Met Phe Gln Ile Pro Glu Phe Glu Pro Ser
        115                 120                 125

Glu Gln Glu Asp Ser Ser Ala Glu Arg Gly Leu Gly Pro Ser Pro
    130                 135                 140

```
Ala Gly Asp Gly Pro Ser Gly Ser Gly Lys His His Arg Gln Ala Pro
145                 150                 155                 160

Gly Leu Leu Trp Asp Ala Ser His Gln Gln Glu Gln Pro Thr Ser Ser
                165                 170                 175

Ser His His Gly Gly Ala Gly Ala Val Glu Ile Arg Ser Arg His Ser
            180                 185                 190

Ala Tyr Pro Ala Gly Thr Glu Asp Asp Glu Gly Met Gly Glu Glu Pro
        195                 200                 205

Ser Pro Phe Arg Gly Arg Ser Arg Ala Ala Pro Pro Asn Leu Trp Ala
    210                 215                 220

Ala Gln Arg Tyr Gly Arg Glu Leu Arg Arg Met Ser Asp Glu Phe Val
225                 230                 235                 240

Asp Ser Phe Lys Lys Gly Leu Pro Arg Pro Lys Ser Ala Gly Thr Ala
                245                 250                 255

Thr Gln Met Arg Gln Ser Ser Ser Trp Thr Arg Val Phe Gln Ser Trp
            260                 265                 270

Trp Asp Arg Asn Leu Gly Arg Gly Ser Ser Ala Pro Ser Gln
        275                 280                 285

<210> SEQ ID NO 58
<211> LENGTH: 301
<212> TYPE: PRT
<213> ORGANISM: Artificial Sequence
<220> FEATURE:
<223> OTHER INFORMATION: Cytokine Fusion containing either IL-4 or IL-13

<400> SEQUENCE: 58

Lys Cys Asp Ile Thr Leu Gln Glu Ile Ile Lys Thr Leu Asn Ser Leu
1               5                   10                  15

Thr Glu Gln Lys Thr Leu Cys Thr Glu Leu Thr Val Thr Asp Ile Phe
            20                  25                  30

Ala Ala Ser Lys Asn Thr Thr Glu Lys Glu Thr Phe Cys Arg Ala Ala
        35                  40                  45

Thr Val Leu Arg Gln Phe Tyr Ser His His Glu Lys Asp Thr Arg Cys
    50                  55                  60

Leu Gly Ala Thr Ala Gln Gln Phe His Arg His Lys Gln Leu Ile Arg
65                  70                  75                  80

Phe Leu Lys Arg Leu Asp Arg Asn Leu Trp Gly Leu Ala Gly Leu Asn
                85                  90                  95

Ser Cys Pro Val Lys Glu Ala Asn Gln Ser Thr Leu Glu Asn Phe Leu
            100                 105                 110

Glu Arg Leu Lys Thr Ile Met Lys Glu Lys Phe Arg Lys Cys Ser Ser
        115                 120                 125

Gly Gly Gly Gly Ser Met Phe Gln Ile Pro Glu Phe Glu Pro Ser Glu
    130                 135                 140

Gln Glu Asp Ser Ser Ser Ala Glu Arg Gly Leu Gly Pro Ser Pro Ala
145                 150                 155                 160

Gly Asp Gly Pro Ser Gly Ser Gly Lys His His Arg Gln Ala Pro Gly
                165                 170                 175

Leu Leu Trp Asp Ala Ser His Gln Gln Glu Gln Pro Thr Ser Ser Ser
            180                 185                 190

His His Gly Gly Ala Gly Ala Val Glu Ile Arg Ser Arg His Ser Ala
        195                 200                 205

Tyr Pro Ala Gly Thr Glu Asp Asp Glu Gly Met Gly Glu Glu Pro Ser
    210                 215                 220
```

```
Pro Phe Arg Gly Arg Ser Arg Ala Ala Pro Pro Asn Leu Trp Ala Ala
225                 230                 235                 240

Gln Arg Tyr Gly Arg Glu Leu Arg Arg Met Ser Asp Glu Phe Val Asp
            245                 250                 255

Ser Phe Lys Lys Gly Leu Pro Arg Pro Lys Ser Ala Gly Thr Ala Thr
            260                 265                 270

Gln Met Arg Gln Ser Ser Ser Trp Thr Arg Val Phe Gln Ser Trp Trp
            275                 280                 285

Asp Arg Asn Leu Gly Arg Gly Ser Ser Ala Pro Ser Gln
            290                 295                 300

<210> SEQ ID NO 59
<211> LENGTH: 309
<212> TYPE: PRT
<213> ORGANISM: Artificial Sequence
<220> FEATURE:
<223> OTHER INFORMATION: Cytokine Fusion containing either IL-4 or IL-13

<400> SEQUENCE: 59

Met Asp Thr Thr Glu Lys Glu Thr Phe Cys Arg Ala Ala Thr Val Leu
1               5                   10                  15

Arg Gln Phe Tyr Ser His His Glu Lys Asp Thr Arg Cys Leu Gly Ala
            20                  25                  30

Thr Ala Gln Gln Phe His Arg His Lys Gln Leu Ile Arg Phe Leu Lys
        35                  40                  45

Arg Leu Asp Arg Asn Leu Trp Gly Leu Ala Gly Leu Asn Ser Cys Pro
50                  55                  60

Val Lys Glu Ala Asn Gln Ser Thr Leu Glu Asn Phe Leu Glu Arg Leu
65                  70                  75                  80

Lys Thr Ile Met Lys Glu Lys Phe Arg Lys Cys Ser Ser Gly Gly Asn
                85                  90                  95

Gly Gly His Lys Cys Asp Ile Thr Leu Gln Glu Ile Ile Lys Thr Leu
            100                 105                 110

Asn Ser Leu Thr Glu Gln Lys Thr Leu Cys Thr Glu Leu Thr Val Thr
        115                 120                 125

Asp Ile Phe Ala Ala Ser Gly Ser Phe Gln Ile Pro Glu Phe Glu Pro
130                 135                 140

Ser Glu Gln Glu Asp Ser Ser Ala Glu Arg Gly Leu Gly Pro Ser
145                 150                 155                 160

Pro Ala Gly Asp Gly Pro Ser Gly Ser Gly Lys His His Arg Gln Ala
            165                 170                 175

Pro Gly Leu Leu Trp Asp Ala Ser His Gln Gln Glu Gln Pro Thr Ser
        180                 185                 190

Ser Ser His His Gly Gly Ala Gly Ala Val Glu Ile Arg Ser Arg His
    195                 200                 205

Ser Ala Tyr Pro Ala Gly Thr Glu Asp Asp Glu Gly Met Gly Glu Glu
210                 215                 220

Pro Ser Pro Phe Arg Gly Arg Ser Arg Ala Ala Pro Pro Asn Leu Trp
225                 230                 235                 240

Ala Ala Gln Arg Tyr Gly Arg Glu Leu Arg Arg Met Ser Asp Glu Phe
            245                 250                 255

Val Asp Ser Phe Lys Lys Gly Leu Pro Arg Pro Lys Ser Ala Gly Thr
            260                 265                 270

Ala Thr Gln Met Arg Gln Ser Ser Ser Trp Thr Arg Val Phe Gln Ser
        275                 280                 285
```

Trp Trp Asp Arg Asn Leu Gly Arg Gly Ser Ser Ala Pro Ser Gln His
    290                 295                 300

His His His His His
305

<210> SEQ ID NO 60
<211> LENGTH: 303
<212> TYPE: PRT
<213> ORGANISM: Artificial Sequence
<220> FEATURE:
<223> OTHER INFORMATION: Cytokine Fusion containing either IL-4 or IL-13

<400> SEQUENCE: 60

Met Asp Thr Thr Glu Lys Glu Thr Phe Cys Arg Ala Ala Thr Val Leu
1               5                   10                  15

Arg Gln Phe Tyr Ser His His Glu Lys Asp Thr Arg Cys Leu Gly Ala
            20                  25                  30

Thr Ala Gln Gln Phe His Arg His Lys Gln Leu Ile Arg Phe Leu Lys
        35                  40                  45

Arg Leu Asp Arg Asn Leu Trp Gly Leu Ala Gly Leu Asn Ser Cys Pro
    50                  55                  60

Val Lys Glu Ala Asn Gln Ser Thr Leu Glu Asn Phe Leu Glu Arg Leu
65                  70                  75                  80

Lys Thr Ile Met Lys Glu Lys Phe Arg Lys Cys Ser Ser Gly Gly Asn
                85                  90                  95

Gly Gly His Lys Cys Asp Ile Thr Leu Gln Glu Ile Ile Lys Thr Leu
            100                 105                 110

Asn Ser Leu Thr Glu Gln Lys Thr Leu Cys Thr Glu Leu Thr Val Thr
        115                 120                 125

Asp Ile Phe Ala Ala Ser Gly Ser Phe Gln Ile Pro Glu Phe Glu Pro
    130                 135                 140

Ser Glu Gln Glu Asp Ser Ser Ala Glu Arg Gly Leu Gly Pro Ser
145                 150                 155                 160

Pro Ala Gly Asp Gly Pro Ser Gly Ser Gly Lys His His Arg Gln Ala
                165                 170                 175

Pro Gly Leu Leu Trp Asp Ala Ser His Gln Gln Glu Gln Pro Thr Ser
            180                 185                 190

Ser Ser His His Gly Gly Ala Gly Ala Val Glu Ile Arg Ser Arg His
        195                 200                 205

Ser Ala Tyr Pro Ala Gly Thr Glu Asp Asp Glu Gly Met Gly Glu Glu
    210                 215                 220

Pro Ser Pro Phe Arg Gly Arg Ser Arg Ala Ala Pro Pro Asn Leu Trp
225                 230                 235                 240

Ala Ala Gln Arg Tyr Gly Arg Glu Leu Arg Arg Met Ser Asp Glu Phe
                245                 250                 255

Val Asp Ser Phe Lys Lys Gly Leu Pro Arg Pro Lys Ser Ala Gly Thr
            260                 265                 270

Ala Thr Gln Met Arg Gln Ser Ser Ser Trp Thr Arg Val Phe Gln Ser
        275                 280                 285

Trp Trp Asp Arg Asn Leu Gly Arg Gly Ser Ser Ala Pro Ser Gln
    290                 295                 300

<210> SEQ ID NO 61
<211> LENGTH: 303
<212> TYPE: PRT
<213> ORGANISM: Artificial Sequence
<220> FEATURE:
<223> OTHER INFORMATION: Cytokine Fusion containing either IL-4 or IL-13

<400> SEQUENCE: 61

Met Asp Thr Thr Glu Lys Glu Thr Phe Cys Arg Ala Ala Thr Val Leu
1               5                   10                  15

Arg Gln Phe Tyr Ser His His Glu Lys Asp Thr Arg Cys Leu Gly Ala
            20                  25                  30

Thr Ala Gln Gln Phe His Arg His Lys Gln Leu Ile Arg Phe Leu Lys
        35                  40                  45

Arg Leu Asp Arg Asn Leu Trp Gly Leu Ala Gly Leu Asn Ser Cys Pro
50                  55                  60

Val Lys Glu Ala Asn Gln Ser Thr Leu Glu Asn Phe Leu Glu Arg Leu
65                  70                  75                  80

Lys Thr Ile Met Arg Glu Lys Tyr Ser Lys Cys Ser Ser Gly Gly Asn
                85                  90                  95

Gly Gly His Lys Cys Asp Ile Thr Leu Gln Glu Ile Ile Lys Thr Leu
            100                 105                 110

Asn Ser Leu Thr Glu Gln Lys Thr Leu Cys Thr Glu Leu Thr Val Thr
        115                 120                 125

Asp Ile Phe Ala Ala Ser Gly Ser Phe Gln Ile Pro Glu Phe Glu Pro
130                 135                 140

Ser Glu Gln Glu Asp Ser Ser Ala Glu Arg Gly Leu Gly Pro Ser
145                 150                 155                 160

Pro Ala Gly Asp Gly Pro Ser Gly Ser Gly Lys His His Arg Gln Ala
                165                 170                 175

Pro Gly Leu Leu Trp Asp Ala Ser His Gln Glu Gln Pro Thr Ser
            180                 185                 190

Ser Ser His His Gly Gly Ala Gly Ala Val Glu Ile Arg Ser Arg His
        195                 200                 205

Ser Ala Tyr Pro Ala Gly Thr Glu Asp Asp Glu Gly Met Gly Glu Glu
210                 215                 220

Pro Ser Pro Phe Arg Gly Arg Ser Arg Ala Ala Pro Pro Asn Leu Trp
225                 230                 235                 240

Ala Ala Gln Arg Tyr Gly Arg Glu Leu Arg Arg Met Ser Asp Glu Phe
                245                 250                 255

Val Asp Ser Phe Lys Lys Gly Leu Pro Arg Pro Lys Ser Ala Gly Thr
            260                 265                 270

Ala Thr Gln Met Arg Gln Ser Ser Ser Trp Thr Arg Val Phe Gln Ser
        275                 280                 285

Trp Trp Asp Arg Asn Leu Gly Arg Gly Ser Ala Pro Ser Gln
290                 295                 300

<210> SEQ ID NO 62
<211> LENGTH: 309
<212> TYPE: PRT
<213> ORGANISM: Artificial Sequence
<220> FEATURE:
<223> OTHER INFORMATION: Cytokine Fusion containing either IL-4 or IL-13

<400> SEQUENCE: 62

Met Asp Thr Thr Glu Lys Glu Thr Phe Cys Arg Ala Ala Thr Val Leu
1               5                   10                  15

Arg Gln Phe Tyr Ser His His Glu Lys Asp Thr Arg Cys Leu Gly Ala
            20                  25                  30

Thr Ala Gln Gln Phe His Arg His Lys Gln Leu Ile Arg Phe Leu Lys

```
        35                  40                  45
Arg Leu Asp Arg Asn Leu Trp Gly Leu Ala Gly Leu Asn Ser Cys Pro
    50                  55                  60

Val Lys Glu Ala Asn Gln Ser Thr Leu Glu Asn Phe Leu Glu Arg Leu
65                  70                  75                  80

Lys Thr Ile Met Arg Glu Lys Tyr Ser Lys Cys Ser Ser Gly Gly Asn
                85                  90                  95

Gly Gly His Lys Cys Asp Ile Thr Leu Gln Glu Ile Ile Lys Thr Leu
            100                 105                 110

Asn Ser Leu Thr Glu Gln Lys Thr Leu Cys Thr Glu Leu Thr Val Thr
        115                 120                 125

Asp Ile Phe Ala Ala Ser Gly Ser Phe Gln Ile Pro Glu Phe Glu Pro
    130                 135                 140

Ser Glu Gln Glu Asp Ser Ser Ser Ala Glu Arg Gly Leu Gly Pro Ser
145                 150                 155                 160

Pro Ala Gly Asp Gly Pro Ser Gly Ser Gly Lys His His Arg Gln Ala
                165                 170                 175

Pro Gly Leu Leu Trp Asp Ala Ser His Gln Gln Glu Gln Pro Thr Ser
            180                 185                 190

Ser Ser His His Gly Gly Ala Gly Ala Val Glu Ile Arg Ser Arg His
        195                 200                 205

Ser Ala Tyr Pro Ala Gly Thr Glu Asp Asp Glu Gly Met Gly Glu Glu
    210                 215                 220

Pro Ser Pro Phe Arg Gly Arg Ser Arg Ala Ala Pro Pro Asn Leu Trp
225                 230                 235                 240

Ala Ala Gln Arg Tyr Gly Arg Glu Leu Arg Arg Met Ser Asp Glu Phe
                245                 250                 255

Val Asp Ser Phe Lys Lys Gly Leu Pro Arg Pro Lys Ser Ala Gly Thr
            260                 265                 270

Ala Thr Gln Met Arg Gln Ser Ser Ser Trp Thr Arg Val Phe Gln Ser
        275                 280                 285

Trp Trp Asp Arg Asn Leu Gly Arg Gly Ser Ser Ala Pro Ser Gln His
    290                 295                 300

His His His His His
305
```

<210> SEQ ID NO 63
<211> LENGTH: 295
<212> TYPE: PRT
<213> ORGANISM: Artificial Sequence
<220> FEATURE:
<223> OTHER INFORMATION: Cytokine Fusion containing either IL-4 or IL-13

<400> SEQUENCE: 63

```
Pro Gly Pro Val Pro Pro Ser Thr Ala Val Arg Ala Leu Ile Glu Glu
1               5                   10                  15

Leu Ile Asn Ile Thr Gln Asn Gln Lys Ala Pro Leu Cys Asn Gly Ser
            20                  25                  30

Met Val Trp Ser Ile Asn Arg Thr Ala Gly Met Tyr Cys Ala Ala Leu
        35                  40                  45

Glu Ser Leu Ile Asn Val Ser Gly Cys Ser Ala Ile Glu Lys Thr Gln
    50                  55                  60

Asp Met Leu Ser Gly Phe Cys Pro His Lys Val Ser Ala Gly Gln Phe
65                  70                  75                  80

Ser Ser Leu His Val Arg Ser Ser Lys Ile Glu Val Ala Gln Phe Val
```

```
                    85                  90                  95
Lys Asp Leu Leu Phe His Leu Arg Thr Leu Phe Arg Glu Gly Gln Phe
                100                 105                 110

Asn Gly Gly Gly Ser Gly Gly Gly Ser Gly Gly Gly Ser
                115                 120                 125

Phe Gln Ile Pro Glu Phe Glu Pro Ser Glu Gln Asp Ser Ser Ser
            130                 135                 140

Ala Glu Arg Gly Leu Gly Pro Ser Pro Ala Gly Asp Gly Pro Ser Gly
145                 150                 155                 160

Ser Gly Lys His His Arg Gln Ala Pro Gly Leu Leu Trp Asp Ala Ser
                165                 170                 175

His Gln Gln Glu Gln Pro Thr Ser Ser Ser His His Gly Gly Ala Gly
                180                 185                 190

Ala Val Glu Ile Arg Ser Arg His Ser Ala Tyr Pro Ala Gly Thr Glu
                195                 200                 205

Asp Asp Glu Gly Met Gly Glu Glu Pro Ser Pro Phe Arg Gly Arg Ser
            210                 215                 220

Arg Ala Ala Pro Pro Asn Leu Trp Ala Ala Gln Arg Tyr Gly Arg Glu
225                 230                 235                 240

Leu Arg Arg Met Ser Asp Glu Phe Val Asp Ser Phe Lys Lys Gly Leu
                245                 250                 255

Pro Arg Pro Lys Ser Ala Gly Thr Ala Thr Gln Met Arg Gln Ser Ser
                260                 265                 270

Ser Trp Thr Arg Val Phe Gln Ser Trp Trp Asp Arg Asn Leu Gly Arg
                275                 280                 285

Gly Ser Ser Ala Pro Ser Gln
                290                 295

<210> SEQ ID NO 64
<211> LENGTH: 366
<212> TYPE: PRT
<213> ORGANISM: Artificial Sequence
<220> FEATURE:
<223> OTHER INFORMATION: Cytokine Fusion containing either IL-4 or IL-13

<400> SEQUENCE: 64

Lys Cys Asp Ile Thr Leu Gln Glu Ile Ile Lys Thr Leu Asn Ser Leu
1               5                   10                  15

Thr Glu Gln Lys Thr Leu Cys Thr Glu Leu Thr Val Thr Asp Ile Phe
                20                  25                  30

Ala Ala Ser Lys Asn Thr Thr Glu Lys Glu Thr Phe Cys Arg Ala Ala
            35                  40                  45

Thr Val Leu Arg Gln Phe Tyr Ser His His Glu Lys Asp Thr Arg Cys
50                  55                  60

Leu Gly Ala Thr Ala Gln Gln Phe His Arg His Lys Gln Leu Ile Arg
65                  70                  75                  80

Phe Leu Lys Arg Leu Asp Arg Asn Leu Trp Gly Leu Ala Gly Leu Asn
                85                  90                  95

Ser Cys Pro Val Lys Glu Ala Asn Gln Ser Thr Leu Glu Asn Phe Leu
                100                 105                 110

Glu Arg Leu Lys Thr Ile Met Arg Glu Lys Tyr Ser Lys Cys Ser Ser
                115                 120                 125

Gly Gly Gly Gly Ser Met Ser Gln Ser Asn Arg Glu Leu Val Val Asp
            130                 135                 140

Phe Leu Ser Tyr Lys Leu Ser Gln Lys Gly Tyr Ser Trp Ser Gln Phe
```

```
        145                 150                 155                 160
    Ser Asp Val Glu Glu Asn Arg Thr Glu Ala Pro Glu Gly Thr Glu Ser
                        165                 170                 175

Glu Met Glu Thr Pro Ser Ala Ile Asn Gly Asn Pro Ser Trp His Leu
                        180                 185                 190

Ala Asp Ser Pro Ala Val Asn Gly Ala Thr Gly His Ser Ser Ser Leu
                    195                 200                 205

Asp Ala Arg Glu Val Ile Pro Met Ala Ala Val Lys Gln Ala Leu Arg
                210                 215                 220

Glu Ala Gly Asp Glu Phe Glu Leu Arg Tyr Arg Arg Ala Phe Ser Asp
    225                 230                 235                 240

Leu Thr Ser Gln Leu His Ile Thr Pro Gly Thr Ala Tyr Gln Ser Phe
                        245                 250                 255

Glu Gln Val Val Asn Glu Leu Phe Arg Asp Gly Val Asn Trp Gly Arg
                    260                 265                 270

Ile Val Ala Phe Phe Ser Phe Gly Gly Ala Leu Cys Val Glu Ser Val
                275                 280                 285

Asp Lys Glu Met Gln Val Leu Val Ser Arg Ile Ala Ala Trp Met Ala
                290                 295                 300

Thr Tyr Leu Asn Asp His Leu Glu Pro Trp Ile Gln Glu Asn Gly Gly
    305                 310                 315                 320

Trp Asp Thr Phe Val Glu Leu Tyr Gly Asn Asn Ala Ala Ala Glu Ser
                        325                 330                 335

Arg Lys Gly Gln Glu Arg Phe Asn Arg Trp Phe Leu Thr Gly Met Thr
                    340                 345                 350

Val Ala Gly Val Val Leu Leu Gly Ser Leu Phe Ser Arg Lys
                355                 360                 365

<210> SEQ ID NO 65
<211> LENGTH: 485
<212> TYPE: PRT
<213> ORGANISM: Artificial Sequence
<220> FEATURE:
<223> OTHER INFORMATION: Cytokine Fusion containing either IL-4 or IL-13

<400> SEQUENCE: 65

Met Asp Thr Thr Glu Lys Glu Thr Phe Cys Arg Ala Ala Thr Val Leu
1               5                   10                  15

Arg Gln Phe Tyr Ser His His Glu Lys Asp Thr Arg Cys Leu Gly Ala
                20                  25                  30

Thr Ala Gln Gln Phe His Arg His Lys Gln Leu Ile Arg Phe Leu Lys
            35                  40                  45

Leu Arg Asp Arg Asn Leu Trp Gly Leu Ala Gly Leu Asn Ser Cys Pro
        50                  55                  60

Val Lys Glu Ala Asn Gln Ser Thr Leu Glu Asn Phe Leu Glu Arg Leu
65                  70                  75                  80

Lys Thr Ile Met Arg Glu Lys Tyr Ser Lys Cys Ser Ser Gly Gly Asn
                85                  90                  95

Gly Gly His Lys Cys Asp Ile Thr Leu Gln Glu Ile Ile Lys Thr Leu
                100                 105                 110

Asn Ser Leu Thr Glu Gln Lys Thr Leu Cys Thr Glu Leu Thr Val Thr
            115                 120                 125

Asp Ile Phe Ala Ala Ser Lys Ala Ser Gly Gly Pro Glu Gly Gly Ser
        130                 135                 140

Leu Ala Ala Leu Thr Ala His Gln Ala Cys His Leu Pro Leu Glu Thr
```

145 150 155 160

Phe Thr Arg His Arg Gln Pro Arg Gly Trp Glu Gln Leu Glu Gln Cys
165 170 175

Gly Tyr Pro Val Gln Arg Leu Val Ala Leu Tyr Leu Ala Ala Arg Leu
180 185 190

Ser Trp Asn Gln Val Asp Gln Val Ile Arg Asn Ala Leu Ala Ser Pro
195 200 205

Gly Ser Gly Gly Asp Leu Gly Glu Ala Ile Arg Glu Gln Pro Glu Gln
210 215 220

Ala Arg Leu Ala Leu Thr Leu Ala Ala Ala Glu Ser Glu Arg Phe Val
225 230 235 240

Arg Gln Gly Thr Gly Asn Asp Glu Ala Gly Ala Ala Asn Gly Pro Ala
245 250 255

Asp Ser Gly Asp Ala Leu Leu Glu Arg Asn Tyr Pro Thr Gly Ala Glu
260 265 270

Phe Leu Gly Asp Gly Gly Asp Val Ser Phe Ser Thr Arg Gly Thr Gln
275 280 285

Asn Trp Thr Val Glu Arg Leu Leu Gln Ala His Arg Gln Leu Glu Glu
290 295 300

Arg Gly Tyr Val Phe Val Gly Tyr His Gly Thr Phe Leu Glu Ala Ala
305 310 315 320

Gln Ser Ile Val Phe Gly Gly Val Arg Ala Arg Ser Gln Asp Leu Asp
325 330 335

Ala Ile Trp Arg Gly Phe Tyr Ile Ala Gly Asp Pro Ala Leu Ala Tyr
340 345 350

Gly Tyr Ala Gln Asp Gln Glu Pro Asp Ala Arg Gly Arg Ile Arg Asn
355 360 365

Gly Ala Leu Leu Arg Val Tyr Val Pro Arg Ser Ser Leu Pro Gly Phe
370 375 380

Tyr Arg Thr Ser Leu Thr Leu Ala Ala Pro Glu Ala Ala Gly Glu Val
385 390 395 400

Glu Arg Leu Ile Gly His Pro Leu Pro Leu Arg Leu Asp Ala Ile Thr
405 410 415

Gly Pro Glu Glu Glu Gly Gly Arg Leu Glu Thr Ile Leu Gly Trp Pro
420 425 430

Leu Ala Glu Arg Thr Val Val Ile Pro Ser Ala Ile Pro Thr Asp Pro
435 440 445

Arg Asn Val Gly Gly Asp Leu Asp Pro Ser Ser Ile Pro Asp Lys Glu
450 455 460

Gln Ala Ile Ser Ala Leu Pro Asp Tyr Ala Ser Gln Pro Gly Lys Pro
465 470 475 480

Pro Lys Asp Glu Leu
485

<210> SEQ ID NO 66
<211> LENGTH: 309
<212> TYPE: PRT
<213> ORGANISM: Artificial Sequence
<220> FEATURE:
<223> OTHER INFORMATION: Cytokine Fusion containing either IL-4 or IL-13

<400> SEQUENCE: 66

Met Asp Thr Thr Glu Lys Glu Thr Phe Cys Arg Ala Ala Thr Val Leu
1 5 10 15

Arg Gln Phe Tyr Ser His His Glu Lys Asp Thr Arg Cys Leu Gly Ala

```
            20                  25                  30
Thr Ala Gln Gln Phe His Arg His Lys Gln Leu Ile Arg Phe Leu Lys
        35                  40                  45

Arg Leu Asp Arg Asn Leu Trp Gly Leu Ala Gly Leu Asn Ser Cys Pro
 50                  55                  60

Val Lys Glu Ala Asn Gln Ser Thr Leu Glu Asn Phe Leu Glu Arg Leu
 65                  70                  75                  80

Arg Val Ile Met Gln Ser Lys Trp Phe Lys Cys Gly Ala Gly Gly Asn
                 85                  90                  95

Gly Gly His Lys Cys Asp Ile Thr Leu Gln Glu Ile Ile Lys Thr Leu
            100                 105                 110

Asn Ser Leu Thr Glu Gln Lys Thr Leu Cys Thr Glu Leu Thr Val Thr
            115                 120                 125

Asp Ile Phe Ala Ala Ser Gly Ser Phe Gln Ile Pro Glu Phe Glu Pro
        130                 135                 140

Ser Glu Gln Glu Asp Ser Ser Ala Glu Arg Gly Leu Gly Pro Ser
145                 150                 155                 160

Pro Ala Gly Asp Gly Pro Ser Gly Ser Gly Lys His His Arg Gln Ala
                165                 170                 175

Pro Gly Leu Leu Trp Asp Ala Ser His Gln Gln Gln Pro Thr Ser
            180                 185                 190

Ser Ser His His Gly Gly Ala Gly Ala Val Glu Ile Arg Ser Arg His
            195                 200                 205

Ser Ala Tyr Pro Ala Gly Thr Glu Asp Asp Glu Gly Met Gly Glu Glu
        210                 215                 220

Pro Ser Pro Phe Arg Gly Arg Ser Arg Ala Ala Pro Pro Asn Leu Trp
225                 230                 235                 240

Ala Ala Gln Arg Tyr Gly Arg Glu Leu Arg Arg Met Ser Asp Glu Phe
                245                 250                 255

Val Asp Ser Phe Lys Lys Gly Leu Pro Arg Pro Lys Ser Ala Gly Thr
            260                 265                 270

Ala Thr Gln Met Arg Gln Ser Ser Ser Trp Thr Arg Val Phe Gln Ser
        275                 280                 285

Trp Trp Asp Arg Asn Leu Gly Arg Gly Ser Ser Ala Pro Ser Gln His
        290                 295                 300

His His His His His
305

<210> SEQ ID NO 67
<211> LENGTH: 303
<212> TYPE: PRT
<213> ORGANISM: Artificial Sequence
<220> FEATURE:
<223> OTHER INFORMATION: Cytokine Fusion containing either IL-4 or IL-13

<400> SEQUENCE: 67

Met Asp Thr Thr Glu Lys Glu Thr Phe Cys Arg Ala Ala Thr Val Leu
 1               5                  10                  15

Arg Gln Phe Tyr Ser His His Glu Lys Asp Thr Arg Cys Leu Gly Ala
                 20                  25                  30

Thr Ala Gln Gln Phe His Arg His Lys Gln Leu Ile Arg Phe Leu Lys
        35                  40                  45

Arg Leu Asp Arg Asn Leu Trp Gly Leu Ala Gly Leu Asn Ser Cys Pro
 50                  55                  60

Val Lys Glu Ala Asn Gln Ser Thr Leu Glu Asn Phe Leu Glu Arg Leu
```

```
                65                  70                  75                  80
Arg Val Ile Met Gln Ser Lys Trp Phe Lys Cys Gly Ala Gly Gly Asn
                85                  90                  95

Gly Gly His Lys Cys Asp Ile Thr Leu Gln Glu Ile Ile Lys Thr Leu
                100                 105                 110

Asn Ser Leu Thr Glu Gln Lys Thr Leu Cys Thr Glu Leu Thr Val Thr
                115                 120                 125

Asp Ile Phe Ala Ala Ser Gly Ser Phe Gln Ile Pro Glu Phe Glu Pro
            130                 135                 140

Ser Glu Gln Glu Asp Ser Ser Ala Glu Arg Gly Leu Gly Pro Ser
145                 150                 155                 160

Pro Ala Gly Asp Gly Pro Ser Gly Ser Gly Lys His His Arg Gln Ala
                165                 170                 175

Pro Gly Leu Leu Trp Asp Ala Ser His Gln Gln Glu Gln Pro Thr Ser
            180                 185                 190

Ser Ser His His Gly Gly Ala Gly Ala Val Glu Ile Arg Ser Arg His
                195                 200                 205

Ser Ala Tyr Pro Ala Gly Thr Glu Asp Asp Glu Gly Met Gly Glu Glu
            210                 215                 220

Pro Ser Pro Phe Arg Gly Arg Ser Arg Ala Ala Pro Pro Asn Leu Trp
225                 230                 235                 240

Ala Ala Gln Arg Tyr Gly Arg Glu Leu Arg Arg Met Ser Asp Glu Phe
                245                 250                 255

Val Asp Ser Phe Lys Lys Gly Leu Pro Arg Pro Lys Ser Ala Gly Thr
            260                 265                 270

Ala Thr Gln Met Arg Gln Ser Ser Ser Trp Thr Arg Val Phe Gln Ser
        275                 280                 285

Trp Trp Asp Arg Asn Leu Gly Arg Gly Ser Ser Ala Pro Ser Gln
            290                 295                 300

<210> SEQ ID NO 68
<211> LENGTH: 305
<212> TYPE: PRT
<213> ORGANISM: Artificial Sequence
<220> FEATURE:
<223> OTHER INFORMATION: Cytokine Fusion containing either IL-4 or IL-13

<400> SEQUENCE: 68

Met His Lys Cys Asp Ile Thr Leu Gln Glu Ile Ile Lys Thr Leu Asn
1               5                   10                  15

Ser Leu Thr Glu Gln Lys Thr Leu Cys Thr Glu Leu Thr Val Thr Asp
                20                  25                  30

Ile Phe Ala Ala Ser Lys Asp Thr Thr Glu Lys Glu Thr Phe Cys Arg
            35                  40                  45

Ala Ala Thr Val Leu Arg Gln Phe Tyr Ser His His Glu Lys Asp Thr
        50                  55                  60

Arg Cys Leu Gly Ala Thr Ala Gln Gln Phe His Arg His Lys Gln Leu
65                  70                  75                  80

Ile Arg Phe Leu Lys Arg Leu Asp Arg Asn Leu Trp Gly Leu Ala Gly
                85                  90                  95

Leu Asn Ser Cys Pro Val Lys Glu Ala Asn Gln Ser Thr Leu Glu Asn
                100                 105                 110

Phe Leu Glu Arg Leu Lys Thr Ile Met Arg Glu Lys Tyr Ser Lys Cys
            115                 120                 125

Ser Ser Gly Ser Phe Gln Ile Pro Glu Phe Glu Pro Ser Glu Gln Glu
```

```
            130                 135                 140
Asp Ser Ser Ala Glu Arg Gly Leu Gly Pro Ser Pro Ala Gly Asp
145                 150                 155                 160

Gly Pro Ser Gly Ser Gly Lys His His Arg Gln Ala Pro Gly Leu Leu
                165                 170                 175

Trp Asp Ala Ser His Gln Gln Glu Gln Pro Thr Ser Ser His His
            180                 185                 190

Gly Gly Ala Gly Ala Val Glu Ile Arg Ser Arg His Ser Ala Tyr Pro
                195                 200                 205

Ala Gly Thr Glu Asp Asp Glu Gly Met Gly Glu Glu Pro Ser Pro Phe
            210                 215                 220

Arg Gly Arg Ser Arg Ala Ala Pro Pro Asn Leu Trp Ala Ala Gln Arg
225                 230                 235                 240

Tyr Gly Arg Glu Leu Arg Arg Met Ser Asp Glu Phe Val Asp Ser Phe
                245                 250                 255

Lys Lys Gly Leu Pro Arg Pro Lys Ser Ala Gly Thr Ala Thr Gln Met
                260                 265                 270

Arg Gln Ser Ser Ser Trp Thr Arg Val Phe Gln Ser Trp Trp Asp Arg
                275                 280                 285

Asn Leu Gly Arg Gly Ser Ser Ala Pro Ser Gln His His His His
            290                 295                 300

His
305

<210> SEQ ID NO 69
<211> LENGTH: 299
<212> TYPE: PRT
<213> ORGANISM: Artificial Sequence
<220> FEATURE:
<223> OTHER INFORMATION: Cytokine Fusion containing either IL-4 or IL-13

<400> SEQUENCE: 69

Met His Lys Cys Asp Ile Thr Leu Gln Glu Ile Ile Lys Thr Leu Asn
1               5                   10                  15

Ser Leu Thr Glu Gln Lys Thr Leu Cys Thr Glu Leu Thr Val Thr Asp
                20                  25                  30

Ile Phe Ala Ala Ser Lys Asp Thr Thr Glu Lys Glu Thr Phe Cys Arg
            35                  40                  45

Ala Ala Thr Val Leu Arg Gln Phe Tyr Ser His His Glu Lys Asp Thr
        50                  55                  60

Arg Cys Leu Gly Ala Thr Ala Gln Gln Phe His Arg His Lys Gln Leu
65                  70                  75                  80

Ile Arg Phe Leu Lys Arg Leu Asp Arg Asn Leu Trp Gly Leu Ala Gly
                85                  90                  95

Leu Asn Ser Cys Pro Val Lys Glu Ala Asn Gln Ser Thr Leu Glu Asn
            100                 105                 110

Phe Leu Glu Arg Leu Lys Thr Ile Met Arg Glu Lys Tyr Ser Lys Cys
        115                 120                 125

Ser Ser Gly Ser Phe Gln Ile Pro Glu Phe Glu Pro Ser Glu Gln Glu
    130                 135                 140

Asp Ser Ser Ala Glu Arg Gly Leu Gly Pro Ser Pro Ala Gly Asp
145                 150                 155                 160

Gly Pro Ser Gly Ser Gly Lys His His Arg Gln Ala Pro Gly Leu Leu
                165                 170                 175

Trp Asp Ala Ser His Gln Gln Glu Gln Pro Thr Ser Ser His His
```

```
                    180                 185                 190
Gly Gly Ala Gly Ala Val Glu Ile Arg Ser Arg His Ser Ala Tyr Pro
            195                 200                 205
Ala Gly Thr Glu Asp Asp Glu Gly Met Gly Glu Glu Pro Ser Pro Phe
        210                 215                 220
Arg Gly Arg Ser Arg Ala Ala Pro Pro Asn Leu Trp Ala Ala Gln Arg
225                 230                 235                 240
Tyr Gly Arg Glu Leu Arg Arg Met Ser Asp Glu Phe Val Asp Ser Phe
                245                 250                 255
Lys Lys Gly Leu Pro Arg Pro Lys Ser Ala Gly Thr Ala Thr Gln Met
            260                 265                 270
Arg Gln Ser Ser Ser Trp Thr Arg Val Phe Gln Ser Trp Trp Asp Arg
        275                 280                 285
Asn Leu Gly Arg Gly Ser Ser Ala Pro Ser Gln
    290                 295

<210> SEQ ID NO 70
<211> LENGTH: 10
<212> TYPE: PRT
<213> ORGANISM: Artificial Sequence
<220> FEATURE:
<223> OTHER INFORMATION: IL-4 and IL-13 linker

<400> SEQUENCE: 70

Gly Gly Gly Gly Ser Gly Gly Gly Gly Ser
1               5                   10

<210> SEQ ID NO 71
<211> LENGTH: 15
<212> TYPE: PRT
<213> ORGANISM: Artificial Sequence
<220> FEATURE:
<223> OTHER INFORMATION: IL-4 and IL-13 linker

<400> SEQUENCE: 71

Gly Gly Gly Gly Ser Gly Gly Gly Gly Ser Gly Gly Gly Gly Ser
1               5                   10                  15

<210> SEQ ID NO 72
<211> LENGTH: 20
<212> TYPE: PRT
<213> ORGANISM: Artificial Sequence
<220> FEATURE:
<223> OTHER INFORMATION: IL-4 and IL-13 linker

<400> SEQUENCE: 72

Gly Gly Gly Gly Ser Gly Gly Gly Ser Gly Gly Gly Gly Ser Gly
1               5                   10                  15

Gly Gly Gly Ser
            20

<210> SEQ ID NO 73
<211> LENGTH: 20
<212> TYPE: PRT
<213> ORGANISM: Artificial Sequence
<220> FEATURE:
<223> OTHER INFORMATION: IL-4 and IL-13 linker

<400> SEQUENCE: 73

Gly Gly Gly Gly Ser Gly Gly Gly Ser Gly Gly Gly Gly Ser Gly
1               5                   10                  15

Gly Gly Gly Ser
```

-continued

20

<210> SEQ ID NO 74
<211> LENGTH: 168
<212> TYPE: PRT
<213> ORGANISM: Artificial Sequence
<220> FEATURE:
<223> OTHER INFORMATION: Cytokine Fusion containing either IL-4 or IL-13

<400> SEQUENCE: 74

Met Phe Gln Ile Pro Glu Phe Glu Pro Ser Glu Gln Glu Asp Ser Ser
1               5                   10                  15

Ser Ala Glu Arg Gly Leu Gly Pro Ser Pro Ala Gly Asp Gly Pro Ser
            20                  25                  30

Gly Ser Gly Lys His His Arg Gln Ala Pro Gly Leu Leu Trp Asp Ala
        35                  40                  45

Ser His Gln Gln Glu Gln Pro Thr Ser Ser His His Gly Gly Ala
    50                  55                  60

Gly Ala Val Glu Ile Arg Ser Arg His Ser Ala Tyr Pro Ala Gly Thr
65                  70                  75                  80

Glu Asp Asp Glu Gly Met Gly Glu Glu Pro Ser Pro Phe Arg Gly Arg
                85                  90                  95

Ser Arg Ala Ala Pro Pro Asn Leu Trp Ala Ala Gln Arg Tyr Gly Arg
            100                 105                 110

Glu Leu Arg Arg Met Ser Asp Glu Phe Val Asp Ser Phe Lys Lys Gly
        115                 120                 125

Leu Pro Arg Pro Lys Ser Ala Gly Thr Ala Thr Gln Met Arg Gln Ser
130                 135                 140

Ser Ser Trp Thr Arg Val Phe Gln Ser Trp Trp Asp Arg Asn Leu Gly
145                 150                 155                 160

Arg Gly Ser Ser Ala Pro Ser Gln
                165

<210> SEQ ID NO 75
<211> LENGTH: 239
<212> TYPE: PRT
<213> ORGANISM: Artificial Sequence
<220> FEATURE:
<223> OTHER INFORMATION: Cytokine Fusion containing either IL-4 or IL-13

<400> SEQUENCE: 75

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Val Val His Leu Thr
                85                  90                  95

Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
        115                 120                 125

```
Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
                180                 185                 190

Gly Gly Trp Asp Ala Phe Val Glu Leu Tyr Gly Pro Ser Met Arg Pro
            195                 200                 205

Leu Phe Asp Phe Ser Trp Leu Ser Leu Lys Thr Leu Leu Ser Leu Ala
    210                 215                 220

Leu Val Gly Ala Cys Ile Thr Leu Gly Ala Tyr Leu Gly His Lys
225                 230                 235

<210> SEQ ID NO 76
<211> LENGTH: 168
<212> TYPE: PRT
<213> ORGANISM: Artificial Sequence
<220> FEATURE:
<223> OTHER INFORMATION: Cytokine Fusion containing either IL-4 or IL-13

<400> SEQUENCE: 76

Met Phe Gln Ile Pro Glu Phe Glu Pro Ser Glu Gln Glu Asp Ser Ser
1               5                   10                  15

Ser Ala Glu Arg Gly Leu Gly Pro Ser Pro Ala Gly Asp Gly Pro Ser
                20                  25                  30

Gly Ser Gly Lys His His Arg Gln Ala Pro Gly Leu Leu Trp Asp Ala
            35                  40                  45

Ser His Gln Gln Glu Gln Pro Thr Ser Ser His His Gly Gly Ala
    50                  55                  60

Gly Ala Val Glu Ile Arg Ser Arg His Ser Ser Tyr Pro Ala Gly Thr
65                  70                  75                  80

Glu Asp Asp Glu Gly Met Gly Glu Gly Pro Ser Pro Phe Arg Gly Arg
                85                  90                  95

Ser Arg Ser Ala Pro Pro Asn Leu Trp Ala Ala Gln Arg Tyr Gly Arg
                100                 105                 110

Glu Leu Arg Arg Met Ser Asp Glu Phe Val Asp Ser Phe Lys Lys Gly
            115                 120                 125

Leu Pro Arg Pro Lys Ser Ala Gly Thr Ala Thr Gln Met Arg Gln Ser
    130                 135                 140

Ser Ser Trp Thr Arg Val Phe Gln Ser Trp Trp Asp Arg Asn Leu Gly
145                 150                 155                 160

Arg Gly Ser Ser Ala Pro Ser Gln
                165

<210> SEQ ID NO 77
<211> LENGTH: 192
<212> TYPE: PRT
<213> ORGANISM: Artificial Sequence
<220> FEATURE:
<223> OTHER INFORMATION: Cytokine Fusion containing either IL-4 or IL-13

<400> SEQUENCE: 77

Met Asp Gly Ser Gly Glu Gln Pro Arg Gly Gly Pro Thr Ser Ser
1               5                   10                  15

Glu Gln Ile Met Lys Thr Gly Ala Leu Leu Leu Gln Gly Phe Ile Gln
                20                  25                  30
```

```
Asp Arg Ala Gly Arg Met Gly Gly Glu Ala Pro Glu Leu Ala Leu Asp
        35                  40                  45

Pro Val Pro Gln Asp Ala Ser Thr Lys Lys Leu Ser Glu Cys Leu Lys
    50                  55                  60

Arg Ile Gly Asp Glu Leu Asp Ser Asn Met Glu Leu Gln Arg Met Ile
65                  70                  75                  80

Ala Ala Val Asp Thr Asp Ser Pro Arg Glu Val Phe Phe Arg Val Ala
                85                  90                  95
Ala Asp Met Phe Ser Asp Gly Asn Phe Asn Trp Gly Arg Val Val Ala
            100                 105                 110
Leu Phe Tyr Phe Ala Ser Lys Leu Val Leu Lys Ala Leu Cys Thr Lys
        115                 120                 125

Val Pro Glu Leu Ile Arg Thr Ile Met Gly Trp Thr Leu Asp Phe Leu
    130                 135                 140

Arg Glu Arg Leu Leu Gly Trp Ile Gln Asp Gln Gly Gly Trp Asp Gly
145                 150                 155                 160
Leu Leu Ser Tyr Phe Gly Thr Pro Thr Trp Gln Thr Val Thr Ile Phe
                165                 170                 175
Val Ala Gly Val Leu Thr Ala Ser Leu Thr Ile Trp Lys Lys Met Gly
            180                 185                 190

<210> SEQ ID NO 78
<211> LENGTH: 211
<212> TYPE: PRT
<213> ORGANISM: Artificial Sequence
<220> FEATURE:
<223> OTHER INFORMATION: Cytokine Fusion containing either IL-4 or IL-13

<400> SEQUENCE: 78

Met Ala Ser Gly Gln Gly Pro Gly Pro Pro Arg Gln Glu Cys Gly Glu
1               5                   10                  15

Pro Ala Leu Pro Ser Ala Ser Glu Glu Gln Val Ala Gln Asp Thr Glu
            20                  25                  30

Glu Val Phe Arg Ser Tyr Val Phe Tyr Arg His Gln Gln Glu Gln Glu
        35                  40                  45

Ala Glu Gly Val Ala Ala Pro Ala Asp Pro Glu Met Val Thr Leu Pro
    50                  55                  60

Leu Gln Pro Ser Ser Thr Met Gly Gln Val Gly Arg Gln Leu Ala Ile
65                  70                  75                  80

Ile Gly Asp Asp Ile Asn Arg Arg Tyr Asp Ser Glu Phe Gln Thr Met
                85                  90                  95

Leu Gln His Leu Gln Pro Thr Ala Glu Asn Ala Tyr Glu Tyr Phe Thr
            100                 105                 110

Lys Ile Ala Thr Ser Leu Phe Glu Ser Gly Ile Asn Trp Gly Arg Val
        115                 120                 125

Val Ala Leu Leu Gly Phe Gly Tyr Arg Leu Ala Leu His Val Tyr Gln
    130                 135                 140

His Gly Leu Thr Gly Phe Leu Gly Gln Val Thr Arg Phe Val Val Asp
145                 150                 155                 160

Phe Met Leu His His Cys Ile Ala Arg Trp Ile Ala Gln Arg Gly Gly
                165                 170                 175

Trp Val Ala Ala Leu Asn Leu Gly Asn Gly Pro Ile Leu Asn Val Leu
            180                 185                 190

Val Val Leu Gly Val Val Leu Leu Gly Gln Phe Val Val Arg Arg Phe
        195                 200                 205
```

Phe Lys Ser
    210

<210> SEQ ID NO 79
<211> LENGTH: 160
<212> TYPE: PRT
<213> ORGANISM: Artificial Sequence
<220> FEATURE:
<223> OTHER INFORMATION: Cytokine Fusion containing either IL-4 or IL-13

<400> SEQUENCE: 79

Met Ser Glu Val Arg Pro Leu Ser Arg Asp Ile Leu Met Glu Thr Leu
1               5                   10                  15

Leu Tyr Glu Gln Leu Leu Glu Pro Pro Thr Met Glu Val Leu Gly Met
            20                  25                  30

Thr Asp Ser Glu Glu Asp Leu Asp Pro Met Glu Asp Phe Asp Ser Leu
        35                  40                  45

Glu Cys Met Glu Gly Ser Asp Ala Leu Ala Leu Arg Leu Ala Cys Ile
50                  55                  60

Gly Asp Glu Met Asp Val Ser Leu Arg Ala Pro Arg Leu Ala Gln Leu
65                  70                  75                  80

Ser Glu Val Ala Met His Ser Leu Gly Leu Ala Phe Ile Tyr Asp Gln
                85                  90                  95

Thr Glu Asp Ile Arg Asp Val Leu Arg Ser Phe Met Asp Gly Phe Thr
            100                 105                 110

Thr Leu Lys Glu Asn Ile Met Arg Phe Trp Arg Ser Pro Asn Pro Gly
        115                 120                 125

Ser Trp Val Ser Cys Glu Gln Val Leu Leu Ala Leu Leu Leu Leu Leu
130                 135                 140

Ala Leu Leu Leu Pro Leu Leu Ser Gly Gly Leu His Leu Leu Leu Lys
145                 150                 155                 160

<210> SEQ ID NO 80
<211> LENGTH: 195
<212> TYPE: PRT
<213> ORGANISM: Artificial Sequence
<220> FEATURE:
<223> OTHER INFORMATION: Cytokine Fusion containing either IL-4 or IL-13

<400> SEQUENCE: 80

Met Asp Cys Glu Val Asn Asn Gly Ser Ser Leu Arg Asp Glu Cys Ile
1               5                   10                  15

Thr Asn Leu Leu Val Phe Gly Phe Leu Gln Ser Cys Ser Asp Asn Ser
            20                  25                  30

Phe Arg Arg Glu Leu Asp Ala Leu Gly His Glu Leu Pro Val Leu Ala
        35                  40                  45

Pro Gln Trp Glu Gly Tyr Asp Glu Leu Gln Thr Asp Gly Asn Arg Ser
    50                  55                  60

Ser His Ser Arg Leu Gly Arg Ile Glu Ala Asp Ser Glu Ser Gln Glu
65                  70                  75                  80

Asp Ile Ile Arg Asn Ile Ala Arg His Leu Ala Gln Val Gly Asp Ser
                85                  90                  95

Met Asp Arg Ser Ile Pro Pro Gly Leu Val Asn Gly Leu Ala Leu Gln
            100                 105                 110

Leu Arg Asn Thr Ser Arg Ser Glu Glu Asp Arg Asn Arg Asp Leu Ala
        115                 120                 125

Thr Ala Leu Glu Gln Leu Leu Gln Ala Tyr Pro Arg Asp Met Glu Lys

```
                130                 135                 140
Glu Lys Thr Met Leu Val Leu Ala Leu Leu Ala Lys Lys Val Ala
145                 150                 155                 160

Ser His Thr Pro Ser Leu Leu Arg Asp Val Phe His Thr Val Asn
                165                 170                 175

Phe Ile Asn Gln Asn Leu Arg Thr Tyr Val Arg Ser Leu Ala Arg Asn
                180                 185                 190

Gly Met Asp
        195

<210> SEQ ID NO 81
<211> LENGTH: 133
<212> TYPE: PRT
<213> ORGANISM: Artificial Sequence
<220> FEATURE:
<223> OTHER INFORMATION: Exemplary IL-2 Mutein

<400> SEQUENCE: 81

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
                35                  40                  45

Lys Ala Thr Glu Leu Lys His Leu Gln Cys Leu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
                115                 120                 125

Ile Ser Thr Leu Thr
        130

<210> SEQ ID NO 82
<211> LENGTH: 133
<212> TYPE: PRT
<213> ORGANISM: Artificial Sequence
<220> FEATURE:
<223> OTHER INFORMATION: Exemplary IL-2 Mutein

<400> SEQUENCE: 82

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Ala Lys Phe Tyr Met Pro Lys
                35                  40                  45

Lys Ala Thr Glu Leu Lys His Leu Gln Cys Leu Glu Glu Leu Lys
        50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                85                  90                  95
```

```
Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 83
<211> LENGTH: 133
<212> TYPE: PRT
<213> ORGANISM: Artificial Sequence
<220> FEATURE:
<223> OTHER INFORMATION: Exemplary IL-2 Mutein

<400> SEQUENCE: 83

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Asn Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 84
<211> LENGTH: 133
<212> TYPE: PRT
<213> ORGANISM: Artificial Sequence
<220> FEATURE:
<223> OTHER INFORMATION: Exemplary IL-2 Mutein

<400> SEQUENCE: 84

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Ala Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125
```

```
Ile Ser Thr Leu Thr
    130

<210> SEQ ID NO 85
<211> LENGTH: 133
<212> TYPE: PRT
<213> ORGANISM: Artificial Sequence
<220> FEATURE:
<223> OTHER INFORMATION: Exemplary IL-2 Mutein

<400> SEQUENCE: 85

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Tyr Met Pro Lys
        35                  40                  45

Lys Ala Thr Glu Leu Lys His Leu Gln Cys Leu Glu Glu Ala Leu Lys
    50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 86
<211> LENGTH: 133
<212> TYPE: PRT
<213> ORGANISM: Artificial Sequence
<220> FEATURE:
<223> OTHER INFORMATION: Exemplary IL-2 Mutein

<400> SEQUENCE: 86

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Ala Lys Phe Ala Met Pro Lys
        35                  40                  45

Lys Ala Thr Glu Leu Lys His Leu Gln Cys Leu Glu Glu Ala Leu Lys
    50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130
```

<210> SEQ ID NO 87
<211> LENGTH: 133
<212> TYPE: PRT
<213> ORGANISM: Artificial Sequence
<220> FEATURE:
<223> OTHER INFORMATION: Exemplary IL-2 Mutein

<400> SEQUENCE: 87

```
Ala Pro Thr Ser Ser Ser Thr Lys Lys Thr Gln Leu Gln Leu Glu His
1               5                   10                  15

Leu Leu Leu Asp Leu Gln Met Val Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Ser Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130
```

<210> SEQ ID NO 88
<211> LENGTH: 133
<212> TYPE: PRT
<213> ORGANISM: Artificial Sequence
<220> FEATURE:
<223> OTHER INFORMATION: Exemplary IL-2 Mutein

<400> SEQUENCE: 88

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

His Leu Glu Glu Val Leu Asn Leu Ala Asn Ser Lys Asn Phe His Val
65                  70                  75                  80

Thr Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130
```

<210> SEQ ID NO 89
<211> LENGTH: 133
<212> TYPE: PRT
<213> ORGANISM: Artificial Sequence
<220> FEATURE:

<223> OTHER INFORMATION: Exemplary IL-2 Mutein

<400> SEQUENCE: 89

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala His Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 90
<211> LENGTH: 133
<212> TYPE: PRT
<213> ORGANISM: Artificial Sequence
<220> FEATURE:
<223> OTHER INFORMATION: Exemplary IL-2 Mutein

<400> SEQUENCE: 90

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Ser Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 91
<211> LENGTH: 133
<212> TYPE: PRT
<213> ORGANISM: Artificial Sequence
<220> FEATURE:
<223> OTHER INFORMATION: Exemplary IL-2 Mutein

<400> SEQUENCE: 91

Ala Pro Thr Ser Ser Ser Thr Lys Lys Thr Gln Leu Gln Leu Glu His

```
1               5                   10                  15
Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
            50                  55                  60

Pro Leu Glu Glu Val Leu Asn Leu Ala Asn Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
                115                 120                 125

Ile Ser Thr Leu Thr
                130

<210> SEQ ID NO 92
<211> LENGTH: 375
<212> TYPE: PRT
<213> ORGANISM: Artificial Sequence
<220> FEATURE:
<223> OTHER INFORMATION: Exemplary IL-2 Mutein

<400> SEQUENCE: 92

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
            50                  55                  60

Pro Leu Glu Glu Val Leu Asn Leu Ala Ser Ser Lys Asn Phe His Leu
65                  70                  75                  80

Asp Pro Arg Asp Val Ile Ser Asn Ile Asn Val Phe Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
                115                 120                 125

Ile Ser Thr Leu Thr Gly Gly Gly Ser Gly Gly Gly Ser Gly
        130                 135                 140

Gly Gly Gly Ser Asp Lys Thr His Thr Cys Pro Pro Cys Pro Ala Pro
145                 150                 155                 160

Glu Leu Leu Gly Gly Pro Ser Val Phe Leu Phe Pro Pro Lys Pro Lys
                165                 170                 175

Asp Thr Leu Met Ile Ser Arg Thr Pro Glu Val Thr Cys Val Val Val
                180                 185                 190

Asp Val Ser His Glu Asp Pro Glu Val Lys Phe Asn Trp Tyr Val Asp
                195                 200                 205

Gly Val Glu Val His Asn Ala Lys Thr Lys Pro Arg Glu Glu Gln Tyr
                210                 215                 220

Ala Ser Thr Tyr Arg Val Val Ser Val Leu Thr Val Leu His Gln Asp
```

```
225                 230                 235                 240
Trp Leu Asn Gly Lys Glu Tyr Lys Cys Lys Val Ser Asn Lys Ala Leu
                245                 250                 255
Pro Ala Pro Ile Glu Lys Thr Ile Ser Lys Ala Lys Gly Gln Pro Arg
            260                 265                 270
Glu Pro Gln Val Tyr Thr Leu Pro Pro Ser Arg Glu Met Thr Lys
            275                 280                 285
Asn Gln Val Ser Leu Thr Cys Leu Val Lys Gly Phe Tyr Pro Ser Asp
            290                 295                 300
Ile Ala Val Glu Trp Glu Ser Asn Gly Gln Pro Glu Asn Asn Tyr Lys
305                 310                 315                 320
Thr Thr Pro Pro Val Leu Asp Ser Asp Gly Ser Phe Phe Leu Tyr Ser
                325                 330                 335
Lys Leu Thr Val Asp Lys Ser Arg Trp Gln Gln Gly Asn Val Phe Ser
                340                 345                 350
Cys Ser Val Met His Glu Ala Leu His Asn His Tyr Thr Gln Lys Ser
                355                 360                 365
Leu Ser Leu Ser Pro Gly Lys
    370                 375

<210> SEQ ID NO 93
<211> LENGTH: 133
<212> TYPE: PRT
<213> ORGANISM: Artificial Sequence
<220> FEATURE:
<223> OTHER INFORMATION: Exemplary IL-2 Mutein

<400> SEQUENCE: 93

Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
                20                  25                  30
Asn Pro Lys Leu Thr Arg Met Leu Thr Phe Lys Phe Tyr Met Pro Lys
            35                  40                  45
Lys Ala Thr Glu Leu Lys His Leu Gln Cys Leu Glu Glu Glu Leu Lys
50                  55                  60
Pro Leu Glu Glu Val Leu Asn Leu Ala Gln Ser Lys Asn Phe His Phe
65                  70                  75                  80
Asp Pro Arg Asp Val Val Ser Asn Ile Asn Val Phe Val Leu Glu Leu
                85                  90                  95
Lys Gly Ser Glu Thr Thr Phe Met Cys Glu Tyr Ala Asp Glu Thr Ala
            100                 105                 110
Thr Ile Val Glu Phe Leu Asn Arg Trp Ile Thr Phe Cys Gln Ser Ile
            115                 120                 125
Ile Ser Thr Leu Thr
        130

<210> SEQ ID NO 94
<211> LENGTH: 133
<212> TYPE: PRT
<213> ORGANISM: Artificial Sequence
<220> FEATURE:
<223> OTHER INFORMATION: Exemplary IL-2 Mutein

<400> SEQUENCE: 94

Ala Pro Thr Ser Ser Ser Thr Lys Lys Thr Gln Leu Gln Leu Glu His
1               5                   10                  15
```

```
Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Asn Ser Lys Asn Phe His Phe
65                  70                  75                  80

Asp Pro Arg Asp Val Val Ser Asn Val Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 95
<211> LENGTH: 133
<212> TYPE: PRT
<213> ORGANISM: Artificial Sequence
<220> FEATURE:
<223> OTHER INFORMATION: Exemplary IL-2 Mutein

<400> SEQUENCE: 95

Ala Pro Thr Ser Ser Ser Thr Lys Lys Thr Gln Leu Gln Leu Glu His
1               5                   10                  15

Leu Leu Leu Asp Leu Gln Met Val Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Ser Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 96
<211> LENGTH: 133
<212> TYPE: PRT
<213> ORGANISM: Artificial Sequence
<220> FEATURE:
<223> OTHER INFORMATION: Exemplary IL-2 Mutein

<400> SEQUENCE: 96

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45
```

```
Lys Ala Thr Glu Leu Lys His Leu Gln Cys Leu Glu Glu Leu Lys
    50                  55                  60

His Leu Glu Glu Val Leu Asn Leu Ala Asn Ser Lys Asn Phe His Val
65                  70                  75                  80

Thr Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 97
<211> LENGTH: 133
<212> TYPE: PRT
<213> ORGANISM: Artificial Sequence
<220> FEATURE:
<223> OTHER INFORMATION: Exemplary IL-2 Mutein

<400> SEQUENCE: 97

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala His Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 98
<211> LENGTH: 133
<212> TYPE: PRT
<213> ORGANISM: Artificial Sequence
<220> FEATURE:
<223> OTHER INFORMATION: Exemplary IL-2 Mutein

<400> SEQUENCE: 98

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Ser Ser Lys Asn Phe His Phe
```

```
                65                  70                  75                  80
Asp Pro Arg Asp Val Val Ser Asn Ile Asn Val Phe Val Leu Glu Leu
                    85                  90                  95
Lys Gly Ser Glu Thr Thr Phe Met Cys Glu Tyr Ala Asp Glu Thr Ala
                100                 105                 110
Thr Ile Val Glu Phe Leu Asn Arg Trp Ile Thr Phe Cys Gln Ser Ile
                115                 120                 125
Ile Ser Thr Leu Thr
            130

<210> SEQ ID NO 99
<211> LENGTH: 133
<212> TYPE: PRT
<213> ORGANISM: Artificial Sequence
<220> FEATURE:
<223> OTHER INFORMATION: Exemplary IL-2 Mutein

<400> SEQUENCE: 99

Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
                20                  25                  30
Asn Pro Lys Leu Thr Arg Met Leu Thr Phe Lys Phe Tyr Met Pro Lys
                35                  40                  45
Lys Ala Thr Glu Leu Lys His Leu Gln Cys Leu Glu Glu Glu Leu Lys
            50                  55                  60
Pro Leu Glu Glu Val Leu Asn Leu Ala Asn Ser Lys Asn Phe His Phe
65                  70                  75                  80
Asp Pro Arg Asp Val Val Ser Asn Ile Asn Val Phe Val Leu Glu Leu
                    85                  90                  95
Lys Gly Ser Glu Thr Thr Phe Met Cys Glu Tyr Ala Asp Glu Thr Ala
                100                 105                 110
Thr Ile Val Glu Phe Leu Asn Arg Trp Ile Thr Phe Cys Gln Ser Ile
                115                 120                 125
Ile Ser Thr Leu Thr
            130

<210> SEQ ID NO 100
<211> LENGTH: 133
<212> TYPE: PRT
<213> ORGANISM: Artificial Sequence
<220> FEATURE:
<223> OTHER INFORMATION: Exemplary IL-2 Mutein

<400> SEQUENCE: 100

Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
                20                  25                  30
Asn Pro Lys Leu Thr Arg Met Leu Thr Phe Lys Phe Tyr Met Pro Lys
                35                  40                  45
Lys Ala Thr Glu Leu Lys His Leu Gln Cys Leu Glu Glu Glu Leu Lys
            50                  55                  60
Pro Leu Glu Glu Val Leu Asn Leu Ala Ser Ser Lys Asn Phe His Leu
65                  70                  75                  80
Thr Pro Arg Asp Val Ile Ser Asn Ile Asn Val Phe Val Leu Glu Leu
                    85                  90                  95
```

```
Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 101
<211> LENGTH: 133
<212> TYPE: PRT
<213> ORGANISM: Artificial Sequence
<220> FEATURE:
<223> OTHER INFORMATION: Exemplary IL-2 Mutein

<400> SEQUENCE: 101

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 102
<211> LENGTH: 133
<212> TYPE: PRT
<213> ORGANISM: Artificial Sequence
<220> FEATURE:
<223> OTHER INFORMATION: Exemplary IL-2 Mutein - IL-2 agonist H9D10

<400> SEQUENCE: 102

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala His Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125
```

Ile Ser Thr Leu Thr
    130

<210> SEQ ID NO 103
<211> LENGTH: 133
<212> TYPE: PRT
<213> ORGANISM: Artificial Sequence
<220> FEATURE:
<223> OTHER INFORMATION: Exemplary IL-2 Mutein - IL-2 agonist H9E10

<400> SEQUENCE: 103

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Ser Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 104
<211> LENGTH: 133
<212> TYPE: PRT
<213> ORGANISM: Artificial Sequence
<220> FEATURE:
<223> OTHER INFORMATION: Exemplary IL-2 Mutein - IL-2 agonist H9G8

<400> SEQUENCE: 104

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Asn Ser Lys Asn Phe His Phe
65                  70                  75                  80

Asp Pro Arg Asp Val Val Ser Asn Ile Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

```
<210> SEQ ID NO 105
<211> LENGTH: 133
<212> TYPE: PRT
<213> ORGANISM: Artificial Sequence
<220> FEATURE:
<223> OTHER INFORMATION: Exemplary IL-2 Mutein - IL-2 agonist H9B1

<400> SEQUENCE: 105

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Asn Ser Lys Asn Phe His Phe
65                  70                  75                  80

Asp Pro Arg Asp Val Val Ser Asn Val Asn Val Phe Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 106
<211> LENGTH: 133
<212> TYPE: PRT
<213> ORGANISM: Artificial Sequence
<220> FEATURE:
<223> OTHER INFORMATION: Exemplary IL-2 Mutein

<400> SEQUENCE: 106

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Arg Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 107
<211> LENGTH: 133
<212> TYPE: PRT
<213> ORGANISM: Artificial Sequence
<220> FEATURE:
```

<223> OTHER INFORMATION: Exemplary IL-2 Mutein

<400> SEQUENCE: 107

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Arg Ser Lys Asn Phe His Leu
65                  70                  75                  80

Arg Pro Arg Asp Val Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 108
<211> LENGTH: 133
<212> TYPE: PRT
<213> ORGANISM: Artificial Sequence
<220> FEATURE:
<223> OTHER INFORMATION: Exemplary IL-2 Mutein

<400> SEQUENCE: 108

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Arg Ser Lys Asn Phe His Leu
65                  70                  75                  80

Ile Pro Arg Asp Val Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 109
<211> LENGTH: 133
<212> TYPE: PRT
<213> ORGANISM: Artificial Sequence
<220> FEATURE:
<223> OTHER INFORMATION: Exemplary IL-2 Mutein

<400> SEQUENCE: 109

Ala Pro Thr Ser Ser Ser Thr Lys Lys Thr Gln Leu Gln Leu Glu His

```
1               5                   10                  15
Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
            50                  55                  60

Pro Leu Glu Glu Val Leu Asn Leu Ala His Ser Lys Asn Phe His Leu
65                  70                  75                  80

Thr Pro Arg Asp Val Val Ser Asn Ile Asn Val Phe Ile Leu Glu Leu
            85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
            130

<210> SEQ ID NO 110
<211> LENGTH: 133
<212> TYPE: PRT
<213> ORGANISM: Artificial Sequence
<220> FEATURE:
<223> OTHER INFORMATION: Exemplary IL-2 Mutein

<400> SEQUENCE: 110

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
            50                  55                  60

Pro Leu Glu Glu Val Leu Asn Leu Ala Ser Ser Lys Asn Phe His Leu
65                  70                  75                  80

Asp Pro Arg Asp Val Ile Ser Asn Ile Asn Val Phe Val Leu Glu Leu
            85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
            130

<210> SEQ ID NO 111
<211> LENGTH: 113
<212> TYPE: PRT
<213> ORGANISM: Artificial Sequence
<220> FEATURE:
<223> OTHER INFORMATION: IL-13 Amino Acid

<400> SEQUENCE: 111

Pro Gly Pro Val Pro Pro Ser Thr Ala Val Arg Glu Leu Ile Glu Glu
1               5                   10                  15

Leu Ile Asn Ile Thr Gln Asn Gln Lys Ala Pro Leu Cys Asn Gly Ser
            20                  25                  30
```

```
Met Val Trp Ser Ile Asn Arg Thr Ala Gly Met Tyr Cys Ala Ala Leu
         35                  40                  45

Glu Ser Leu Ile Asn Val Ser Gly Cys Ser Ala Ile Glu Lys Thr Gln
     50                  55                  60

Arg Met Leu Ser Gly Phe Cys Pro His Lys Val Ser Ala Gly Gln Phe
 65              70                  75                      80

Ser Ser Leu His Val Arg Ser Ser Lys Ile Glu Val Ala Gln Phe Val
             85                  90                  95

Lys Asp Leu Leu Phe His Leu Arg Thr Leu Phe Arg Glu Gly Gln Phe
         100                 105                 110

Asn

<210> SEQ ID NO 112
<211> LENGTH: 5
<212> TYPE: PRT
<213> ORGANISM: Artificial Sequence
<220> FEATURE:
<223> OTHER INFORMATION: IL-4 and IL-13 linker

<400> SEQUENCE: 112

Gly Gly Gly Gly Ser
1               5
```

USES AND METHODS FOR ONCOLYTIC VIRUS TARGETING OF IL-4/IL-13 AND FUSIONS THEREOF

CROSS-REFERENCE TO RELATED APPLICATIONS

The present application claims priority to U.S. Provisional Application No. 62/679,689, filed Jun. 1, 2018; and U.S. Provisional Application No. 62/687,228 filed Jun. 19, 2018, the disclosures of which are hereby incorporated by reference in their entireties for all purposes.

BACKGROUND OF THE INVENTION

Cytokines are small cell-signaling molecules that are secreted by numerous cells and are a category of signaling molecules used extensively in intercellular communication. Cytokines regulate key cellular functions, including differentiation, proliferation and apoptosis/anti-apoptosis.

Many cytokines mediate stimulation by first interacting with a relatively high affinity cytokine receptor chain, usually designated "a" or "alpha" or "a" followed by a relatively low affinity interaction with a receptor chain that is shared among different cytokines, a shared receptor chain. While not being bound by theory, generally, binding of a cytokine to the first high affinity receptor creates a composite surface that the shared receptor chain can then bind.

Interleukin-4 (IL-4) typifies such cytokines. The primary binding chain of IL-4 is IL-4 Receptor α(IL-4Rα). The IL-4/IL-4Rα complex serves as a ligand for the second component of the IL-4 receptor, γc. Additionally, the IL-4/IL-4Rα complex serves as a ligand for the interleukin-13 (IL-13) Receptor α1 (IL-13Rα1). Unlike IL-4, IL-13 does not bind to IL-4Rα however, IL-13/IL-13Rα1 complex binds does bind to IL-4Rα.

Because IL-4 and IL-13 can signal through distinct receptors, while not being bound by theory, it can be postulated that they are able to activate different signal transduction pathways. Indeed, γc activates the tyrosine kinase Janus kinase 3 (JAK3), whereas IL-13Rα1 activates Tyk2 and JAK2. Activated JAKs mediate the phosphorylation of the cytoplasmic tail of IL-4R on conserved tyrosine residues that serve as docking sites for proteins containing Src homology 2 (SH2) domains. Three closely clustered tyrosine residues serve as docking sites for signal transducer and activator of transcription 6 (STAT6), a transcription factor selectively coupled to the IL-4Rα chain. The binding of IL-13 to IL-13Rα1 also activates STAT6 through the binding of IL-4Rα by IL-13/IL-13Rα1 complex.

In addition to STAT6, IL-4 recruits and activates IRS-2. Structure-function analyses have revealed that a tyrosine residue [$Tyr_{497}$, part of the insulin/IL-4R motif (14-R)] on the transmembrane domain of IL-4Rα is necessary for the docking of IRS-2 to IL-4Rα after IL-4Rα has been activated by IL-4. JAK1 and JAK3 then phosphorylate IL-4Rα-bound IRS-2. The activation of IRS-2 leads to the activation of phosphoinositide 3-kinase (PI3K) and the downstream protein serine/threonine kinase Akt, a pathway that is thought to mediate growth and survival signals in many cell types. Indeed, this pathway is important in IL-4-mediated growth in cells expressing the type I IL-4R (NK cells, T cells, and B cells).

Although IL-4Rα is ubiquitously present, γc, but not IL-13Rα1 is found on T cells, natural killer (NK) cells, basophils, mast cells, and most mouse B cells (most human B cells express both γc, and IL-13Rα1). IL-4, but not IL-13, promotes the differentiation of naive T cells into $T_{H2}$ cells, and IL-4 appears much more important than IL-13 for the induction of mouse IgE responses. Some bone marrow-derived cells, including macrophages and dendritic cells, express both γc and IL-13Rα1, but little or no γc subunit, is found on most non-bone marrow-derived cells, including smooth muscle and epithelial cells; IL-4 has no inherent advantage over IL-13 in stimulating these cells.

IL-4R, is an ideal but under-exploited target for the development of cancer therapeutics. Expression levels of IL-4R are low on the surface of healthy and normal cells, but increase several-fold on cancer cells. For example, a majority of cancer biopsy and autopsy samples from adult and pediatric central nervous system (CNS) tumors, including recurrent GB biopsies, have been shown to over-express the TL-4R. There is little or no IL-4R expression in normal adult and pediatric brain tissue (Joshi, et al., 2001; see Table 2 of the reference).

Interleukin-13 (IL-13) is a cytokine secreted by T lymphocytes and mast cells, which shares several biological activities with IL-4, as a mediator of allergic inflammation and disease. IL-13 is involved in the allergic response via its actions on epithelial and smooth muscle cells. IL-13 induces many features of allergic lung disease, including airway hyperresponsiveness, goblet cell metaplasia and mucus hypersecretion, which all contribute to airway obstruction. IL-13 also induces secretion of chemokines that are required for recruitment of allergic effector cells to the lung.

An important factor in IL-13 biology is the nature of its receptor interactions. Its diverse functions are mediated by a complex receptor system including IL-4 receptor α (IL-4Rα; CD124) and two other cognate cell surface proteins, IL-13Rα1 (CD213a1) and IL-13Rα2 (CD213a2). IL-13Rα1 forms a heterodimer with IL-4Rα that is a signaling IL-13 receptor. In contrast, IL-13Rα2 has been thought to be a decoy receptor due to its short cytoplasmic tail. IL-13Rα2 exists on the cell membrane, intracellularly, and in soluble form. IL-13Rα2 has an extremely high affinity for IL-13, and can out-compete antibodies for IL-13 binding. The other receptor, IL-13Rα1, has a much lower affinity, but is associated with signaling events mediated by IL-4Rα. It induces its effects through a multi-subunit receptor that includes the alpha chain of the IL-4 receptor (IL-4Rα) and IL-13Rα1. Most of the biological effects of IL-13, like those of IL-4, are linked to a single transcription factor, signal transducer and activator of transcription 6 (STAT6).

IL13Rα2 is highly expressed in many tumor types, such as colorectal, glioblastoma, ovarian, head and neck, breast, pancreatic, kidney, and mesothelioma, but not by most normal cells such as immune cells or endothelial cells. IL13Rα2 is also associated with poor prognosis in human cancers and a target for cancer therapy. High IL13Rα2 expression levels have been shown to promote invasion and metastasis of brain, pancreatic, ovarian, breast and colorectal cancers. Increased IL13Rα2 levels were also associated with poor metastasis-free survival of patients with breast cancer. IL13Rα2 expression is also a prognostic marker for glioma malignancy grade and for poor patient survival.

Targeted immunotherapy has emerged as promising field of research in the treatment of malignancies and has received a great deal of interest in recent years. There are many different approaches among which, oncolytic virus therapy is one of them. Oncolytic virus therapy takes advantage of the oncolytic nature of some viruses (oncolytic viruses (OVs)) in order to kill tumor cells. The advantage of these viruses is their ability to infect and replicate in tumor cells without harming normal tissues. Tumor cells are indeed a good target for OVs. They show a reduction in many of the specific mechanisms used by host cells to respond to viral infection (such as the type I IFN pathway) allowing viruses to replicate successfully in these cells. Moreover, advances in genetic engineering have led to the production of viruses lacking the thymidine kinase gene forcing the virus to replicate only in those cells that have an up-regulation of the RAS pathway like cancer cells. Furthermore, oncolytic viral therapy not only kill cancer cells but also activate the immune system, silenced by the tumor microenvironment.

The present invention meets the need for further cancer therapies by providing targeted immunotherapies employing oncolytic viruses and targeting moieties containing IL-4 and/or IL-13 and/or the variants thereof for use in cancer therapies. The present invention provides methods for using oncolytic viruses to target IL-4 and/or IL-13 muteins to cancer cells and/or the tumor microenvironment (TME), as well as methods for using IL-4 and/or IL-13 muteins to target oncolytic viruses to cancer cells and/or the tumor microenvironment (TME).

BRIEF SUMMARY OF THE INVENTION

In one aspect, the present invention provides a modified oncolytic virus vector comprising at least one nucleic acid sequence encoding an IL-4 receptor targeted cargo protein, wherein the oncolytic virus is selected from the group consisting of an adenovirus, a self-replicating alphavirus, a vaccinia virus, a Seneca Valley Virus, a Newcastle disease Virus, a Maraba virus, vesicular stomatitis virus (VSV), a Herpes virus (including HSV-1 and HSV-2), a measles virus, a poliovirus, a reovirus, a coxsackie virus, a lentivirus, a morbillivirus, an influenza virus, Sinbis virus, myxoma virus, and a retrovirus.

In one aspect, the present invention provides a modified oncolytic vaccinia virus vector comprising a modified vaccinia virus genome and at least one nucleic acid sequence encoding an IL-4 receptor targeted cargo protein, wherein the modified oncolytic vaccinia virus vector encodes a modified oncolytic vaccinia virus characterized by inactivation or partial inactivation of thymidine kinase (TK) and vaccinia growth factor.

In some embodiments, the modified oncolytic vaccinia virus vector as described herein, wherein the modified vaccinia virus genome comprises a substitution and/or an open reading frame ablating deletion of at least one nucleotide in the thymidine kinase gene and deletion of vaccinia growth factor gene, resulting in the inactivation of thymidine kinase and vaccinia growth factor.

In one aspect, the present invention provides a modified oncolytic virus encoded by the modified vector as described herein.

In one aspect, the modified oncolytic vaccinia virus encoded by the modified vector as described herein.

In one aspect, the present invention provides a modified oncolytic adenovirus vector comprising (i) an adenovirus genome, wherein optionally the nucleotides encoding amino acids 122-129 of E1A polypeptide are deleted, and (ii) at least one nucleic acid sequence encoding an IL-4 receptor targeted cargo protein.

In one aspect, the present invention provides a modified oncolytic adenovirus encoded by the modified vector as described herein.

In one aspect, the present invention provides a modified oncolytic rhabdovirus vector or virus comprising at least one nucleic acid sequence encoding an IL-4 receptor targeted cargo protein.

In some embodiments, the modified oncolytic rhabdovirus virus is encoded by the modified vector as described herein.

In some embodiments, the IL-4 receptor targeted cargo protein directs the modified oncolytic virus to the tumor and/or tumor microenvironment.

In some embodiments, the IL-4 receptor targeted cargo protein directs the modified oncolytic virus to the immunosuppressive cells of the tumor microenvironment (TME), such as tumor associated macrophages and MDSCs (myeloid-derived suppressor cells) in order to have an improved therapeutic benefit.

In some embodiments, the IL-4 target cargo protein directs the modified oncolytic virus to one or more tumor antigens.

In some embodiments, the vaccinia virus comprises a modified vaccinia virus vector and at least one nucleic acid sequence encoding an IL-2 mutein, wherein the modified vaccinia virus vector comprises a substitution and/or an open reading frame ablating deletion of at least one nucleotide in the thymidine kinase gene, and deletion of vaccinia growth factor gene.

In some embodiments, the in vivo contacting results in an increased concentration of the IL-4 or IL-13 mutein protein in the tumor microenvironment as compared to the concentration of an IL-4 or IL-13 mutein protein not conjugated to an oncolytic virus.

In some embodiments, the IL-4 or IL-13 mutein comprises any one of the IL-4 or IL-13 mutein sequences described in Table 3, Table 4 and/or Table 5.

In some embodiments, the IL-4 or IL-13 mutein comprises a sequence including any one of SEQ ID NOs:2-55.

In some embodiments, the IL-13 mutein comprises a sequence including any one of SEQ ID NOs:2-48.

In some embodiments, the IL-4 mutein comprises a sequence including any one of SEQ ID NOs:50-55.

In some embodiments, the IL-4 or IL-13 mutein comprises a sequence including any one of SEQ ID NOs:56-69.

In some embodiments, the IL-13 mutein comprises the amino acid sequence (SEQ ID NO: 2)
PGPVPPSTAVRALIEELINITQNQKAPLCNGSMVWSINRTAGMYCAALE

SLINVSGCSAIEKTQDMLSGFCPHKVSAGQFSSLHVRSSKIEVAQFVKD

LLFHLRTLFREGQFN.

In some embodiments, the IL-13 mutein comprises the amino acid sequence (SEQ ID NO: 18)
PGPVPPSTAHRELIEELVNITQNQKAPLCNGSMVWSINLTAGMYCAALE

SLINVSGCSAIEKTQRMLSGFCPHKVSAGQFSSLHVTGRKIEVAQFVKD

LLLHLKKLFKEGQFN.

In some embodiments, the IL-4 mutein comprises the amino acid sequence (SEQ ID NO: 51)
KCDITLQEIIKTLNSLTEQKTLCTELTVTDIFAASKNTTEKETFCRAAT

VLRQFYSHHEKDTRCLGATAQQFHRHKQLIRFLKRLDRNLWGLAGLNSC

PVKEANQSTLENFLERLKTIMKEKFRKCSS.

In some embodiments, the oncolytic virus further comprises a transgene capable of expressing an IL-2 mutein.

In some embodiments, the IL-2 mutein protein enhances effector T cells and NK cells.

In some embodiments, the IL-2 mutein suppresses regulatory T cell (Treg) activity.

In some embodiments, the IL-2 mutein comprises amino acid substitutions L80F, R81D, L85V, I86V, and I92F in comparison to wild-type human IL-2 of SEQ ID NO:81.

In some embodiments, the IL-2 mutein further comprises at least one amino acid substitution selected from the group consisting of F42A, E62A, and Y45A in comparison to wild-type human IL-2 of SEQ ID NO:81.

In some embodiments, the IL-2 mutein further comprises amino acid substitutions F42A and E62A in comparison to wild-type human IL-2 of SEQ ID NO:81.

In some embodiments, the IL-2 mutein further comprises amino acid substitutions F42A, E62A, and Y45A in comparison to wild-type human IL-2 of SEQ ID NO:81.

In some embodiments, the IL-2 mutein further comprises amino acid substitutions F42A and Y45A in comparison to wild-type human IL-2 of SEQ ID NO:81.

In some embodiments, the IL-2 mutein comprises any one of the IL-2 mutein sequences described in Table 7.

In some embodiments, the IL-2 mutein comprises any one of the IL-2 mutein comprises a sequence including any one of SEQ ID NOs:82-109.

In some embodiments, the IL-2 mutein comprises the amino acid sequence (SEQ ID NO: 93)
APTSSSTKKTQLQLEHLLLDLQMILNGINNYKNPKLTRMLTFKFYMPKK

ATELKHLQCLEEELKPLEEVLNLAQSKNFHFDPRDVVSNINVFVLELKG

SETTFMCEYADETATIVEFLNRWITFCQSIISTLT.

In some embodiments, the IL-2 mutein comprises the amino acid sequence (SEQ ID NO: 82)
APTSSSTKKTQLQLEHLLLDLQMILNGINNYKNPKLTRMLTAKFYMPKK

ATELKHLQCLEEELKPLEEVLNLAQSKNFHFDPRDVVSNINVFVLELKG

SETTFMCEYADETATIVEFLNRWITFCQSIISTLT.

In some embodiments, the IL-2 mutein comprises the amino acid sequence (SEQ ID NO: 84)
APTSSSTKKTQLQLEHLLLDLQMILNGINNYKNPKLTRMLTAKFAMPKK

ATELKHLQCLEEELKPLEEVLNLAQSKNFHFDPRDVVSNINVFVLELKG

SETTFMCEYADETATIVEFLNRWITFCQSIISTLT.

In some embodiments, the IL-2 mutein comprises the amino acid sequence (SEQ ID NO: 85)
APTSSSTKKTQLQLEHLLLDLQMILNGINNYKNPKLTRMLTAKFYMPKK

ATELKHLQCLEEALKPLEEVLNLAQSKNFHFDPRDVVSNINVFVLELKG

SETTFMCEYADETATIVEFLNRWITFCQSIISTLT.

In some embodiments the IL-2 mutein comprises the amino acid sequence (SEQ ID NO: 86)
APTSSSTKKTQLQLEHLLLDLQMILNGINNYKNPKLTRMLTAKFAMPKK

ATELKHLQCLEEALKPLEEVLNLAQSKNFHFDPRDVVSNINVFVLELKG

SETTFMCEYADETATIVEFLNRWITFCQSIISTLT.

In some aspects, the present invention provides a method of treating cancer comprising administering an oncolytic virus capable of expressing an IL-4 or IL-13 mutein to a subject in need thereof, including an oncolytic virus disclosed herein.

In some aspects, the present invention provides a method for treating a brain tumor in a patient comprising:

a) identifying a patient having a brain tumor; and b) contacting the tumor with the oncolytic virus disclosed herein.

In some aspects, the present invention provides a method of targeting an IL-4 or IL-13 mutein protein to a cancer cell comprising contacting the cancer cell with an IL-4 or IL-13 mutein oncolytic virus combination, wherein the combination comprises an IL-4 or IL-13 mutein conjugated to or expressed by an oncolytic virus, and wherein the oncolytic virus is capable of targeting the cancer cell, including an oncolytic virus disclosed herein.

In some embodiments, the contacting occurs in vitro.

In some embodiments, the contacting occurs in vivo.

In some embodiments, the oncolytic virus is selected from the group consisting of an adenovirus, a self-replicating alphavirus, a vaccinia virus, a Seneca Valley Virus, a Newcastle disease Virus, a Maraba virus, vesicular stomatitis virus (VSV), a Herpes virus (including HSV-1 and HSV-2), a measles virus, a poliovirus, a reovirus, a coxsackie virus, a lentivirus, a morbillivirus, an influenza virus, Sinbis virus, myxoma virus, and a retrovirus.

In some embodiments, the vaccinia virus comprises a modified vaccinia virus vector and at least one nucleic acid sequence encoding an IL-2 mutein, wherein the modified vaccinia virus vector comprises a substitution and/or an open reading frame ablating deletion of at least one nucleotide in the thymidine kinase gene, and deletion of vaccinia growth factor gene.

In some embodiments, the in vivo contacting results in an increased concentration of the IL-4 or IL-13 mutein protein in the tumor microenvironment as compared to the concentration of an IL-4 or IL-13 mutein protein not conjugated to an oncolytic virus.

In some embodiments, the IL-4 or IL-13 mutein comprises any one of the IL-4 or IL-13 mutein sequences described in Table 3, Table 4 and/or Table 5.

In some embodiments, the IL-4 or IL-13 mutein comprises a sequence including any one of SEQ ID NOs:2-55.

In some embodiments, the IL-13 mutein comprises a sequence including any one of SEQ ID NOs:2-48.

In some embodiments, the IL-4 mutein comprises a sequence including any one of SEQ ID NOs:50-55.

In some embodiments, the IL-4 or IL-13 mutein comprises a sequence including any one of SEQ ID NOs:56-69.

In some embodiments, the IL-13 mutein comprises the amino acid sequence (SEQ ID NO: 2)
PGPVPPSTAVRALIEELINITQNQKAPLCNGSMVWSINRTAGMYCAALE

SLINVSGCSAIEKTQDMLSGFCPHKVSAGQFSSLHVRSSKIEVAQFVKD

LLFHLRTLFREGQFN.

In some embodiments, the IL-13 mutein comprises the amino acid sequence (SEQ ID NO: 18)
PGPVPPSTAHRELIEELVNITQNQKAPLCNGSMVWSINLTAGMYCAALE

SLINVSGCSAIEKTQRMLSGFCPHKVSAGQFSSLHVTGRKIEVAQFVKD

LLLHLKKLFKEGQFN.

In some embodiments, the IL-4 mutein comprises the amino acid sequence (SEQ ID NO: 51)
KCDITLQEIIKTLNSLTEQKTLCTELTVTDIFAASKNTTEKETFCRAAT

VLRQFYSHHEKDTRCLGATAQQFHRHKQLIRFLKRLDRNLWGLAGLNSC

PVKEANQSTLENFLERLKTIMKEKFRKCSS.

In some embodiments, the oncolytic virus further comprises a transgene capable of expressing an IL-2 mutein.

In some embodiments, the IL-2 mutein protein enhances effector T cells and NK cells.

In some embodiments, the IL-2 mutein suppresses regulatory T cell (Treg) activity.

In some embodiments, the IL-2 mutein further comprises at least one amino acid substitution selected from the group consisting of F42A, E62A, and Y45A in comparison to wild-type human IL-2 of SEQ ID NO:81.

In some embodiments, the IL-2 mutein further comprises amino acid substitutions F42A and E62A in comparison to wild-type human IL-2 of SEQ ID NO:81.

In some embodiments, the IL-2 mutein further comprises amino acid substitutions F42A, E62A, and Y45A in comparison to wild-type human IL-2 of SEQ ID NO:81.

In some embodiments, the IL-2 mutein further comprises amino acid substitutions F42A and Y45A in comparison to wild-type human IL-2 of SEQ ID NO:81.

In some embodiments, the IL-2 mutein comprises any one of the IL-2 mutein sequences described in Table 7.

In some embodiments, the IL-2 mutein comprises any one of the IL-2 mutein comprises a sequence including any one of SEQ ID NOs:82-109.

In some embodiments, the IL-2 mutein comprises the amino acid sequence (SEQ ID NO: 93)
APTSSSTKKTQLQLEHLLLDLQMILNGINNYKNPKLTRMLTFKFYMPKK

ATELKHLQCLEEELKPLEEVLNLAQSKNFHFDPRDVVSNINVFVLELKG

SETTFMCEYADETATIVEFLNRWITFCQSIISTLT.

In some embodiments, the IL-2 mutein comprises the amino acid sequence (SEQ ID NO: 82)
APTSSSTKKTQLQLEHLLLDLQMILNGINNYKNPKLTRMLTAKFYMPKK

ATELKHLQCLEEELKPLEEVLNLAQSKNFHFDPRDVVSNINVFVLELKG

SETTFMCEYADETATIVEFLNRWITFCQSIISTLT.

In some embodiments, the IL-2 mutein comprises the amino acid sequence (SEQ ID NO: 84)
APTSSSTKKTQLQLEHLLLDLQMILNGINNYKNPKLTRMLTAKFAMPKK

ATELKHLQCLEEELKPLEEVLNLAQSKNFHFDPRDVVSNINVFVLELKG

SETTFMCEYADETATIVEFLNRWITFCQSIISTLT.

In some embodiments, the IL-2 mutein comprises the amino acid sequence (SEQ ID NO: 85)
APTSSSTKKTQLQLEHLLLDLQMILNGINNYKNPKLTRMLTAKFYMPKK

ATELKHLQCLEEALKPLEEVLNLAQSKNFHFDPRDVVSNINVFVLELKG

SETTFMCEYADETATIVEFLNRWITFCQSIISTLT.

In some embodiments, the IL-2 mutein comprises the amino acid sequence (SEQ ID NO: 86)
APTSSSTKKTQLQLEHLLLDLQMILNGINNYKNPKLTRMLTAKFAMPKK

ATELKHLQCLEEALKPLEEVLNLAQSKNFHFDPRDVVSNINVFVLELKG

SETTFMCEYADETATIVEFLNRWITFCQSIISTLT.

BRIEF DESCRIPTION OF THE DRAWINGS

FIGS. 1A and 1B: Exemplary oncolytic viruses.

DETAILED DESCRIPTION OF THE INVENTION

I. Definitions

Abbreviations and Terms

| | |
|---|---|
| PA | Proaerolysin |
| BAD | BCL2-associated agonist of cell death |
| BAX | BCL2-associated X protein |
| EGF | Epidermal growth factor |
| EpCAM | Epithelial protein cell adhesion molecule |
| GMCSF | Granulocyte-macrophage colony-stimulating factor |
| IL-4 | Interleukin-4 |
| IL-13 | Interleukin-13 |
| PSMA | Prostate specific membrane antigen |

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a IL-4 receptor targeted cargo protein" includes single or plural IL-4 receptor targeted cargo proteins and is considered equivalent to the phrase "comprising at least about one IL-4 receptor targeted cargo protein." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Unless explained otherwise, all technical and scientific terms used herein have the same meaning as commonly understood to one of ordinary skill in the art to which this disclosure belongs.

Accession Numbers: Reference numbers assigned to various nucleic acid and amino acid sequences in the NCBI database (National Center for Biotechnology Information) that is maintained by the National Institute of Health, U.S.A. The accession numbers listed in this specification are herein incorporated by reference as provided in the database as of the date of filing this application.

Administration: Providing or giving a subject an agent, such as a composition that includes a IL-4 receptor targeted cargo protein. Exemplary routes of administration include, but are not limited to, oral, injection (such as subcutaneous, intramuscular, intradermal, intraperitoneal, intratumoral and intravenous), sublingual, rectal or transrectal, transdermal, intranasal, vaginal, cervical, and inhalation routes. In specific examples, intratumoral includes local, regional, focal, or convection enhanced delivery. In other specific examples, administration includes transurethral or transperineal administration. In one example, surrogate magnetic resonance imaging tracers (e.g., gadolinium-bound albumin (Gd-albumin)) can be administered in combination with the IL-4 receptor targeted cargo protein to determine if the IL-4 receptor targeted cargo protein is delivered to a tumor, such as a brain tumor, safely at therapeutic doses while monitoring its distribution in real-time (see for example, Murad et al., Clin. Cancer Res. 12(10):3145-51 2006).

Antibody: Immunoglobulin molecules and immunologically active portions of immunoglobulin molecules, that is, molecules that contain an antigen binding site that specifically binds (immunoreacts with) an epitope, such as an epitope displayed by cancer cells and/or cancer stem cells. Antibodies include monoclonal antibodies, polyclonal antibodies, as well as humanized antibodies. Antibodies also include affibodies. Affibodies mimic monoclonal antibodies in function but are based on Protein A. Affibodies can be engineered as high-affinity ligands for binding to a targeting moiety.

A naturally occurring antibody (e.g., IgG, IgM, IgD) includes four polypeptide chains, two heavy (H) chains and two light (L) chains interconnected by disulfide bonds. However, it has been shown that the antigen-binding function of an antibody can be performed by fragments of a naturally occurring antibody. Thus, these antigen-binding fragments are also intended to be designated by the term "antibody." Specific, non-limiting examples of binding fragments encompassed within the term antibody include (i) a Fab fragment consisting of the VL, VH, CL and CH1 domains; (ii) an Fd fragment consisting of the VH and CH1 domains; (iii) an Fv fragment consisting of the VL and VH domains of a single arm of an antibody (scFv) and scFv molecules linked to each other to form a bivalent dimer (diabody) or trivalent trimer (triabody); (iv) a dAb fragment (Ward et al., Nature 341:544-546, 1989) which consists of a VH domain; (v) an isolated complementarity determining region (CDR); and (vi) a F(ab')2 fragment, a bivalent fragment comprising two Fab fragments linked by a disulfide bridge at the hinge region.

Methods of producing polyclonal and monoclonal antibodies are known to those of ordinary skill in the art, and many antibodies are available. See, e.g., Coligan, Current Protocols in Immunology Wiley/Greene, N.Y., 1991; and Harlow and Lane, Antibodies: A Laboratory Manual Cold Spring Harbor Press, NY, 1989; Stites et al., (eds.) Basic and Clinical Immunology (4th ed.) Lange Medical Publications, Los Altos, Calif., and references cited therein; Goding, Monoclonal Antibodies: Principles and Practice (2d ed.) Academic Press, New York, N.Y., 1986; and Kohler and Milstein, Nature 256: 495-497, 1975. Other suitable techniques for antibody preparation include selection of libraries of recombinant antibodies in phage or similar vectors. See, Huse et al., Science 246: 1275-1281, 1989; and Ward et al., Nature 341: 544-546, 1989.

Immunoglobulins and certain variants thereof are known and many have been prepared in recombinant cell culture (e.g., see U.S. Pat. Nos. 4,745,055; 4,444,487; WO 88/03565; EP 256,654; EP 120,694; EP 125,023; Faoulkner et al., Nature 298:286, 1982; Morrison, J. Immunol. 123: 793, 1979; Morrison et al., Ann Rev. Immunol 2:239, 1984). Detailed methods for preparation of chimeric (humanized) antibodies can be found in U.S. Pat. No. 5,482,856. Additional details on humanization and other antibody production and engineering techniques can be found in Borrebaeck (ed), Antibody Engineering, 2nd Edition Freeman and Company, NY, 1995; McCafferty et al., Antibody Engineering, A Practical Approach, IRL at Oxford Press, Oxford, England, 1996, and Paul Antibody Engineering Protocols Humana Press, Towata, N.J., 1995.

In some examples, an antibody specifically binds to a target protein (e.g., a cell surface receptor such as an IL4 receptor) with a binding constant that is at least $10^3$ $M^{-1}$ greater, $10^4$ $M^{-1}$ greater or $10^5$ $M^{-1}$ greater than a binding constant for other molecules in a sample. In some examples, a specific antibody (e.g., a monoclonal antibody or fragments thereof) has an equilibrium constant ($K_d$) of 1 nM or less. For example, a specific binding agent may bind to a target protein with a binding affinity of at least about $0.1 \times 10^{-8}$ M, at least about $0.3 \times 10^{-8}$M, at least about $0.5 \times 10^{-8}$ M, at least about $0.75 \times 10^{-8}$ M, at least about $1.0 \times 10^{-8}$ M, at least about $1.3 \times 10^{-8}$ M at least about $1.5 \times 10^{-8}$ M, or at least about $2.0 \times 10^{-8}$ M. Kd values can, for example, be determined by competitive ELISA (enzyme-linked immunosorbent assay) or using a surface-plasmon resonance device such as the Biacore T100, which is available from Biacore, Inc., Piscataway, N.J.

Binds or binding: The association between two or more molecules, wherein the two or more molecules are in close physical proximity to each other, such as the formation of a complex. An exemplary complex is a receptor-ligand pair or an antibody-antigen pair. Generally, the stronger the binding of the molecules in a complex, the slower their rate of dissociation. Specific binding refers to a preferential binding between an agent and a specific target. For example, specific binding refers to when a IL-4 receptor targeted cargo protein that includes a targeting moiety specific for a cancer stem cell antigen binds to the cancer stem cell, but does not significantly bind to other cells that do not display the target in close proximity to the cancer stem cell. Such binding can be a specific non-covalent molecular interaction between the ligand and the receptor. In a particular example, binding is assessed by detecting cancer stem cell growth inhibition using one of the methods described herein after the IL-4 receptor targeted cargo protein has been contacted with the cancer stem cell.

Such interaction is mediated by one or, typically, more noncovalent bonds between the binding partners (or, often, between a specific region or portion of each binding partner). In contrast to non-specific binding sites, specific binding sites are saturable. Accordingly, one exemplary way to characterize specific binding is by a specific binding curve. A specific binding curve shows, for example, the amount of one binding partner (the first binding partner) bound to a fixed amount of the other binding partner as a function of the first binding partner concentration. As the first binding partner concentration increases under these conditions, the amount of the first binding partner bound will saturate. In another contrast to non-specific binding sites, specific binding partners involved in a direct association with each other (e.g., a protein-protein interaction) can be competitively removed (or displaced) from such association (e.g., protein complex) by excess amounts of either specific binding partner. Such competition assays (or displacement assays) are very well known in the art.

Cancer: Malignant neoplasm that has undergone characteristic anaplasia with loss of differentiation, increased rate of growth, invasion of surrounding tissue, and is capable of metastasis. Residual cancer is cancer that remains in a subject after any form of treatment given to the subject to reduce or eradicate a cancer and recurrent cancer is cancer that recurs after such treatment. Metastatic cancer is a cancer at one or more sites in the body other than the site of origin of the original (primary) cancer from which the metastatic cancer is derived. In the case of a metastatic cancer originating from a solid tumor, one or more (for example, many) additional tumor masses can be present at sites near or distant to the site of the original tumor. The phrase "disseminated metastatic nodules" or "disseminated metastatic tumors" refers to a plurality (typically many) metastatic tumors dispersed to one or more anatomical sites. For example, disseminated metastatic nodules within the peritoneum (that is a disseminated intraperitoneal cancer) can arise from a tumor of an organ residing within or outside the peritoneum, and can be localized to numerous sites within the peritoneum. Such metastatic tumors can themselves be discretely localized to the surface of an organ, or can invade the underlying tissue.

Cargo Moiety: A peptide (e.g., protein fragment or full length protein) or other molecule that can function to significantly reduce or inhibit the growth of a cancer stem cell. In some examples a cargo moiety can trigger cell death (e.g., apoptosis). Exemplary cargo moieties include toxins, such as toxins derived from plants, microorganisms, and animals. In other examples, cargo moieties are proteins that normally contribute to the control of cell life cycles, for example cargo moieties can be any protein that triggers cell death, such as via apoptotic or non-apoptotic pathways. In some examples, the cargo moiety is not a protein, but another molecule that can function to significantly reduce or inhibit the growth of a cancer stem cell, such as thapsigargin. In some examples, a cargo moiety is activated by a tumor-associated protease, such as PSA. Exemplary cargo moieties, and exemplary GenBank accession numbers, are provided in Table 1, below. In addition to native cargo sequences, variant sequences can also be used, such as mutant sequences with greater biological activity than that of the native sequence.

TABLE 1

Exemplary cargo moiety sequences

| Cargo Moiety | Accession Numbers* |
|---|---|
| Aerolysin | ABR14715.1; ABR14714.1 |
| Proaerolysin | AAA21938.1; P09167.2; U.S. Pat. No. 7,282,476 (proaerolysin sequences therein herein incorporated by reference) |
| Bouganin | AAL35962 and SEQ ID NO: 9 in U.S. Pat. No. 6,737,511, as well as variant sequences provided in U.S. Pat. No. 7,339,031 and WO 2005/090579 (bouganin sequences therein herein incorporated by reference) |
| *Pseudomonas* exotoxin | 1IKP A; AAB59097.1; AAF90003.1 (also see SEQ ID NO: 1 of U.S. Pat. No. 6,011,002) |
| Bcl-2 pro-apoptotic proteins such as BAD and BAX | BAD: CAG46757; AAH01901.1; CAG46733.1; and sequences provided in U.S. Pat. No. 6,737,511 BAX: CAE52909.1; AAO22992.1; EAW52418.1 |
| Cholera toxin | BAA06291.1; ACF35010.1; BAA06288.1; as well as variant sequences provided in U.S. patent application Ser. No. 61/058,872 (variant cholera toxin sequences therein herein incorporated by reference) |
| Ribonuclease A | BAA05124.1; NP_937877.1; NP_115961.2; Q5GAN4.1; and sequences provided in PCT Publication No. WO2007/041361 (rapLR1 sequences therein herein incorporated by reference) |

*GenBank Numbers are herein incorporated by reference, as well as their corresponding nucleic acid sequences.

Contact or contacting: Refers to the relatively close physical proximity of one object to another object. Generally, contacting involves placing two or more objects in close physical proximity to each other to give the objects and opportunity to interact. For example, contacting a IL-4 receptor targeted cargo protein with a cancer stem cell can be accomplished by placing the IL-4 receptor targeted cargo protein (which can be in a solution) in proximity to the cell, for example by injecting the IL-4 receptor targeted cargo protein into a subject having the cancer. Similarly, a IL-4 receptor targeted cargo protein can be contacted with a cell in vitro, for example by adding the IL-4 receptor targeted cargo protein to culture media in which the cell is growing.

Decrease: To reduce the quality, amount, or strength of something. In one example, a therapy (such as treatment with a IL-4 receptor targeted cargo protein) decreases a cancer stem cell population (such as by decreasing the size of a tumor, the volume of a tumor, the metastasis of a tumor, the number of cancer cells and/or cancer stem cells, or combinations thereof), or one or more symptoms associated with cancer, for example as compared to the response in the absence of the therapy. In a particular example, a therapy decreases the size of a tumor, volume of a tumor, number of cancer cells and/or cancer stem cells, or the metastasis of a cancer, or combinations thereof, subsequent to the therapy, such as a decrease of at least about 10%, at least about 20%, at least about 50%, or even at least about 90%. Such decreases can be measured using the methods disclosed herein.

Diagnose: The process of identifying a medical condition or disease, for example from the results of one or more diagnostic procedures. In particular examples, includes determining the prognosis of a subject (e.g., likelihood of survival over a period of time, such as likelihood of survival in 6-months, 1-year, or 5-years). In a specific example, cancer is diagnosed by detecting the presence of a cancer stem cell in a sample using one or more of the targets on the cancer stem cell surface. For example, diagnoses can include determining the particular stage of cancer or the presence of a site of metastasis.

Linker: A molecule used to connect one or more agents to one or more other agents. For example, a linker can be used to connect one or more cargo moieties to one or more targeting moieties. Particular non-limiting examples of linkers include dendrimers, such as synthetic polymers, peptides, proteins and carbohydrates. Linkers additionally can contain one or more protease cleavage sites or be sensitive to cleavage via oxidation and/or reduction.

Pharmaceutically acceptable carriers: The term "pharmaceutically acceptable carriers" refers to pharmaceutically acceptable carriers (vehicles) useful in this disclosure are conventional. Remington's Pharmaceutical Sciences, by E. W. Martin, Mack Publishing Co., Easton, Pa., 15th Edition (1975), describes compositions and formulations suitable for pharmaceutical delivery of one or more therapeutic or diagnostic agents, such as one or more of the IL-4 receptor targeted cargo protein molecules provided herein.

In general, the nature of the carrier will depend on the particular mode of administration being employed. For instance, parenteral formulations can include injectable fluids that include pharmaceutically and physiologically acceptable fluids such as water, physiological saline, balanced salt solutions, aqueous dextrose, glycerol or the like as a vehicle. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate, sodium lactate, potassium chloride, calcium chloride, and triethanolamine oleate.

Pharmaceutical agent or drug: A chemical compound or composition capable of inducing a desired therapeutic effect when administered to a subject, alone or in combination with another therapeutic agent(s) or pharmaceutically acceptable carriers. In a particular example, a pharmaceutical agent (such as one that includes a IL-4 receptor targeted cargo protein) treats a cancer, for example by reducing the size of the tumor (such as the volume or reducing the number of cancer cells and/or cancer stem cells), reducing metastasis of the cancer, or combinations thereof.

Recombinant: A recombinant molecule (such as a recombinant nucleic acid molecule or protein) has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques. A recombinant protein is one that results from expressing a recombinant nucleic acid encoding the protein. IL-4 receptor targeted cargo proteins of the present disclosure are generally recombinant.

Sample: Biological specimens such as samples containing biomolecules, such as nucleic acid molecules, proteins, or both. Exemplary samples are those containing cells or cell lysates from a subject, such as those present in peripheral blood (or a fraction thereof such as serum), urine, saliva, tissue biopsy, cheek swabs, surgical specimen, fine needle aspirates, cervical samples, and autopsy material. In a specific example, a sample is obtained from a tumor (for example a section of tissue from a biopsy), which can include tumor cells that are both non-cancer cells and/or cancer stem cells and cancer cells and/or cancer stem cells. In some embodiments, the tumor sample is from a central nervous system (CNS) tumor.

Sequence identity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods.

Methods of alignment of sequences for comparison are well known in the art. Various programs and alignment algorithms are described in: Smith & Waterman, Adv. Appl. Math. 2:482, 1981; Needleman & Wunsch, J. Mol. Biol. 48:443, 1970; Pearson & Lipman, Proc. Natl. Acad. Sci. USA 85:2444, 1988; Higgins & Sharp, Gene, 73:237-44, 1988; Higgins & Sharp, CABIOS 5:151-3, 1989; Corpet et al., Nuc. Acids Res. 16:10881-90, 1988; Huang et al. Computer Appls. in the Biosciences 8, 155-65, 1992; and Pearson et al., Meth. Mol. Bio. 24:307-31, 1994. Altschul et al., J. Mol. Biol. 215:403-10, 1990, presents a detailed consideration of sequence alignment methods and homology calculations.

The NCBI Basic Local Alignment Search Tool (BLAST) (Altschul et al., J. Mol. Biol. 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN can be used to compare nucleic acid sequences, while BLASTP can be used to compare amino acid sequences. To compare two nucleic acid sequences, the options can be set as follows: -i is set to a file containing the first nucleic acid sequence to be compared (such as C:\seq1.txt); --j is set to a file containing the second nucleic acid sequence to be compared (such as C:\seq2.txt); --p is set to blastn; --o is set to any desired file name (such as C:\output.txt); --q is set to --1; --r is set to 2; and all other options are left at their default setting. For example, the following command can be used to generate an output file containing a comparison between two sequences: C:\B12seq --i c:\seq1.txt --j c:\seq2.txt --p blastn --o c:\output.txt --q --1 --r 2.

To compare two amino acid sequences, the options of B12seq can be set as follows: -i is set to a file containing the first amino acid sequence to be compared (such as C:\seq1.txt); --j is set to a file containing the second amino acid sequence to be compared (such as C:\seq2.txt); --p is set to blastp; --o is set to any desired file name (such as C:\output.txt); and all other options are left at their default setting. For example, the following command can be used to generate an output file containing a comparison between two amino acid sequences: C:\B12seq --i c:\seq1.txt --j c:\seq2.txt --p blastp --o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (1166/1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer.

For comparisons of amino acid sequences of greater than about 30 amino acids, the Blast 2 sequences function is employed using the default BLOSUM62 matrix set to default parameters, (gap existence cost of 11, and a per residue gap cost of 1). Homologs are typically characterized by possession of at least 70% sequence identity counted over the full-length alignment with an amino acid sequence using the NCBI Basic Blast 2.0, gapped blastp with databases such as the nr or swissprot database. Queries searched with the blastn program are filtered with DUST (Hancock and Armstrong, 1994, Comput. Appl. Biosci. 10:67-70). Other programs use SEG. In addition, a manual alignment can be performed. Proteins with even greater similarity will show increasing percentage identities when assessed by this method, such as at least about 75%, 80%, 85%, 90%, 95%, 98%, or 99% sequence identity to a cargo protein or targeting moiety provided herein.

When aligning short peptides (fewer than around 30 amino acids), the alignment is performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least about 60%, 70%, 75%, 80%, 85%, 90%, 95%, 98%, 99% sequence identity to a cargo moiety or targeting moiety provided herein. When less than the entire sequence is being compared for sequence identity, homologs will typically possess at least 75% sequence identity over short windows of 10-20 amino acids, and can possess sequence identities of at least 85%, 90%, 95% or 98% depending on their identity to the reference sequence. Methods for determining sequence identity over such short windows are described at the NCBI web site.

Subject: Living multi-cellular vertebrate organisms, a category that includes human and non-human mammals (such as laboratory or veterinary subjects).

IL-4 receptor targeted cargo protein: Any protein that binds specifically to a cancer stem cell and reduces or inhibits cancer stem cell growth, or kills cancer cells and/or cancer stem cells. In some examples, IL-4 receptor targeted cargo proteins can target both cancer cells and/or cancer stem cells and tumor (e.g., cancer) cells that are not cancer cells and/or cancer stem cells. IL-4 receptor targeted cargo proteins include a targeting moiety and a cargo moiety, the targeting moiety specifically binds with the cancer stem cell and the cargo moiety significantly reduces or inhibits the growth of the cancer stem cell or kills cancer stern cells. In some examples the cargo moiety causes the death of the cancer stem cell that it is associated with. In some examples the cargo moiety is not a protein, such as a chemotherapeutic agent, and in some examples the targeting moiety is not a protein. IL-4 receptor targeted cargo proteins include IL-4 and/or IL-13 muteins as described herein.

Targeting moiety: Any compound that binds to a molecule (herein referred to as a target) displayed by a cancer stem cell, for example a targeting moiety can be an antibody that binds to a target (e.g., receptor), a ligand (e.g., a cytokine or growth factor) that binds to a receptor, a permuted ligand that binds to a receptor, or a peptide sequence sensitive to cleavage by a tumor-associated protease. In some examples, a targeting moiety is activated by a tumor-associated protease, such as PSA. Typically, targeting moieties selectively bind to one type of cell displaying a target more effectively than they bind to other types of cells that do not display the target. Targeting moieties can be chosen to selectively bind to subsets of tumor cells, such as cancer cells and/or cancer stem cells. Targeting moieties include specific binding agents such as antibodies, natural ligands of the target on the stern cell, such as IL-4, derivatives of such natural ligands, and immunoglobulin A. In some examples, the targeting moiety is not biologically active (e.g., cannot activate a receptor), but retains the ability to bind to the target and thus direct the IL-4 receptor targeted cargo protein to the appropriate cells.

Table 2 provides information relating to the sequences of exemplary natural ligands as well as other antigens that can be used as targeting moieties. In some examples, circular permuted ligands, such as circular permuted IL-4, can be used to bind cancer cells and/or cancer stem cells. As additional research is performed, new cancer stem cell specific targets will be identified. These additional markers can be used as targets for binding to targeting moieties and IL-4 receptor targeted cargo proteins can be made to inhibit the growth of (or kill) cancer cells and/or cancer stem cells displaying such ligands. One of ordinary skill in the art will appreciate that once a marker is known, standard methods of making antibodies to the identified marker can be used to make targeting moieties specific for the cancer stem cell marker, thus, allowing for the development of a specific IL-4 receptor targeted cargo protein.

TABLE 2

Exemplary targeting moiety sequences

| Receptor or Antigen to be Targeted | Accession Numbers* |
|---|---|
| IL-4 | AAH70123; CAA57444.1; AAH67515.1 (also see SEQ ID NO: 2 and various circularly permuted ligands described in U.S. Pat. No. 6,011,002) |
| IL-13 | AAH96141.2; AAH96138.1; AAH96139.1 |

*GenBank Numbers are herein incorporated by reference, as well as their corresponding nucleic acid sequences.

Targets on cancer cells and/or cancer cells and/or cancer stem cells include small molecules displayed on the surface of cancer cells and/or cancer stem cells. Antibodies directed to such targets can be used as targeting moieties as well as the natural ligands of the targets and derivatives thereof.

Therapeutically effective amount: An amount of an agent that alone, or together with a pharmaceutically acceptable carrier or one or more additional therapeutic agents, induces the desired response. A therapeutic agent, such as a IL-4 receptor targeted cargo protein, is administered in therapeutically effective amounts that stimulate the desired response, for example reduction of symptoms of cancer in subjects known to have a cancer that includes cancer cells and/or cancer stem cells.

Effective amounts of a therapeutic agent can be determined in many different ways, such as assaying for improvement of a physiological condition of a subject having cancer. Effective amounts also can be determined through various in vitro, in vivo or in situ assays.

Therapeutic agents can be administered in a single dose, or in several doses, for example weekly, monthly, or bi-monthly, during a course of treatment. However, the effective amount of can be dependent on the source applied, the subject being treated, the severity and type of the condition being treated, and the manner of administration.

In one example, it is an amount sufficient to partially or completely alleviate symptoms of cancer in a subject. Treatment can involve only slowing the progression of the cancer temporarily, but can also include halting or reversing the progression of the cancer permanently. For example, a pharmaceutical preparation can decrease one or more symptoms of the cancer (such as the size of a tumor or the number of tumors or number of cancer cells and/or cancer stem cells), for example decrease a symptom by at least about 20%, at least about 50%, at least about 70%, at least about 90%, at least about 98%, or even at least about 100%, as compared to an amount in the absence of the therapeutic preparation.

Treating a disease: A therapeutic intervention that ameliorates a sign or symptom of a disease or pathological condition, such a sign or symptom of cancer. Treatment can also induce remission or cure of a condition, such as cancer and in particular a central nervous system (CNS) cancer or tumor. In particular examples, treatment includes preventing a disease, for example by inhibiting the full development of a disease, such as preventing development of tumor metastasis. Prevention of a disease does not require a total absence of a dysplasia or cancer. For example, a decrease of at least about 50% can be sufficient.

Tumor: Is a neoplasm or an abnormal mass of tissue that is not inflammatory, which arises from cells of preexistent tissue. A tumor can be either benign (noncancerous) or malignant (cancerous). Examples of tumors include, but are not limited to central nervous system (CNS) cancers or tumors. Examples of solid tumors, such as sarcomas and carcinomas, include, but are not limited to brain tumors, and CNS tumors (such as a glioma, glioblastoma, astrocytoma, medulloblastoma, craniopharyogioma, ependymoma, pinealoma, hemangioblastoma, acoustic neuroma, oligodendroglioma, menangioma, meningioma, neuroblastoma and retinoblastoma). Tumors can include recurrent and/or refractory tumors, including CNS tumors.

Refractory: A disease or condition which does not respond to attempted forms of treatment, for example a tumor that does not respond to the standard treatment methods.

Under conditions sufficient for: A phrase that is used to describe any environment that permits the desired activity. In one example, includes incubating a IL-4 receptor targeted cargo protein with tumor stern cell under conditions that allow the IL-4 receptor targeted cargo protein to specifically bind to a cancer stem cell in the sample. In another example, includes contacting one or more IL-4 receptor targeted cargo proteins with one or more cancer cells and/or cancer stem cells in a subject sufficient to allow the desired activity. In particular examples, the desired activity is decreasing growth or multiplication of such cancer cells and/or cancer stem cells or killing cancer cells and/or cancer stem cells.

Unit dose: A physically discrete unit containing a predetermined quantity of an active material (such as IL-4 receptor targeted cargo protein) calculated to individually or collectively produce a desired effect such as a therapeutic effect. A single unit dose or a plurality of unit doses can be used to provide the desired effect, such as a therapeutic effect.

II. IL-4 AND IL-13 Fusions

Described herein are IL-4 and/or IL-13 fusion proteins that target cancer cells and/or cancer stem cells and inhibit growth of and/or kill cancer cells and/or cancer stem cells. These molecules, herein after collectively referred to as IL-4 receptor targeted cargo proteins, include a targeting moiety that binds to a target (e.g., in some embodiments IL-4R) displayed by the cancer stem cell as well as a cargo moiety that provides the cell growth inhibiting (or cell killing) activity. The targeting moiety can be bound to the cargo moiety directly or through one or more of a variety of linkers that are further described herein. Cancer cells and/or cancer stem cells generally have the ability to self-renew and thus generate progeny with similar properties as themselves. In some examples, the disclosed IL-4 receptor targeted cargo proteins can target both cancer cells and/or cancer stem cells and tumor (e.g., cancer) cells that are not cancer cells and/or cancer stem cells. Therefore, in some examples IL-4 receptor targeted cargo proteins can kill or inhibit the growth of cancer cells and/or cancer stem cells and tumor (e.g., cancer) cells that are not cancer cells and/or cancer stem cells. In other examples, such as with a targeting moiety directed to CD 133, the IL-4 receptor targeted cargo proteins kill or inhibit the growth of cancer cells and/or cancer stem cells in the tumor, but not tumor cells that are not cancer cells and/or cancer stem cells.

Targeting moieties include proteins and other agents that function to specifically bind to a target on a cancer stem cell (but in some examples the target may also be present on other cancer cells). Targeting moieties include specific binding agents, such as antibodies, affibodies, or receptor ligands. In some examples, the targeting moiety is derived from the natural ligand to the target (e.g., cell surface receptor) displayed by the cancer stem cell. The targeting moiety that is derived from a natural ligand can include the complete amino acid sequence of the ligand (e.g. the same sequence that the ligand would have if it was isolated from nature), or the amino acid sequence of the targeting moiety can share at least about 95%, at least about 90%, at least about 80%, at least about 70%, at least about 60%, at least about 50%, or at least about 40% sequence identity with the natural ligand (e.g., at least about this amount of sequence identity to the GenBank Accession Nos. listed in Table 2), as long as the variant retains or has enhanced biological activity of the native ligand. In some examples, such variants have an increased binding affinity for their target relative to the native ligand. A targeting moiety that is derived from a natural ligand can also be a fragment of the native sequence that is capable of binding to the target displayed by the cancer stem cell. In some examples, the ligand is a circularly permuted version of a natural ligand (e.g., see U.S. Pat. No. 6,011,002).

Circularly permuted molecules include those in which the termini of a linear molecule (e.g., ligand) have been joined together, either directly or via a linker, to produce a circular molecule, and then the circular molecule is opened at another location to produce a new linear molecule with termini different from the termini in the original molecule. In some examples, the targeting moiety has one or more amino acid mutations (relative to the native sequence), which alters binding to the target, such as mutations that increase binding of a ligand to its target.

Cargo moieties can reduce, inhibit the growth of, and/or kill cancer cells and/or cancer stem cells, and in some examples also inhibit the growth of, and/or kill bulk cancer cells (e.g., non stem cancer cells). These molecules can be native proteins, or proteins that have been engineered, as well as other molecules that inhibit the growth of, and/or kill cancer cells and/or cancer stem cells, and in some examples also inhibit the growth of, and/or kill bulk cancer cells (e.g., non stem cancer cells). One example of such a molecule is a chemotherapeutic agent, such as thapsigargin. Cargo moieties can be linked to targeting moieties (a linked cargo moiety and targeting moiety is referred to herein as a IL-4 receptor targeted cargo protein) that bind to cancer cells and/or cancer stem cells. Thus, the cargo moiety linked to the targeting moiety will bind to the cancer stem cell and inhibit the growth of (or kill) the cancer stem cell. In some examples, the cargo moiety can cause cancer stem cell death and in some examples the cancer stem cell death is caused by apoptosis. In some examples cargo moieties are toxins (including plant or microorganism derived toxins), active fragments of toxins, or derivatives of toxins that share at least about 95%, at least about 90%, at least about 80%, at least about 70%, at least about 60%, at least about 50%, or at least about 40% sequence identity with the natural toxin and retains or has enhanced biological activity of the native toxin, for example with the cargo moieties provided in Table 1. In other examples the cargo moieties are derived from proteins that modulate cell life cycles or are part of natural immune responses in animals. For example, some cargo moieties are derived from proteins that are known to induce apoptosis. In some examples cargo moieties are derived from pro-apoptotic proteins, active fragments of such proteins, or derivatives of such proteins that share at least about 95%, at least about 90%, at least about 80%, at least about 70%, at least about 60%, at least about 50%, or at least about 40% sequence identity with the natural moiety (see Table 1 for sequence accession numbers), as long as the variant retains or has enhanced biological activity of the native moiety. In additional examples a cargo moiety can be inactive when administered as part of a IL-4 receptor targeted cargo protein, and then upon contacting another molecule in the subject become active. A more detailed description of cargo moieties is provided herein.

The description also includes methods of treating subjects having (or had) cancer with the IL-4 receptor targeted cargo protein. For example, the method can include administering one or more disclosed IL-4 receptor targeted cargo proteins to the subject, thereby treating cancer cells and/or cancer stem cells in the subject (e.g., reducing the number or volume of stem cells). For example, the IL-4 receptor targeted cargo proteins can be used to treat subjects with recurrent cancer or cancer that is refractory. In such examples the subject is treated with a traditional anti-cancer therapy, for example radiation, surgery, or chemotherapy and then tested to determine the effectiveness of the treatment. If the traditional therapy did not alter the cancer in a desired way, the subject can then be treated with a IL-4 receptor targeted cargo protein.

In some examples treatment regimes that include IL-4 receptor targeted cargo proteins and additional anticancer therapeutics can be administered to a subject. The IL-4 receptor targeted cargo protein and the additional anticancer therapeutic will vary depending upon the type of cancer stem cell being targeted.

In specific examples, a subject is administered one or more of the following specific IL-4 receptor targeted cargo proteins to treat cancer cells and/or cancer stem cells: circularly permuted IL-4-*Pseudomonas* exotoxin (see U.S. Pat. No. 6,011,002), IL-4-BAD, as well as PRX 321.

A. IL-4 and/or IL-13 Mutein Fusion Proteins

The IL-4 and/or IL-13 muteins can be prepared as fusion or chimeric polypeptides that include a subject IL-4 and/or IL-13 mutein and a heterologous polypeptide (i.e., a polypeptide that is not IL-4 and/or IL-13 or a mutant thereof) (see, e.g., U.S. Pat. No. 6,451,308). Exemplary heterologous polypeptides can increase the circulating half-life of the chimeric polypeptide in vivo, and may, therefore, further enhance the properties of the mutant IL-4 and/or IL-13 polypeptides. In various embodiments, the polypeptide that increases the circulating half-life may be a serum albumin, such as human serum albumin, PEG, PEG-derivatives, or the Fc region of the IgG subclass of antibodies that lacks the IgG heavy chain variable region. Exemplary Fc regions can include a mutation that inhibits complement fixation and Fc receptor binding, or it may be lytic, i.e., able to bind complement or to lyse cells via another mechanism, such as antibody-dependent complement lysis (ADCC; U.S. Ser. No. 08/355,502 filed Dec. 12, 1994).

The "Fc region" can be a naturally occurring or synthetic polypeptide that is homologous to the IgG C-terminal domain produced by digestion of IgG with papain. IgG Fc has a molecular weight of approximately 50 kDa. The mutant IL-4 and/or IL-13 polypeptides can include the entire Fc region, or a smaller portion that retains the ability to extend the circulating half-life of a chimeric polypeptide of which it is a part. In addition, full-length or fragmented Fc regions can be variants of the wild-type molecule. In some embodiments, the IL-4 and/or IL-13 mutein fusion protein (e.g., an IL-4 and/or IL-13 mutein as described herein) includes an IgG1, IgG2, IgG3, or IgG4 Fc region (see, for example, sequences in FIG. 2A-2B). In some embodiments, the Fc region comprises the substitution N297A.

In some embodiments, the IL-4 and/or IL-13 mutein is linked directly or indirectly to the heterologous fusion polypeptide.

In some embodiments, the IL-4 and/or IL-13 mutein is linked directly to the Fc region. In some embodiments, the IL-4 and/or IL-13 mutein is linked to the Fc region via a linker peptide, such as GGGGS. In some embodiments, the linker is (GGGGS)n, wherein n is an integer between 1 and 10. In some embodiments, the linker is GGGGS. In some embodiments, the linker is GGGGSGGGGS (SEQ ID NO: 70). In some embodiments, the linker is GGGGSGGGGSGGGGS (SEQ ID NO: 71). In some embodiments, the linker is GGGGSGGGGSGGGGSGGGGS (SEQ ID NO: 72). In some embodiments, the linker is GGGGSGGGGSGGGGSGGGGSGGGGS (SEQ ID NO: 73).

The Fc region can be "lytic" or "non-lytic," but is typically non-lytic. A non-lytic Fc region typically lacks a high affinity Fc receptor binding site and a C'1q binding site. The high affinity Fc receptor binding site of murine IgG Fc includes the Leu residue at position 235 of IgG Fc. Thus, the Fc receptor binding site can be destroyed by mutating or deleting Leu 235. For example, substitution of Glu for Leu 235 inhibits the ability of the Fc region to bind the high affinity Fc receptor. The murine C'1q binding site can be functionally destroyed by mutating or deleting the Glu 318, Lys 320, and Lys 322 residues of IgG. For example, substitution of Ala residues for Glu 318, Lys 320, and Lys 322 renders IgG1 Fc unable to direct antibody-dependent complement lysis. In contrast, a lytic IgG Fc region has a high affinity Fc receptor binding site and a C'1q binding site. The high affinity Fc receptor binding site includes the Leu residue at position 235 of IgG Fc, and the C'1q binding site includes the Glu 318, Lys 320, and Lys 322 residues of IgG1. Lytic IgG Fc has wild-type residues or conservative amino acid substitutions at these sites. Lytic IgG Fc can target cells for antibody dependent cellular cytotoxicity or complement directed cytolysis (CDC). Appropriate mutations for human IgG are also known (see, e.g., Morrison et al., The Immunologist 2:119-124, 1994; and Brekke et al., The Immunologist 2: 125, 1994).

In other embodiments, the chimeric polypeptide can include a subject IL-4 and/or IL-13 mutein and a polypeptide that functions as an antigenic tag, such as a FLAG sequence. FLAG sequences are recognized by biotinylated, highly specific, anti-FLAG antibodies, as described herein (see also Blanar et al., Science 256:1014, 1992; LeClair et al., Proc. Natl. Acad. Sci. USA 89:8145, 1992). In some embodiments, the chimeric polypeptide further comprises a C-terminal c-myc epitope tag.

In other embodiments, the chimeric polypeptide includes the mutant IL-4 and/or IL-13 polypeptide and a heterologous polypeptide that functions to enhance expression or direct cellular localization of the mutant IL-4 and/or IL-13 polypeptide, such as the Aga2p agglutinin subunit (see, e.g., Boder and Wittrup, Nature Biotechnol. 15:553-7, 1997).

In other embodiments, a chimeric polypeptide including a mutant IL-4 and/or IL-13 and an antibody or antigen-binding portion thereof can be generated. The antibody or antigen-binding component of the chimeric protein can serve as a targeting moiety. For example, it can be used to localize the chimeric protein to a particular subset of cells or target molecule. Methods of generating cytokine-antibody chimeric polypeptides are described, for example, in U.S. Pat. No. 6,617,135.

In some embodiments, the chimeric polypeptide comprises a fusion to an antibody or an antigen-binding portion thereof that disrupts the interaction between the PD-1 receptor and its ligand, PD-L1, and or is an antibody to a component of the PD-1/PD-L1 signaling pathway. Antibodies known in the art which bind to PD-1 and disrupt the interaction between the PD-1 and its ligand, PD-L1, and stimulate an anti-tumor immune response, are suitable for use in the chimeric polypeptides disclosed herein. In some embodiments, the antibody or antigen-binding portion thereof binds specifically to PD-1. For example, antibodies that target PD-1 and which can find used in the present invention include, e.g., but are not limited to nivolumab (BMS-936558, Bristol-Myers Squibb), pembrolizumab (lambrolizumab, MK03475 or MK-3475, Merck), humanized anti-PD-1 antibody JS001 (ShangHai JunShi), monoclonal anti-PD-1 antibody TSR-042 (Tesaro, Inc.), Pidilizumab (anti-PD-1 mAb CT-011, Medivation), anti-PD-1 monoclonal Antibody BGB-A317 (BeiGene), and/or anti-PD-1 antibody SHR-1210 (ShangHai HengRui), human monoclonal antibody REGN2810 (cemiplimab, Regeneron), human monoclonal antibody MDX-1106 (Bristol-Myers Squibb), and/or humanized anti-PD-1 IgG4 antibody PDR001 (Novartis). In some embodiments, the PD-1 antibody is from clone: RMP1-14 (rat IgG)-BioXcell cat #BP0146. Other suitable antibodies include anti-PD-1 antibodies disclosed in U.S. Pat. No. 8,008,449, herein incorporated by reference. In some embodiments, the antibody or antigen-binding portion thereof binds specifically to PD-L1 and inhibits its interaction with PD-1, thereby increasing immune activity. Any antibodies known in the art which bind to PD-L1 and disrupt the interaction between the PD-1 and PD-L1, and stimulates an anti-tumor immune response, are suitable for use in the chimeric polypeptides disclosed herein. For example, antibodies that target PD-L1 and are in clinical trials, include BMS-936559 (Bristol-Myers Squibb) and MPDL3280A (Genetech). Other suitable antibodies that target PD-L1 are disclosed in U.S. Pat. No. 7,943,743, herein incorporated by reference. It will be understood by one of ordinary skill that any antibody which binds to PD-1 or PD-L1, disrupts the PD-1/PD-L1 interaction, and stimulates an anti-tumor immune response, is suitable for use in the chimeric polypeptides disclosed herein. In some embodiments, the chimeric polypeptide comprises a fusion to an anti-PD-1 antibody. In some embodiments, the chimeric polypeptide comprises a fusion to an anti-PD-L1 antibody.

In some embodiments, the chimeric polypeptide comprises a fusion to an antibody or an antigen-binding portion thereof that targets CTLA-4 and disrupts its interaction with CD80 and CD86. Exemplary antibodies that target CTLA-4 include ipilimumab (MDX-010, MDX-101, Bristol-Myers Squibb), which is FDA approved, and tremelimumab (ticilimumab, CP-675, 206, Pfizer), currently undergoing human trials. Other suitable antibodies that target CTLA-4 are disclosed in WO 2012/120125, U.S. Pat. Nos. 6,984,720, 6,682,7368, and U.S. Patent Applications 2002/0039581, 2002/0086014, and 2005/0201994, herein incorporated by reference. It will be understood by one of ordinary skill that any antibody which binds to CTLA-4, disrupts its interaction with CD80 and CD86, and stimulates an anti-tumor immune response, is suitable for use in the chimeric polypeptides disclosed herein. In some embodiments, the chimeric polypeptide comprises a fusion to an anti-CTLA-4 antibody.

In some embodiments, the chimeric polypeptide comprises a fusion to an antibody or an antigen-binding portion thereof that targets LAG-3 and disrupts its interaction with MHC class II molecules. An exemplary antibody that targets LAG-3 is IMP321 (Immutep), currently undergoing human trials. Other suitable antibodies that target LAG-3 are disclosed in U.S. Patent Application 2011/0150892, herein incorporated by reference. It will be understood by one of ordinary skill that any antibody which binds to LAG-3, disrupts its interaction with MHC class II molecules, and stimulates an anti-tumor immune response, is suitable for use in the chimeric polypeptides disclosed herein. In some embodiments, the chimeric polypeptide comprises a fusion to an anti-LAG-3 antibody.

In some embodiments, the chimeric polypeptide comprises a fusion to an antibody or an antigen-binding portion thereof that targets B7-H3 or B7-H4. The B7 family does not have any defined receptors but these ligands are upregulated on tumor cells or tumor-infiltrating cells. An exemplary antibody that targets B7-H3 is MGA271 (Macrogenics) is currently undergoing human trials. Other suitable antibodies that target B7 family members are disclosed in U.S. Patent Application 2013/0149236, herein incorporated by reference. It will be understood by one of ordinary skill that any antibody which binds to B7-H3 or H4, and stimulates an anti-tumor immune response, is suitable for use in the chimeric polypeptides disclosed herein. In some embodiments, the chimeric polypeptide comprises a fusion to an anti-B7-H3 or B7-H4 antibody.

In some embodiments, the chimeric polypeptide comprises a fusion to an antibody or an antigen-binding portion thereof that targets TIM-3 and disrupts its interaction with galectin 9. Suitable antibodies that target TIM-3 are disclosed in U.S. Patent Application 2013/0022623, herein incorporated by reference. It will be understood by one of ordinary skill that any antibody which binds to TIM-3, disrupts its interaction with galectin 9, and stimulates an anti-tumor immune response, is suitable for use in the chimeric polypeptides disclosed herein. In some embodiments, the chimeric polypeptide comprises a fusion to an anti-TIM-3 antibody.

In some embodiments, the chimeric polypeptide comprises a fusion to an antibody or an antigen-binding portion thereof that targets 4-1BB/CD137 and disrupts its interaction with CD137L. It will be understood by one of ordinary skill that any antibody which binds to 4-1BB/CD137, disrupts its interaction with CD137L or another ligand, and stimulates an anti-tumor immune response or an immune stimulatory response that results in anti-tumor activity overall, is suitable for use in the chimeric polypeptides disclosed herein. In some embodiments, the chimeric polypeptide comprises a fusion to an anti-4-1BB/CD137 antibody.

In some embodiments, the chimeric polypeptide comprises a fusion to an antibody or an antigen-binding portion thereof that targets GITR and disrupts its interaction with its ligand. It will be understood by one of ordinary skill that any antibody which binds to GITR, disrupts its interaction with GITRL or another ligand, and stimulates an anti-tumor immune response or an immune stimulatory response that results in anti-tumor activity overall, is suitable for use in the chimeric polypeptides disclosed herein. In some embodiments, the chimeric polypeptide comprises a fusion to an anti-GITR antibody.

In some embodiments, the chimeric polypeptide comprises a fusion to an antibody or an antigen-binding portion thereof that targets OX40 and disrupts its interaction with its ligand. It will be understood by one of ordinary skill that any antibody which binds to OX40, disrupts its interaction with OX40L or another ligand, and stimulates an anti-tumor immune response or an immune stimulatory response that results in anti-tumor activity overall, is suitable for use in the chimeric polypeptides disclosed herein. In some embodiments, the chimeric polypeptide comprises a fusion to an anti-OX40 antibody.

In some embodiments, the chimeric polypeptide comprises a fusion to an antibody or an antigen-binding portion thereof that targets CD40 and disrupts its interaction with its ligand. It will be understood by one of ordinary skill that any antibody which binds to CD40, disrupts its interaction with its ligand, and stimulates an anti-tumor immune response or an immune stimulatory response that results in anti-tumor activity overall, is suitable for use in the chimeric polypeptides disclosed herein. In some embodiments, the chimeric polypeptide comprises a fusion to an anti-CD40 antibody.

In some embodiments, the chimeric polypeptide comprises a fusion to an antibody or an antigen-binding portion thereof that targets ICOS and disrupts its interaction with its ligand. It will be understood by one of ordinary skill that any antibody which binds to ICOS, disrupts its interaction with its ligand, and stimulates an anti-tumor immune response or an immune stimulatory response that results in anti-tumor activity overall, is suitable for use in the chimeric polypeptides disclosed herein. In some embodiments, the chimeric polypeptide comprises a fusion to an anti-ICOS antibody.

In some embodiments, the chimeric polypeptide comprises a fusion to an antibody or an antigen-binding portion thereof that targets CD28 and disrupts its interaction with its ligand. It will be understood by one of ordinary skill that any antibody which binds to CD28, disrupts its interaction with its ligand, and stimulates an anti-tumor immune response or an immune stimulatory response that results in anti-tumor activity overall, is suitable for use in the chimeric polypeptides disclosed herein. In some embodiments, the chimeric polypeptide comprises a fusion to an anti-CD28 antibody.

In some embodiments, the chimeric polypeptide comprises a fusion to an antibody or an antigen-binding portion thereof that targets IFNα and disrupts its interaction with its ligand. It will be understood by one of ordinary skill that any antibody which binds to IFNα, disrupts its interaction with its ligand, and stimulates an anti-tumor immune response or an immune stimulatory response that results in anti-tumor activity overall, is suitable for use in the chimeric polypeptides disclosed herein. In some embodiments, the chimeric polypeptide comprises a fusion to an anti-IFNα antibody.

In some embodiments, the chimeric polypeptide comprises a fusion to a tumor antigen or polypeptide targeting a tumor antigen. Generally, tumor antigens allow for distinguishing the tumor cells from their normal cellular counterparts and can include, for example, tumor-specific antigens (TSA) as well as tumor-associated antigens (TAA). In some embodiments, a tumor antigen is a protooncogene and/or a tumor suppressor, as well as overexpressed or aberrantly expressed cellular proteins, tumor antigens produced by oncogenic viruses, oncofetal antigens, altered cell surface glycolipids and glycoproteins, and/or cell type-specific differentiation antigens. Such tumor antigens can include melanoma antigens, cancer-testis antigens, epithelial tumor antigens, cell cycle regulatory proteins, prostate specific antigens (including prostate carcinoma antigens, such as for example those disclosed in U.S. Pat. No. 5,538,866) lymphoma (U.S. Pat. Nos. 4,816,249; 5,068,177; and 5,227,159). Tumor antigens can include for example, but are not limited to, HIMW mucins bound by 2G3 and 369F10, c-erbB-2 related tumor antigen (an approximately 42 kD or 55 kD glycoprotein), the approximately 40, 60, 100 and 200 kD antigens bound by 113F1, 9-O-acetyl GD3, p97, alphafetoprotein (AFP) (for example, for germ cell tumors and/or hepatocellular carcinoma), carcinoembryonic antigen (CEA) (for example, for bowel cancers occasional lung or breast cancer), CA-125 (for example, for ovarian cancer), MUC-1 (for example, for breast cancer), epithelial tumor antigen (ETA) (for example, for breast cancer), tyrosinase (for example, for malignant melanoma), melanoma-associated antigen (MAGE) (for example, for malignant melanoma), cancer/testis antigen 1 (CTAG1B), melanoma-associated antigen 1 (MAGEA1), abnormal Ras products, abnormal p53 products, overexpression of cyclins (including, for example, cyclin B1), mutation in fibronectin, post-translational alteration in the MUC1 glycoprotein, secreted tumor antigens (including, for example, gangliosides).

B. IL-4 Receptor Targeted Cargo Proteins

IL-4 receptor targeted cargo proteins are proteins that include a targeting moiety linked to a cargo moiety. IL-4 receptor targeted cargo proteins function to specifically bind to cancer cells and/or cancer stem cells and reduce or inhibit cancer stem cell growth, as well as targeting the immunosuppressive cells in the tumor microenvironment (TME). In some embodiments, IL-4 receptor targeted cargo proteins comprise an IL-4R targeting moiety. In some embodiments, IL-4 receptor targeted cargo proteins comprise an IL-4R targeting moiety comprising IL-4 or a variant thereof as described herein. In some embodiments, IL-4 receptor targeted cargo proteins comprise an IL-4R targeting moiety comprising IL-13 or a variant thereof as described herein.

The IL-4R targeting moiety can comprise an IL-4 sequence or variant thereof. Exemplary polypeptide sequences are provided in SEQ ID NO:51-SEQ ID NO:55, SEQ ID NO:58-SEQ ID NO:62, and SEQ ID NO:64-SEQ ID NO:69. In some embodiments, the polypeptide sequence is as provided in any one of SEQ ID NO through 51-SEQ ID NO:55, SEQ ID NO:58 through SEQ ID NO:62, and/or SEQ ID NO:64 through SEQ ID NO:69. In some embodiments, the polypeptide sequence is SEQ ID NO:51. In some embodiments, the polypeptide sequence is SEQ ID NO:52. In some embodiments, the polypeptide sequence is SEQ ID NO:53. In some embodiments, the polypeptide sequence is SEQ ID NO:54. In some embodiments, the polypeptide sequence is SEQ ID NO:55. In some embodiments, the polypeptide sequence is SEQ ID NO:58. In some embodiments, the polypeptide sequence is SEQ ID NO:59. In some embodiments, the polypeptide sequence is SEQ ID NO:60. In some embodiments, the polypeptide sequence is SEQ ID NO:61. In some embodiments, the polypeptide sequence is SEQ ID NO:62. In some embodiments, the polypeptide sequence is SEQ ID NO:64. In some embodiments, the polypeptide sequence is SEQ ID NO:65. In some embodiments, the polypeptide sequence is SEQ ID NO:66. In some embodiments, the polypeptide sequence is SEQ ID NO:67. In some embodiments, the polypeptide sequence is SEQ ID NO:68. In some embodiments, the polypeptide sequence is SEQ ID NO:69. In some embodiments, the polypeptide sequence is 98% identical to any one of SEQ ID NO through 51-SEQ ID NO:55, SEQ ID NO:58 through SEQ ID NO:62, and/or SEQ ID NO:64 through SEQ ID NO:69. In some embodiments, the polypeptide sequence is 99% identical to any one of SEQ ID NO through 51-SEQ ID NO:55, SEQ ID NO:58 through SEQ ID NO:62, and/or SEQ ID NO:64 through SEQ ID NO:66. In some embodiments, any one of SEQ ID NO through 51-SEQ ID NO:55, SEQ ID NO:58 through SEQ ID NO:62, and/or SEQ ID NO:64 through SEQ ID NO:69 are part of the IL-4R targeting moiety. In some embodiments, SEQ ID NO:51 is part of the IL-4R targeting moiety. In some embodiments, SEQ ID NO:52 is part of the IL-4R targeting moiety. In some embodiments, SEQ ID NO:53 is part of the IL-4R targeting moiety. In some embodiments, SEQ ID NO:54 is part of the IL-4R targeting moiety. In some embodiments, SEQ ID NO:55 is part of the IL-4R targeting moiety. In some embodiments, SEQ ID NO:58 is part of the IL-4R targeting moiety. In some embodiments, SEQ ID NO:59 is part of the IL-4R targeting moiety. In some embodiments, SEQ ID NO:60 is part of the IL-4R targeting moiety. In some embodiments, SEQ ID NO:61 is part of the IL-4R targeting moiety. In some embodiments, SEQ ID NO:62 is part of the IL-4R targeting moiety. In some embodiments, SEQ ID NO:64 is part of the IL-4R targeting moiety. In some embodiments, SEQ ID NO:65 is part of the IL-4R targeting moiety. In some embodiments, SEQ ID NO:66 is part of the IL-4R targeting moiety. In some embodiments, SEQ ID NO:67 is part of the IL-4R targeting moiety. In some embodiments, SEQ ID NO:68 is part of the IL-4R targeting moiety. In some embodiments, SEQ ID NO:69 is part of the IL-4R targeting moiety.

The IL-13 superkine component of the construct may be at least about 50 amino acids in length, at least about 75, at least about 100, at least about 110, at least about 115 amino acids in length, up to the full-length of the wild-type protein at the transmembrane domain, i.e. about 116 amino acids in length. For example, the superkine may be fused to the hinge, transmembrane or signaling domains of a CAR. Exemplary polypeptide sequences are provided in SEQ ID NO:2-SEQ ID NO:48, SEQ ID NO:56, SEQ ID NO:57, and SEQ ID NO:63. In some embodiments, the polypeptide sequence is as provided in any one of SEQ ID NO:2 through SEQ ID NO:38. In some embodiments, the polypeptide sequence is SEQ ID NO:2. In some embodiments, the polypeptide sequence is SEQ ID NO:3. In some embodiments, the polypeptide sequence is SEQ ID NO:4. In some embodiments, the polypeptide sequence is SEQ ID NO:5. In some embodiments, the polypeptide sequence is SEQ ID NO:6. In some embodiments, the polypeptide sequence is SEQ ID NO:7. In some embodiments, the polypeptide sequence is SEQ ID NO:8. In some embodiments, the polypeptide sequence is SEQ ID NO:9. In some embodiments, the polypeptide sequence is SEQ ID NO:10. In some embodiments, the polypeptide sequence is SEQ ID NO:11. In some embodiments, the polypeptide sequence is SEQ ID NO:12. In some embodiments, the polypeptide sequence is SEQ ID NO:13. In some embodiments, the polypeptide sequence is SEQ ID NO:14. In some embodiments, the polypeptide sequence is SEQ ID NO:15. In some embodiments, the polypeptide sequence is SEQ ID NO:16. In some embodiments, the polypeptide sequence is SEQ ID NO:17. In some embodiments, the polypeptide sequence is SEQ ID NO:18. In some embodiments, the polypeptide sequence is SEQ ID NO:19. In some embodiments, the polypeptide sequence is SEQ ID NO:20. In some embodiments, the polypeptide sequence is SEQ ID NO:21. In some embodiments, the polypeptide sequence is SEQ ID NO:22. In some embodiments, the polypeptide sequence is SEQ ID NO:23. In some embodiments, the polypeptide sequence is SEQ ID NO:24. In some embodiments, the polypeptide sequence is SEQ ID NO:25. In some embodiments, the polypeptide sequence is SEQ ID NO:26. In some embodiments, the polypeptide sequence is SEQ ID NO:27. In some embodiments, the polypeptide sequence is SEQ ID NO:28. In some embodiments, the polypeptide sequence is SEQ ID NO:29. In some embodiments, the polypeptide sequence is SEQ ID NO:30. In some embodiments, the polypeptide sequence is SEQ ID NO:31. In some embodiments, the polypeptide sequence is SEQ ID NO:32. In some embodiments, the polypeptide sequence is SEQ ID NO:33. In some embodiments, the polypeptide sequence is SEQ ID NO:34. In some embodiments, the polypeptide sequence is SEQ ID NO:35. In some embodiments, the polypeptide sequence is SEQ ID NO:36. In some embodiments, the polypeptide sequence is SEQ ID NO:37. In some embodiments, the polypeptide sequence is SEQ ID NO:38. In some embodiments, the polypeptide sequence is 90% identical to any one of SEQ ID NO:2 through SEQ ID NO:38. In some embodiments, the polypeptide sequence is 95% identical to any one of SEQ ID NO:2 through SEQ ID NO:38. In some embodiments, the polypeptide sequence is 98% identical to any one of SEQ ID NO:2 through SEQ ID NO:38. In some embodiments, the polypeptide sequence is 99% identical to any one of SEQ ID NO:2 through SEQ ID NO:38. In some embodiments, any one of SEQ ID NO:2 through SEQ ID NO:38 is part of the IL-4R targeting moiety. In some embodiments, SEQ ID NO:2 is part of the IL-4R targeting moiety. In some embodiments, SEQ ID NO:3 is part of the IL-4R targeting moiety. In some embodiments, SEQ ID NO:4 is part of the IL-4R targeting moiety. In some embodiments, SEQ ID NO:5 is part of the IL-4R targeting moiety. In some embodiments, SEQ ID NO:6 is part of the IL-4R targeting moiety. In some embodiments, SEQ ID NO:7 is part of the IL-4R targeting moiety. In some embodiments, SEQ ID NO:8 is part of the IL-4R targeting moiety. In some embodiments, SEQ ID NO:9 is part of the IL-4R targeting moiety. In some embodiments, SEQ ID NO:10 is part of the IL-4R targeting moiety. In some embodiments, SEQ ID NO:11 is part of the IL-4R targeting moiety. In some embodiments, SEQ ID NO:12 is part of the IL-4R targeting moiety. In some embodiments, SEQ ID NO:13 is part of the IL-4R targeting moiety. In some embodiments, SEQ ID NO:14 is part of the IL-4R targeting moiety. In some embodiments, SEQ ID NO:15 is part of the IL-4R targeting moiety. In some embodiments, SEQ ID NO:16 is part of the IL-4R targeting moiety. In some embodiments, SEQ ID NO:17 is part of the IL-4R targeting moiety. In some embodiments, SEQ ID NO:18 is part of the IL-4R targeting moiety. In some embodiments, SEQ ID NO:19 is part of the IL-4R targeting moiety. In some embodiments, SEQ ID NO:20 is part of the IL-4R targeting moiety. In some embodiments, SEQ ID NO:21 is part of the IL-4R targeting moiety. In some embodiments, SEQ ID NO:22 is part of the IL-4R targeting moiety. In some embodiments, SEQ ID NO:23 is part of the IL-4R targeting moiety. In some embodiments, SEQ ID NO:24 is part of the IL-4R targeting moiety. In some embodiments, SEQ ID NO:25 is part of the IL-4R targeting moiety. In some embodiments, SEQ ID NO:26 is part of the IL-4R targeting moiety. In some embodiments, SEQ ID NO:27 is part of the IL-4R targeting moiety. In some embodiments, SEQ ID NO:28 is part of the IL-4R targeting moiety. In some embodiments, SEQ ID NO:29 is part of the IL-4R targeting moiety. In some embodiments, SEQ ID NO:30 is part of the IL-4R targeting moiety. In some embodiments, SEQ ID NO:31 is part of the IL-4R targeting moiety. In some embodiments, SEQ ID NO:32 is part of the IL-4R targeting moiety. In some embodiments, SEQ ID NO:33 is part of the IL-4R targeting moiety. In some embodiments, SEQ ID NO:34 is part of the IL-4R targeting moiety. In some embodiments, SEQ ID NO:35 is part of the IL-4R targeting moiety. In some embodiments, SEQ ID NO:36 is part of the IL-4R targeting moiety. In some embodiments, SEQ ID NO:37 is part of the IL-4R targeting moiety. In some embodiments, SEQ ID NO:38 is part of the TL-4R targeting moiety. In some embodiments, SEQ ID NO: 40 is part of the IL-4R targeting moiety. In some embodiments, SEQ ID NO: 43 is part of the IL-4R targeting moiety. In some embodiments, SEQ ID NO:43 is part of the IL-4R targeting moiety. In some embodiments, SEQ ID NO:44 is part of the TL-4R targeting moiety. In some embodiments, SEQ ID NO:45 is part of the IL-4R targeting moiety. In some embodiments, SEQ ID NO:46 is part of the IL-4R targeting moiety. In some embodiments, SEQ ID NO:47 is part of the IL-4R targeting moiety. In some embodiments, SEQ ID NO:48 is part of the IL-4R targeting moiety.

Table of IL-13 sequences is provided below.

TABLE 3

List of IL-13 Amino Acid Sequences

| SEQ ID NO: (Information) | Amino acid sequence |
|---|---|
| SEQ ID NO: 1 (IL-13 wildtype) | PGPVPPSTALRELIEELVNITQNQKAPLCN GSMVWSINLTAGMYCAALESLINVSGCSA IEKTQRMLSGFCPHKVSAGQFSSLHVRDT KIEVAQFVKDLLLHLKKLFREGQFN |
| SEQ ID NO: 2 | PGPVPPSTAVRALIEELINITQNQKAPLCNG SMVWSINRTAGMYCAALESLINVSGCSAI EKTQDMLSGFCPHKVSAGQFSSLHVRSSKI EVAQFVKDLLFHLRTLFREGQFN |
| SEQ ID NO: 3 | PGPVPPSTAIRELIEELINITQNQKAPLQNGS MVWSINLTAGMYCAALESLINVSGCSAIE KTQRMLSGFCPHKVSAGQFSSLHVRGSKI EVAQFVKDLLHHLRALFREGQFN |
| SEQ ID NO: 4 | PGPVPPSTAVRELIEELINITQNQKAPLCNG SMVWSINRTAGMYCAALESLINVSGCSAI EKTQRMLSGFCPHKVSAGQFSSLHVRSSKI EVAQFVKDLLFHLRTLFREGQFN |
| SEQ ID NO: 5 | PGPVPPSTALIELIEELINITQNQKAPLQNGS MVWSINLTAGIYCAALESLINVSGCSAIEK TQRMLSGFCPHKVSAGQFSSLHVKGSKIE VAQFVKDLLHHLRALMREGQFN |
| SEQ ID NO: 6 | PGPVPPSTAIRELIEELLNITQNQKAPLCNG SMVWSINLTAGMYCAALESLINVSGCSAI EKTQRMLSGFCPHKVSAGQFSSLHVMKSK IEVAQFVKDLLHHLRALFREGQFN |
| SEQ ID NO: 7 | PGPVPPSTAIRELIEELINITQNQKAPLQNGS MVWSINLTAGMYCAALESLINVSGCSAIE KTQRMLSGFCPHKVSAGQFSSLHVRSSRIE VAQFVKDLLHHLRTLFREGQFN |
| SEQ ID NO: 8 | PGPVPPSTALRELIEELINITQNEKAPLCNG SMVWSINLTAGIYCAALESLINVSGCSAIE KTQRMLSGFCPHKVSAGQFSSLHVTGSKI EVAQFVKDLLYHLRALFREGQFN |
| SEQ ID NO: 9 | PGPVPPSTALSELIEELINITQNQKAPLCNG SMVWSINPTAGMYCAALESLINVSGCSAIE KTQRMLSGFCPHKVAAGQFSSLHDKGSMI EVAQFVKDLLYHLRTLFREGQFN |
| SEQ ID NO: 10 | PGPVPPSTATRELIEELINITQNQKAPLCNG SMVWSINLTADMYCAALESLINVSGCSAI EKTQRMLSGFCPHKVSVGQFSSLHVRGSK IEVAQFVKDLLYHLRTLFREGQFN |

TABLE 3-continued

List of IL-13 Amino Acid Sequences

| SEQ ID NO:<br>(Information) | Amino acid sequence |
|---|---|
| SEQ ID NO: 11 | PGPVPPSTADIELIAELINITQNQKAPLONG<br>SMVWSINLTADMYCAALESLINVSGCSAI<br>EKTQRMLSGFCPHKVSAGQFSSLHVKKTR<br>IEVAQFVKDLLLHLKKLFKEGQFN |
| SEQ ID NO: 12 | PGPVPPSTAARELIEELVNITQNQKAPLCN<br>GSMVWSINLTAGMYCAALESLINVSGCSA<br>IEKTQRMLSGFCPHKVSAGQLSSLHVTGK<br>RIEVAQFVKDLLNHLRALFKEGQFN |
| SEQ ID NO: 13 | PGPVPPSTAVRELIEELVNITQNQKAPLCN<br>GSMVWSINLTAGMYCAALESLINVSGCSA<br>IEKTQRMLSGFCPHKVSAGQFSSLHVRDT<br>RIEVAQFVKDLLNHLKELFTEGQFN |
| SEQ ID NO: 14 | PGPVPPSTALSELMEELVNITQNQKAPLCN<br>GSMVWSINLTAGMYCAALESLINVSGCSA<br>IEKTQRMLSGFCPHKVSAGQFSSLHVRDS<br>KIEVAQFVKDLLNHLKALFKEGQFN |
| SEQ ID NO: 15 | GPVPPSTAFRELIEELVNITQNQKAPLCNG<br>SMVWSINLTAGMYCAALESLINVSGCSAI<br>EKTQRMLSGFCPHKVSPGQFSSLHVTNSRI<br>EVAQFVKDLLNHLKALFKEGQYN |
| SEQ ID NO: 16 | GPVPPSTAHLELIEELINITQNQKAPLCNGS<br>MVWSINLTAGMYCAALESLINVSGCSAIE<br>KTQRMLSGFCPHKVSAGQFSSLHVKETRI<br>EVAQFVKDLLNHLKTLFKEGQFN |
| SEQ ID NO: 17 | PGPVPPSTAHLELIEELINITQNQKAPLCNG<br>SMVWSINPTAGMYCAALESLINVSGCSAIE<br>KTQRMLSGFCPHKVSAGQFSSLHVMDTRI<br>EVAQFVKDLLLHLKKLFKEGQFN |
| SEQ ID NO: 18 | PGPVPPSTAHRELIEELVNITQNQKAPLCN<br>GSMVWSINLTAGMYCAALESLINVSGCSA<br>IEKTQRMLSGFCPHKVSAGQFSSLHVTGR<br>KIEVAQFVKDLLLHLKKLFKEGQFN |
| SEQ ID NO: 19 | PGPVPPSTAHRELIEELVNITQNQKAPLCN<br>GSMVWRINRTAGMYCAALESLINVSGCSA<br>IEKTQRMLSGFCPHKVSAGQFSSLHVMDS<br>RIEVAQFVKDLLNHLRALFKEGQFN |
| SEQ ID NO: 20 | PGPVPPSTAARELIEELFNITQNQKAPLCN<br>GSMVWSINLTAGMYCAALESLINVSGCSA<br>IEKTKRMLSGFCPHKVSAGQFPSLHVKKT<br>RIEVAQFVKDLLIHLRKLFKEGQFN |
| SEQ ID NO: 21<br>(Exemplary sequence comprising<br>R11I, V18I, R86K, D87G, T88S,<br>L101H, K104R, K105A, F107M,<br>referred to herein as A5) | PGPVPPSTALIELIEELINITQNQKAPLONGS<br>MVWSINLTAGMYCAALESLINVSGCSAIEK<br>TQRMLSGFCPHKVSAGQFSSLHVKGSKIEV<br>AQFVKDLLHHLRALMREGQFN |
| SEQ ID NO: 22<br>(Exemplary sequence comprising<br>L10I, V18L, R86M, D87K,<br>T88S, L101H, K104R, K105A,<br>referred to herein as A6) | PGPVPPSTAIRELIEELLNITQNQKAPLONGS<br>MVWSINLTAGMYCAALESLINVSGCSAIEK<br>TQRMLSGFCPHKVSAGQFSSLHVMKSKIEV<br>AQFVKDLLHHLRALFREGQFN |
| SEQ ID NO: 23<br>(Exemplary sequence comprising<br>L10I, V18I, D87G, T88S,<br>L101H, K104R, K105A, referred<br>to herein as A7) | PGPVPPSTAIRELIEELINITQNQKAPLONGS<br>MVWSINLTAGMYCAALESLINVSGCSAIEK<br>TQRMLSGFCPHKVSAGQFSSLHVRGSKIEV<br>AQFVKDLLHHLRALFREGQFN |
| SEQ ID NO: 24<br>(Exemplary sequence comprising<br>L10I, V18I, D87S, T88S, K89R,<br>L101H, K104R, K105T; referred<br>to herein as A8) | PGPVPPSTAIRELIEELINITQNQKAPLONGS<br>MVWSINLTAGMYCAALESLINVSGCSAIEK<br>TQRMLSGFCPHKVSAGQFSSLHVRSSRIEVA<br>QFVKDLLHHLRTLFREGQFN |

TABLE 3-continued

List of IL-13 Amino Acid Sequences

| SEQ ID NO: (Information) | Amino acid sequence |
|---|---|
| SEQ ID NO: 25 (Exemplary sequence comprising L10V, V18I, D87S, T88S, L101F, K104R, K105T, referred to herein as A11 variant 1) | PGPVPPSTAVRELIEELINITQNQKAPLQNGS MVWSINLTAGMYCAALESLINVSGCSAIEK TQRMLSGFCPHKVSAGQFSSLHVRSSKIEVA QFVKDLLFHLRTLFREGQFN |
| SEQ ID NO: 25 (Exemplary sequence comprising L10V, V18I, D87S, T88S, L101F, K104R, K105T, referred to herein as A11 variant 2) | PGPVPPSTAVRELIEELINITQNQKAPLCNGS MVWSIN*R*TAGMYCAALESLINVSGCSAIEK TQRMLSḠFCPHKVSAGQFSSLHVRSSKIEVA QFVKDLLFHLRTLFREGQFN |
| SEQ ID NO: 26 (Exemplary sequence comprising V18I, R86T, D87G, T88S, L101Y, K104R, K105A, referred to herein as B2) | PGPVPPSTALRELIEELINITQNQKAPLCNG SMVWSINLTAGMYCAALESLINVSGCSAI EKTQRMLSGFCPHKVSAGQFSSLHVTGSK IEVAQFVKDLLYHLRALFREGQFN |
| SEQ ID NO: 27 (Exemplary sequence comprising R11S, V18I, R86K, D87G, T88S, K89M, L101Y, K104R, K105T, referred to herein as B4) | PGPVPPSTALSELIEELINITQNQKAPLCNG SMVWSINLTAGMYCAALESLINVSGCSAI EKTQRMLSGFCPHKVSAGQFSSLHVKGSM IEVAQFVKDLLYHLRTLFREGQFN |
| SEQ ID NO: 28 (Exemplary sequence comprising L10T, V18I, D87G, T88S, K89K, L10Y1, K104R, K105T, referred to herein as B6) | PGPVPPSTATRELIEELINITQNQKAPLCNG SMVWSINLTAGMYCAALESLINVSGCSAI EKTQRMLSGFCPHKVSAGQFSSLHVRGSK IEVAQFVKDLLYHLRTLFREGQFN |
| SEQ ID NO: 29 (Exemplary sequence comprising L10D, R11I, V18I, R86K, D87K, K89R, R108K, referred to herein as C2) | PGPVPPSTADIELIEELINITQNQKAPLCNG SMVWSINLTAGMYCAALESLINVSGCSAI EKTQRMLSGFCPHKVSAGQFSSLHVKKTR IEVAQFVKDLLLHLKKLFKEGQFN |
| SEQ ID NO: 30 (Exemplary sequence comprising L10A, R86T, D87G, T88K, K89R, L101N, K104R, K105A, R108K, referred to herein as C3) | PGPVPPSTAARELIEELVNITQNQKAPLCN GSMVWSINLTAGMYCAALESLINVSGCSA IEKTQRMLSGFCPHKVSAGQFSSLHVTGK RIEVAQFVKDLLNHLRALFKEGQFN |
| SEQ ID NO: 31 (Exemplary sequence comprising L10V, K89R, L101N, K105E, R108T, referred to herein as C4) | PGPVPPSTAVRELIEELVNITQNQKAPLCN GSMVWSINLTAGMYCAALESLINVSGCSA IEKTQRMLSGFCPHKVSAGQFSSLHVRDT RIEVAQFVKDLLNHLKELFTEGQFN |
| SEQ ID NO: 32 (Exemplary sequence comprising R11S, I14M, T88S, L101N, K105A, R108K, referred to herein as C7) | PGPVPPSTALSELMEELVNITQNQKAPLCN GSMVWSINLTAGMYCAALESLINVSGCSA IEKTQRMLSGFCPHKVSAGQFSSLHVRDS KIEVAQFVKDLLNHLKALFKEGQFN |
| SEQ ID NO: 33 (Exemplary sequence comprising L10H, R11L, V18I, R86K, D87E, K89R, L10IN, K105T, R108K, refered to herein as C9) | PGPVPPSTAHLELIEELINITQNQKAPLCNG SMVWSINLTAGMYCAALESLINVSGCSAI EKTQRMLSGFCPHKVSAGQFSSLHVKETR IEVAQFVKDLLNHLKTLFKEGQFN |
| SEQ ID NO: 34 (Exemplary sequence comprising L10H, R11L, V18I, R86M, K89R, R108K, referred to herein as C10) | PGPVPPSTAHLELIEELINITQNQKAPLCNG SMVWSINLTAGMYCAALESLINVSGCSAI EKTQRMLSGFCPHKVSAGQFSSLHVMDTR IEVAQFVKDLLLHLKKLFKEGQFN |
| SEQ ID NO: 35 (Exemplary sequence comprising L10H, R86T, D87G, T88R, R108K, referred to herein as C11) | PGPVPPSTAHRELIEELVNITQNQKAPLCN GSMVWSINLTAGMYCAALESLINVSGCSA IEKTQRMLSGFCPHKVSAGQFSSLHVTGR KIEVAQFVKDLLLHLKKLFKEGQFN |
| SEQ ID NO: 36 (Exemplary sequence comprising | PGPVPPSTAHRELIEELVNITQNQKAPLCN GSMVWSINLTAGMYCAALESLINVSGCSA |

TABLE 3-continued

List of IL-13 Amino Acid Sequences

| SEQ ID NO:<br>(Information) | Amino acid sequence |
|---|---|
| L10H, R86M, T88S, K89R, L101N, K104R, K105A, R108K, referred to herein as C12) | IEKTQRMLSGFCPHKVSAGQFSSLHVMDS RIEVAQFVKDLLNHLRALFKEGQFN |
| SEQ ID NO: 37<br>(Exemplary sequence comprising L10A, V18F, R86F, D87F, K89R, L101I, K104R, R108K, referred to herein as D7) | PGPVPPSTAARELIEELFNITQNQKAPLCN GSMVWSINLTAGMYCAALESLINVSGCSA IEKTQRMLSGFCPHKVSAGQFSSLHVKKT RIEVAQFVKDLLIHLRKLFKEGQFN |
| SEQ ID NO: 38<br>(Exemplary sequence comprising L10V, E12A, V18I, R65D, D87S, T88S, L101F, K104R, K105T, referred to herein as IL-13dn) | PGPVPPSTAVRALIEELINITQNQKAPLQNG SMVWSINLTAGMYCAALESLINVSGCSAI EKTQDMLSGFCPHKVSAGQFSSLHVRSSKI EVAQFVKDLLFHLRTLFREGQFN |
| SEQ ID NO: 39<br>signal peptide | MHPLLNPLLLALGLMALLLTTVIALTCL GGFASPGPVPPSTAHRELIEELVNITQNQK APLCNGSMVWSINLTAGMYCAALESLINV SGCSAIEKTQRMLSGFCPHKVSAGQFSSLH VTGRKIEVAQFVKDLLLHLKKLFKEGQFN |
| SEQ ID NO: 40<br>(Exemplary sequence comprising L10V, E12A, V18I, R65D, D87S, T88S, L101F, K104R, K105T, referred to herein as IL-13DN variant 1) | PGPVPPSTAVRALIEELINITQNQKAPLQNG SMVWSIN<u>R</u>TAGMYCAALESLINVSGCSAI EKTQDML<u>S</u>GFCPHKVSAGQFSSLHVRSSKI EVAQFVKDLLFHLRTLFREGQFN |
| SEQ ID NO: 41<br>(Exemplary sequence comprising L10V, E12A, V18I, R65D, D87S, T88S, L101F, K104R, K105T, referred to herein as IL-13DN variant 2) | PGPVPPSTAVRALIEELINITQNQKAPLCNG SMVWSIN<u>L</u>TAGMYCAALESLINVSGCSAI EKTQDML<u>S</u>GFCPHKVSAGQFSSLHVRSSKI EVAQFVKDLLFHLRTLFREGQFN |
| SEQ ID NO: 42<br>wild-type IL-13 including an additional methionine at the N-terminus | MPGPVPPSTALRELIEELVNITQNQKAPLC NGSMVWSINLTAGMYCAALESLINVSGCS AIEKTQRMLSGFCPHKVSAGQFSSLHVRD TKIEVAQFVKDLLLHLKKLFREGQFN |
| SEQ ID NO: 43<br>circularly permuted IL-13 | MYCAALESLINVSGCSAIEKTQRMLSGFCP HKVSAGQFSSLHVRDTKIEVAQFVKDLLL HLKKLFREGQFNGGSGPGPVPPSTALRELI EELVNITQNQKAPLCNGSMVWSINLTAG |
| SEQ ID NO: 44<br>Circularly permuted IL-13 | MYCAALESLINVSGCSAIEKTQRMLSGFCP HKVSAGQFSSLHVRDTKIEVAQFVKDLLL HLKKLFREGQFNGGSGMPGPVPPSTALRE LIEELVNITQNQKAPLCNGSMVWSINLTA G |
| SEQ ID NO: 45<br>circularly permuted IL-13 "A11" variant | MYCAALESLINVSGCSAIEKTQRMLSGFCP HKVSAGQFSSLHVRSSKIEVAQFVKDLLF HLRTLFREGQFNGGSGPGPVPPSTAVRELI EELINITQNQKAPLCNGSMVWSINRTAG |
| SEQ ID NO: 46<br>circularly permuted IL-13 | MYCAALESLINVSGCSAIEKTQRMLSGFCP HKVSAGQFSSLHVRSSKIEVAQFVKDLLF HLRTLFREGQFNGGSGMPGPVPPSTAVRE LIEELINITQNQKAPLCNGSMVWSINRTAG |
| SEQ ID NO: 47<br>circularly permuted IL-13 "DN" variant | MYCAALESLINVSGCSAIEKTQDMLSGFCP HKVSAGQFSSLHVRSSKIEVAQFVKDLLF HLRTLFREGQFNGGSGPGPVPPSTAVRALI EELINITQNQKAPLCNGSMVWSINLTAG |
| SEQ ID NO: 48<br>circular permuted IL-13 | MYCAALESLINVSGCSAIEKTQDMLSGFCP HKVSAGQFSSLHVRSSKIEVAQFVKDLLF HLRTLFREGQFNGGSGMPGPVPPSTAVRA LIEELINITQNQKAPLCNGSMVWSINLTAG |

Table of IL-4 sequences is provided below.

TABLE 4

List of IL-4 Amino Acid Sequences

| SEQ ID NO: (Information) | Amino acid sequence |
| --- | --- |
| SEQ ID NO: 49 (IL-4 wildtype with signal peptide) | MGLTSQLLPPLFFLLACAGNFVHGHKCDITLQEIIKTLNSLTEQKTLCTELTVTDIFAASKNTTEKETFCRAATVLRQFYSHHEKDTRCLGATAQQFHRHKQLIRFLKRLDRNLWGLAGLNSCPVKEANQSTLENFLERLKTIMREKYSKCSS |
| SEQ ID NO: 50 IL-4 including an additional methionine at the N-terminus" starting | MHKCDITLQEIIKTLNSLTEQKTLCTELTVTDIFAASKDTTEKETFCRAATVLRQFYSHHEKDTRCLGATAQQFHRHKQLIRFLKRLDRNLWGLAGLNSCPVKEANQSTLENFLERLKTIMREKYSKCSS |
| SEQ ID NO: 51 KFR | KCDITLQEIIKTLNSLTEQKTLCTELTVTDIFAASKNTTEKETFCRAATVLRQFYSHHEKDTRCLGATAQQFHRHKQLIRFLKRLDRNLWGLAGLNSCPVKEANQSTLENFLERLKTIMKEKFRKCSS |
| SEQ ID NO: 52 RGA | MDTTEKETFCRAATVLRQFYSHHEKDTRCLGATAQQFHRHKQLIRFLKRLDRNLWGLAGLNSCPVKEANQSTLENFLERLRVIMQSKWFKCGAGGNGGHKCDITLQEIIKTLNSLTEQKTLCTELTVTDIFAAS |
| SEQ ID NO: 53 cirularly permuted wild-type IL-4 | MDTTEKETFCRAATVLRQFYSHHEKDTRCLGATAQQFHRHKQLIRFLKRLDRNLWGLAGLNSCPVKEANQSTLENFLERLKTIMREKYSKCSSGGNGGHKCDITLQEIIKTLNSLTEQKTLCTELTVTDIFAAS |
| SEQ ID NO: 54 circularly permuted "KFR" IL-4 variant | MDTTEKETFCRAATVLRQFYSHHEKDTRCLGATAQQFHRHKQLIRFLKRLDRNLWGLAGLNSC TABLE 5-continued List of Amino Acid Sequences

| SEQ ID NO:<br>(Information) | Amino acid sequence |
|---|---|
| agonist; GGGGS linker) | TQRMLSGFCPHKVSAGQFSSLHVRSSKIEVA<br>QFVKDLLFHLRTLFREGQFNGGGGSMFQIP<br>EFEPSEQEDSSSAERGLGPSPAGDGPSGSGK<br>HHRQAPGLLWDASHQQEQPTSSSHHGGAG<br>AVEIRSRHSAYPAGTEDDEGMGEEPSPFRG<br>RSRAAPPNLWAAQRYGRELRRMSDEFVDS<br>FKKGLPRPKSAGTATQMRQSSSWTRVFQS<br>WWDRNLGRGSSAPSQ |
| SEQ ID NO: 58<br>KFR-BAD (KFR targets Type 2<br>IL-4R; GGGGS linker) | KCDITLQEIIKTLNSLTEQKTLCTELTVTDIF<br>AASKNTTEKETFCRAATVLRQFYSHHEKDT<br>RCLGATAQQFHRHKQLIRFLKRLDRNLWGL<br>AGLNSCPVKEANQSTLENFLERLKTIMKEK<br>FRKCSSGGGGSMFQIPEFEPSEQEDSSSAER<br>GLGPSPAGDGPSGSGKHHRQAPGLLWDAS<br>HQQEQPTSSSHHGGAGAVEIRSRHSAYPAG<br>TEDDEGMGEEPSPFRGRSRAAPPNLWAAQR<br>YGRELRRMSDEFVDSFKKGLPRPKSAGTAT<br>QMRQSSSWTRVFQSWWDRNLGRGSSAPSQ |
| SEQ ID NO: 59<br>pKFR4-Bad-H6 | MDTTEKETFCRAATVLRQFYSHHEKDTRCL<br>GATAQQFHRHKQLIRFLKRLDRNLWGLAG<br>LNSCPVKEANQSTLENFLERLKTIMKEKFRK<br>CSSGGNGGHKCDITLQEIIKTLNSLTEQKTL<br>CTELTVTDIFAASGSFQIPEFEPSEQEDSSSAE<br>RGLGPSPAGDGPSGSGKHHRQAPGLLWDA<br>SHQQEQPTSSSHHGGAGAVEIRSRHSAYPA<br>GTEDDEGMGEEPSPFRGRSRAAPPNLWAAQ<br>RYGRELRRMSDEFVDSFKKGLPRPKSAGTA<br>TQMRQSSSWTRVFQSWWDRNLGRGSSAPS<br>QHHHHHH |
| SEQ ID NO: 60<br>cpKFR4-Bad fusion; GS linker | MDTTEKETFCRAATVLRQFYSHHEKDTRCL<br>GATAQQFHRHKQLIRFLKRLDRNLWGLAG<br>LNSCPVKEANQSTLENFLERLKTIMKEKFRK<br>CSSGGNGGHKCDITLQEIIKTLNSLTEQKTL<br>CTELTVTDIFAASGSFQIPEFEPSEQEDSSSAE<br>RGLGPSPAGDGPSGSGKHHRQAPGLLWDA<br>SHQQEQPTSSSHHGGAGAVEIRSRHSAYPA<br>GTEDDEGMGEEPSPFRGRSRAAPPNLWAAQ<br>RYGRELRRMSDEFVDSFKKGLPRPKSAGTA<br>TQMRQSSSWTRVFQSWWDRNLGRGSSAPS<br>Q |
| SEQ ID NO: 61<br>cpIL4-BAD; GS linker | MDTTEKETFCRAATVLRQFYSHHEKDTRCL<br>GATAQQFHRHKQLIRFLKRLDRNLWGLAG<br>LNSCPVKEANQSTLENFLERLKTIMREKYSK<br>CSSGGNGGHKCDITLQEIIKTLNSLTEQKTL<br>CTELTVTDIFAASGSFQIPEFEPSEQEDSSSAE<br>RGLGPSPAGDGPSGSGKHHRQAPGLLWDA<br>SHQQEQPTSSSHHGGAGAVEIRSRHSAYPA<br>GTEDDEGMGEEPSPFRGRSRAAPPNLWAAQ<br>RYGRELRRMSDEFVDSFKKGLPRPKSAGTA<br>TQMRQSSSWTRVFQSWWDRNLGRGSSAPS<br>Q |
| SEQ ID NO: 62<br>cpIL-4-BAD H6; GS linker | MDTTEKETFCRAATVLRQFYSHHEKDTRCL<br>GATAQQFHRHKQLIRFLKRLDRNLWGLAG<br>LNSCPVKEANQSTLENFLERLKTIMREKYSK<br>CSSGGNGGHKCDITLQEIIKTLNSLTEQKTL<br>CTELTVTDIFAASGSFQIPEFEPSEQEDSSSAE<br>RGLGPSPAGDGPSGSGKHHRQAPGLL<br>WDASHQQEQPTSSSHHGGAGAVEIRSRHSA<br>YPAGTEDDEGMGEEPSPFRGRSRAAPPNLW<br>AAQRYGRELRRMSDEFVDSFKKGLPRPKSA<br>GTATQMRQSSSWTRVFQSWWDRNLGRGSS<br>APSQHHHHHH |
| SEQ ID NO: 63<br>IL13-BAD (targets IL13Ral and<br>is referred to as IL13DN) | PGPVPPSTAVRALIEELINITQNQKAPLNGS<br>MVWSINRTAGMYCAALESLINVSGCSAIEK<br>TQDMLSGFCPHKVSAGQFSSLHVRSSKIEV<br>AQFVKDLLFHLRTLFREGQFNGGGGSGGGG<br>SGGGGSFQIPEFEPSEQEDSSSAERGLGPSPA<br>GDGPSGSGKHHRQAPGLLWDASHQQEQPT<br>SSSHHGGAGAVEIRSRHSAYPAGTEDDEGM |

TABLE 5-continued

List of Amino Acid Sequences

| SEQ ID NO: (Information) | Amino acid sequence |
|---|---|
| | GEEPSPFRGRSRAAPPNLWAAQRYGRELRR MSDEFVDSFKKGLPRPKSAGTATQMRQSSS WTRVFQSWWDRNLGRGSSAPSQ |
| SEQ ID NO: 64 IL-4-BclxL; GGGGS linker | KCDITLQEIIKTLNSLTEQKTLCTELTVTDIF AASKNTTEKETFCRAATVLRQFYSHHEKDT RCLGATAQQFHRHKQLIRFLKRLDRNLWGL AGLNSCPVKEANQSTLENFLERLKTIMREK YSKCSSGGGGSMSQSNRELVVDFLSYKLSQ KGYSWSQFSDVEENRTEAPEGTESEMETPS AINGNPSWHLADSPAVNGATGHSSSLDARE VIPMAAVKQALREAGDEFELRYRRAFSDLT SQLHITPGTAYQSFEQVVNELFRDGVNWGR IVAFFSFGGALCVESVDKEMQVLVSRIAAW MATYLNDHLEPWIQENGGWDTFVELYGNN AAAESRKGQERFNRWFLTGMTVAGVVLLG SLFSRK |
| SEQ ID NO: 65 PRX321 | MDTTEKETFCRAATVLRQFYSHHEKDTRCL GATAQQFHRHKQLIRFLKLRDRNLWGLAG LNSCPVKEANQSTLENFLERLKTIMREKYSK CSSGGNGGHKCDITLQEIIKTLNSLTEQKTL CTELTVTDIFAASKASGGPEGGSLAALTAH QACHLPLETFTRHRQPRGWEQLEQCGYPVQ RLVALYLAARLSWNQVDQVIRNALASPGS GGDLGEAIREQPEQARLALTLAAAESERFV RQGTGNDEAGAANGPADSGDALLERNYPT GAEFLGDGGDVSFSTRGTQNWTVERLLQA HRQLEERGYVFVGYHGTFLEAAQSIVFGGV RARSQDLDAIWRGFYIAGDPALAYGYAQD QEPDARGRIRNGALLRVYVPRSSLPGFYRTS LTLAAPEAAGEVERLIGHPLPLRLDAITGPE EEGGRLETILGWPLAERTVVIPSAIPTDPRNV GGDLDPSSIPDKEQAISALPDYASQPGKPPK DEL |
| SEQ ID NO: 66 cpS4-Bad-H6 | MDTTEKETFCRAATVLRQFYSHHEKDTRCL GATAQQFHRHKQLIRFLKRLDRNLWGLAG LNSCPVKEANQSTLENFLERLRVIMQSKWF KCGAGGNGGHKCDITLQEIIKTLNSLTEQKT LCTELTVTDIFAASGSFQIPEFEPSEQEDSSSA ERGLGPSPAGDGPSGSGKHHRQAPGLLWD ASHQQEQPTSSSHHGGAGAVEIRSRHSAYP AGTEDDEGMGEEPSPFRGRSRAAPPNLWAA QRYGRELRRMSDEFVDSFKKGLPRPKSAGT ATQMRQSSSWTRVFQSWWDRNLGRGSSAP SQHHHHHH |
| SEQ ID NO: 67 cpS4-Bad | MDTTEKETFCRAATVLRQFYSHHEKDTRCL GATAQQFHRHKQLIRFLKRLDRNLWGLAG LNSCPVKEANQSTLENFLERLRVIMQSKWF KCGAGGNGGHKCDITLQEIIKTLNSLTEQKT ICTELTVTDIFA ASGSFQIPFFEPSENENSESA ERGLGPSPAGDGPSGSGKHHRQAPGLLWD ASHQQEQPTSSSHHGGAGAVEIRSRHSAYP AGTEDDEGMGEEPSPFRGRSRAAPPNLWAA QRYGRELRRMSDEFVDSFKKGLPRPKSAGT ATQMRQSSSWTRVFQSWWDRNLGRGSSAP SQ |
| SEQ ID NO: 68 IL-4-Bad-H6 | MHKCDITLQEIIKTLNSLTEQKTLCTELTVT DIFAASKDTTEKETFCRAATVLRQFYSHHE KDTRCLGATAQQFHRHKQLIRFLKRLDRNL WGLAGLNSCPVKEANQSTLENFLERLKTIM REKYSKCSSGSFQIPEFEPSEQEDSSSAERGL GPSPAGDGPSGSGKHHRQAPGLLWDASHQ QEQPTSSSHHGGAGAVEIRSRHSAYPAGTE DDEGMGEEPSPFRGRSRAAPPNLWAAQRY GRELRRMSDEFVDSFKKGLPRPKSAGTATQ MRQSSSWTRVFQSWWDRNLGRGSSAPSQH HHHH |
| SEQ ID NO: 69 IL-4-Bad-H6 | MHKCDITLQEIIKTLNSLTEQKTLCTELTVT DIFAASKDTTEKETFCRAATVLRQFYSHHE KDTRCLGATAQQFHRHKQLIRFLKRLDRNL |

TABLE 5-continued

List of Amino Acid Sequences

| SEQ ID NO:<br>(Information) | Amino acid sequence |
|---|---|
| | WGLAGLNSCPVKEANQSTLENFLERLKTIM<br>REKYSKCSSGSFQIPEFEPSEQEDSSSAERGL<br>GPSPAGDGPSGSGKHHRQAPGLLWDASHQ<br>QEQPTSSSHHGGAGAVEIRSRHSAYPAGTE<br>DDEGMGEEPSPFRGRSRAAPPNLWAAQRY<br>GRELRRMSDEFVDSFKKGLPRPKSAGTATQ<br>MRQSSSWTRVFQSWWDRNLGRGSSAPSQ |

In some embodiments, the fusion partner is included in Table 6 below.

TABLE 6

List of Selected Fusion Partners

| SEQ ID NO:<br>(Information) | Amino acid sequence |
|---|---|
| SEQ ID NO: 74<br>BAD amino acid sequence | MFQIPEFEPSEQEDSSSAERGLGPSPAGDGPS<br>GSGKHHRQAPGLLWDASHQQEQPTSSSHH<br>GGAGAVEIRSRHSAYPAGTEDDEGMGEEPS<br>PFRGRSRAAPPNLWAAQRYGRELRRMSDEF<br>VDSFKKGLPRPKSAGTATQMRQSSSWTRVF<br>QSWWDRNLGRGSSAPSQ |
| SEQ ID NO: 75<br>Bcl-2 amino acid sequence | MAHAGRTGYDNREIVMKYIHYKLSQRGYE<br>WDAGDVGAAPPGAAPAPGIFSSQPGHTPHP<br>AASRDPVARTSPLQTPAAPGAAAGPALSPV<br>PPVVHLTLRQAGDDFSRRYRRDFAEMSSQL<br>HLTPFTARGRFATVVEELFRDGVNWGRIVA<br>FFEFGGVMCVESVNREMSPLVDNIALWMT<br>EYLNRHLHTWIQDNGGWDAFVELYGPSMR<br>PLFDFSWLSLKTLLSLALVGACITLGAYLGH<br>K |
| SEQ ID NO: 76<br>>HsBAD_Q92934-1(UniProtKB) | MFQIPEFEPSEQEDSSSAERGLGPSPAGDG<br>PSGSGKHHRQAPGLLWDASHQQEQPTSSSH<br>HGGAGAVEIRSRHSSYPAGTEDDEGMGEEP<br>SPFRGRSRSAPPNLWAAQRYGRELRRMSDE<br>FVDSFKKGLPRPKSAGTATQMRQSSSWTRV<br>FQSWWDRNLGRGSSAPSQ |
| SEQ ID NO: 77<br>>HsBAX_Q07812-1(UniProtKB) | MDGSGEQPRGGGPTSSEQIMKTGALLLQGF<br>IQDRAGRMGGEAPELALDPVPQDASTKKLS<br>ECLKRIGDELDSNMELQRMIAAVDTDSPRE<br>VFFRVAADMFSDGNFNWGRVVALFYFASK<br>LVLKALCTKVPELIRTIMGWTLDFLRERLLG<br>WIQDQGGWDGLLSYFGTPTWQTVTIFVAG<br>VLTASLTIWKK MG |
| SEQ ID NO: 78<br>>HsBAK1_Q16611-1(UniProtKB) | MASGQGPGPPRQECGEPALPSASEEQVAQD<br>TEEVFRSYVFYRHQQEQEAEGVAAPADPE<br>MVTLPLQPSSTMGQVGRQLAIIGDDINRRY<br>DSEFQTMLQHLQPTAENAYEYFTKIATSLFE<br>SGINWGRVVALLGFGYRLALHVYQHGLTG<br>FLGQVTRFVVDFMLHHCIARWIAQRGGWV<br>AALNLGNGPILNVLVVLGVVLLGQFVVRRF<br>FKS |
| SEQ ID NO: 79<br>>HsBIK_Q13323-1(UniProtKB) | MSEVRPLSRDILMETLLYEQLLEPPTMEVL<br>GMTDSEEDLDPMEDFDSLECMEGSDALAL<br>RLACIGDEMDVSLRAPRLAQLSEVAMHSLG<br>LAFIYDQTEDIRDVLRSFMDGFTTLKENIMR<br>FWRSPNPGSWVSCEQVLLALLLLLALLLPL<br>LSGGLHLLLK |
| SEQ ID NO: 80<br>>HsBID_P55957-1(UniProtKB) | MDCEVNNGSSLRDECITNLLVFGFLQSCSD<br>NSFRRELDALGHELPVLAPQWEGYDELQTD<br>GNRSSHSRLGRIEADSESQEDIIRNIARHLAQ<br>VGDSMDRSIPPGLVNGLALQLRNTSRSEED |

TABLE 6-continued

List of Selected Fusion Partners

SEQ ID NO:
(Information)  Amino acid sequence

RNRDLATALEQLLQAYPRDMEKEKTMLV
LALLLAKKVASHTPSLLRDVFHTTVNFINQ
NLRTYVRSLARNGMD

C. IL-2 Muteins

IL-2 muteins contemplated for use with the present invention include any of the IL-2 muteins described herein. The substituted amino acid residue(s) can be, but are not necessarily, conservative substitutions, which typically include substitutions within the following groups: glycine, alanine; valine, isoleucine, leucine; aspartic acid, glutamic acid; asparagine, glutamine; serine, threonine; lysine, arginine; and phenylalanine, tyrosine. These mutations can be at amino acid residues that contact the IL-2Rβ and/or the IL-2Rγ.

More specifically, a mutation (whether conservative or non-conservative, by way of addition(s) or deletion(s)) can be made at one or more of positions. For example, the mutation can be: I24V, P65H, Q74R, Q74H, Q74N, Q74S, L80F, L80V, R81I, R81T, R81D, L85V, I86V, I89V, I92F, V93I. The sequences of exemplary IL-2 muteins are as follows: 5-1 SEQ ID NO: 5; 5-2 SEQ ID NO: 82; 6-6 SEQ ID NO: 83; A2 SEQ ID NO: 84; B1 SEQ ID NO:85; B11 SEQ ID NO:86; C5 SEQ ID NO:87; D10 SEQ ID NO:88; E10 SEQ ID NO:89; G8 SEQ ID NO:90; H4 SEQ ID NO:91; and H9 SEQ ID NO:92.

In some embodiments, the substitutions in the IL-2 mutein comprise L80F, R81D, L85V, I86V, and I92F, numbered in accordance with wild-type human IL-2 of SEQ ID NO:81. In some embodiments, the IL-2 mutein further comprises F42A substitution, wherein numbering is in accordance with the wild-type human IL-2 of SEQ ID NO:81. In some embodiments, the IL-2 mutein further comprises Y45A substitution, wherein numbering is in accordance with the wild-type human IL-2 of SEQ ID NO:81. In some embodiments, the IL-2 mutein further comprises E62A substitution, wherein numbering is in accordance with the wild-type human IL-2 of SEQ ID NO:81. In some embodiments, the substitutions in the IL-2 mutein comprise F42A, L80F, R81D, L85V, I86V, and I92F, numbered in accordance with wild-type human IL-2 of SEQ ID NO:81. In some embodiments, the substitutions in the IL-2 mutein comprise F42A, Y45A, L80F, R81D, L85V, I86V, and I92F, numbered in accordance with wild-type human IL-2 of SEQ ID NO:81. In some embodiments, the substitutions in the IL-2 mutein comprise F42A, E62A, L80F, R81D, L85V, I86V, and I92F, numbered in accordance with wild-type human IL-2 of SEQ ID NO:81. In some embodiments, the substitutions in the IL-2 mutein comprise F42A, Y45A, E62A, L80F, R81D, L85V, I86V, and I92F, numbered in accordance with wild-type human IL-2 of SEQ ID NO:81. In some embodiments, the substitutions in the IL-2 mutein comprise E62A, L80F, R81D, L85V, I86V, and I92F, numbered in accordance with wild-type human IL-2 of SEQ ID NO:81. In some embodiments, the substitutions in the IL-2 mutein comprise Y45A, E62A, L80F, R81D, L85V, I86V, and I92F, numbered in accordance with wild-type human IL-2 of SEQ ID NO:81. In some embodiments, the substitutions in the IL-2 mutein comprise Y45A and E62A, numbered in accordance with wild-type human IL-2 of SEQ ID NO:81.

In some embodiments, the substitutions in the IL-2 mutein that lead to increased and/or enhanced IL-2Rβ binding include L80F, R81D, L85V, I86V, and I92F, numbered in accordance with wild-type human IL-2 of SEQ ID NO:81. In some embodiments, an IL-2 mutein for use in the invention comprises L80F, R81D, L85V, I86V, and I92F and exhibits increased IL-2Rβ binding. In some embodiments, an IL-2 mutein for use in the invention further comprises a substitution at position F42A. In some embodiments, the IL-2 mutein for use in the invention further comprises a substitution at position K43N. In some embodiments, the mutein comprises substitutions L80F, R81D, L85V, I86V, and I92F, and one or more substitutions selected from the group consisting of F42A, Y45A, and E62A, all as compared to wild-type human IL-2 (SEQ ID NO:81). In some embodiments, the mutein comprises substitutions L80F, R81D, L85V, I86V, and I92F, and further comprises the substitutions F42A, Y45A, and E62A, all as compared to wild-type human IL-2 (SEQ ID NO:81). In some embodiments, the mutein comprises substitutions L80F, R81D, L85V, I86V, and I92F, and further comprises the substitutions F42A and Y45A, all as compared to wild-type human IL-2 (SEQ ID NO:81). In some embodiments, the mutein comprises substitutions L80F, R81D, L85V, I86V, and I92F, and further comprises the substitutions F42A and E62A, all as compared to wild-type human IL-2 (SEQ ID NO:81).

In some embodiments, the amino acid substitutions increasing IL-2Rβ binding affinity include: L80F, R81D, L85V, I86V, and I92F. In some embodiments, the amino acid substitutions that increase IL-2Rβ binding affinity include: L80F, R81D, L85V, I86V, and I92F.

In some embodiments, the subject IL-2 mutein having a greater binding affinity for IL-2Rβ as compared to wild-type human IL-2, includes the amino acid substitutions L80F, R81D, L85V, I86V, and I92F. In some embodiments, the IL-2 mutein has the amino acid sequence:

(SEQ ID NO: 93; H9)
APTSSSTKKTQLQLEHLLLDLQMILNGINNYKNPKLTRMLTFKFYMPKK

ATELKHLQCLEEELKPLEEVLNLAQSKNFHFDPRDVVSNINVFVLELKG

SETTFMCEYADETATIVEFLNRWITFCQSIISTLT.

In some embodiments, the IL-2 mutein has increased capabilities to stimulate one or more signaling pathways that are dependent on IL-2Rβ/IL-2Rγ, heterodimerization. In some embodiments, the subject IL-2 mutein has an enhanced capability to stimulate STAT5 phosphorylation in an IL-2Rβ+ cell as compared to wild-type human IL-2. In some embodiments, the IL-2 mutein stimulates STAT5 phosphorylation in an IL-2Rβ+ cell at a level that is 1%, 5%, 10%, 15%, 20%, 25%, 30%, 35%, 40%, 45%, 50%, 55%, 60%, 65%, 70%, 75%, 80%, 85%, 90%, 95% or more of the level that wild-type IL-2 stimulates STAT5 phosphorylation in the same cell. In some embodiments, the IL-2 mutein stimulates STAT5 phosphorylation in an IL-2Rβ+ cell at a level that is 105%, 110%, 115%, 120%, 125%, 130%, 135%, 140%, 145%, 150%, 155%, 160%, 165%, 170%, 175%, 180%, 185%, 190%, 195% or more as compared to the level that wild-type IL-2 stimulates STAT5 phosphorylation in the same cell. In some embodiments, the IL-2Rβ+ cell is a T cell. In particular embodiments, the T cell is a CD8+ T cell. In some embodiments, the CD8+ T cell is a freshly isolated CD8+ T cell. In other embodiments, the CD8+ T cell T cell is an activated CD8+ T cell. In other embodiments, the IL-2Rβ+ cell is a natural killer (NK) cell. In some embodiments, the IL-2 mutein comprises substitutions L80F, R81D, L85V, I86V, and I92F, as compared to wild-type human IL-2 (SEQ ID NO:81).

In some embodiments, the mutein has an enhanced capability to stimulate ERK1/ERK2 signaling in an IL-2Rβ+ cell as compared to wild-type human IL-2. In some embodiments, the IL-2 mutein stimulates pERK1/ERK2 signaling in an IL-2Rβ+ cell at a level that is 1%, 5%, 10%, 15%, 20%, 25%, 30%, 35%, 40%, 45%, 50%, 55%, 60%, 65%, 70%, 75%, 80%, 85%, 90%, 95% or more of the level that wild-type IL-2 stimulates pERK1/ERK2 signaling in the same cell. In some embodiments, the IL-2 mutein stimulates pERK1/ERK2 phosphorylation in an IL-2Rβ+ cell at a level that is 105%, 110%, 115%, 120%, 125%, 130%, 135%, 140%, 145%, 150%, 155%, 160%, 165%, 170%, 175%, 180%, 185%, 190%, 195% or more as compared to the level that wild-type IL-2 stimulates pERK1/ERK2 phosphorylation in the same cell. In some embodiments, the IL-2Rβ+ cell is a T cell. In particular embodiments, the T cell is a CD8+ T cell. In some embodiments, the CD8+ T cell is a freshly isolated CD8+ T cell. In other embodiments, the CD8+ T cell T cell is an activated CD8+ T cell. In other embodiments, the IL-2Rβ+ cell is a natural killer (NK) cell. In some embodiments, the IL-2 mutein comprises substitutions L80F, R81D, L85V, I86V, and I92F, as compared to wild-type human IL-2 (SEQ ID NO:81).

STAT5 and ERK1/2 signaling can be measured, for example, by phosphorylation of STAT5 and ERK1/2 using any suitable method known in the art. For example, STAT5 and ERK1/2 phosphorylation can be measured using antibodies specific for the phosphorylated version of these molecules in combination with flow cytometry analysis as described herein. In some embodiments, the mutein has an enhanced capability to stimulate PI 3-kinase signaling in a IL-2Rβ+ cell as compared to wild-type human IL-2. In some embodiments, the IL-2 mutein stimulates PI 3-kinase signaling in an IL-2Rβ+ cell at a level that is 1%, 5%, 10%, 15%, 20%, 25%, 30%, 35%, 40%, 45%, 50%, 55%, 60%, 65%, 70%, 75%, 80%, 85%, 90%, 95% or less of the level that wild-type IL-2 stimulates PI 3-kinase signaling in the same cell. In some embodiments, the IL-2 mutein stimulates PI 3-kinase signaling in an IL-2Rβ+ cell at a level that is 105%, 110%, 115%, 120%, 125%, 130%, 135%, 140%, 145%, 150%, 155%, 160%, 165%, 170%, 175%, 180%, 185%, 190%, 195% or more as compared to the level that wild-type IL-2 stimulates PI 3-kinase signaling phosphorylation in the same cell. In some embodiments, the IL-2Rβ+ cell is a T cell. In particular embodiments, the T cell is a CD8+ T cell. In some embodiments, the CD8+ T cell T cell is an activated CD8+ T cell. In other embodiments, the IL-2Rβ+ cell is a natural killer (NK) cell. In some embodiments, the IL-2 mutein comprises substitutions L80F, R81D, L85V, I86V, and I92F, as compared to wild-type human IL-2 (SEQ ID NO:81). PI3-kinase signaling can be measured using any suitable method known in the art. For example, PI 3-kinase signaling can be measured using antibodies that are specific for phospho-S6 ribosomal protein in conjunction with flow cytometry analysis as described herein.

In some embodiments, the IL-2 mutein is a stimulator of IL-2 and/or IL-15 STAT5 phosphorylation in CD8+ T cells. In some embodiments, the mutein is a promoter of IL-2 and/or IL-15 induced proliferation of CD8+ T cells. In some embodiments, the mutein is a stimulator of IL-2 dependent, TCR-induced cell proliferation. In some embodiments, the IL-2 mutein comprises substitutions L80F, R81D, L85V, I86V, and I92F, as compared to wild-type human IL-2 (SEQ ID NO:81).

IL-2 promotes Th1, Th9, and Treg T cell differentiation and inhibits Th17 differentiation. Therefore, without being bound by any particular theory of operation, it is believed that IL-2 muteins that function as IL-2 superagonists are capable of promoting Th1, Th9, and/or Treg cell differentiation or inhibiting Th17 cell differentiation. In some embodiments, the IL-2 mutein is a promoter of IL-2 dependent Th1, Th9 and/or Treg differentiation. In some embodiments, the mutein is an inhibitor of Th17 differentiation. In some embodiments, the IL-2 mutein comprises substitutions L80F, R81D, L85V, I86V, and I92F, as compared to wild-type human IL-2 (SEQ ID NO:81).

In some embodiments, the IL-2 mutein signals less and/or independently of CD25 (for example, has reduced or ablated CD25 binding) as compared to wild-type human IL-2. In some embodiments the reduced and/or independent signaling with regard to CD25 allows for preferential activation of effector T-cells while limiting the stimulation of Tregs. In some embodiments the reduced and/or independent signaling with regard to CD25 allows for reduced toxicity. In some embodiments, the mutein comprises substitutions L80F, R81D, L85V, I86V, and I92F, and one or more substitutions selected from the group consisting of F42A, Y45A, and E62A, all as compared to wild-type human IL-2 (SEQ ID NO:81).

In some embodiments, the IL-2 mutein is capable of increasing and/or restoring responsiveness to anergic NK cells. In some embodiments, the IL-2 mutein is capable of increasing and/or restoring responsiveness to anergic NK cells in the tumor microenvironment. In some embodiments, the IL-2 mutein comprises substitutions L80F, R81D, L85V, I86V, and I92F, as compared to wild-type human IL-2 (SEQ ID NO:81).

In some embodiments the mutein is an inhibitor an inhibitor of IL-2 dependent activation of natural killer (NK) cells. IL-2 activation of NK cells can be measured by any suitable method known in the art, for example, by measuring IL-2 induced CD69 expression and/or cytotoxicity, as described herein.

In some embodiments, an increase in IL-2Rβ binding affinity is any binding affinity for IL-2Rβ that is greater than the wild-type human IL-2 binding affinity for IL-2Rβ. In some embodiments, the binding affinity is a 2-fold, 5-fold, 10-fold, 20-fold, 30-fold, 40-fold, 50-fold, 60-fold, 70-fold, 80-fold, 90-fold, 100-fold, 120-fold, 150-fold, 170-fold, 190-fold, 200-fold, 220-fold, 240-fold or more increase in binding affinity for IL-2Rβ as compared to the wild-type human IL-2 binding affinity for IL-2Rβ.

In some embodiments, an increase in binding capacity for IL-2Rβ is any binding capacity for IL-2Rβ that is greater than the wild-type human IL-2 binding capacity for IL-2Rβ. In some embodiments, the binding capacity is a 2-fold, 5-fold, 10-fold, 20-fold, 30-fold, 40-fold, 50-fold, 60-fold, 70-fold, 80-fold, 90-fold, 100-fold, 120-fold, 150-fold, 170- fold, 190-fold, 200-fold, 220-fold, 240-fold or more increase in binding capacity for IL-2Rβ as compared to the wild-type human IL-2 binding capacity for IL-2Rβ.

In some embodiments, the subject IL-2 mutein having a greater binding affinity for IL-2Rβ as compared to wild-type human IL-2 also exhibits reduced binding to CD25 and includes the amino acid substitutions F42A, L80F, R81D, L85V, I86V, and I92F. In some embodiments, the reduce binding affinity is about 220-fold, i.e., from about Kd of 6.6 nM for wild-type human IL-2 to about 1.4 μM for the mutein comprising F42A, L80F, R81D, L85V, I86V, and I92F. In some embodiments, the IL-2 mutein has the amino acid sequence:

(SEQ ID NO: 82; also referred to as H9-F42A)
APTSSSTKKTQLQLEHLLLDLQMILNGINNYKNPKLTRMLTAKFYMPKK

ATELKHLQCLEEELKPLEEVLNLAQSKNFHFDPRDVVSNINVFVLELKG

SETTFMCEYADETATIVEFLNRWITFCQSIISTLT.

In some embodiments, the subject IL-2 mutein having a greater binding affinity for IL-2Rβ as compared to wild-type human IL-2 also exhibits reduced binding to CD25 and includes the amino acid substitutions K43N, L80F, R81D, L85V, I86V, and I92F. In some embodiments, the reduce binding affinity is due to allowing for glycosylation at position 43 with the K43N substitution. By substituting lysine for asparagine (K43N), CD25 binding is reduced and/or ablated in the IL-2 mutein comprising the amino acid substitutions K43N, L80F, R81D, L85V, I86V, and I92F. In some embodiments, the IL-2 mutein has the amino acid sequence:

(SEQ ID NO: 83; also referred to as H9-K43N)
APTSSSTKKTQLQLEHLLLDLQMILNGINNYKNPKLTRMLTFNFYMPKK

ATELKHLQCLEEELKPLEEVLNLAQSKNFHFDPRDVVSNINVFVLELKG

SETTFMCEYADETATIVEFLNRWITFCQSIISTLT.

In some embodiments, a reduction in binding affinity for CD25 is any binding affinity for CD25 that is less than the wild-type human IL-2 binding affinity. In some embodiments, the binding affinity is a 10-fold, 20-fold, 30-fold, 40-fold, 50-fold, 60-fold, 70-fold, 80-fold, 90-fold, 100-fold, 120-fold, 150-fold, 170-fold, 190-fold, 200-fold, 220-fold, 240-fold or more decrease in binding affinity for CD25 as compared to the wild-type human IL-2 binding affinity for CD25.

In some embodiments, the subject IL-2 mutein having a greater binding affinity for IL-2Rβ and a reduced binding affinity for CD25 as compared to wild-type human IL-2 includes the amino acid substitutions F42A, Y45A L80F, R81D, L85V, I86V, and I92F. In some embodiments, the IL-2 mutein has the amino acid sequence:

(SEQ ID NO: 84; H9-F42A/Y45A; H9-FYAA)
APTSSSTKKTQLQLEHLLLDLQMILNGINNYKNPKLTRMLTAKFAMPKK

ATELKHLQCLEEELKPLEEVLNLAQSKNFHFDPRDVVSNINVFVLELKG

SETTFMCEYADETATIVEFLNRWITFCQSIISTLT.

In some embodiments, the subject IL-2 mutein having a greater binding affinity for IL-2Rβ and a reduced binding affinity for CD25 as compared to wild-type human IL-2 includes the amino acid substitutions F42A, E62A L80F, R81D, L85V, I86V, and I92F. In some embodiments, the IL-2 mutein has the amino acid sequence:

(SEQ ID NO: 85; H9-F42A/E62A; H9-FEAA)
APTSSSTKKTQLQLEHLLLDLQMILNGINNYKNPKLTRMLTAKFYMPKK

ATELKHLQCLEEALKPLEEVLNLAQSKNFHFDPRDVVSNINVFVLELKG

SETTFMCEYADETATIVEFLNRWITFCQSIISTLT.

In some embodiments, the subject IL-2 mutein having a greater binding affinity for IL-2Rβ and a reduced binding affinity for CD25 as compared to wild-type human IL-2 includes the amino acid substitutions F42A, Y45A, E62A, L80F, R81D, L85V, I86V, and I92F. In some embodiments, the IL-2 mutein has the amino acid sequence:

(SEQ ID NO: 86; H9-F42A/Y45A/E62A; H9-FYEAAA)
APTSSSTKKTQLQLEHLLLDLQMILNGINNYKNPKLTRMLTAKFAMPKK

ATELKHLQCLEEALKPLEEVLNLAQSKNFHFDPRDVVSNINVFVLELKG

SETTFMCEYADETATIVEFLNRWITFCQSIISTLT.

In some embodiments, the IL-2 mutein sequence is 90% identical to any one of SEQ ID NO:81 or SEQ ID NO:82 through SEQ ID NO:109. In some embodiments, the IL-2 mutein sequence is 95% identical to any one of SEQ ID NO:81 or SEQ ID NO:82 through SEQ ID NO:109. In some embodiments, the IL-2 mutein sequence is 98% identical to any one of SEQ ID NO:81 or SEQ ID NO:82 through SEQ ID NO:109. In some embodiments, the IL-2 mutein sequence is 99% identical to any one of SEQ ID NO:81 or SEQ ID NO:82 through SEQ ID NO:109.

Further exemplary IL-2 sequences are provided in the table below.

TABLE 7

List of Exemplary IL-2 Muteins

| Amino Acid Sequences SEQ ID NO: (Information) | Amino acid sequence |
|---|---|
| SEQ ID NO: 81 Wild type IL-2 | APTSSSTKKTQLQLEHLLLDLQMILNGINNYKNPKL TRMLTFKFYMPKKATELKHLQCLEEELKPLEEVLN LAQSKNFHLRPRDLISNINVIVLELKGSETTFMCEY ADETATIVEFLNRWITFCQSIISTLT |
| SEQ ID NO: 82 (also referred to as H9-F42A) | APTSSSTKKTQLQLEHLLLDLQMILNGINNYKNPKL TRMLTAKFYMPKKATELKHLQCLEEELKPLEEVLN LAQSKNFHFDPRDVVSNINVFVLELKGSETTFMCE YADETATIVEFLNRWITFCQSIISTLT ( |

TABLE 7-continued

List of Exemplary IL-2 Muteins

| Amino Acid Sequences SEQ ID NO: (Information) | Amino acid sequence |
|---|---|
| (SEQ ID NO: 83 (also referred to as H9-K43N) | APTSSSTKKTQLQLEHLLLDLQMILNGINNYKNPKL TRMLTFNFYMPKKATELKHLQCLEEELKPLEEVLN LAQSKNFHFDPRDVVSNINVFVLELKGSETTFMCE YADETATIVEFLNRWITFCQSIISTLT |
| SEQ ID NO: 84 (H9-F42A/Y45A; H9-FYAA) | APTSSSTKKTQLQLEHLLLDLQMILNGINNYKNPKL TRMLTAKFAMPKKATELKHLQCLEEELKPLEEVLN LAQSKNFHFDPRDVVSNINVFVLELKGSETTFMCE YADETATIVEFLNRWITFCQSIISTLT |
| SEQ ID NO: 85 (H9-F42A/E62A; H9-FEAA) | APTSSSTKKTQLQLEHLLLDLQMILNGINNYKNPKL TRMLTAKFYMPKKATELKHLQCLEEALKPLEEVLN LAQSKNFHFDPRDVVSNINVFVLELKGSETTFMCE YADETATIVEFLNRWITFCQSIISTLT |
| SEQ ID NO: 86 H9-F42A/Y45A/E62A; H9-FYEAAA). | APTSSSTKKTQLQLEHLLLDLQMILNGINNYKNPKL TRMLTAKFAMPKKATELKHLQCLEEALKPLEEVLN LAQSKNFHFDPRDVVSNINVFVLELKGSETTFMCE YADETATIVEFLNRWITFCQSIISTLT |
| SEQ ID NO: 87 B11 | APTSSSTKKTQLQLEHLLLDLQMVLNGINNYKNPK LTRMLTFKFYMPKKATELKHLQCLEEELKPLEEVL NLASSKNFHFDPRDVVSNINVFVLELKGSETTFMC EYADETATIVEFLNRWITFCQSIISTLT |
| SEQ ID NO: 88 C5 | APTSSSTKKTQLQLEHLLLDLQMILNGINNYKNPKL TRMLTFKFYMPKKATELKHLQCLEEELKHLEEVLN LANSKNFHVTPRDVVSNINVFVLELKGSETTFMCE YADETATIVEFLNRWITFCQSIISTLT |
| SEQ ID NO: 89 D10 | APTSSSTKKTQLQLEHLLLDLQMILNGINNYKNPKL TRMLTFKFYMPKKATELKHLQCLEEELKPLEEVLN LAHSKNFHFDPRDVVSNINVFVLELKGSETTFMCE YADETATIVEFLNRWITFCQSIISTLT |
| SEQ ID NO: 90 E10 | APTSSSTKKTQLQLEHLLLDLQMILNGINNYKNPKL TRMLTFKFYMPKKATELKHLQCLEEELKPLEEVLN LASSKNFHFDPRDVVSNINVFVLELKGSETTFMCE YADETATIVEFLNRWITFCQSIISTLT |
| SEQ ID NO: 91 G8 | APTSSSTKKTQLQLEHLLLDLQMILNGINNYKNPKL TRMLTFKFYMPKKATELKHLQCLEEELKPLEEVLN LANSKNFHFDPRDVVSNINVFVLELKGSETTFMCE YADETATIVEFLNRWITFCQSIISTLT |
| SEQ ID NO: 92 H4 (with linker) | APTSSSTKKTQLQLEHLLLDLQMILNGINNYKNPKL TRMLTFKFYMPKKATELKHLQCLEEELKPLEEVLN LASSKNFHLDPRDVISNINVFVLELKGSETTFMCEY ADETATIVEFLNRWITFCQSI-ISTLTGGGGSGGGGSG GGGSDKTHTCPPCPAPELLGGPSVFLFPPKPKDTLM ISRTPEVTCVVVDVSHEDPEVKFNWYVDGVEVHN AKTKPREEQYASTYRVVSVLTVLHQDWLNGKEYK CKVSNKALPAPIEKTISKAKGQPREPQVYTLPPSRE EMTKNQVSLTCLVKGFYPSDIAVEWESNGQPENNY KTTPPVLDSDGSFFLYSKLTVDKSRWQQGNVFSCS VMHEALHNHYTQKSLSLSPGK* |
| SEQ ID NO: 93 H9 | APTSSSTKKTQLQLEHLLLDLQMILNGINNYKNPKL TRMLTFKFYMPKKATELKHLQCLEEELKPLEEVLN LAQSKNFHFDPRDVVSNINVFVLELKGSETTFMCE YADETATIVEFLNRWITFCQSIISTLT |
| SEQ ID NO: 94 | APTSSSTKKTQLQLEHLLLDLQMILNGINNYKNPKL TRMLTFKFYMPKKATELKHLQCLEEELKPLEEVLN LANSKNFHFDPRDVVSNVNVFVLELKGSETTFMCE YADETATIVEFLNRWITFCQSIISTLT |
| SEQ ID NO: 95 | APTSSSTKKTQLQLEHLLLDLQMVLNGINNYKNPK LTRMLTFKFYMPKKATELKHLQCLEEELKPLEEVL NLASSKNFHFDPRDVVSNINVFVLELKGSETTFMC EYADETATIVEFLNRWITFCQSIISTLT |

TABLE 7-continued

List of Exemplary IL-2 Muteins

| Amino Acid Sequences SEQ ID NO: (Information) | Amino acid sequence |
|---|---|
| SEQ ID NO: 96 | APTSSSTKKTQLQLEHLLLDLQMILNGINNYKNPKL<br>TRMLTFKFYMPKKATELKHLQCLEEELKHLEEVLN<br>LANSKNFHVTPRDVVSNINVFVLELKGSETTFMCE<br>YADETATIVEFLNRWITFCQSIISTLT |
| SEQ ID NO: 97 | APTSSSTKKTQLQLEHLLLDLQMILNGINNYKNPKL<br>TRMLTFKFYMPKKATELKHLQCLEEELKPLEEVLN<br>LAHSKNFHFDPRDVVSNINVFVLELKGSETTFMCE<br>YADETATIVEFLNRWITFCQSIISTLT |
| SEQ ID NO: 98 | APTSSSTKKTQLQLEHLLLDLQMILNGINNYKNPKL<br>TRMLTFKFYMPKKATELKHLQCLEEELKPLEEVLN<br>LASSKNFHFDPRDVVSNINVFVLELKGSETTFMCE<br>YADETATIVEFLNRWITFCQSIISTLT |
| SEQ ID NO: 99 | APTSSSTKKTQLQLEHLLLDLQMILNGINNYKNPKL<br>TRMLTFKFYMPKKATELKHLQCLEEELKPLEEVLN<br>LANSKNFHFDPRDVVSNINVFVLELKGSETTFMCE<br>YADETATIVEFLNRWITFCQSIISTLT |
| SEQ ID NO: 100 | APTSSSTKKTQLQLEHLLLDLQMILNGINNYKNPKL<br>TRMLTFKFYMPKKATELKHLQCLEEELKPLEEVLN<br>LASSKNFHLTPRDVISNINVFVLELKGSETTFMCEY<br>ADETATIVEFLNRWITFCQSIISTLT |
| SEQ ID NO: 101 | APTSSSTKKTQLQLEHLLLDLQMILNGINNYKNPKL<br>TRMLTFKFYMPKKATELKHLQCLEEELKPLEEVLN<br>LAQSKNFHFDPRDVVSNINVFVLELKGSETTFMCE<br>YADETATIVEFLNRWITFCQSIISTLT |
| SEQ ID NO: 102<br>IL-2 agonist | H9D10<br>APTSSSTKKTQLQLEHLLLDLQMILNGINNYKNPKL<br>TRMLTFKFYMPKKATELKHLQCLEEELKPLEEVLN<br>LAHSKNFHFDPRDVVSNINVFVLELKGSETTFMCE<br>YADETATIVEFLNRWITFCQSIISTLT |
| SEQ ID NO: 103<br>IL-2 agonist | H9E10<br>APTSSSTKKTQLQLEHLLLDLQMILNGINNYKNPKL<br>TRMLTFKFYMPKKATELKHLQCLEEELKPLEEVLN<br>LASSKNFHFDPRDVVSNINVFVLELKGSETTFMCEY<br>ADETATIVEFLNRWITFCQSIISTLT |
| SEQ ID NO: 104<br>IL-2 agonist | H9G8<br>APTSSSTKKTQLQLEHLLLDLQMILNGINNYKNPKL<br>TRMLTFKFYMPKKATELKHLQCLEEELKPLEEVLN<br>LANSKNFHFDPRDVVSNINVFVLELKGSETTFMCE<br>YADETATIVEFLNRWITFCQSIISTLT |
| SEQ ID NO: 105<br>IL-2 agonist | H9B1<br>APTSSSTKKTQLQLEHLLLDLQMILNGINNYKNPKL<br>TRMLTFKFYMPKKATELKHLQCLEEELKPLEEVLN<br>LANSKNFHFDPRDVVSNVNVFVLELKGSETTFMCE<br>YADETATIVEFLNRWITFCQSIISTLT |
| SEQ ID NO: 106 | APTSSSTKKTQLQLEHLLLDLQMILNGINNYKNPKL<br>TRMLTFKFYMPKKATELKHLQCLEEELKPLEEVLN<br>LARSKNFHLRPRDLISNINVIVLELKGSETTFMCEY<br>ADETATIVEFLNRWITFCQSIISTLT |
| SEQ ID NO: 107 | APTSSSTKKTQLQLEHLLLDLQMILNGINNYKNPKL<br>TRMLTFKFYMPKKATELKHLQCLEEELKPLEEVLN<br>LARSKNFHLRPRDVISNINVIVLELKGSETTFMCEY<br>ADETATIVEFLNRWITFCQSIISTLT |
| SEQ ID NO: 108 | APTSSSTKKTQLQLEHLLLDLQMILNGINNYKNPKL<br>TRMLTFKFYMPKKATELKHLQCLEEELKPLEEVLN<br>LARSKNFHLIPRDVISNINVIVLELKGSETTFMC-<br>EYA<br>DETATIVEFLNRWITFCQSIISTLT |

TABLE 7-continued

List of Exemplary IL-2 Muteins

Amino Acid Sequences
SEQ ID NO:
(Information)                  Amino acid sequence SEQ ID NO: 109                 APTSSSTKKTQLQLEHLLLDLQMILNGINNYKNPKL
                               TRMLTFKFYMPKKATELKHLQCLEEELKPLEEVLN
                               LA<u>H</u>SKNFHLTPRDVVSNINV<u>F</u>ILELKGSETTFMCEY
                               AD<u>E</u>TATIVEFLNR<u>WI</u>TFCQS<u>II</u>STLT SEQ ID NO: 110                 APTSSSTKKTQLQLEHLLLDLQMILNGINNYKNPKL
H4 (without linker)            TRMLTFKFYMPKKATELKHLQCLEEELKPLEEVLN
                               LA<u>SS</u>KNFHL<u>D</u>PRDV<u>I</u>SNINV<u>F</u>VLELKGSETTFMCEY
                               AD<u>E</u>TATIVEFLNR<u>WI</u>TFCQS<u>II</u>STLT D. Cargo Moieties Cargo moieties reduce or inhibit cancer stem cell growth, or kill cancer cells and/or cancer stem cells. In some examples cargo moieties are not proteins, but other molecules that reduce or inhibit cancer stem cell growth, or kill cancer cells and/or cancer stem cells, such as chemotherapeutic agents. In some examples, cargo moieties also reduce or inhibit bulk cancer cell growth, or kill cancer cells. Any protein or other agent that functions to reduce or inhibit cancer stem cell growth, or kill such cells, can be used as a cargo moiety. For example, toxins and proteins that function to control cell life cycles can be used as cargo moieties. Toxins that can be used as cargo moieties include toxins made by microorganisms, plants or animals, as well as toxins made by human cells. Similarly, any natural cell growth controlling protein can be used as a cargo moiety. For example, proteins that trigger cell death during the normal life cycle of an organism can be used as cargo moieties. In some examples, an oncolytic virus (e.g., see Allen et al., Mol. Ther. 16:1556-64, 2008) or liposomes carrying cytotoxic agents (e.g., see Madhankumar et al., Mol. Cancer. Ther. 5:3162-9, 2006) is used as the cargo protein.

In one example, the cargo moiety is a toxin. Exemplary toxins that can be used include pore-forming toxins, and toxins that upon internalization inhibit cell growth. In other examples, cargo moieties are proteins that are apoptotic triggering proteins, and cell growth inhibiting proteins. In some examples, the toxin is a modified bacterial toxin such that the resulting toxin is less immunogenic than the native toxin. Such modified toxins, such as a modified *Pseudomonas* exotoxin A, can reduce the patient's immunogenic response, thereby allowing repeated administration.

Pore forming toxins are toxins that form pores in the cell membrane thereby killing the cell via cell lyses. Exemplary pore forming toxins include but are not limited to human toxins such as perforin or bacterial toxins such as aerolysin as well as modified pore-forming protein toxins that are derived from naturally occurring pore-forming protein toxins (nPPTs) such as aerolysin or aerolysin-related polypeptides. Suitable aerolysin-related nPPTs have the following features: a pore-forming activity that is activated by removal of an inhibitory domain via protease cleavage, and the ability to bind to receptors that are present on cell membranes through one or more binding domains. In some examples the linker can be engineered to be sensitive to a protease or be chemically liable. Additional examples of pore forming toxins that can be used as cargo moieties include, but are not limited to, proaerolysin from *Aeromonas hydrophila*, *Aeromonas trota* and *Aeromonas salmonicida*, alpha toxin from *Clostridium septicum*, anthrax protective antigen, *Vibrio cholerae* VCC toxin, epsilon toxin from *Clostridium perfringens*, and *Bacillus thuringiensis* delta toxins. A detailed description of the engineering of proaerolysin can be found in U.S. Pat. No. 7,282,476, which is herein incorporated by reference.

Additional toxins that can be used as cargo moieties include toxins that act within a cell. For example, anthrax, diphtheria, cholera, and botulinum toxins include a portion that acts in the cytoplasm, as well as a portion that acts to bind to the cell surface. These toxins, or portions thereof, can be linked to a targeting moiety and used to inhibit cancer stem cell growth. Select members of the ribonuclease A (RNase A) superfamily are potent cytotoxins. These cytotoxic ribonucleases enter the cytosol, where they degrade cellular RNA and cause cell death.

In some examples ribosome inactivating proteins can be used as toxins. In these examples the cargo moiety is a polypeptide having ribosome-inactivating activity including, without limitation, gelonin, bouganin, saporin, ricin, ricin A chain, bryodin, restrictocin, and variants thereof. Diphtheria toxin and *Pseudomonas* exotoxin A inhibit protein synthesis via ADP-ribosylation of elongation factor 2. When the cargo moiety is a ribosome-inactivating protein or inhibits protein synthesis via ADP-ribosylation of elongation factor 2, the IL-4 receptor targeted cargo protein can be internalized upon binding to the cancer stem cell. Cargo moieties that induce apoptosis can also be used to target cancer cells and/or cancer stem cells. Examples of cargo moieties that induce apoptosis include caspases, granzymes and BCL-2 pro-apoptotic related proteins such as BAX (e.g., Accession no: CAE52910), BAD (e.g., Accession no: CAG46757), BAT (e.g., Accession no: AA107425), BAK (e.g., Accession no: AAA74466), BIK (e.g., Accession no: CAG30276), BOK (e.g., Accession no: AAH06203), BID (e.g., Accession no: CAG28531), BIM (e.g., Accession no: NP_619527) and BMF (e.g., Accession no: AAH69328). These cargo moieties can be used alone of in combination to reduce or inhibit cancer stem cell growth.

Aerolysin is a channel-forming toxin produced as an inactive protoxin called proaerolysin (PA). Exemplary aerolysin and PA sequences that can be used in a IL-4 receptor targeted cargo protein are provided in Table 1. The PA protein contains many discrete functionalities that include a binding domain, a toxin domain, and a C-terminal inhibitory peptide domain that contains a protease activation site. The binding domain recognizes and binds to glycophosphatidylinositol (GPI) membrane anchors, such as are found in Thy-1 on T lymphocytes, the PIGA gene product found in erythrocyte membranes and Prostate Stem Cell Antigen (PSCA). The activation or proteolysis site within proaerolysin is a six amino acid sequence that is recognized as a proteolytic substrate by the furin family of proteases. PA is activated upon hydrolysis of a C-terminal inhibitory segment by furin. Activated aerolysin binds to GPI-anchored proteins in the cell membrane and forms a heptamer that inserts into the membrane producing well-defined channels of about .17 angstroms. Channel formation leads to rapid cell death. Wild-type aerolysin is toxic to mammalian cells, including erythrocytes, for example at 1 nanomolar or less.

In some examples, a target cargo protein is an PA molecule with the native furin site replaced with a different cleavage site, such as prostate-specific protease cleavage site (e.g., a PSA-specific cleavage site, which permits activation of the variant PA in the presence of a prostate-specific protease such as PSA, PMSA, or HK2). In one example, a prostate-specific protease cleavage site is inserted into the native furin cleavage site of PA, such that PA is activated in the presence of a prostate-specific protease, but not furin. In another example, a variant PA molecule further includes a functionally deleted binding domain (e.g., about amino acids 1-83 of a native PA protein sequence). Functional deletions can be made using any method known in the art, such as deletions, insertions, mutations, or substitutions. In some examples, IL-4 receptor targeted cargo proteins include variant PA molecules in which the native binding domain is functionally deleted and replaced with a prostate-tissue or other tissue-specific binding domain. In other examples, variant PA molecules include a furin cleavage site and a functionally deleted binding domain which is replaced with a prostate-tissue specific binding domain. Such variant PA molecules are targeted to prostate cells via the prostate-tissue specific binding domain, and activated in the presence of furin.

Bouganin is a ribosome-binding protein originally isolated from *Bougainvillea speotabilis* (see U.S. Pat. No. 6,680,296). Exemplary modified bouganins are described in WO 2005/090579 and U.S. Pat. No. 7,339,031. Bouganin damages ribosomes and leads to a cessation of protein synthesis and cell death. Exemplary bouganin proteins that can be used in the IL-4 receptor targeted cargo proteins of the present disclosure include those in GenBank Accession No. AAL35962, as well as those native and modified bouganin sequences provided in U.S. Pat. Nos. 6,680,296; 7,339,031 and PCT publication WO 2005/090579 (bouganin sequences herein incorporated by reference), as well as sequences having at least 60% sequence identity, at least 75%, at least 80%, at least 85%, at least 90%, at least 95%, at least 98% or even at least 99% sequence identity to such sequences. BAD, BCL2-associated agonist of cell death, is a regulator of programmed cell death (apoptosis). BAD positively regulates cell apoptosis by forming heterodimers with BCL-xL and BCL-2, and reversing their death repressor activity. Proapoptotic activity of BAD is regulated through its phosphorylation. Exemplary BAD proteins that can be used in the IL-4 receptor targeted cargo proteins of the present disclosure include those in GenBank Accession Nos. CAG46757; AAH01901.1; and CAG46733.1, as well as those sequences provided in U.S. Pat. No. 6,737,511 (sequences herein incorporated by reference), as well as sequences having at least 60% sequence identity, at least 75%, at least 80%, at least 85%, at least 90%, at least 95%, at least 98% or even at least 99% sequence identity to such sequences, as long as the variant retains or has enhanced biological activity of the native BAD protein.

BAX, BCL2-associated X protein, is a regulator of programmed cell death (apoptosis). This protein forms a heterodimer with BCL2, and functions as an apoptotic activator. BAX interacts with, and increases the opening of, the mitochondrial voltage-dependent anion channel (VDAC), which leads to the loss in membrane potential and the release of cytochrome c. Exemplary BAX proteins that can be used in the IL-4 receptor targeted cargo proteins of the present disclosure include those provided by GenBank Accession Nos. CAE52909.1; AA022992.1; EAW52418.1, U.S. Pat. No. 6,645,490 (Bax in the IL2-Bax construct is a Bax-alpha variant that can be used in the present disclosure), as well as sequences having at least 60% sequence identity, at least 75%, at least 80%, at least 85%, at least 90%, at least 95%, at least 98% or even at least 99% sequence identity to such sequences, as long as the variant retains or has enhanced biological activity of the native BAX protein.

In some examples, the BAX protein of a IL-4 receptor targeted cargo protein may be modified such that the C-terminal anchor domain has been deleted and replaced with a CaaX sequence. CaaX is a peptide with the sequence Cysteine-a-a-X where "X" is any amino acid and "a" is an aliphatic amino acid. Because membrane association of BAX is needed for optimal apoptosis activity, addition of membrane binding domains such as CaaX can enhance their pro-apoptotic activities. Proteins with CaaX sequence are farnesylated. Farnesylated proteins are targeted to membranes (e.g., see Wright and Philip, J. Lipid Res., 2006, 47(5): 883-91). Potential BAX variants containing a CaaX sequence may or may not contain the C-terminal anchor domain.

*Pseudomonas* exotoxin (PE) is a toxin secreted by *Pseudomonas*. Native PE is cytotoxic for mammalian cells due to its ability to enter cells by receptor-mediated endocytosis and then, after a series of intracellular processing steps, translocate to the cell cytosol and ADP-ribosylate elongation factor 2. This results in the inhibition of protein synthesis and cell death. PE has three functional domains: an amino-terminal receptor-binding domain, a middle translocation domain, and a carboxyl-terminal ADP-ribosylation domain. Modified PE molecules can include elimination of domain Ia, as well as deletions in domains II and III. Exemplary PE proteins that can be used in the IL-4 receptor targeted cargo proteins of the present disclosure include those provided in Table 1, as well as sequences having at least 60% sequence identity, at least 75%, at least 80%, at least 85%, at least 90%, at least 95%, at least 98% or even at least 99% sequence identity to such sequences, as long as the variant retains or has enhanced biological activity of the native PE protein.

Thapsigargin is an inhibitor of sarco/endoplasmic reticulum Ca2+ ATPases. Thapsigargin is classified as a sesquiterpene lactone, and raises cytosolic calcium concentration by blocking the ability of the cell to pump calcium into the sarcoplasmic and endoplasmic reticulum which causes these stores to become depleted. Store-depletion can secondarily activate plasma membrane calcium channels, allowing an influx of calcium into the cytosol.

Ribonuclease A (RNAseA) is an endonuclease that cleaves single-stranded RNA. RNAse A toxins can be obtained from mammals and reptiles. Exemplary RNAse A proteins that can be used in the IL-4 receptor targeted cargo proteins of the present disclosure include those provided in Table 1, as well as sequences having at least 60% sequence identity, at least 75%, at least 80%, at least 85%, at least 90%, at least 95%, at least 98% or even at least 99% sequence identity to such sequences, as long as the variant retains or has enhanced biological activity of the native RNAseA toxin.

The cargo moiety used can include native sequences (such as the GenBank Accession Nos. and sequences present in the patents referenced in Table 1 and listed above), as well as variants thereof, such as a variant having at least 98%, at least 95%, at least 90%, at least 80%, at least 70%, or at least 60% sequence identity with the native cargo moiety, as long as the variant retains or has enhanced biological activity of the native cargo moiety (e.g., at least about this amount of sequence identity to the GenBank Accession Nos. listed in Table 1 and listed above). In some examples, variant sequences retain substantially the same amount (or even more) of the native biological function of the cargo moiety, such as the ability to kill or inhibit the growth of a cancer stem cell. A cargo moiety can also be a fragment of the native sequence that retains a substantial amount of the native biological function of the protein.

The cargo moieties are engineered to target cancer cells and/or cancer stem cells by linking them to targeting moieties. Targeting moieties include agents that can bind to cancer stem cell surface targets.

E. Oncolytic Viruses

A variety of oncolytic viruses can be used with the methods according to the present invention. In some examples, oncolytic viruses described below can be employed to target and/or deliver the IL-4 targeted cargo moieties of the present invention. In some examples, the IL-4 targeted cargo moieties of the present invention can be employed to target an oncolytic virus (e.g., see Allen et al., Mol. Ther. 16:1556-64, 2008). Numerous virus can be employed as the oncolytic virus, including adenoviruses as well as self-replicating alphavirus such for example those provided in FIG. 17, as well as oncolytic vaccinia viruses (see, for example WO2013038066, incorporated herein by reference in its entirety), and oncolytic rhabdovirus.

Other oncolytic viruses can include Seneca Valley Virus, Newcastle disease Virus (also referred to as Newcastle virus), Maraba virus, VSV, Herpes virus (including HSV-1), Measles virus, poliovirus, reovirus, coxsackie virus, a lentivirus, a morbillivirus, an influenza virus, Sinbis virus, myxoma virus, and/or retrovirus (see, for example, Twumasi-Boateng, et al., "Oncolytic viruses as engineering platforms for combination immunotherapy", Nature Reviews Cancer, 2018), and Kaufman et al., Cancer Immunotherapy, 14:642-662 (2015), all of which are incorporated by reference herein their entireties). In some embodiments, the oncolytic virus includes but is not limited to an adenovirus, a self-replicating alphavirus, a vaccinia virus, a Seneca Valley Virus, a Newcastle disease Virus, vesicular stomatitis virus (VSV), a Herpes virus (including HSV-1 and HSV-2), a measles virus, a poliovirus, a reovirus, a coxsackie virus, a lentivirus, a morbillivirus, an influenza virus, Sinbis virus, myxoma virus, and/or a retrovirus.

Other oncolytic viruses can include, for example, oncoVex/T-VEC, which involves the intratumoral injection of replication-conditional herpes simplex virus which preferentially infects cancer cells. The virus, which is also engineered to express GM-CSF, is able to replicate inside a cancer cell causing its lysis, releasing new viruses and an array of tumor antigens, and secreting GM-CSF in the process. Such oncolytic virus vaccines enhance DCs function in the tumor microenvironment to stimulate anti-tumor immune responses.

Any of the oncolytic viruses described herein can be used to target or deliver the IL-4 and/or IL-13 muteins described herein to the tumor. In some embodiments, the IL-4 and/or IL-13 mutein is any IL-4 and/or IL-13 mutein or variant disclosed herein. In some embodiments, the IL-4 and/or IL-13 mutein sequence is 90% identical to any one of SEQ ID NO:2-SEQ ID NO:48 and/or SEQ ID NO:51-SEQ ID NO:69. In some embodiments, the IL-4 and/or IL-13 mutein incudes any one of SEQ ID NO:2-SEQ ID NO:48 and/or SEQ ID NO:51-SEQ ID NO:69. In some embodiments, the oncolytic virus comprises a transgene capable of expressing an IL-4 and/or IL-13 mutein as described herein. In some embodiments, the oncolytic virus comprises a transgene capable of expressing an IL-4 and/or IL-13 mutein comprising any one of SEQ ID NO:2-SEQ ID NO:48 and/or SEQ ID NO:51-SEQ ID NO:69. In some embodiments, the oncolytic virus comprises a nucleic acid encoding an IL-4 and/or IL-13 mutein comprising any one of SEQ ID NO:2-SEQ ID NO:48 and/or SEQ ID NO:51-SEQ ID NO:69. In some embodiments, the oncolytic virus comprises a transgene that is expressed as a therapeutic payload. In some embodiments, the therapeutic payload is an IL-4 and/or IL-13 as described herein. In some embodiments, the therapeutic payload is IL-4 and/or IL-13 mutein comprises any one of SEQ ID NO:2-SEQ ID NO:48 and/or SEQ ID NO:51-SEQ ID NO:69. In some embodiments, an IL-13 Rα2 targeting moeity could be used as a targeting moeity and an IL-2 mutein could be the transgene expressed by the oncolytic virus.

Any of the oncolytic viruses described herein can include an IL-4R targeting moiety. In some embodiments, the IL-4R targeting moiety comprises an IL-4 sequence or variant thereof that targets immunosuppressive cells of the TME (tumor microenvironment) such as tumor associated macrophages and MDSCs (myeloid-derived suppressor cells) in order for oncolytic viruses to provide an improved therapeutic benefit. In some embodiments, the IL-4R targeting moiety comprises any one of IL-13 and/or IL-4 sequences as described herein. In some embodiments, the IL-4R targeting moiety comprises any one of SEQ ID NO:2-SEQ ID NO:48 and/or SEQ ID NO:51-SEQ ID NO:69. In some embodiments, IL-4R targeting moiety comprises an IL-13 variant/IL-13 superkine including those targeting Type 2 IL4R and/or targeting IL13Rα2 which can direct the oncolytic viruses to tumor antigens. In some embodiments, the IL-4R targeting moiety comprises an IL-13 variant/IL-13 superkine including any one of those provided in SEQ ID NO:2-SEQ ID NO:48, SEQ ID NO:56, SEQ ID NO:57, and/or SEQ ID NO:63, can also direct the oncyltic viruses to tumor antigens. In some embodiments, the oncolytic virus is targeted by one cytokine and expresses another cytokine. In some embodiments, the oncolytic virus comprises a transgene that is expressed as a therapeutic payload. In some embodiments, the therapeutic payload expressed is any one of the IL-4 sequence as described herein. In some embodiments, the the therapeutic payload expressed is any one of the IL-13 sequence as described herein.

In some embodiments, the oncolytic virus is an oncolytic vaccinia virus. In some embodiments, the oncolytic vaccinia virus vector is characterized in that the virus particle is of the type intracellular mature virus (IMV), intracellular enveloped virus (IEV), cell-associated enveloped virus (CEV), or extracellular enveloped virus (EEV). In some embodiments, the oncolytic vaccinia virus particle is of the type EEV or IMV. In some embodiments, the oncolytic vaccinia virus particle is of the type EEV.

The current disclosure provides construction of recombinant oncolytic vectors and the virus encoded by such vectors, which preferentially replicate in tumor cells and express at least one transgene to facilitate antitumor efficacy, induce apoptosis induction and modulate host immune responses in a subject. The current disclosure also provides cells and pharmaceutical compositions containing such recombinant oncolytic virus. Accordingly, oncolytic viruses, such as but is not limited to, adenoviruses, rhabdovirus virus and oncolytic vaccinia viruses can be combined with any one or more of the IL-4 and/or IL-13 targeting moieties as described herein in order to target the oncolytic virus. Oncolysis releases tumor antigens and provides costimulatory danger signals. However, arming the virus can improve efficacy further. For example, CD40 ligand (CD40L, CD154) is known to induce apoptosis of tumor cells and it also triggers several immune mechanisms. One of these is a T-helper type 1 (Th1) response that leads to activation of cytotoxic T-cells and reduction of immune suppression. The present invention provides for oncolytic viruses that are targeted (for example, "armed") with the IL-4 and/or IL-13 targeting moieties.

In some embodiments, this invention provides a modified vaccinia virus vector, a virus particle, a host cell, a pharmaceutical composition and a kit comprising vaccinia virus genome wherein the thymidine kinase gene is inactivated by either a substitution in the thymidine kinase (TK) gene and/or an open reading frame ablating deletion of at least one nucleotide providing a partially deleted thymidine kinase gene, and the vaccinia growth factor gene is deleted, and wherein the modified vaccinia virus vector comprises at least one nucleic acid sequence encoding a non-viral protein (e.g., an IL-4 and/or IL-13 targeting moiety as described herein). Such modified vaccinia virus vector, the virus particle, the pharmaceutical composition or the kit can be used for cancer therapy, for eliciting immune response in a subject, for use in a method of inhibiting malignant cell proliferation in a mammal, for use in a therapy or prophylaxis of cancer, for detecting the presence of the modified vaccinia virus in a subject, and as an in situ cancer vaccine, optionally in combination with other oncolytic virus, such as but is not limited to an adenovirus or rhabdovirus virus. In some embodiments, the invention provides method of producing a modified vaccinia virus comprising vaccinia virus genome wherein the thymidine kinase gene is inactivated by a substitution in the thymidine kinase (TK) gene and/or an open reading frame ablating deletion of at least one nucleotide providing a partially deleted thymidine kinase gene, and the vaccinia growth factor gene is deleted, and wherein the modified vaccinia virus vector comprises at least one nucleic acid sequence encoding a non-viral protein (e.g., an IL-4 and/or IL-13 targeting moiety as described herein), the method comprising the steps of providing producer cells capable of sustaining production of vaccinia virus particles and carrying the modified vaccinia vector; culturing the producer cells in conditions suitable for virus replication and production; and harvesting the virus particles.

In some embodiments, this invention provides a modified adenovirus vector, a virus particle, a host cell, a pharmaceutical composition and a kit comprising such modified adenovirus vector, wherein the modified adenovirus vector comprises at least one nucleic acid sequence encoding a non-viral protein (e.g., an IL-4 and/or IL-13 targeting moiety as described herein) and optionally wherein the nucleotides encoding amino acids 122-129 of the encoded E1A polypeptide of the adenovirus vector are deleted. Such modified adenovirus virus vector, the virus particle, the pharmaceutical composition or the kit can be used for cancer therapy, for eliciting immune response in a subject, for use in a method of inhibiting malignant cell proliferation in a mammal, for use in a therapy or prophylaxis of cancer, for detecting the presence of the modified adenovirus virus in a subject, and as an in situ cancer vaccine, optionally in combination with other oncolytic virus, such as but is not limited to a rhabdovirus or vaccinia virus. In some embodiments, the invention provides method of producing a modified adenovirus virus vector comprising at least one nucleic acid sequence encoding a non-viral protein (e.g., an IL-4 and/or IL-13 targeting moiety as described herein), the method comprising the steps of providing producer cells capable of sustaining production of adenovirus virus particles and carrying the modified adenovirus virus vector; culturing the producer cells in conditions suitable for virus replication and production; and harvesting the virus particles.

In some embodiments, this invention provides a modified rhabdovirus virus vector, a virus particle, a host cell, a pharmaceutical composition and a kit comprising such modified rhabdovirus virus vector, wherein the modified rhabdovirus virus vector comprises at least one nucleic acid sequence encoding a non-viral protein (e.g., an IL-4 and/or IL-13 targeting moiety as described herein) inserted therein. Such modified rhabdovirus virus vector, the virus particle, the pharmaceutical composition or the kit can be used for cancer therapy, for eliciting immune response in a subject, for use in a method of inhibiting malignant cell proliferation in a mammal, for use in a therapy or prophylaxis of cancer, for detecting the presence of the modified rhabdovirus virus in a subject, and as an in situ cancer vaccine, optionally in combination with other oncolytic virus, such as but is not limited to an adenovirus or vaccinia virus. In some embodiments, the invention provides method of producing a modified rhabdovirus virus vector comprising at least one nucleic acid sequence encoding a non-viral protein (e.g., an IL-4 and/or IL-13 targeting moiety as described herein), the method comprising the steps of providing producer cells capable of sustaining production of rhabdovirus virus particles and carrying the modified rhabdovirus virus vector; culturing the producer cells in conditions suitable for virus replication and production; and harvesting the virus particles.

Generally, the present invention also provides methods of administering an oncolytic virus "armed" or targeted with an IL-4 and/or IL-13 moiety as described herein. The routes of administration vary, naturally, with the location and nature of the tumor, and include, e.g., intradermal, transdermal, parenteral, intravenous, intramuscular, intranasal, subcutaneous, regional (e.g., in the proximity of a tumor, particularly with the vasculature or adjacent vasculature of a tumor), percutaneous, intratracheal, intraperitoneal, intraarterial, intravesical, intratumoral, inhalation, perfusion, lavage, and oral administration. Compositions are formulated relative to the particular administration route.

1. Oncolytic Vaccinia Virus

Vaccinia virus is a member of the Orthopoxvirus genus of the Poxviridae. It has large double-stranded DNA genome (~200 kb, ~200 genes) and a complex morphogenic pathway produces distinct forms of infectious virions from each infected cell. Viral particles contain lipid membranes(s) around a core. Virus core contains viral structural proteins, tightly compacted viral DNA genome, and transcriptional enzymes. Dimensions of vaccinia virus are ~360×270×250 nm, and weight of ~5-10 fg. Genes are tightly packed with little non-coding DNA and open-reading frames (ORFs) lack introns. Three classes of genes (early, intermediate, late) exists. Early genes (~100 genes; immediate and delayed) code for proteins mainly related to immune modulation and virus DNA replication. Intermediate genes code for regulatory proteins which are required for the expression of late genes (e.g. transcription factors) and late genes code for proteins required to make virus particles and enzymes that are packaged within new virions to initiate the next round of infection. Vaccinia virus replicates in the cell cytoplasm.

Different strains of vaccinia viruses have been identified (as an example: Copenhagen, modified virus Ankara (MVA), Lister, Tian Tan, Wyeth (New York City Board of Health), Western Reserve (WR)). The genome of WR vaccinia has been sequenced (Accession number AY243312). In some embodiments, the oncolytic vaccinia virus is a Copenhagen, modified virus Ankara (MVA), Lister, Tian Tan, Wyeth, or Western Reserve (WR) vaccinia virus.

Different forms of viral particles have different roles in the virus life cycle Several forms of viral particles exist: intracellular mature virus (IMV), intracellular enveloped virus (IEV), cell-associated enveloped virus (CEV), extracellular enveloped virus (EEV). EEV particles have an extra membrane derived from the trans-Golgi network. This outer membrane has two important roles: a) it protects the internal IMV from immune aggression and, b) it mediates the binding of the virus onto the cell surface.

CEVs and EEVs help virus to evade host antibody and complement by being wrapped in a host-derived membrane. IMV and EEV particles have several differences in their biological properties and they play different roles in the virus life cycle. EEV and IMV bind to different (unknown) receptors (1) and they enter cells by different mechanisms. EEV particles enter the cell via endocytosis and the process is pH sensitive. After internalization, the outer membrane of EEV is ruptured within an acidified endosome and the exposed IMV is fused with the endosomal membrane and the virus core is released into the cytoplasm. IMV, on the other hand, enters the cell by fusion of cell membrane and virus membrane and this process is pH-independent. In addition to this, CEV induces the formation of actin tails from the cell surface that drive virions towards uninfected neighboring cells.

Furthermore, EEV is resistant to neutralization by antibodies (NAb) and complement toxicity, while IMV is not. Therefore, EEV mediates long range dissemination in vitro and in vivo. Comet-inhibition test has become one way of measuring EEV-specific antibodies since even if free EEV cannot be neutralized by EEV NAb, the release of EEV from infected cells is blocked by EEV NAb and comet shaped plaques cannot be seen. EEV has higher specific infectivity in comparison to IMV particles (lower particle/pfu ratio) which makes EEV an interesting candidate for therapeutic use. However, the outer membrane of EEV is an extremely fragile structure and EEV particles need to be handled with caution which makes it difficult to obtain EEV particles in quantities required for therapeutic applications. EEV outer membrane is ruptured in low pH (pH ~6). Once EEV outer membrane is ruptured, the virus particles inside the envelope retain full infectivity as an IMV.

Some host-cell derived proteins co-localize with EEV preparations, but not with IMV, and the amount of cell-derived proteins is dependent on the host cell line and the virus strain. For instance, WR EEV contains more cell-derived proteins in comparison to VV IHD-J strain. Host cell derived proteins can modify biological effects of EEV particles. As an example, incorporation of the host membrane protein CD55 in the surface of EEV makes it resistance to complement toxicity. In the present invention it is shown that human A549 cell derived proteins in the surface of EEV particles may target virus towards human cancer cells. Similar phenomenon has been demonstrated in the study with human immunodeficiency virus type 1, where host-derived ICAM-1 glycoproteins increased viral infectivity. IEV membrane contains at least 9 proteins, two of those not existing in CEV/EEV. F12L and A36R proteins are involved in IEV transport to the cell surface where they are left behind and are not part of CEV/EEV (9, 11). 7 proteins are common in (IEV)/CEV/EEV: F13L, A33R, A34R, A56R, B5R, E2, (K2L). For Western Reserve strain of vaccinia virus, a maximum of 1% of virus particles are normally EEV and released into the culture supernatant before oncolysis of the producer cell. 50-fold more EEV particles are released from International Health Department (IHD)-J strain of vaccinia. IHD has not been studied for use in cancer therapy of humans however. The IHD-W phenotype was attributed largely to a point mutation within the A34R EEV lectin-like protein. Also, deletion of A34R increases the number of EEVs released. EEV particles can be first detected on cell surface 6 hours post-infection (as CEV) and 5 hours later in the supernatant (IHD-J strain). Infection with a low multiplicity of infection (MOI) results in higher rate of EEV in comparison to high viral dose. The balance between CEV and EEV is influenced by the host cell and strain of virus.

Vaccinia has been used for eradication of smallpox and later, as an expression vector for foreign genes and as a live recombinant vaccine for infectious diseases and cancer. Vaccinia virus is the most widely used pox virus in humans and therefore safety data for human use is extensive. During worldwide smallpox vaccination programs, hundreds of thousands humans have been vaccinated safety with modified vaccinia virus strains and only very rare severe adverse events have been reported. Those are generalized vaccinia (systemic spread of vaccinia in the body), erythema multiforme (toxic/allergic reaction), eczema vaccinatum (widespread infection of the skin), progressive vaccinia (tissue destruction), and postvaccinia! encephalitis.

All together 44 melanoma patients have been treated in early clinical trials with wild type vaccinia virus in 1960s-1990s and the overall objective response rate of injected tumors was 50%. Also some beneficial immunological responses were seen (36). Wild type vaccinia virus has been used also for treatment of bladder cancer, lung and kidney cancer, and myeloma and only mild adverse events were seen. JX-594, an oncolytic Wyeth strain vaccinia virus coding for GM-CSF, has been successfully evaluated in three phase I studies and preliminary results from randomized phase II trial has been presented in the scientific meeting.

Vaccinia virus is appealing for cancer gene therapy due to several characteristics. It has natural tropism towards cancer cells and the selectivity can be significantly enhanced by deleting some of the viral genes. The present invention relates to the use of double deleted vaccinia virus (vvdd) in which two viral genes, viral thymidine kinase (TK) and vaccinia growth factor (VGF), are at least partially deleted. TK and VGF genes are needed for virus to replicate in normal but not in cancer cells. The partial TK deletion may be engineered in the TK region conferring activity.

TK deleted vaccinia viruses are dependent on cellular nucleotide pool present in dividing cells for DNA synthesis and replication. In some embodiments, the TK deletion limits virus replication significantly in resting cells allowing efficient virus replication to occur only in actively dividing cells (e.g., cancer cells). VGF is secreted from infected cells and has a paracrine priming effect on surrounding cells by acting as a mitogen. Replication of VGF deleted vaccinia viruses is highly attenuated in resting (non-cancer) cells. The effects of TK and VGF deletions have been shown to be synergistic.

2. Oncolytic Adenovirus

Generally, adenovirus is a 36 kb, linear, double-stranded DNA virus (Grunhaus and Horwitz, 1992). The term "adenovirus" or "AAV" includes AAV type 1 (AAV1), AAV type 2 (AAV2), AAV type 3 (AAV3), AAV type 4 (AAV4), AAV type 5 (AAV5), AAV type 6 (AAV6), AAV type 7 (AAV7), AAV type 8 (AAV8), AAV type 9 (AAV9), AAV 9_hu14, avian AAV, bovine AAV, canine AAV, equine AAV, primate AAV, non-primate AAV, and ovine AAV. "Primate AAV" refers to AAV capable of infecting primates, "non-primate AAV" refers to AAV capable of infecting non-primate mammals, "bovine AAV" refers to AAV capable of infecting bovine mammals, etc.

Adenoviral infection of host cells results in adenoviral DNA being maintained episomally, which reduces the potential genotoxicity associated with integrating vectors. Also, adenoviruses are structurally stable, and no genome rearrangement has been detected after extensive amplification Adenovirus can infect virtually all epithelial cells regardless of their cell cycle stage. (See, for example, US20060147420, incorporated by reference herein in its entirety.) Moreover, the E1a and E4 regions of adenovirus are essential for an efficient and productive infection of human cells. The E1a gene is the first viral gene to be transcribed in a productive infection, and its transcription is not dependent on the action of any other viral gene products. However, the transcription of the remaining early viral genes requires E1a gene expression. The E1a promoter, in addition to regulating the expression of the E1a gene, also integrates signals for packaging of the viral genome as well as sites required for the initiation of viral DNA replication. See, Schmid, S. I., and Hearing, P. in Current Topics in Microbiology and Immunology, vol. 199: pages 67-80 (1995).

In some embodiments, the oncolytic virus is an oncolytic adenovirus. It has been established that naturally occurring viruses can be engineered to produce an oncolytic effect in tumor cells (Wildner, 2001; Jacotat, 1967; Kim, 2001; Geoerger et al., 2002; Yan et al., 2003; Vile et al., 2002, each of which is incorporated herein by reference). In the case of adenoviruses, specific deletions within their adenoviral genome can attenuate their ability to replicate within normal quiescent cells, while they retain the ability to replicate in tumor cells. One such conditionally replicating adenovirus, A24, has been described by Fueyo et al. (2000), see also U.S. Patent Application No. 20030138405, each of which are incorporated herein by reference. The A24 adenovirus is derived from adenovirus type 5 (Ad-5) and contains a 24-base-pair deletion within the CR2 portion of the E1A gene. See, for example WO2001036650A2 (incorporated by reference herein in its entirety.

Oncolytic adenoviruses include conditionally replicating adenoviruses (CRADs), such as Delta 24, which have several properties that make them candidates for use as biotherapeutic agents. One such property is the ability to replicate in a permissive cell or tissue, which amplifies the original input dose of the oncolytic virus and helps the agent spread to adjacent tumor cells providing a direct antitumor effect.

In some embodiments, the oncolytic component of Delta 24 with a transgene expression approach to produce an armed Delta 24. Armed Delta 24 adenoviruses may be used for producing or enhancing bystander effects within a tumor and/or producing or enhancing detection/imaging of an oncolytic adenovirus in a patient, or tumor associated tissue and/or cell. In some embodiments, the combination of oncolytic adenovirus with various transgene strategies (e.g., targeting with an IL-4 and/or IL-13 moiety) will improve the therapeutic potential, including for example, potential against a variety of refractory tumors, as well as provide for improved imaging capabilities. In certain embodiments, an oncolytic adenovirus may be administered with a replication defective adenovirus, another oncolytic virus, a replication competent adenovirus, and/or a wildtype adenovirus. Each of which may be adminstered concurrently, before or after the other adenoviruses.

In some embodiments, an E1a adenoviral vectors involves the replacement of the basic adenovirus E1a promoter, including the CAAT box, TATA box and start site for transcription initiation, with a basic promoter that exhibits tumor specificity, and preferably is E2F responsive, and more preferably is the human E2F-1 promoter. Thus, this virus will be repressed in cells that lack molecules, or such molecules are non functional, that activate transcription from the E2F responsive promoter. Normal non dividing, or quiescent cells, fall in this class, as the transcription factor, E2F, is bound to pRb, or retinoblastoma protein, thus making E2F unavailable to bind to and activate the E2F responsive promoter. In contrast, cells that contain free E2F should support E2F based transcription. An example of such cells are neoplastic cells that lack pRb function, allowing for a productive viral infection to occur. In some embodiments, an E1a adenoviral vector is targeted use an IL-4 and/or IL-13 moiety as described herein.

Retention of the enhancer sequences, packaging signals, and DNA replication start sites which lie in the E1a promoter will ensure that the adenovirus infection proceeds to wild type levels in the neoplastic cells that lack pRb function. In essence, the modified E1a promoter confers tumor specific transcriptional activation resulting in substantial tumor specific killing, yet provides for enhanced safety in normal cells.

In some embodiments, an E1a adenoviral vector is prepared by substituting the endogenous E1a promoter with the E2F responsive promoter, the elements upstream of nucleotide 375 in the adenoviral 5 genome are kept intact. The nucleotide numbering is as described by See, Schmid, S. I., and Hearing, P. Current Topics in Microbiology and Immunology, vol. 199: pages 67-80 (1995). This includes all of the seven A repeat motifs identified for packaging of the viral genome (See FIG. 2 of Schmid and Hearing, above.) Sequences from nucleotide 375 to nucleotide 536 are deleted by a BsaAI to BsrBI restriction start site, while still retaining 23 base pairs upstream of the translational initiation codon for the E1A protein. An E2F responsive promoter, preferably human E2F-1 is substituted for the deleted endogenous E1a promoter sequences using known materials and methods. The E2F-1 promoter may be isolated as described in Example 1.

The E4 region has been implicated in many of the events that occur late in adenoviral infection, and is required for efficient viral DNA replication, late mRNA accumulation and protein synthesis, splicing, and the shutoff of host cell protein synthesis. Adenoviruses that are deficient for most of the E4 transcription unit are severely replication defective and, in general, must be propagated in E4 complementing cell lines to achieve high titers. The E4 promoter is positioned near the right end of the viral genome and governs the transcription of multiple open reading frames (ORF). A number of regulatory elements have been characterized in this promoter that are critical for mediating maximal transcriptional activity.

In addition to these sequences, the E4 promoter region contains regulatory sequences that are required for viral DNA replication. A depiction of the E4 promoter and the position of these regulatory sequences can be seen in FIGS. 2 and 3 of U.S. Pat. No. 7,001,596, incorporated by reference herein in it entirety.

In some embodiments, the adenoviral vector that has the E4 basic promoter substituted with one that has been demonstrated to show tumor specificity, preferably an E2F responsive promoter, and more preferably the human E2F-1 promoter. The reasons for preferring an E2F responsive promoter to drive E4 expression are the same as were discussed above in the context of an E1a adenoviral vector having the E1a promoter substituted with an E2F responsive promoter. The tumor suppressor function of pRb correlates with its ability to repress E2F-responsive promoters such as the E2F-1 promoter (Adams, P. D., and W. G. Kaelin, Jr. 1995, Cancer Biol. 6:99-108; Sellers, W. R., and W. G. Kaelin. 1996, published erratum appears in Biochim Biophys Acta 1996 Dec. 9; 1288(3):E-1, Biochim Biophys Acta. 1288:M1-5. Sellers, W. R., J. W. Rodgers, and W. G. Kaelin, Jr. 1995, Proc Natl Acad Sci USA. 92:11544-8.) The human E2F-1 promoter has been extensively characterized and shown to be responsive to the pRb signaling pathway, including pRb/p107, E2F-1/-2/-3, and G1 cyclin/cdk complexes, and E1A (Johnson, D. G., K. Ohtani, and J. R. Nevins. 1994, Genes Dev. 8:1514-25; Neuman, E., E. K. Flemington, W. R. Sellers, and W. G. Kaelin, Jr. 1995. Mol Cell Biol. 15:4660; Neuman, E., W. R. Sellers, J. A. McNeil, J. B. Lawrence, and W. G. Kaelin, Jr. 1996, Gene. 173:163-9.) Most, if not all, of this regulation has been attributed to the presence of multiple E2F sites present within the E2F-1 promoter. Hence, a virus carrying this (these) modification (s) would be expected to be attenuated in normal cells that contain an intact (wild type) pRb pathway, yet exhibit a normal infection/replication profile in cells that are deficient for pRb's repressive function. In order to maintain the normal infection/replication profile of this mutant virus we have retained the inverted terminal repeat (ITR) at the distal end of the E4 promoter as this contains all of the regulatory elements that are required for viral DNA replication (Hatfield, L. and P. Hearing. 1993, J. Virol. 67:3931-9; Rawlins, D. R., P. J. Rosenfeld, R. J. Wides, M. D. Challberg, and T. J. Kelly, Jr. 1984, Cell. 37:309-19; Rosenfeld, P. J., E. A. O'Neill, R. J. Wides, and T. J. Kelly. 1987, Mol Cell Biol. 7:875-86; Wides, R. J., M. D. Challberg, D. R. Rawlins, and T. J. Kelly. 1987, Mol Cell Biol. 7:864-74). This facilitates attaining wild type levels of virus in pRb pathway deficient tumor cells infected with this virus.

In some embodiments, the E4 promoter is positioned near the right end of the viral genome and it governs the transcription of multiple open reading frames (ORFs) (Freyer, G. A., Y. Katoh, and R. J. Roberts. 1984, Nucleic Acids Res. 12:3503-19; Tigges, M. A., and H. J. Raskas. 1984. Splice junctions in adenovirus 2 early region 4 mRNAs: multiple splice sites produce 18 to 24 RNAs. J. Virol. 50:106-17; Virtanen, A. P. Gilardi, A. Naslund, J. M. LeMoullec, U. Pettersson, and M. Perricaudet. 1984, J. Virol. 51:822-31.) A number of regulatory elements have been characterized in this promoter that mediate transcriptional activity (Berk, A. J. 1986, Annu Rev Genet. 20:45-79; Gilardi, P., and M. Perricaudet. 1986, Nucleic Acids Res. 14:9035-49; Gilardi, P., and M. Perricaudet. 1984, Nucleic Acids Res. 12:7877-88; Hanaka, S., T. Nishigaki, P. A. Sharp, and H. Handa. 1987, Mol Cell Biol. 7:2578-87; Jones, C., and K. A. Lee. 1991, Mol Cell Biol. 11:4297-305; Lee, K. A., and M. R. Green. 1987, Embo J. 6:1345-53.) In addition to these sequences, the E4 promoter region contains elements that are involved in viral DNA replication (Hatfield, L., and P. Hearing. 1993, J Virol. 67:3931-9; Rawlins, D. R., P. J. Rosenfeld, R. J. Wides, M. D. Challberg, and T. J. Kelly, Jr. 1984, Cell. 37:309-19; Rosenfeld, P. J., E. A. O'Neill, R. J. Wides, and T. J. Kelly. 1987, Mol Cell Biol. 7:875-86; Wides, R. J., M. D. Challberg, D. R. Rawlins, and T. J. Kelly. 1987, Mol Cell Biol. 7:864-74.) A depiction of the E4 promoter and the position of these regulatory sequences can be seen in FIGS. 1 and 2. See, also, Jones, C., and K. A. Lee. Mol Cell Biol. 11:4297-305 (1991). With these considerations in mind, an E4 promoter shuttle was designed by creating two novel restriction endonuclease sites: a XhoI site at nucleotide 35,576 and a SpeI site at nucleotide 35,815 (see FIG. 3). Digestion with both XhoI and SpeI removes nucleotides from 35,581 to 35,817. This effectively eliminates bases −208 to +29 relative to the E4 transcriptional start site, including all of the sequences that have been shown to have maximal influence on E4 transcription. In particular, this encompasses the two inverted repeats of E4F binding sites that have been demonstrated to have the most significant effect on promoter activation. However, all three Sp1 binding sites, two of the five ATF binding sites, and both of the NF1 and NFIII/Oct-1 binding sites that are critical for viral DNA replication are retained.

In some embodiments, the E2F responsive promoter is the human E2F-1 promoter. Key regulatory elements in the E2F-1 promoter that mediate the response to the pRb pathway have been mapped both in vitro and in vivo (Johnson, D. G., K. Ohtani, and J. R. Nevins. 1994, Genes Dev. 8:1514-25; Neuman, E., E. K. Flemington, W. R. Sellers, and W. G. Kaelin, Jr. 1995, Mol Cell Biol. 15:4660; Parr, M. J., Y. Manome, T. Tanaka, P. Wen, D. W. Kufe, W. G. Kaelin, Jr., and H. A. Fine. 1997, Nat Med. 3:1145-9.) Thus, we isolated the human E2F-1 promoter fragment from base pairs −218 to +51, relative to the transcriptional start site, by PCR with primers that incorporated a SpeI and XhoI site into them. This creates the same sites present within the E4 promoter shuttle and allows for direct substitution of the E4 promoter with the E2F-1 promoter.

3. Oncolytic Rhabdovirus

In some embodiments, the oncolytic virus is a replication competent oncolytic rhabdovirus. Such oncolytic rhabdovirusus include, without limitation, wild type or genetically modified Arajas virus, Chandipura virus, Cocal virus, Isfahan virus, Maraba virus, Piry virus, Vesicular stomatitis Alagoas virus, BeAn 157575 virus, Boteke virus, Calchaqui virus, Eel virus American, Gray Lodge virus, Jurona virus, Klamath virus, Kwatta virus, La Joya virus, Malpais Spring virus, Mount Elgon bat virus, Perinet virus, Tupaia virus, Farmington virus, Bahia Grande virus, Muir Springs virus, Reed Ranch virus, Hart Park virus, Flanders virus, Kamese virus, Mosqueiro virus, Mossuril virus, Barur virus, Fukuoka virus, Kern Canyon virus, Nkolbisson virus, Le Dantec virus, Keuraliba virus, Connecticut virus, New Minto virus, Sawgrass virus, Chaco virus, Sena Madureira virus, Timbo virus, Almpiwar virus, Aruac virus, Bangoran virus, Bimbo virus, Bivens Arm virus, Blue crab virus, Charleville virus, Coastal Plains virus, DakArK 7292 virus, Entamoeba virus, Garba virus, Gossas virus, Humpty Doo virus, Joinjakaka virus, Kannamangalam virus, Kolongo virus, Koolpinyah virus, Kotonkon virus, Landjia virus, Manitoba virus, Marco virus, Nasoule virus, Navarro virus, Ngaingan virus, Oak Vale virus, Obodhiang virus, Oita virus, Ouango virus, Parry Creek virus, Rio Grande cichlid virus, Sandjimba virus, Sigma virus, Sripur virus, Sweetwater Branch virus, Tibrogargan virus, Xiburema virus, Yata virus, Rhode Island virus, Adelaide River virus, Berrimah virus, Kimberley virus, or Bovine ephemeral fever virus. In some embodiments, the oncolytic rhabdovirus is a wild type or recombinant vesiculovirus. In other embodiments, the oncolytic rhabdovirus is a wild type or recombinant vesicular stomatitis virus (VSV), Farmington, Maraba, Carajas, Muir Springs or Bahia grande virus, including variants thereof. In some embodiments, the oncolytic rhabdovirus is a VSV or Maraba rhabdovirus comprising one or more genetic modifications that increase tumor selectivity and/or oncolytic effect of the virus. In some embodiments, the oncolytic virus is VSV, VSVΔ51 (VSVdelta51), VSV IFN-β, maraba virus or MG1 virus (see, for example, U.S. Patent Application Publication US 2019/0022203A1, which is incorporated herein by reference in its entirety).

In some embodiments, the oncolytic virus can be engineered to express one or more tumor antigens, such as those mentioned in paragraphs [0071]-[0082] of WIPO publication no. WO 2014/127478 and paragraph [0042] of U.S. Patent Application Publication No. 2012/0014990, as well as the database summarizing antigenic epitopes provided by Van der Bruggen P, Stroobant V, Vigneron N, Van den Eynde B in "Database of T cell-defined human tumor antigens: the 2013 update." Cancer Immun 2013 13:15 and on the World Wide Web at cancerimmunity.org/peptide/, the contents all of which are incorporated herein by reference. In preferred embodiments, the oncolytic virus is an oncolytic rhabdovirus (e.g. VSV or Maraba strain) that expresses MAGEA3, Human Papilloma Virus E6/E7 fusion protein, human Six-Transmembrane Epithelial Antigen of the Prostate protein, or Cancer Testis Antigen 1, or a variant thereof. In particularly preferred embodiments, the oncolytic virus is an oncolytic rhadovirus selected from Maraba MGI and VSVΔ51 that expresses MAGEA3, Human Papilloma Virus E6/E7 fusion protein, human Six-Transmembrane Epithelial Antigen of the Prostate protein, or Cancer Testis Antigen 1, or a variant thereof. In some embodiments, the one or more tumor antigens are selected from the group consisting o Melanoma antigen, family A,3 (MAGEA3), Human Papilloma Virus (HPV) oncoproteins E6/E7, six-Transmembrane Epithelial Antigen of the Prostate (huSTEAP), Cancer Testis Antigen 1 (NYES01), and Placenta-specific protein 1 (PLAC-1).

In some embodiments, the oncolytic habdovirus is a pseudotyped replicative oncolytic rhabdovirus comprising an arenavirus envelope glycoprotein in place of the rhabdvirus glycoprotein. In some embodiments, the pseudotyped replicative oncolytic rhabdovirus is a wild type or recombinant vesiculovirus, particularly a wild type or recombinant vesicular stomatitis virus (VSV) or Maraba virus (MRB) with an arenavirus glycoprotein replacing the VSV or MRB glycoprotein. In some embodiments, the pseudotyped oncolytic rhabdovirus is a VSV or MRB comprising one or more genetic modifications that increase tumor selectivity and/or oncolytic effect of the virus. In other preferred embodiments, the arenavirus glycoprotein is a lymphocytic choriomeningitis virus (LCMV) glycoprotein, a Lassa virus glycoprotein, a Junin virus glycoprotein or a variant thereof. In particularly preferred embodiments, a pseudotyped oncolytic VSV or Maraba virus with a Lassa or Junin glycoprotein replacing the VSV or Maraba glycoprotein is provided. In some embodiments, the pseudotyped replicative oncolytic rhabdovirus exhibits reduced neurotropism compared to a non-pseudotyped replicative oncolytic rhabodvirus with the same genetic background. In other embodiments, the pseudotyped replicative oncolytic rhabdovirus comprises heterologous nucleic acid sequence encoding one or more tumor antigens such as those mentioned in paragraphs [0071]-[0082] of WIPO publication no. WO 2014/127478 and paragraph [0042] of U.S. Patent Application Publication No. 2012/0014990, the contents of both of which are incorporated herein by reference and/or comprises heterologous nucleic acid sequence encoding one or more cytokines and/or comprises heterologous nucleic acid sequence encoding one or more immune checkpoint inhibitors. In other embodiments, the pseudotyped replicative oncolytic rhabdovirus comprises heterologous nucleic acid sequence encoding one or more tumor antigens selected from the group consisting o Melanoma antigen, family A,3 (MAGEA3), Human Papilloma Virus (HPV) oncoproteins E6/E7, six-Transmembrane Epithelial Antigen of the Prostate (huSTEAP), Cancer Testis Antigen 1 (NYES01), and Placenta-specific protein 1 (PLAC-1).

In related embodiments, the pseudotyped oncolytic rhabdovirus is engineered to express one or more tumor antigens, such as those mentioned in paragraphs [0071]-[0082] of WIPO publication no. WO 2014/127478 and paragraph [0042] of U.S. Patent Application Publication No. 2012/0014990. In some embodiments, the pseudotyped oncolytic rhabdovirus (e.g. VSV or Maraba strain) expresses MAGEA3, Human Papilloma Virus E6/E7 fusion protein, human Six-Transmembrane Epithelial Antigen of the Prostate protein, or Cancer Testis Antigen 1, or a variant thereof. In some embodiments, the oncolytic virus is an oncolytic rhadovirus selected from Maraba and VSVΔ51 that expresses MAGEA3, Human Papilloma Virus E6/E7 fusion protein, human Six-Transmembrane Epithelial Antigen of the Prostate protein, or Cancer Testis Antigen 1, or a variant thereof.

In some aspects, a combination therapy for treating and/or preventing cancer in a mammal is provided comprising co-administering to the mammal (i) an oncolytic rhabdovirus expressing a tumor antigen to which the mammal has a pre-existing immunity selected from MAGEA3, Human Papilloma Virus E6/E7 fusion protein, human Six-Transmembrane Epithelial Antigen of the Prostate protein, or Cancer Testis Antigen 1, or a variant thereof and (ii) a checkpoint inhibitor (e.g. a monoclonal antibody against CTLA4 or PD-1/PD-L1). In preferred embodiments, the pre-existing immunity in the mammal is established by vaccinating the mammal with the tumor antigen prior to administration of the oncolytic virus. In related embodiments, a first dose of checkpoint inhibitor is administered prior to a first dose of oncolytic rhabdovirus expressing the tumor antigen and subsequent doses of checkpoint inhibitor may be administered after a first (or second, third and so on) of oncolytic rhabdovirus expressing the tumor antigen.

(1) Maraba Virus

Maraba is a member of the Rhabdovirus family and is also classified in the Vesiculovirus Genus. As used herein, rhabdovirus can be Maraba virus or an engineered variant of Maraba virus.

Maraba virus has been shown to have a potent oncolytic effect on tumour cells in vitro and in vivo, for example, in WO 2009/016433, which is incorporated by reference in its entirety.

As used herein, a Maraba virus can be a non-VSV rhabdovirus, and includes one or more of the following viruses or variants thereof: Arajas virus, Chandipura virus, Cocal virus, Isfahan virus, Maraba virus, Piry virus, Vesicular stomatitis Alagoas virus, BeAn 157575 virus, Boteke virus, Calchaqui virus, Eel virus American, Gray Lodge virus, Jurona virus, Klamath virus, Kwatta virus, La Joya virus, Malpais Spring virus, Mount Elgon bat virus, Perinet virus, Tupaia virus, Farmington, Bahia Grande virus, Muir Springs virus, Reed Ranch virus, Hart Park virus, Flanders virus, Kamese virus, Mosqueiro virus, Mossuril virus, Barur virus, Fukuoka virus, Kern Canyon virus, Nkolbisson virus, Le Dantec virus, Keuraliba virus, Connecticut virus, New Minto virus, Sawgrass virus, Chaco virus, Sena Madureira virus, Timbo virus, Almpiwar virus, Aruac virus, Bangoran virus, Bimbo virus, Bivens Arm virus, Blue crab virus, Charleville virus, Coastal Plains virus, DakArK 7292 virus, Entamoeba virus, Garba virus, Gossas virus, Humpty Doo virus, Joinjakaka virus, Kannamangalam virus, Kolongo virus, Koolpinyah virus, Kotonkon virus, Landjia virus, Manitoba virus, Marco virus, Nasoule virus, Navarro virus, Ngaingan virus, Oak-Vale virus, Obodhiang virus, Oita virus, Ouango virus, Parry Creek virus, Rio Grande cichlid virus, Sandjimba virus, Sigma virus, Sripur virus, Sweetwater Branch virus, Tibrogargan virus, Xiburema virus, Yata virus, Rhode Island, Adelaide River virus, Berrimah virus, Kimberley virus, or Bovine ephemeral fever virus. In certain aspects, non-VSV rhabdovirus can refer to the supergroup of Dimarhabdovirus (defined as rhabdovirus capable of infection both insect and mammalian cells). In specific embodiments, the rhabdovirus is not VSV. In particular aspects the non-VSV rhabdovirus is a Carajas virus, Maraba virus, Farmington, Muir Springs virus, and/or Bahia grande virus, including variants thereof.

In some embodiments, an oncolytic non-VSV rhabdovirus or a recombinant oncolytic non-VSV rhabdovirus encodes one or more of rhabdoviral N, P, M, G and/or L protein, or variant thereof (including chimeras and fusion proteins thereof), having an amino acid identity of at least or at most 20, 30, 40, 50, 60, 65, 70, 75, 80, 85, 90, 92, 94, 96, 98, 99, 100%, including all ranges and percentages there between, to the N, P, M, G and/or L protein of Arajas virus, Chandipura virus, Cocal virus, Isfahan virus, Maraba virus, Piry virus, Vesicular stomatitis Alagoas virus, BeAn 157575 virus, Boteke virus, Calchaqui virus, Eel virus American, Gray Lodge virus, Jurona virus, Klamath virus, Kwatta virus, La Joya virus, Malpais Spring virus, Mount Elgon bat virus, Perinet virus, Tupaia virus, Farmington, Bahia Grande virus, Muir Springs virus, Reed Ranch virus, Hart Park virus, Flanders virus, Kamese virus, Mosqueiro virus, Mossuril virus, Barur virus, Fukuoka virus, Kern Canyon virus, Nkolbisson virus, Le Dantec virus, Keuraliba virus, Connecticut virus, New Minto virus, Sawgrass virus, Chaco virus, Sena Madureira virus, Timbo virus, Almpiwar virus, Aruac virus, Bangoran virus, Bimbo virus, Bivens Arm virus, Blue crab virus, Charleville virus, Coastal Plains virus, DakArK 7292 virus, Entamoeba virus, Garba virus, Gossas virus, Humpty Doo virus, Joinjakaka virus, Kannamangalam virus, Kolongo virus, Koolpinyah virus, Kotonkon virus, Landjia virus, Manitoba virus, Marco virus, Nasoule virus, Navarro virus, Ngaingan virus, Oak-Vale virus, Obodhiang virus, Oita virus, Ouango virus, Parry Creek virus, Rio Grande cichlid virus, Sandjimba virus, Sigma virus, Sripur virus, Sweetwater Branch virus, Tibrogargan virus, Xiburema virus, Yata virus, Rhode Island, Adelaide River virus, Berrimah virus, Kimberley virus, or Bovine ephemeral fever virus. VSV or any non-VSV rhabdovirus can be the background sequence into which a variant G-protein or other viral protein can be intergrated.

In some embodiments, a non-VSV rhabdovirus, or a recombinant there of, can comprise a nucleic acid segment encoding at least or at most 10, 20, 30, 40, 45, 50, 60, 65, 70, 80, 90, 100, 125, 175, 250 or more contiguous amino acids, including all value and ranges there between, of N, P, M, G or L protein of one or more non-VSV rhabdovirus, including chimeras and fusion proteins thereof. In certain embodiments a chimeric G protein will include a cytoplasmic, transmembrane, or both cytoplasmic and transmembrane portions of a VSV or non-VSV G protein.

As used herein, a heterologous G protein can include that of a non-VSV rhabdovirus. Non-VSV rhabdo viruses will include one or more of the following viruses or variants thereof: Arajas virus, Chandipura virus, Cocal virus, Isfahan virus, Maraba virus, Piry virus, Vesicular stomatitis Alagoas virus, BeAn 157575 virus, Boteke virus, Calchaqui virus, Eel virus American, Gray Lodge virus, Jurona virus, Klamath virus, Kwatta virus, La Joya virus, Malpais Spring virus, Mount Elgon bat virus, Perinet virus, Tupaia virus, Farmington, Bahia Grande virus, Muir Springs virus, Reed Ranch virus, Hart Park virus, Flanders virus, Kamese virus, Mosqueiro virus, Mossuril virus, Barur virus, Fukuoka virus, Kern Canyon virus, Nkolbisson virus, Le Dantec virus, Keuraliba virus, Connecticut virus, New Minto virus, Sawgrass virus, Chaco virus, Sena Madureira virus, Timbo virus, Almpiwar virus, Aruac virus, Bangoran virus, Bimbo virus, Bivens Arm virus, Blue crab virus, Charleville virus, Coastal Plains virus, DakArK 7292 virus, Entamoeba virus, Garba virus, Gossas virus, Humpty Doo virus, Joinjakaka virus, Kannamangalam virus, Kolongo virus, Koolpinyah virus, Kotonkon virus, Landjia virus, Manitoba virus, Marco virus, Nasoule virus, Navarro virus, Ngaingan virus, Oak-Vale virus, Obodhiang virus, Oita virus, Ouango virus, Parry Creek virus, Rio Grande cichlid virus, Sandjimba virus, Sigma virus, Sripur virus, Sweetwater Branch virus, Tibrogargan virus, Xiburema virus, Yata virus, Rhode Island, Adelaide River virus, Berrimah virus, Kimberley virus, or Bovine ephemeral fever virus. In certain embodiments, non-VSV rhabdovirus can refer to the supergroup of Dimarhabdovirus (defined as rhabdovirus capable of infection both insect and mammalian cells). In certain embodiments, the non-VSV rhabdovirus is a Carajas virus, Maraba virus, Muir Springs virus, and/or Bahia grande virus, including variants thereof.

MG1 virus is an engineered maraba virus that includes a polynucleotide sequence encoding a mutated matrix (M) protein, a polynucleotide sequence encoding a mutated G protein, or both. An exemplary MG1 virus that encodes a mutated M protein and a mutated G protein is described in WO/2011/070440, which is incorporated herein by reference. This MG1 virus is attenuated in normal cells but hypervirulent in cancer cells.

One embodiment of the invention includes an oncolytic Maraba virus encoding a variant M and/or G protein having an amino acid identity of at least or at most 20, 30, 40, 50, 60, 65, 70, 75, 80, 85, 90, 92, 94, 96, 98, 99, 100%, including all ranges and percentages there between, to the M or G protein of Maraba virus. In certain aspects amino acid 242 of the Maraba G protein is mutated. In further aspects amino acid 123 of the M protein is mutated. In still further aspects both amino acid 242 of the G protein and amino acid 123 of the M protein are mutated. Amino acid 242 can be substituted with an arginine (Q242R) or other amino acid that attenuates the virus. Amino acid 123 can be substituted with a tryptophan (L123W) or other amino acid that attenuates the virus. In certain aspects two separate mutations individually attenuate the virus in normal healthy cells. Upon combination of the mutants the virus becomes more virulent in tumor cells than the wild type virus. Thus, the therapeutic index of the Maraba DM is increased unexpectedly.

In some embodiments, a Maraba virus as described herein may be further modified by association of a heterologous G protein as well. As used herein, a heterologous G protein includes rhabdovirus G protein. Rhabdoviruses will include one or more of the following viruses or variants thereof: Carajas virus, Chandipura virus, Cocal virus, Isfahan virus, Maraba virus, Piry virus, Vesicular stomatitis Alagoas virus, BeAn 157575 virus, Boteke virus, Calchaqui virus, Eel virus American, Gray Lodge virus, Jurona virus, Klamath virus, Kwatta virus, La Joya virus, Malpais Spring virus, Mount Elgon bat virus, Perinet virus, Tupaia virus, Farmington, Bahia Grande virus, Muir Springs virus, Reed Ranch virus, Hart Park virus, Flanders virus, Kamese virus, Mosqueiro virus, Mossuril virus, Barur virus, Fukuoka virus, Kern Canyon virus, Nkolbisson virus, Le Dantec virus, Keuraliba virus, Connecticut virus, New Minto virus, Sawgrass virus, Chaco virus, Sena Madureira virus, Timbo virus, Almpiwar virus, Aruac virus, Bangoran virus, Bimbo virus, Bivens Arm virus, Blue crab virus, Charleville virus, Coastal Plains virus, DakArK 7292 virus, Entamoeba virus, Garba virus, Gossas virus, Humpty Doo virus, Joinjakaka virus, Kannamangalam virus, Kolongo virus, Koolpinyah virus, Kotonkon virus, Landjia virus, Manitoba virus, Marco virus, Nasoule virus, Navarro virus, Ngaingan virus, Oak-Vale virus, Obodhiang virus, Oita virus, Ouango virus, Parry Creek virus, Rio Grande cichlid virus, Sandjimba virus, Sigma virus, Sripur virus, Sweetwater Branch virus, Tibrogargan virus, Xiburema virus, Yata virus, Rhode Island, Adelaide River virus, Berrimah virus, Kimberley virus, or Bovine ephemeral fever virus. In certain aspects, rhabdovirus can refer to the supergroup of Dimarhabdovirus (defined as rhabdovirus capable of infection both insect and mammalian cells). In particular aspects the rhabdovirus is a Carajas virus, Maraba virus, Muir Springs virus, and/or Bahia grande virus, including variants thereof.

The Maraba viruses described herein can be used in combination with other rhabdoviruses. Other rhabdovirus include one or more of the following viruses or variants thereof: Carajas virus, Chandipura virus, Cocal virus, Isfahan virus, Piry virus, Vesicular stomatitis Alagoas virus, BeAn 157575 virus, Boteke virus, Calchaqui virus, Eel virus American, Gray Lodge virus, Jurona virus, Klamath virus, Kwatta virus, La Joya virus, Malpais Spring virus, Mount Elgon bat virus, Perinet virus, Tupaia virus, Farmington, Bahia Grande virus, Muir Springs virus, Reed Ranch virus, Hart Park virus, Flanders virus, Kamese virus, Mosqueiro virus, Mossuril virus, Barur virus, Fukuoka virus, Kern Canyon virus, Nkolbisson virus, Le Dantec virus, Keuraliba virus, Connecticut virus, New Minto virus, Sawgrass virus, Chaco virus, Sena Madureira virus, Timbo virus, Almpiwar virus, Aruac virus, Bangoran virus, Bimbo virus, Bivens Arm virus, Blue crab virus, Charleville virus, Coastal Plains virus, DakArK 7292 virus, Entamoeba virus, Garba virus, Gossas virus, Humpty Doo virus, Joinjakaka virus, Kannamangalam virus, Kolongo virus, Koolpinyah virus, Kotonkon virus, Landjia virus, Manitoba virus, Marco virus, Nasoule virus, Navarro virus, Ngaingan virus, Oak-Vale virus, Obodhiang virus, Oita virus, Ouango virus, Parry Creek virus, Rio Grande cichlid virus, Sandjimba virus, Sigma virus, Sripur virus, Sweetwater Branch virus, Tibrogargan virus, Xiburema virus, Yata virus, Rhode Island, Adelaide River virus, Berrimah virus, Kimberley virus, or Bovine ephemeral fever virus. In certain aspects, rhabdovirus can refer to the supergroup of Dimarhabdovirus (defined as rhabdovirus capable of infection both insect and mammalian cells). In specific embodiments, the rhabdovirus is not VSV. In particular aspects the rhabdovirus is a Carajas virus, Maraba virus, Farmington, Muir Springs virus, and/or Bahia grande virus, including variants thereof.

In some embodiments, Maraba viruses is engineered by other ways. For example, Maraba viruses can be engineered to be chimeric for BG or Ebola glycoproteins, which is shown to be potent and selective oncolytic activity when tested against brain cancer cell lines; and alternatively, Maraba virus may be attenuated through replacement of its glycoprotein (Maraba-G protein) with LCMV-G protein. A chimeric Maraba virus having LCMV-G protein is produced by swapping out the MRB G glycoprotein for the LCMV glycoprotein to create a chimeric virus, termed "Maraba LCMV-G" or "Maraba. LCMV(G)" as described in WO2014089668, incorporated by reference herein.

(2) VSV Virus

Vesicular stomatitis virus (VSV) is a member of the Rhabdovirus family and is classified in the Vesiculovirus Genus. VSV has been shown to be a potent oncolytic virus capable of inducing cytotoxicity in many types of human tumour cells in vitro and in vivo (see, for example, WO 2001/19380; incorporated by reference herein in its entirety). VSV infections in humans are either asymptomatic or manifest as a mild "flu." There have been no reported cases of severe illness or death among VSV-infected humans. Other useful characteristics of VSV include the fact that it replicates quickly and can be readily concentrated to high titres, it is a simple virus comprising only five genes and is thus readily amenable to genetic manipulation, and it has a broad host range and is capable of infecting most types of human cells. In one embodiment of the present invention, the mutant virus is a mutant VSV. A number of different strains of VSV are known in the art and are suitable for use in the present invention. Examples include, but are not limited to, the Indiana and New Jersey strains. A worker skilled in the art will appreciate that new strains of VSV will emerge and/or be discovered in the future which are also suitable for use in the present invention. Such strains are also considered to fall within the scope of the invention.

In some embodiments, VSV is engineered to comprising one or more mutation in a gene which encodes a protein that is involved in blocking nuclear transport of mRNA or protein in an infected host cell. As a result, the mutant viruses have a reduced ability to block nuclear transport and are attenuated in vivo. Blocking nuclear export of mRNA or protein cripples the anti-viral systems within the infected cell, as well as the mechanism by which the infected cell can protect surrounding cells from infection (i.e. the early warning system), and ultimately leads to cytolysis.

An example of a suitable gene encoding a non-structural protein is the gene encoding the matrix, or M, protein of Rhabdoviruses. The M protein from VSV has been well studied and has been shown to be a multifunctional protein required for several key viral functions including: budding (Jayakar, et al. 2000, J Virol? 74(21): 9818-27), virion assembly (Newcomb, et al. 1982, J Virol, 41(3): 1055-62), cytopathic effect (Blondel, et al. 1990, J Virol s 64(4): 1716-25), and inhibition of host gene expression (Lyles, et al. 1996, Virology 225(1): 172-80). The latter property has been shown herein to be due to inhibition of the nuclear transport of both proteins and mRNAs into and out of the host nucleus. Examples of suitable mutations that can be made in the gene encoding the VSV M protein include, but are not limited to, insertions of heterologous nucleic acids into the coding region, deletions of one or more nucleotide in the coding region, or mutations that result in the substitution or deletion of one or more of the amino acid residues at positions 33, 51, 52, 53, 54, 221, 226 of the M protein, or a combination thereof.

The amino terminus of VSV M protein has been shown to target the protein to the mitochondria, which may contribute to the cytotoxicity of the protein. A mutation introduced into this region of the protein, therefore, could result in increased or decreased virus toxicity. Examples of suitable mutations that can be made in the region of the M protein gene encoding the N-terminus of the protein include, but are not limited to, those that result in one or more deletion, insertion or substitution in the first (N-terminal) 72 amino acids of the protein.

The amino acid numbers referred to above describe positions in the M protein of the Indiana strain of VSV. It will be readily apparent to one skilled in the art that the amino acid sequence of M proteins from other VSV strains and Rhabdoviridae may be slightly different to that of the Indiana VSV M protein due to the presence or absence of some amino acids resulting in slightly different numbering of corresponding amino acids. Alignments of the relevant protein sequences with the Indiana VSV M protein sequence in order to identify suitable amino acids for mutation that correspond to those described herein can be readily carried out by a worker skilled in the art using standard techniques and software (such as the BLASTX program available at the National Center for Biotechnology Information website). The amino acids thus identified are candidates for mutation in accordance with the present invention.

In one embodiment of the present invention, the mutant virus is a VSV with one or more of the following mutations introduced into the gene encoding the M protein (notation is: wild-type amino acid/amino acid position/mutant amino acid; the symbol Δ indicates a deletion and X indicates any amino acid): M51R, M51A, M51-54A, ΔM51, ΔM51-54, ΔM51-57, V221F, S226R, ΔV221-S226, M51X, V221X, S226X, or combinations thereof. In another embodiment, the mutant virus is a VSV with one of the following combinations of mutations introduced into the gene encoding the M protein: double mutations—M51R and V221F; M51A and V221F; M51-54A and V221F; ΔM51 and V221F; ΔM51-54 and V221F; ΔM51-57 and V221F; M51R and S226R; M51A and S226R; M51-54A and S226R; ΔM51 and S226R; ΔM51-54 and S226R; ΔM51-57 and S226R; triple mutations—M51R, V221F and S226R; M51A, V221F and S226R; M51-54A, V221F and S226R; ΔM51, V221F and S226R; ΔM51-54, V221F and S226R; ΔM51-57, V221F and S226R.

For example, VSVΔ51 is an engineered attenuated mutant of the natural wild-type isolate of VSV. The Δ51 mutation renders the virus sensitive to IFN signaling via a mutation of the Matrix (M) protein. An exemplary VSVΔ51 is described in WO 2004/085658, which is incorporated herein by reference.

VSV IFN-β is an engineered VSV that includes a polynucleotide sequence encoding interferon-β. An exemplary VSV that encodes interferon-β is described in Jenks N, et al., "Safety studies on intrahepatic or intratumoral injection of oncolytic vesicular stomatitis virus expressing interferon-beta in rodents and nonhuman primates." Hum Gene Ther. 2010 April; 21 (4):451-62, which is incorporated herein by reference.

In some embodiments, an oncolytic VSV rhabdovirus comprises a heterologous G protein. In some embodiments, an oncolytic VSV rhabdovirus is a recombinant oncolytic VSV rhabdovirus encoding one or more of non-VSV rhabdoviral N, P, M, G and/or L protein, or variant thereof (including chimeras and fusion proteins thereof), having an amino acid identity of at least or at most 20, 30, 40, 50, 60, 65, 70, 75, 80, 85, 90, 92, 94, 96, 98, 99, 100%, including all ranges and percentages there between, to the N, P, M, G, and/or L protein of a non-VSV rhabdovirus. In another aspect of the invention, a VSV rhabdovirus comprising a heterologous G protein or recombinant thereof, can comprise a nucleic acid comprising a nucleic acid segment encoding at least or at most 10, 20, 30, 40, 45, 50, 60, 65, 70, 80, 90, 100, 125, 175, 250 or more contiguous amino acids, including all value and ranges there between, of N, P, M, G, or L protein of a non-VSV rhabdovirus, including chimeras and fusion proteins thereof. In certain aspects, a chimeric G protein may comprise a cytoplasmic, transmembrane, or both a cytoplasmic and transmembrane portion of VSV or a second non-VSV virus or non-VSV rhabdovirus.

F. Cancer Stem Cell Targeting Moieties

Targeting moieties are the portion of the IL-4 receptor targeted cargo proteins that target the IL-4 receptor targeted cargo protein to cancer cells, and including cancer cells and/or cancer stem cells and bulk cancer cells. Targeting moieties function to specifically bind to a cancer stem cell. However, it is appreciated that the targeting moiety need not retain its native biological activity (e.g., the ability to activate a receptor or ability to prevent a ligand from binding to its receptor) as long as it permits the IL-4 receptor targeted cargo protein to bind with high specificity to cancer cells and/or cancer stem cells (and in some examples also cancer cells). In certain examples, the targeting moiety is a natural ligand of a target displayed by the cancer stem cell or a derivative of a natural ligand. In other examples the targeting moiety is an antibody, such as a humanized antibody or antibody fragment, which specifically binds to a target displayed on the surface of the cancer stem cell (e.g., targets a receptor). Targeting moieties can be linked to cargo moieties using any method known in the art, for example via chemical or recombinant technology.

A non-limiting list of compounds that could be used to target cancer cells and/or cancer stem cells includes antibodies, natural ligands, engineered ligands and combinations thereof that bind to one or more cancer cells and/or cancer stem cells. Exemplary ligands include cytokines and growth factors. Exemplary targets on cancer cells and/or cancer stem cells include, for example, IL-4R.

Of particular interest are targeting moieties that are molecules that are natural ligands or derivatives of the natural ligands to the target on the cancer cells and/or cancer stem cells. For example, if the cancer stem cell expresses IL-4 receptors (IL-4R), IL-4 ligand can be used as the targeting moiety. The IL-4 can be chemically or recombinantly linked to one or more of the cargo moieties described herein. Examples of derivatives of natural ligands include the circularized cytokine ligands described in U.S. Pat. No. 6,011,002 to Pastan et al., which is herein incorporated by reference. In addition to IL-4 ligands, IL-13 can also be used as a ligand targeting moiety since the IL-4 and IL-13 receptors share some sequence and biological functions. IL-4 receptor targeted cargo proteins include those comprising IL-4 and IL-13 ligands and variants thereof.

In some examples, antibodies (including fragments, humanized antibodies and the like as described above) that target IL-4R. Antibodies are commercially available from various companies such as Millipore, Bedford, Mass. or custom made antibodies can be ordered from companies such as Cambridge Research Biochemicals, Billingham, Cleveland. Methods routine in the art can be used to generate such antibodies if desired. Such antibodies will specifically bind to cancer cells and/or cancer stem cells (and may also bind to bulk cancer cells) and function to place the cargo moiety in contact with a cancer stem cell.

IL-4 is a pleiotropic cytokine produced by activated T cells, and is the ligand for the IL-4 receptor. The IL-4 receptor also binds to IL-13. Thus, IL-13 can also be used as a targeting moiety to target the IL-4 receptor. IL-4, IL-3, IL-5, IL-13, and CSF2 form a cytokine gene cluster on human chromosome 5q, with this gene particularly close to IL-13. Exemplary IL-4 and IL-13 proteins that can be used in the IL-4 receptor targeted cargo proteins of the present disclosure include those provided in Table 2, as well as sequences having at least 60% sequence identity, at least 75%, at least 80%, at least 85%, at least 90%, at least 95%, at least 98% or even at least 99% sequence identity to such sequences, as long as the variant retains the ability to bind the IL-4 receptor.

The targeting moiety used can include native sequences (such as the GenBank Accession Nos. and sequences present in the patents referenced in Table 2 and listed above), as well as variants thereof, such as a variant having at least 98%, at least 95%, at least 90%, at least 80%, at least 70%, or at least 60% sequence identity with the native targeting moiety protein (e.g., at least about this amount of sequence identity to the GenBank Accession Nos. listed in Table 2 and listed above). In some examples, variant sequences retain substantially the same amount (or even more) of the native biological function of the targeting moiety protein, such as the ability to activate an intracellular signal cascade. However, variant targeting moiety molecules may in some examples retain little or no native biological activity, but retain the ability to bind the appropriate target (e.g., bind to the appropriate cell surface receptor or protein) with high specificity.

In some embodiments, the cancer stem cells are from a cancer selected from the group consisting of glioblastoma, head and neck cancer, lung cancer, breast cancer, pancreatic cancer, cervical cancer, prostate cancer, and soft tissue sarcoma.

G. Linkers

Linking of a cargo moiety to a targeting moiety may be direct meaning that one portion of the cargo moiety is directly attached to a portion of the targeting moiety. For example, one end of the amino acid sequence of a cargo protein can be directly attached to an end of the amino acid sequence of the targeting moiety. For example, the C-terminus of the cargo protein can be linked to the N-terminus of the targeting moiety, or the C-terminus of the targeting moiety can be linked to the N-terminus of the cargo protein. Methods of generating such fusion proteins are routine in the art, for example using recombinant molecular biology methods.

In another example, the cargo moiety is linked to the targeting moiety indirectly through a linker. The linker can serve, for example, simply as a convenient way to link the two entities, as a means to spatially separate the two entities, to provide an additional functionality to the IL-4 receptor targeted cargo protein, or a combination thereof.

In general, the linker joining the targeting moiety and the cargo moiety can be designed to (1) allow the two molecules to fold and act independently of each other, (2) not have a propensity for developing an ordered secondary structure which could interfere with the functional domains of the two moieties, (3) have minimal hydrophobic or charged characteristic which could interact with the functional protein domains and/or (4) provide steric separation of the two regions. For example, in some instances it may be desirable to spatially separate the targeting moiety and the cargo moiety to prevent the targeting moiety from interfering with the inhibitory activity of the targeted cargo moiety and/or the cargo moiety interfering with the targeting activity of the targeting moiety. The linker can also be used to provide, for example, lability to the connection between the targeting moiety and the cargo moiety, an enzyme cleavage site (for example a cleavage site for a protease), a stability sequence, a molecular tag, a detectable label, or various combinations thereof.

The linker can be bifunctional or polyfunctional, e.g. contains at least about a first reactive functionality at, or proximal to, a first end of the linker that is capable of bonding to, or being modified to bond to, the targeting moiety and a second reactive functionality at, or proximal to, the opposite end of the linker that is capable of bonding to, or being modified to bond to, the cargo moiety being modified. The two or more reactive functionalities can be the same (i.e. the linker is homobifunctional) or they can be different (i.e. the linker is heterobifunctional). A variety of bifunctional or polyfunctional cross-linking agents are known in the art that are suitable for use as linkers (for example, those commercially available from Pierce Chemical Co., Rockford, Ill.), such as avidin and biotin. Alternatively, these reagents can be used to add the linker to the targeting moiety and/or cargo moiety.

The length and composition of the linker can be varied considerably provided that it can fulfill its purpose as a molecular bridge. The length and composition of the linker are generally selected taking into consideration the intended function of the linker, and optionally other factors such as ease of synthesis, stability, resistance to certain chemical and/or temperature parameters, and biocompatibility. For example, the linker should not significantly interfere with the ability of the targeting moiety to target the IL-4 receptor targeted cargo protein to a cancer stem cell, or with the activity of the IL-4 receptor targeted cargo protein relating to activation, pore-forming ability, or toxin activity.

Linkers suitable for use may be branched, unbranched, saturated, or unsaturated hydrocarbon chains, as well as peptides as noted above. Furthermore, if the linker is a peptide, the linker can be attached to the targeting moiety and/or the cargo moiety using recombinant DNA technology. Such methods are well-known in the art and details of this technology can be found, for example, in Sambrook et al., supra.

In one example, the linker is a branched or unbranched, saturated or unsaturated, hydrocarbon chain having from 1 to 100 carbon atoms, wherein one or more of the carbon atoms is optionally replaced by —O— or —NR— (wherein R is H, or C1 to C6 alkyl), and wherein the chain is optionally substituted on carbon with one or more substituents selected from the group of (C1-C6) alkoxy, (C3-C6) cycloalkyl, (C1-C6) alkanoyl, (C1-C6) alkanoyloxy, (C1-C6) alkoxycarbonyl, (C1-C6) alkylthio, amide, azido, cyano, nitro, halo, hydroxy, oxo (.dbd.O), carboxy, aryl, aryloxy, heteroaryl, and heteroaryloxy.

Examples of suitable linkers include, but are not limited to, peptides having a chain length of 1 to 500 amino acid residues (such as 1 to 100, 1 to 50, 6 to 30, such as less than 30 amino acids). Typically surface amino acids in flexible protein regions include Gly, Asn and Ser. Other neutral amino acids, such as Thr and Ala, can also be used in the linker sequence. Additional amino acids can be included in the linker to provide unique restriction sites in the linker sequence to facilitate construction of the fusions. Other exemplary linkers include those derived from groups such as ethanolamine, ethylene glycol, polyethylene with a chain length of 6 to 100 carbon atoms, polyethylene glycol with 3 to 30 repeating units, phenoxyethanol, propanolamide, butylene glycol, butyleneglycolamide, propyl phenyl, and ethyl, propyl, hexyl, steryl, cetyl, and palmitoyl alkyl chains.

In one example, the linker is a branched or unbranched, saturated or unsaturated, hydrocarbon chain, having from 1 to 50 carbon atoms, wherein one or more of the carbon atoms is optionally replaced by —O— or —NR— (wherein R is as defined above), and wherein the chain is optionally substituted on carbon with one or more substituents selected from the group of (C1-C6) alkoxy, (C1-C6) alkanoyl, (C1-C6) alkanoyloxy, (C1-C6) alkoxycarbonyl, (C1-C6) alkylthio, amide, hydroxy, oxo (.dbd.O), carboxy, aryl and aryloxy.

In a specific example, the linker is a peptide having a chain length of 1 to 50 amino acid residues, such as 1 to 40, 1 to 20, or 5 to 10 amino acid residues.

Peptide linkers that are susceptible to cleavage by enzymes of the complement system, urokinase, tissue plasminogen activator, trypsin, plasmin, or another enzyme having proteolytic activity may be used in one example. According to another example, the IL-4 receptor targeted cargo protein includes a targeting moiety attached via a linker susceptible to cleavage by enzymes having a proteolytic activity such as a urokinase, a tissue plasminogen activator, plasmin, thrombin or trypsin. In addition, targeting moieties may be attached to the cargo moiety via disulfide bonds (for example, the disulfide bonds on a cysteine molecule). Since many tumors naturally release high levels of glutathione (a reducing agent) this can reduce the disulfide bonds with subsequent release of the cargo moiety at the site of delivery.

In one example, the IL-4 receptor targeted cargo protein includes a targeting moiety linked by a cleavable linker region. In another example, the cleavable linker region is a protease-cleavable linker, although other linkers, cleavable for example by small molecules, may be used. Examples of protease cleavage sites are those cleaved by factor Xa, thrombin and collagenase. In one example, the protease cleavage site is one that is cleaved by a protease that is associated with a disease. In another example, the protease cleavage site is one that is cleaved by a protease that is up-regulated or associated with cancers in general. Examples of such proteases are uPA, the matrix metalloproteinase (MMP) family, the caspases, elastase, prostate specific antigen (PSA, a serine protease), and the plasminogen activator family, as well as fibroblast activation protein. In still another example, the cleavage site is cleaved by a protease secreted by cancer-associated cells. Examples of these proteases include matrix metalloproteases, elastase, plasmin, thrombin, and uPA. In another example, the protease cleavage site is one that is up-regulated or associated with a specific cancer. The precise sequences are available in the art and the skilled person will have no difficulty in selecting a suitable cleavage site. By way of example, the protease cleavage region targeted by Factor Xa is I E G R. The protease cleavage region targeted by enterokinase is D D D D K. The protease cleavage region targeted by thrombin is L V P R G. In one example, the cleavable linker region is one which is targeted by endocellular proteases.

As known in the art, the attachment of a linker to cargo moiety (or of a linker element to a cleavable element, or a cleavable element to another cargo moiety) need not be a particular mode of attachment or reaction.

H. Exemplary Cargo Moiety/Targeting Moiety Combinations

Any combination of cargo moiety and IL-4 based targeting moiety can be employed according to the present invention. In this section exemplary combinations of targeting moieties and cargo moieties are provided. In all examples that targeting moiety can be an antibody that specifically binds to a target, such as a fully humanized antibody.

IL-4 (including IL-4 circularly permuted ligands and other IL-4 receptor binding proteins such as IL-13) is another targeting moiety that can be linked to BCL-2 family proteins, such as BAX, BAD, BAT, BAK, BIK, BOK, BID BIM, BMF and BOK, or a toxin such as aerolysin, proaerolysin, *Pseudomonas* exotoxin, or combinations thereof. Any form or derivative of IL-4 can be used as the targeting moiety. For example, IL-4 or fragments of IL-4 that bind to the IL-4 receptor can be used. Additionally, multiple cargo moieties can be linked to IL-4 or multiple IL-4 proteins can be linked to cargo moieties.

Any form or derivative of IL-4 can be used as the targeting moiety. For example, IL-4 or fragments of IL-4 that bind to the IL-4 receptor can be used. Additionally, multiple cargo moieties can be linked to IL-4 or multiple IL-2 proteins can be linked to cargo moieties.

A circularly permuted ligand, for example a circularly permuted ligand derived from IL-4 can be employed as the targeting moiety. *Pseudomonas* exotoxin can be employed as the cargo moiety. Any form or derivative of circularly permuted IL-4 ligand can be used as the targeting moiety. Additionally, multiple cargo moieties can be linked to a circularly permuted ligand or multiple circularly permuted ligand proteins can be linked to cargo moieties.

III. Formulations/Compositions

In one aspect, the present invention includes pharmaceutical compositions that contain a modified oncolytic virus comprising an IL-4 receptor targeted cargo protein described herein and one or more non-toxic pharmaceutically acceptable carriers, diluents, excipients and/or adjuvants. In another aspect, the present invention includes pharmaceutical compositions that contain an IL-4 and/or IL-13 mutein oncolytic virus combination described herein and one or more non-toxic pharmaceutically acceptable carriers, diluents, excipients and/or adjuvants.

If desired, other active ingredients may be included in the compositions. As indicated above, such compositions are suitable for use in the treatment of cancer. The term "pharmaceutically acceptable carrier" refers to a carrier medium which does not interfere with the effectiveness of the biological activity of the active ingredients and which is not toxic to the host or patient. Representative examples are provided below.

The pharmaceutical compositions may comprise, for example, from about 1% to about 95% of an oncolytic virus comprising an IL-4 receptor targeted cargo protein or an IL-4 or IL-13 mutein oncolytic virus combination. Compositions formulated for administration in a single dose form may comprise, for example, about 20% to about 90% of the oncolytic virus comprising an IL-4 receptor targeted cargo protein or the IL-4 or IL-13 mutein oncolytic virus combination, whereas compositions that are not in a single dose form may comprise, for example, from about 5% to about 20% of the oncolytic virus comprising an IL-4 receptor targeted cargo protein or the IL-4 or IL-13 mutein oncolytic virus combination.

Concentration of the oncolytic virus comprising an IL-4 receptor targeted cargo protein or an IL-4 or IL-13 mutein oncolytic virus combination in the final formulation can be at least 1 ng/mL, such as at least 1 µg/mL or at least 1 mg/mL. For example, the concentration in the final formulation can be between about 0.01 µg/mL and about 1,000 µg/mL. In one example, the concentration in the final formulation is between about 0.01 mg/mL and about 100 mg/mL.

The composition can be a liquid solution, suspension, emulsion, sustained release formulation, or powder. The composition can be formulated as a suppository, with traditional binders and carriers such as triglycerides.

The oncolytic virus comprising an IL-4 receptor targeted cargo protein or the IL-4 or IL-13 mutein oncolytic virus combination can be delivered along with a pharmaceutically acceptable vehicle. In one example, the vehicle may enhance the stability and/or delivery properties, such as an artificial membrane vesicle (including a liposome, noisome, nanosome and the like), microparticle or microcapsule, or as a colloidal formulation that comprises a pharmaceutically acceptable polymer. The use of such vehicles/polymers may be beneficial in achieving sustained release of the content. Alternatively, or in addition, the formulations can include additives to stabilize the protein and virus in vivo, such as human serum albumin, or other stabilizers for protein therapeutics known in the art. The formulations can also include one or more viscosity enhancing agents which act to prevent backflow of the formulation when it is administered, for example by injection or via catheter. Such viscosity enhancing agents include, but are not limited to, biocompatible glycols and sucrose.

Pharmaceutical compositions formulated as aqueous suspensions contain the active compound(s) in admixture with one or more suitable excipients, for example, with suspending agents, such as sodium carboxymethylcellulose, methyl cellulose, hydropropylmethylcellulose, sodium alginate, polyvinylpyrrolidone, hydroxypropyl-.beta.-cyclodextrin, gum tragacanth and gum acacia; dispersing or wetting agents such as a naturally-occurring phosphatide, for example, lecithin, or condensation products of an alkylene oxide with fatty acids, for example, polyoxyethyene stearate, or condensation products of ethylene oxide with long chain aliphatic alcohols, for example, hepta-decaethyleneoxycetanol, or condensation products of ethylene oxide with partial esters derived from fatty acids and a hexitol for example, polyoxyethylene sorbitol monooleate, or condensation products of ethylene oxide with partial esters derived from fatty acids and hexitol anhydrides, for example, polyethylene sorbitan monooleate. The aqueous suspensions may also contain one or more preservatives, for example ethyl, or n-propyl p-hydroxy-benzoate, or one or more coloring agents.

Pharmaceutical compositions can be formulated as oily suspensions by suspending the active compound(s) in a vegetable oil, for example, *arachis* oil, olive oil, sesame oil or coconut oil, or in a mineral oil such as liquid paraffin. The oily suspensions may contain a thickening agent, for example, beeswax, hard paraffin or cetyl alcohol. Compositions can be preserved by the addition of an anti-oxidant such as ascorbic acid.

The pharmaceutical compositions can be formulated as a dispersible powder or granules, which can subsequently be used to prepare an aqueous suspension by the addition of water. Such dispersible powders or granules provide the active ingredient in admixture with one or more dispersing or wetting agents, suspending agents and/or preservatives. Suitable dispersing or wetting agents and suspending agents are exemplified by those already mentioned above.

Pharmaceutical compositions can also be formulated as oil-in-water emulsions. The oil phase can be a vegetable oil, for example, olive oil or *arachis* oil, or a mineral oil, for example, liquid paraffin, or it may be a mixture of these oils. Suitable emulsifying agents for inclusion in these compositions include naturally-occurring gums, for example, gum acacia or gum tragacanth; naturally-occurring phosphatides, for example, soy bean, lecithin; or esters or partial esters derived from fatty acids and hexitol, anhydrides, for example, sorbitan monoleate, and condensation products of the partial esters with ethylene oxide, for example, polyoxyethylene sorbitan monoleate.

The pharmaceutical compositions containing an oncolytic virus comprising an IL-4 receptor targeted cargo protein or an IL-4 or IL-13 mutein oncolytic virus combination can be formulated as a sterile injectable aqueous or oleaginous suspension according to methods known in the art and using suitable one or more dispersing or wetting agents and/or suspending agents, such as those mentioned above. The sterile injectable preparation can be a sterile injectable solution or suspension in a non-toxic parentally acceptable diluent or solvent, for example, as a solution in 1,3-butanediol. Acceptable vehicles and solvents that can be employed include, but are not limited to, water, Ringer's solution, lactated Ringer's solution and isotonic sodium chloride solution. Other examples include, sterile, fixed oils, which are conventionally employed as a solvent or suspending medium, and a variety of bland fixed oils including, for example, synthetic mono- or diglycerides. Fatty acids such as oleic acid can also be used in the preparation of injectables.

In one example, the oncolytic virus comprising an IL-4 receptor targeted cargo protein or the IL-4 or IL-13 mutein oncolytic virus combination is conjugated to a water-soluble polymer, e.g., to increase stability or circulating half life or reduce immunogenicity. Clinically acceptable, water-soluble polymers include, but are not limited to, polyethylene glycol (PEG), polyethylene glycol propionaldehyde, carboxymethylcellulose, dextran, polyvinyl alcohol (PVA), polyvinylpyrrolidone (PVP), polypropylene glycol homopolymers (PPG), polyoxyethylated polyols (POG) (e.g., glycerol) and other polyoxyethylated polyols, polyoxyethylated sorbitol, or polyoxyethylated glucose, and other carbohydrate polymers. Methods for conjugating polypeptides to water-soluble polymers such as PEG are described, e.g., in U.S. patent Pub. No. 20050106148 and references cited therein. In one example the polymer is a pH-sensitive polymers designed to enhance the release of drugs from the acidic endosomal compartment to the cytoplasm (see for example, Henry et al., Biomacromolecules 7(8):2407-14, 2006).

The oncolytic virus comprising an IL-4 receptor targeted cargo protein or the IL-4 or IL-13 mutein oncolytic virus combination can also be administered in therapeutically effective amounts together with one or more anti-cancer therapeutics. The compound(s) can be administered before, during or after treatment with the anti-cancer therapeutic.

An "anti-cancer therapeutic" is a compound, composition, or treatment (e.g., surgery) that prevents or delays the growth and/or metastasis of cancer cells. Such anti-cancer therapeutics include, but are not limited to, surgery (e.g., removal of all or part of a tumor), chemotherapeutic drug treatment, radiation, gene therapy, hormonal manipulation, immunotherapy (e.g., therapeutic antibodies and cancer vaccines) and antisense or RNAi oligonucleotide therapy. Examples of useful chemotherapeutic drugs include, but are not limited to, hydroxyurea, busulphan, cisplatin, carboplatin, chlorambucil, melphalan, cyclophosphamide, Ifosphamide, danorubicin, doxorubicin, epirubicin, mitoxantrone, vincristine, vinblastine, Navelbine® (vinorelbine), etoposide, teniposide, paclitaxel, docetaxel, gemcitabine, cytosine, arabinoside, bleomycin, neocarcinostatin, suramin, taxol, mitomycin C, Avastin, Herceptin®, flurouracil, and temozolamide and the like. The compounds are also suitable for use with standard combination therapies employing two or more chemotherapeutic agents. It is to be understood that anti-cancer therapeutics includes novel compounds or treatments developed in the future.

The pharmaceutical compositions described above include an oncolytic virus comprising an IL-4 receptor targeted cargo protein or an IL-4 or IL-13 mutein oncolytic virus combination in an amount effective to achieve the intended purpose. Thus the term "therapeutically effective dose" refers to the amount of the oncolytic virus comprising an IL-4 receptor targeted cargo protein or the IL-4 or IL-13 mutein oncolytic virus combination that ameliorates the symptoms of cancer. Determination of a therapeutically effective dose of a compound is well within the capability of those skilled in the art. For example, the therapeutically effective dose can be estimated initially either in cell culture assays, or in animal models, such as those described herein. Animal models can also be used to determine the appropriate concentration range and route of administration. Such information can then be used to determine useful doses and routes for administration in other animals, including humans, using standard methods known in those of ordinary skill in the art.

Therapeutic efficacy and toxicity can also be determined by standard pharmaceutical procedures such as, for example, by determination of the median effective dose, or ED.sub.50 (i.e. the dose therapeutically effective in 50% of the population) and the median lethal dose, or LD.sub.50 (i.e. the dose lethal to 50% of the population). The dose ratio between therapeutic and toxic effects is known as the "therapeutic index," which can be expressed as the ratio, LD.sub.50/ED.sub.50. The data obtained from cell culture assays and animal studies can be used to formulate a range of dosage for human or animal use. The dosage contained in such compositions is usually within a range of concentrations that include the ED.sub.50 and demonstrate little or no toxicity. The dosage varies within this range depending upon the dosage form employed, sensitivity of the subject, and the route of administration and the like. Exemplary dosage ranges that can be used include at least 1 ng/g tumor, at least 1 µg/g tumor, or at least 1 mg/g tumor, such as dosage ranges from about 0.01 µg/g tumor to about 50 µg/g tumor, from about 0.02 µ/g tumor to about 40 µg/g tumor, from about 0.02 µg/g tumor to about 35 µg/g tumor, 0.03 µg/g tumor to about 25 µg/g tumor, from about 0.04 µg/g tumor to about 20 µg/g tumor, from about 0.04 µg/g tumor to about 10 µg/g tumor, and from about 0.5 µg/g tumor to about 2 µg/g tumor.

One of ordinary skill in the art will appreciate that the dosage will depend, among other things, upon the type of IL-4 receptor targeted cargo protein or the IL-4/IL-13 mutein being used and the type of cancer stem cell being treated.

In some embodiments, the formulation and routes of administration described herein allow for about 80%, about 85%, about 90%, about 95%, or about 100% of the tumor and the 1 cm margin around it (at risk for tumor spread) to be successfully covered. In some embodiments, the formulation and routes of administration described herein allow for about 80% to about 100% of the tumor and the 1 cm margin around it (at risk for tumor spread) to be successfully covered. In some embodiments, the formulation and routes of administration described herein allow for about 85% to about 100% of the tumor and the 1 cm margin around it (at risk for tumor spread) to be successfully covered. In some embodiments, the formulation and routes of administration described herein allow for about 90% to about 100% of the tumor and the 1 cm margin around it (at risk for tumor spread) to be successfully covered. In some embodiments, the formulation and routes of administration described herein allow for about 95% to about 100% of the tumor and the 1 cm margin around it (at risk for tumor spread) to be successfully covered. In some embodiments, the formulation and routes of administration described herein allow for about 100% of the tumor and the 1 cm margin around it (at risk for tumor spread) to be successfully covered.

IV. Making IL-4 Receptor Targeted Cargo Proteins

IL-4 receptor targeted cargo proteins can be prepared by many routine methods as known in the art. IL-4 receptor targeted cargo proteins, as well as modifications thereto, can be made, for example, by engineering the nucleic acid encoding the IL-4 receptor targeted cargo protein using recombinant DNA technology or by peptide synthesis. Modifications to the IL-4 receptor targeted cargo protein may be made, for example, by modifying the IL-4 receptor targeted cargo protein polypeptide itself, using chemical modifications and/or limited proteolysis. Combinations of these methods may also be used to prepare the IL-4 receptor targeted cargo proteins.

Methods of cloning and expressing proteins are well-known in the art, detailed descriptions of techniques and systems for the expression of recombinant proteins can be found, for example, in Current Protocols in Protein Science (Coligan, J. E., et al., Wiley & Sons, New York). Those skilled in the art will understand that a wide variety of expression systems can be used to provide the recombinant protein. Accordingly, the IL-4 receptor targeted cargo proteins can be produced in a prokaryotic host (e.g., *E. coli, A. salmonicida* or *B. subtilis*) or in a eukaryotic host (e.g., *Saccharomyces* or *Pichia*; mammalian cells, e.g., COS, NIH 3T3, CHO, BHK, 293, or HeLa cells; or insect cells). The IL-4 receptor targeted cargo proteins can be purified from the host cells by standard techniques known in the art.

Sequences for various exemplary cargo moieties and targeting moieties are provided in the Tables 1 and 2. Variants and homologs of these sequences can be cloned, if an alternative sequence is desired, using standard techniques [see, for example, Ausubel et al., Current Protocols in Molecular Biology, Wiley & Sons, NY (1997 and updates); Sambrook et al., supra]. For example, the nucleic acid sequence can be obtained directly from a suitable organism, such as *Aeromonas hydrophila*, by extracting mRNA and then synthesizing cDNA from the mRNA template (for example by RT-PCR) or by PCR-amplifying the gene from genomic DNA. Alternatively, the nucleic acid sequence encoding either the targeting moiety or the cargo moiety can be obtained from an appropriate cDNA library by standard procedures. The isolated cDNA is then inserted into a suitable vector, such as a cloning vector or an expression vector.

Mutations (if desired) can be introduced at specific, pre-selected locations by in vitro site-directed mutagenesis techniques well-known in the art. Mutations can be introduced by deletion, insertion, substitution, inversion, or a combination thereof, of one or more of the appropriate nucleotides making up the coding sequence.

The expression vector can further include regulatory elements, such as transcriptional elements, required for efficient transcription of the IL-4 receptor targeted cargo protein-encoding sequences. Examples of regulatory elements that can be incorporated into the vector include, but are not limited to, promoters, enhancers, terminators, and polyadenylation signals. Vectors that include a regulatory element operatively linked to a nucleic acid sequence encoding a genetically engineered IL-4 receptor targeted cargo protein can be used to produce the IL-4 receptor targeted cargo protein.

The expression vector may additionally contain heterologous nucleic acid sequences that facilitate the purification of the expressed IL-4 receptor targeted cargo protein, such as affinity tags such (e.g., metal-affinity tags, histidine tags, avidin/streptavidin encoding sequences, glutathione-S-transferase (GST) encoding sequences, and biotin encoding sequences). In one example, such tags are attached to the N- or C-terminus of a IL-4 receptor targeted cargo protein, or can be located within the IL-4 receptor targeted cargo protein. The tags can be removed from the expressed IL-4 receptor targeted cargo protein prior to use according to methods known in the art. Alternatively, the tags can be retained on the IL-4 receptor targeted cargo protein, providing that they do not interfere with the ability of the IL-4 receptor targeted cargo protein to target and kill (or decrease growth of) cancer cells and/or cancer stem cells.

As an alternative to a directed approach to introducing mutations into naturally occurring pore-forming proteins, a cloned gene expressing a pore-forming protein can be subjected to random mutagenesis by techniques known in the art. Subsequent expression and screening of the mutant forms of the protein thus generated would allow the identification and isolation of targeted cargo moieties.

The IL-4 receptor targeted cargo proteins can also be prepared as fragments or fusion proteins. A fusion protein is one which includes a IL-4 receptor targeted cargo protein linked to other amino acid sequences that do not inhibit the ability of the IL-4 receptor targeted cargo protein to selectively target and inhibit cancer stem cell growth or kill cancer cells and/or cancer stem cells. In an alternative example, the other amino acid sequences are short sequences of, for example, up to about 5, about 6, about 7, about 8, about 9, about 10, about 20, about 30, about 50 or about 100 amino acid residues in length. These short sequences can be linker sequences as described above.

Methods for making fusion proteins are well known to those skilled in the art. For example U.S. Pat. No. 6,057,133 discloses methods for making fusion molecules composed of human interleukin-3 (hIL-3) variant or mutant proteins functionally joined to a second colony stimulating factor, cytokine, lymphokine, interleukin, hematopoietic growth factor or IL-3 variant. U.S. Pat. No. 6,072,041 to Davis et al. discloses the generation of fusion proteins comprising a single chain Fv molecule directed against a transcytotic receptor covalently linked to a therapeutic protein.

The IL-4 receptor targeted cargo protein can include one or more linkers, as well as other moieties, as desired. These can include a binding region, such as avidin or an epitope, or a tag such as a polyhistidine tag, which can be useful for purification and processing of the fusion protein. In addition, detectable markers can be attached to the fusion protein, so that the traffic of the fusion protein through a body or cell can be monitored conveniently. Such markers include radionuclides, enzymes, fluorophores, chromophores, and the like.

One of ordinary skill in the art will appreciate that the DNA can be altered in numerous ways without affecting the biological activity of the encoded protein. For example, PCR can be used to produce variations in the DNA sequence which encodes a IL-4 receptor targeted cargo protein. Such variations in the DNA sequence encoding a IL-4 receptor targeted cargo protein can be used to optimize for codon preference in a host cell used to express the protein, or may contain other sequence changes that facilitate expression.

A covalent linkage of a targeting moiety directly to a cargo moiety or via a linker may take various forms as is known in the art. For example, the covalent linkage may be in the form of a disulfide bond. The DNA encoding one of the components can be engineered to contain a unique cysteine codon. The second component can be derivatized with a sulfhydryl group reactive with the cysteine of the first component. Alternatively, a sulfhydryl group, either by itself or as part of a cysteine residue, can be introduced using solid phase polypeptide techniques. For example, the introduction of sulfhydryl groups into peptides is described by Hiskey (Peptides 3:137, 1981).

Proteins also can be chemically modified by standard techniques to add a sulfhydryl group. For example, Traut's reagent (2-iminothiolane-HCl) (Pierce Chemicals, Rockford, Ill.) can be used to introduce a sulfhydryl group on primary amines, such as lysine residues or N-terminal amines. A protein or peptide modified with Traut's reagent can then react with a protein or peptide which has been modified with reagents such as N-succinimidyl 3-(2-pyridyldithio) propionate (SPDP) or succinimidyl 4-(N-maleimidomethyl) cyclohexane-1-carboxylate (SMCC) (Pierce Chemicals, Rockford, Ill.).

The components can also be joined using the polymer, monomethoxy-polyethylene glycol (mPEG), as described in Maiti et al., Int. J. Cancer Suppl., 3:17-22, 1988.

The targeting moiety and the cargo moiety can also be conjugated through the use of standard conjugation chemistries as is known in the art, such as carbodiimide-mediated coupling (for example, DCC, EDC or activated EDC), and the use of 2-iminothiolane to convert epsilon amino groups to thiols for crosslinking and m-maleimidobenzoyl-n-hydroxysuccinimidyl ester (MBS) as a crosslinking agent.

V. Testing IL-4 Receptor Targeted Cargo Proteins

IL-4 receptor targeted cargo proteins can be tested using standard techniques known in the art. Exemplary methods of testing candidate IL-4 receptor targeted cargo proteins are provided below and in the examples included herein. One of ordinary skill in the art will understand that other methods of testing the IL-4 receptor targeted cargo proteins are known in the art and are also suitable for testing candidate IL-4 receptor targeted cargo proteins. For example, methods known in the art for testing for anti-tumor activity can be used. The IL-4 receptor targeted cargo proteins can initially be screened against a panel of cancer cell lines or cancer stem cell lines. A cell proliferation assay, such as the WST-1 kit sold by Roche, can be used. Potency can be evaluated using different drug concentrations in the presence or absence of agents that inhibit cancer cells or sensitize cancer cells and/or cancer stem cells. Selected drug candidates from the initial cancer stem cell screen can be further characterized through additional in vitro assays and in relevant xenograft models to examine anti-tumor activity.

A. In Vitro

IL-4 receptor targeted cargo proteins can be tested for their ability to kill cancer stem cells or significantly reduce or inhibit the growth of cancer cells and/or cancer stem cells using known methods. For example, the ability of the IL-4 receptor targeted cargo proteins to kill or inhibit growth of cells can be assayed in vitro using suitable cells, typically a cell line expressing the target or a stem cancer cell. In general, cells of the selected test cell line are grown to an appropriate density and the candidate IL-4 receptor targeted cargo protein is added. The IL-4 receptor targeted cargo protein can be added to the culture at around at least 1 ng/mL, at least 1 µg/mL, or at least 1 mg/mL, such as from about 0.01 µg/mL to about 1 mg/mL, from about 0.10 µg/mL to about 0.5 mg/mL, from about 1 µg/mL to about 0.4 mg/mL. In some examples, serial dilutions are tested. After an appropriate incubation time (for example, about 48 to 72 hours), cell survival or growth is assessed. Methods of determining cell survival are well known in the art and include, but are not limited to, the resazurin reduction test (see Fields & Lancaster Am. Biotechnol. Lab., 11:48-50, 1993; O'Brien et al., Eur. J. Biochem., 267:5421-5426, 2000 and U.S. Pat. No. 5,501,959), the sulforhodamine assay (Rubinstein et al., J. Natl. Cancer Inst., 82:113-118, 1999) or the neutral red dye test (Kitano et al., Euro. J. Clin. Investg., 21:53-58, 1991; West et al., J. Investigative Derm., 99:95-100, 1992) or trypan blue assay. Numerous commercially available kits may also be used, for example the CellTiter 96® AQueous One Solution Cell Proliferation Assay (Promega). Cytotoxicity is determined by comparison of cell survival in the treated culture with cell survival in one or more control cultures, for example, untreated cultures and/or cultures pre-treated with a control compound (typically a known therapeutic), or other appropriate control. IL-4 receptor targeted cargo proteins considered to be effective in killing or reducing the growth of cancer cells and/or cancer stem cells are capable of decreasing cell survival or growth, for example, by at least about 10%, at least about 20%, at least about 30%, at least about 40%, or at least about 50%.

In some examples the IL-4 receptor targeted cargo protein can be not significantly toxic to non-cancer cells and/or cancer stem cells. For example, the IL-4 receptor targeted cargo protein when incubated at around at least 1 ng/mL, at least 1 µg/mL, or at least 1 mg/mL, such as from about 0.01 µg/mL to about 1 mg/mL, from about 0.10 µg/mL to about 0.5 mg/mL, from about 1 µg/mL to about 0.4 mg/mL in cell culture with cells not displaying the target (e.g., does not express IL-2R) will kill less than about 50%, less than about 40%, less than about 30%, less than about 20%, or less than about 10% of the non-cancer cells and/or cancer stem cells. In some examples, the IL-4 receptor targeted cargo protein when incubated at around at least 1 ng/mL, at least 1 µg/mL, or at least 1 mg/mL, such as from about 0.01 µg/mL to about 1 mg/mL, from about 0.10 µg/mL to about 0.5 mg/mL, from about 1 µg/mL to about 0.4 mg/mL in cell culture with cells not displaying the target (e.g., does not express IL-2R) will have at least a 10-fold greater $LD_{50}$ toward the non-cancer cells and/or cancer stem cells, such as an at least 20-fold greater, at least 50-fold greater, or at least 100-fold greater LD.sub.50 toward the non-cancer cells and/or cancer stem cells.

In some examples IL-4 receptor targeted cargo proteins include a toxin that contains one or more modifications to an activation sequence. These activatable IL-4 receptor targeted cargo proteins can be tested for their ability to be cleaved by the appropriate activating agent according to methods known in the art. For example, if the one or more modifications result in the addition of one or more protease cleavage sites, the IL-4 receptor targeted cargo protein can be incubated with varying concentrations of the appropriate protease(s). The incubation products can be electrophoresed on SDS-PAGE gels and cleavage of the IL-4 receptor targeted cargo protein can be assessed by examining the size of the polypeptide on the gel.

In order to determine if the activatable IL-4 receptor targeted cargo proteins that have been incubated with protease retain pore-forming activity, and thus the ability to kill cells, after incubation with the protease, the reaction products can be tested in a hemolysis assay as is known in the art. An example of a suitable assay is described in Howard and Buckley, J. Bacteriol., 163:336-40, 1985, which is herein incorporated by reference.

IL-4 receptor targeted cargo proteins that confer selectivity for a specific type of cancer may be tested for their ability to target that specific cancer cell type. For example, a IL-4 receptor targeted cargo protein comprising an IL-4 that targets cancer cells and/or cancer stem cells displaying IL-4R can be assessed for its ability to selectively target cancer cells and/or cancer stem cells by comparing the ability of the IL-4 receptor targeted cargo protein to kill cancer cells and/or cancer stem cells to its ability to kill a normal cell, or a different type of cancer cell (e.g., one that does not express IL-4R). Alternatively, flow cytometric methods, as are known in the art, may be used to determine if a IL-4 receptor targeted cargo protein comprising an IL-4 targeting moiety is able to selectively target a specific type of cancer stem cell. Binding of a labeled antibody to the bound IL-4 receptor targeted cargo protein will indicate binding of the IL-4 receptor targeted cargo protein to the target.

A variety of cancer cell-lines suitable for testing the candidate IL-4 receptor targeted cargo proteins are known in the art and many are commercially available (for example, from the American Type Culture Collection, Manassas, Va.). In one example, in vitro testing of the candidate compounds is conducted in a human cancer cell-line. In another example, cancer cells and/or cancer stem cells are isolated and cultured as described in US Patent Application No. 2007/0292389 to Stassi et al. The cultured stem cells are used to test the activity of the IL-4 receptor targeted cargo protein. Initial testing of the targeting moiety can be performed by linking the targeting moiety to a detectable label such as a fluorescent label and contacting a sample known to contain the appropriate cancer cells and/or cancer stem cells with the targeting moiety and observing the associated fluorescent label bound to the cancer stem cell.

Additional in vitro testing of IL-4 receptor targeted cargo proteins can be accomplished using cell lines that have been engineered to express the desired target. An antibody specific for the target can be used to ensure that the target is being expressed. Upon binding to the cell expressing the target, the IL-4 receptor targeted cargo protein may cause cell lysis which can be detected using methods known in the art.

B. In Vivo

The ability of the IL-4 receptor targeted cargo proteins to kill tumor cells in vivo can be determined in an appropriate animal model using standard techniques known in the art (see, for example, Enna, et al., Current Protocols in Pharmacology, J. Wiley & Sons, Inc., New York, N.Y.).

Current animal models for screening anti-tumor compounds include xenograft models, in which a human tumor has been implanted into an animal. Using these techniques cancer cells and/or cancer stem cells can be transplanted and the presence, size and morphology of the resulting tumor can be assessed. Examples of xenograft models of human cancer include, but are not limited to, human solid tumor xenografts, implanted by sub-cutaneous injection or implantation and used in tumor growth assays; human solid tumor isografts, implanted by fat pad injection and used in tumor growth assays; human solid tumor orthotopic xenografts, implanted directly into the relevant tissue and used in tumor growth assays; experimental models of lymphoma and leukemia in mice, used in survival assays, and experimental models of lung metastasis in mice. In addition to the implanted human tumor cells, the xenograft models can further comprise transplanted human peripheral blood leukocytes, which allow for evaluation of the anti-cancer immune response.

Alternatively, murine cancer models can be used for screening anti-tumor compounds. Examples of appropriate murine cancer models are known in the art and include, but are not limited to, implantation models in which murine cancer cells are implanted by intravenous, subcutaneous, fat pad or orthotopic injection; murine metastasis models; transgenic mouse models; and knockout mouse models.

For example, the IL-4 receptor targeted cargo proteins can be tested in vivo on solid tumors using mice that are subcutaneously grafted bilaterally with 30 to 60 mg of a tumor fragment, or implanted with an appropriate number of cancer cells and/or cancer stem cells (e.g., at least 10.sup.3, at least 10.sup.4, or at least at least 10.sup.6 cancer cells and/or cancer stem cells, such as from about 10 to about 10.sup.5, from about 50 to about 10.sup.4, or from about 75 to about 10.sup.3), on day 0. The animals bearing tumors are randomized before being subjected to the various treatments and controls. In the case of treatment of advanced tumors, tumors are allowed to develop to the desired size, animals having insufficiently developed tumors being eliminated. The selected animals are distributed at random to undergo the treatments and controls. Animals not bearing tumors may also be subjected to the same treatments as the tumor-bearing animals in order to be able to dissociate the toxic effect from the specific effect on the tumor. Chemotherapy generally begins from 3 to 22 days after grafting, depending on the type of tumor, and the animals are observed every day. The IL-4 receptor targeted cargo proteins can be administered to the animals, for example, by i.p. injection, intravenous injection, direct injection into the tumor (or into the organ having the tumor), or bolus infusion. The amount of IL-4 receptor targeted cargo protein that is injected can be determined using the in vitro testing results described above. For example, at least about 1 ng/kg body weight, at least 1 µg/kg body weight, or at least 1 mg/kg body weight, such as from about 0.01 µg/kg body weight to about 1 mg/kg body weight, from about 0.10 µg/kg body weight to about 1.0 g/kg body weight, from about 1 mg/kg body weight to about 4 mg/kg body weight. The different animal groups are weighed about 3 or 4 times a week until the maximum weight loss is attained, after which the groups are weighed at least about once a week until the end of the trial.

The tumors are measured after a pre-determined time period, or they can be monitored continuously by measuring about 2 or 3 times a week until the tumor reaches a pre-determined size and/or weight, or until the animal dies if this occurs before the tumor reaches the pre-determined size/weight. The animals are then sacrificed and the tissue histology, size and/or proliferation of the tumor assessed. Orthotopic xenograft models are an alternative to subcutaneous models and may more accurately reflect the cancer development process. In this model, tumor cells are implanted at the site of the organ of origin and develop internally. Daily evaluation of the size of the tumors is thus more difficult than in a subcutaneous model. A recently developed technique using green fluorescent protein (GFP) expressing tumors in non-invasive whole-body imaging can help to address this issue (Yang et al., Proc. Nat. Aca. Sci., 1206-1211, 2000). This technique utilizes human or murine tumors that stably express very high levels of green fluorescent protein (GFP). The GFP expressing tumors can be visualized by means of externally placed video detectors, allowing for monitoring of details of tumor growth, angiogenesis and metastatic spread. Angiogenesis can be measured over time by monitoring the blood vessel density within the tumor(s). The use of this model thus allows for simultaneous monitoring of several features associated with tumor progression and has high preclinical and clinical relevance.

For the study of the effect of the compositions on leukemias, the animals are grafted with a particular number of cells, and the anti-tumor activity is determined by the increase in the survival time of the treated mice relative to the controls.

To study the effect of a particular IL-4 receptor targeted cargo protein on tumor metastasis, tumor cells are typically treated with the composition ex vivo and then injected into a suitable test animal. The spread of the tumor cells from the site of injection is then monitored over a suitable period of time.

IL-4 receptor targeted cargo proteins that are sufficiently effective at inhibiting cancer stem cell growth (as evidenced by in vitro cell survival assays, metastasis inhibition assays, and/or xenograph model systems) can be chosen for use in humans. IL-4 receptor targeted cargo proteins can also be chosen for trial and eventual therapeutic use in humans based upon their relative toxicity at the potential therapeutic dosage range indicated by the assays. Therapeutic dosages and toxicity are further described below.

VI. Therapeutic Uses

The oncolytic virus comprising an IL-4 receptor targeted cargo protein or the IL-4 or IL-13 mutein oncolytic virus combination described herein can be used for a variety of therapeutic purposes. Prior to administration for therapeutic purposes the oncolytic virus comprising an IL-4 receptor targeted cargo protein or the IL-4 or IL-13 mutein oncolytic virus combination may need to be modified or adapted for the particular purpose, for example the concentration needed for whole body administration may differ from that used for local administration. Similarly, the toxicity of the therapeutic may change depending upon the mode of administration and overall composition being used (e.g., buffer, diluent, additional chemotherapeutic, etc.).

A. Toxicity

Therapeutic proteins may elicit some level of antibody response when administered to a subject, which in some cases may lead to undesirable side effects. Therefore, if necessary, the antigenicity of the oncolytic virus comprising an IL-4 receptor targeted cargo protein or the IL-4 or IL-13 mutein oncolytic virus combination can be assessed as known in the art and described below. In addition, methods to reduce potential antigenicity are described.

In vivo toxic effects can be evaluated by measuring their effect on animal body weight during treatment and by performing hematological profiles and liver enzyme analysis after the animal has been sacrificed. The general toxicity can be tested according to methods known in the art. For example, the overall systemic toxicity can be tested by determining the dose that kills 100% of mice (i.e. LD100) following a single intravenous injection. Doses that were at least about 2, 5, or 10-fold less than the LD100 or LD50 can be selected for administration into other mammals, such as a human.

The kinetics and magnitude of the antibody response can be determined, for example, in immunocompetent mice and can be used to facilitate the development of a dosing regimen that can be used in an immunocompetent human. Immunocompetent mice such as the strain C57-BL6 are administered intravenous doses of the oncolytic virus comprising an IL-4 receptor targeted cargo protein or the IL-4 or IL-13 mutein oncolytic virus combination. The mice are sacrificed at varying intervals (e.g. following single dose, following multiple doses) and serum obtained. An ELISA-based assay can be used to detect the presence of anti-virus antibodies.

Antigenicity of IL-4 receptor targeted cargo proteins is also assessed. To decrease antigenicity of IL-4 receptor targeted cargo proteins the native binding domain of the toxin used as the cargo moiety can be functionally deleted and replaced, for example with a targeting moiety to make the IL-4 receptor targeted cargo protein. The antigenicity of such IL-4 receptor targeted cargo proteins can be determined following exposure to varying schedules of the IL-4 receptor targeted cargo protein which lack portions of the native binding domain using the methods described above. IL-4 receptor targeted cargo proteins that utilize fully humanized antibodies can also be used to minimize antigenicity.

Alternatively, sequential administration of alternative IL-4 receptor targeted cargo proteins derived from other cargo proteins with non-overlapping antigenicity can be performed. For example, a IL-4 receptor targeted cargo protein derived from proaerolysin can be used alternately with a IL-4 receptor targeted cargo protein derived from *Clostridium septicum* alpha toxin or *Bacillus thuringiensis* delta-toxin. All of these IL-4 receptor targeted cargo proteins would target cancer cells and/or cancer stem cells, but would not be recognized or neutralized by the same antibodies.

Serum samples from these mice can be assessed for the presence of anti-IL-4 receptor targeted cargo protein antibodies as known in the art. As another example, epitope mapping can also be used to determine antigenicity of proteins as described in Stickler, et al., J. Immunotherapy, 23:654-660, 2000. Briefly, immune cells known as dendritic cells and CD4+ T cells are isolated from the blood of community donors who have not been exposed to the protein of interest. Small synthetic peptides spanning the length of the protein are then added to the cells in culture. Proliferation in response to the presence of a particular peptide suggests that a T cell epitope is encompassed in the sequence. This peptide sequence can subsequently be deleted or modified in the IL-4 receptor targeted cargo protein thereby reducing its antigenicity.

B. Treatment of Cancer

IL-4R is over-expressed in a variety of cancers, and in some embodiments, the oncolytic virus comprising an IL-4 receptor targeted cargo protein or the IL-4 or IL-13 mutein oncolytic virus combination can be used to treat, stabilize or prevent cancer. The oncolytic virus comprising an IL-4 receptor targeted cargo protein or the IL-4 or IL-13 mutein oncolytic virus combination can also be used in the treatment of indolent cancers, recurrent cancers including locally recurrent, distantly recurrent and/or refractory cancers (i.e. cancers that have not responded to other anti-cancer treatments), metastatic cancers, locally advanced cancers and aggressive cancers. In these contexts, the IL-4 receptor targeted cargo proteins may exert either a cytotoxic or cytostatic effect resulting in, for example, a reduction in the number or growth of cancer cells and/or cancer stem cells, a reduction in the size of a tumor, the slowing or prevention of an increase in the size of a tumor, an increase in the disease-free survival time between the disappearance or removal of a tumor and its reappearance, prevention of an initial or subsequent occurrence of a tumor (e.g. metastasis), an increase in the time to progression, reduction of one or more adverse symptoms associated with a tumor, or an increase in the overall survival time of a subject having cancer.

Moreover, IL-4R is overexpressed in non-malignant cells including myeloid derived suppressor cells (MDSCs) and tumor associated macrophages (TAMs) of the immunosuppressive tumor microenvironment (TME). For example, glioblastoma has a robust immunosuppressive TME and may comprise up to 40% of the tumor mass (Kennedy et al., 2013). Recently, it has been shown that malignant gliomas have a T-helper cell type-2 (Th2) bias and are heavily infiltrated by MDSCs and TAMs and that the IL4/IL-4R bias mediates their immunosuppressive functions (Harshyne, et al., 2016). Furthermore, IL-4R is up-regulated on glioma-infiltrating myeloid cells but not in the periphery or in normal brain (Kohanbash et al., 2013). In some embodiments, purging Th2 cells, MDSCs, and TAMs using the oncolytic virus comprising an IL-4 receptor targeted cargo protein or the IL-4 or IL-13 mutein oncolytic virus combination of the present invention may alleviate the immune block associated with cancer. In some embodiments, the alleviation of immune block promotes anti-tumor immunity and aid in long-term disease control and/or disease treatment.

C. Administration and Dosing

Typically, in the treatment of cancer, the oncolytic virus comprising an IL-4 receptor targeted cargo protein or the IL-4 or IL-13 mutein oncolytic virus combination is administered systemically to patients, for example, by bolus injection or continuous infusion into a patient's bloodstream. Alternatively, the oncolytic virus comprising an IL-4 receptor targeted cargo protein or the IL-4 or IL-13 mutein oncolytic virus combination may be administered locally, at the site of a tumor (intratumorally). When administered intratumorally, the administration can be via any route, e.g., locally, regionally, focally, systemic, convection enhanced delivery or combinations thereof.

When used in conjunction with one or more known chemotherapeutic agents, the compounds can be administered prior to, or after, administration of the chemotherapeutic agents, or they can be administered concomitantly. The one or more chemotherapeutics may be administered systemically, for example, by bolus injection or continuous infusion, or they may be administered orally.

For administration to an animal, the pharmaceutical compositions can be formulated for administration by a variety of routes. For example, the compositions can be formulated for topical, rectal or parenteral administration or for administration by inhalation or spray. The term parenteral as used herein includes subcutaneous injections, intravenous, intramuscular, intrathecal, intrasternal injection or infusion techniques. Direct injection or infusion into a tumor is also contemplated. Convection enhanced delivery can also be used to administer the IL-4 receptor targeted cargo protein.

In one example, the oncolytic virus comprising an IL-4 receptor targeted cargo protein or the IL-4 or IL-13 mutein oncolytic virus combination can be injected into a subject having cancer, using an administration approach similar to the multiple injection approach of brachytherapy. For example, multiple aliquots of the oncolytic virus comprising an IL-4 receptor targeted cargo protein or the IL-4 or IL-13 mutein oncolytic virus combination in the form of a pharmaceutical composition or formulation and in the appropriate dosage units, may be injected using a needle. Alternative methods of administration will be evident to one of ordinary skill in the art. Such methods include, for example, the use of catheters, or implantable pumps to provide continuous infusion to the subject in need of therapy.

As is known in the art, software planning programs can be used in combination with brachytherapy treatment and ultrasound, for example, for placement of catheters for infusing the oncolytic virus comprising an IL-4 receptor targeted cargo protein or the IL-4 or IL-13 mutein oncolytic virus combination to treat, for example, brain tumors or other localized tumors. For example, the positioning and placement of the needle can generally be achieved under ultrasound guidance. The total volume, and therefore the number of injections and deposits administered to a patient, can be adjusted, for example, according to the volume or area of the organ to be treated. An example of a suitable software planning program is the brachytherapy treatment planning program Variseed 7.1 (Varian Medical Systems, Palo Alto, Calif.). Such approaches have been successfully implemented in the treatment of prostate cancer among others.

If necessary to reduce a systemic immune response to the oncolytic virus comprising an IL-4 receptor targeted cargo protein or the IL-4 or IL-13 mutein oncolytic virus combination, immunosuppressive therapies can be administered in combination with the oncolytic virus comprising an IL-4 receptor targeted cargo protein or the IL-4 or IL-13 mutein oncolytic virus combination. Examples of immunosuppressive therapies include, but are not limited to, systemic or topical corticosteroids (Suga et al., Ann. Thorac. Surg., 73:1092-7, 2002), cyclosporin A (Fang et al., Hum. Gene Ther., 6:1039-44, 1995), cyclophosphamide (Smith et al., Gene Ther., 3:496-502, 1996), deoxyspergualin (Kaplan et al., Hum. Gene Ther., 8:1095-1104, 1997) and antibodies to T and/or B cells [e.g. anti-CD40 ligand, anti CD4 antibodies, anti-CD20 antibody (Rituximab)](Manning et al., Hum. Gene Ther., 9:477-85, 1998). Such agents can be administered before, during, or subsequent to administration of the IL-4 receptor targeted cargo proteins. Such agents can be administered from about 10 mg/week to about 1000 mg/week, from about 40 mg/week to about 700 mg/week, or from about 200 mg/week to about 500 mg/week for 2, 3, 4, 5, 6, or 7 weeks. Courses of treatment can be repeated as necessary if the subject remains responsive (e.g., the symptoms of cancer are static or decreasing).

The oncolytic virus comprising an IL-4 receptor targeted cargo protein or the IL-4 or IL-13 mutein oncolytic virus combination can also be administered in combination with a sensitizing agent, such as a radio-sensitizers (see for example Diehn et al., J. Natl. Cancer Inst. 98:1755-7, 2006). Generally, a sensitizing agent is any agent that increases the activity of the oncolytic virus comprising an IL-4 receptor targeted cargo protein or the IL-4 or IL-13 mutein oncolytic virus combination. For example, a sensitizing agent will increase the ability of such virus to inhibit cancer stem cell growth or kill cancer cells and/or cancer stem cells. Exemplary sensitizing agents include antibodies to IL-10, bone morphogenic proteins and HDAC inhibitors (see for example Sakariassen et al., Neoplasia 9(11):882-92, 2007). These sensitizing agents can be administered before or during treatment with the oncolytic virus comprising an IL-4 receptor targeted cargo protein or the IL-4 or IL-13 mutein oncolytic virus combination. Exemplary dosages of such sensitizing agents include at least 1 µg/mL, such as at least 10 µg/mL, at least 100 µg/mL, for example 5-100 µg/mL or 10-90 µg/mL. The sensitizing agents can be administered daily, three times a week, twice a week, once a week or once every two weeks. Sensitizing agent can also be administered after treatment with the IL-4 receptor targeted cargo protein is finished.

The oncolytic virus comprising an IL-4 receptor targeted cargo protein or the IL-4 or IL-13 mutein oncolytic virus combination may be used as part of a neo-adjuvant therapy (to primary therapy), as part of an adjuvant therapy regimen, where the intention is to cure the cancer in a subject. The oncolytic virus comprising an IL-4 receptor targeted cargo protein or the IL-4 or IL-13 mutein oncolytic virus combination can also be administered at various stages in tumor development and progression, including in the treatment of advanced and/or aggressive neoplasias (e.g., overt disease in a subject that is not amenable to cure by local modalities of treatment, such as surgery or radiotherapy), metastatic disease, locally advanced disease and/or refractory tumors (e.g., a cancer or tumor that has not responded to treatment).

"Primary therapy" refers to a first line of treatment upon the initial diagnosis of cancer in a subject. Exemplary primary therapies may involve surgery, a wide range of chemotherapies and radiotherapy. "Adjuvant therapy" refers to a therapy that follows a primary therapy and that is administered to subjects at risk of relapsing. Adjuvant systemic therapy is begun soon after primary therapy, for example 2, 3, 4, 5, or 6 weeks after the last primary therapy treatment to delay recurrence, prolong survival or cure a subject. As noted above, it is contemplated that the toncolytic virus comprising an IL-4 receptor targeted cargo protein or the IL-4 or IL-13 mutein oncolytic virus combination can be used alone or in combination with one or more other chemotherapeutic agents as part of an adjuvant therapy. This application can be particularly important in the treatment of drug-resistant cancers which are not responsive to standard treatment. The dosage to be administered is not subject to defined limits, but it will usually be an effective amount. The compositions may be formulated in a unit dosage form. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient. The unit dosage forms may be administered once or multiple unit dosages may be administered, for example, throughout an organ, or solid tumor. However, it will be understood that the actual amount of the compound(s) to be administered will be determined by a physician, in the light of the relevant circumstances, including the condition to be treated, the chosen route of administration, the actual compound administered, the age, weight, and response of the individual patient, and the severity of the patient's symptoms. The above dosage range is given by way of example only and is not intended to limit the scope in any way. In some instances, dosage levels below the lower limit of the aforesaid range may be more than adequate, while in other cases still larger doses may be employed without causing harmful side effects, for example, by first dividing the larger dose into several smaller doses for administration throughout the day.

The oncolytic virus comprising an IL-4 receptor targeted cargo protein or the IL-4 or IL-13 mutein oncolytic virus combination can be used to treat and/or manage cancer, the methods include administering to a subject in need thereof a prophylactically or therapeutically effective regimen, the regimen comprising administering one or more therapies to the subject, wherein the regimen results in the stabilization or reduction in the cancer stem cell population and does not result in a reduction or only results in a small reduction of the circulating endothelial cell population and/or the circulating endothelial progenitor population. In one example, the regimen achieves a 5%-40%, a 10%-60%, or a 20 to 99% reduction in the cancer stem cell population and/or less than a 25%, less than a 15%, or less than a 10% reduction in the circulating endothelial cell population. In another example, the regimen achieves a 5%-40%, a 10%-60%, or a 20 to 99% reduction in the cancer stem cell population and/or less than a 25%, less than a 15%, or less than a 10% reduction in the circulating endothelial progenitor population. In another example, the regimen achieves a 5%-40%, a 10%-60%, or a 20 to 99% reduction in the cancer stem cell population and/or less than a 25%, less than a 15%, or less than a 10% reduction in the circulating endothelial cell population and the circulating endothelial progenitor population. In a specific example, the stabilization or reduction in the cancer stem cell population is achieved after two weeks, a month, two months, three months, four months, six month, nine months, 1 year, 2 years, 3 years, 4 years or more of administration of one or more of the therapies. In a particular example, the stabilization or reduction in the cancer stem cell population can be determined using any method known in the art. In certain examples, in accordance with the regimen, the circulating cancer stem cell population, the circulating endothelial cell population and/or the circulating endothelial progenitor population is monitored periodically (e.g., after 2, 5, 10, 20, 30 or more doses of one or more of the therapies or after 2 weeks, 1 month, 2 months, 6 months, 1 year, or more of receiving one or more therapies).

D. Convection Enhanced Delivery (CED)

The present invention contemplates the use of CED for delivery of therapeutics directly into the tumor. CED has been described in Patel et al., Neurosurgery 56: 1243-52, 2005, (incorporated by reference herein in its entirety). This enables high local drug concentrations to be achieved while limiting systemic toxicity. The procedure has been used in the treatment of recurrent GB and other CNS disorders from early clinical development through to Phase 3 clinical trials with a good safety profile. In some embodiments, the oncolytic virus comprising an IL-4 receptor targeted cargo protein or the IL-4 or IL-13 mutein oncolytic virus combination is delivered by convection-enhanced delivery (CED) intratumorally. In some embodiments, CED is performed by direct infusion through intracranial catheters (1 or more, depending on the size of the tumor) under constant pressure. In some embodiments, MRI imaging prior to, during and following infusion is used to monitor drug distribution and tumor response. In some embodiments, subjects/patients are monitored by clinical evaluation and MRI on an ongoing basis after treatment.

In some embodiments, CED will be employed to administer the oncolytic virus comprising an IL-4 receptor targeted cargo protein or the IL-4 or IL-13 mutein oncolytic virus combination to the CNS tumor. In some embodiments, CED will be employed to administer the oncolytic virus comprising an IL-4 receptor targeted cargo protein or the IL-4 or IL-13 mutein oncolytic virus combination for the treatment of CNS tumors. In some embodiments, CED will be employed to administer the oncolytic virus comprising an IL-4 receptor targeted cargo protein or the IL-4 or IL-13 mutein oncolytic virus combination for the treatment of GB. In some embodiments, CED will be employed to administer the oncolytic virus comprising an IL-4 receptor targeted cargo protein or the IL-4 or IL-13 mutein oncolytic virus combination for the treatment of progressive and/or recurrent GB.

In some embodiments, the CED process will employ the use of planning high precision planning software (e.g. iPlan® Flow Infusion Version 3.0.6, Brainlab AG) for determining catheter placement. In some embodiments, the CED process will employ catheters specifically designed for brain usage. In some embodiments, the CED process will not employ large diameter ventricular catheters, which can be prone to drug leakage from the intended delivery site (see, for example 3).

In some embodiments, the CED process will include co-infusion of a surrogate tracer, for example, a magnetic resonance imaging (MRI) contrast agent, will allow real-time monitoring of the oncolytic virus comprising an IL-4 receptor targeted cargo protein or the IL-4 or IL-13 mutein oncolytic virus combination distribution ensuring adequate coverage of the tumor and the infiltrative edges.

In some embodiments, the surrogate tracer molecule can include but is no limited to any magnetic resonance imaging tracer. In some embodiments, the surrogate tracer is a gadolinium bound tracer. In some embodiments, the surrogate tracer is selected from the group consisting of gadolinium-diethylenetriamine pentaacetic acid [Magnevist®] [Gd-DTPA]; commercially available from Bayer Healthcare Pharmaceuticals, Inc.) and gadolinium-bound albumin (Gd-albumin). In some embodiments, the surrogate tracer used during CED will enable effective real-time monitoring of drug distribution. In some embodiments, the real-time monitoring allows for ensuring adequate coverage of the tumor and the peritumoral infiltrating margin with the oncolytic virus comprising an IL-4 receptor targeted cargo protein or the IL-4 or IL-13 mutein oncolytic virus combination. In some embodiments, the surrogate tracer can be administered in combination with the targeted cargo protein to determine if the targeted cargo protein is delivered to a tumor, such as a brain tumor, safely at therapeutic doses while monitoring its distribution in real-time.

For further information regarding on CED and surrogate tracers, see for example, Chittiboina et al., 2014; Jahangiri et al., 2016; and Murad et al., Clin. Cancer Res. 12(10): 3145-51, 2006), all of which are incorporated herein by reference in their entireties.

E. Monitoring Treatment

Any in vitro or in vivo (ex vivo) assays known to one of ordinary skill in the art that can detect and/or quantify cancer cells and/or cancer stem cells can be used to monitor cancer cells and/or cancer stem cells in order to evaluate the impact of a treatment. These methods can be used to assess the impact in a research setting as well as in a clinical setting. The results of these assays then may be used to alter the targeting moiety, cargo protein or alter the treatment of a subject. Assays for the identification of cancer cells and/or cancer stem cells are provided in US patent application no. 2007/0292389 to Stassi et al. (herein incorporated by reference).

Cancer cells and/or cancer stem cells usually are a subpopulation of tumor cells. Cancer cells and/or cancer stem cells can be found in biological samples derived from cell culture or from subjects (such as a tumor sample). Various compounds such as water, salts, glycerin, glucose, an antimicrobial agent, paraffin, a chemical stabilizing agent, heparin, an anticoagulant, or a buffering agent can be added to the sample. The sample can include blood, serum, urine, bone marrow or interstitial fluid. In another example, the sample is a tissue sample. In a particular example, the tissue sample is breast, brain, skin, colon, lung, liver, ovarian, pancreatic, prostate, renal, bone or skin tissue. In a specific example, the tissue sample is a biopsy of normal or tumor tissue. The amount of biological sample taken from the subject will vary according to the type of biological sample and the method of detection to be employed. In a particular example, the biological sample is blood, serum, urine, or bone marrow and the amount of blood, serum, urine, or bone marrow taken from the subject is 0.1 mL, 0.5 mL, 1 mL, 5 mL, 8 mL, 10 mL or more. In another example, the biological sample is a tissue and the amount of tissue taken from the subject is less than 10 milligrams, less than 25 milligrams, less than 50 milligrams, less than 1 gram, less than 5 grams, less than 10 grams, less than 50 grams, or less than 100 grams.

A test sample can be a sample derived from a subject that has been treated. Test samples can also include control samples. In some examples a control sample is from a subject prior to treatment with the oncolytic virus comprising an IL-4 receptor targeted cargo protein or the IL-4 or IL-13 mutein oncolytic virus combination and in other examples the test sample can be taken from a different location within a subject that has been treated with the oncolytic virus comprising an IL-4 receptor targeted cargo protein or the IL-4 or IL-13 mutein oncolytic virus combination. Control samples can also be derived from cells that have been artificially cultured. The sample can be subjected to one or more pretreatment steps prior to the detection and/or measurement of the cancer stem cell population in the sample. In certain examples, a biological fluid is pretreated by centrifugation, filtration, precipitation, dialysis, or chromatography, or by a combination of such pretreatment steps. In other examples, a tissue sample is pretreated by freezing, chemical fixation, paraffin embedding, dehydration, permeabilization, or homogenization followed by centrifugation, filtration, precipitation, dialysis, or chromatography, or by a combination of such pretreatment steps. In certain examples, the sample is pretreated by removing cells other than stem cells or cancer cells and/or cancer stem cells from the sample, or removing debris from the sample prior to the determination of the amount of cancer cells and/or cancer stem cells in the sample.

In certain examples, the amount of cancer cells and/or cancer stem cells in a subject or a sample from a subject is/are assessed prior to therapy or regimen to establish a baseline. In other examples the sample is derived from a subject that was treated using the oncolytic virus comprising an IL-4 receptor targeted cargo protein or the IL-4 or IL-13 mutein oncolytic virus combination. In some examples the sample is taken from the subject at least about 1, 2, 4, 6, 7, 8, 10, 12, 14, 15, 16, 18, 20, 30, 60, 90 days, 6 months, 9 months, 12 months, or >12 months after the subject begins or terminates treatment. In certain examples, the amount of cancer cells and/or cancer stem cells is assessed after a certain number of doses (e.g., after 2, 5, 10, 20, 30 or more doses of a therapy). In other examples, the amount of cancer cells and/or cancer stem cells is assessed after 1 week, 2 weeks, 1 month, 2 months, 1 year, 2 years, 3 years, 4 years or more after receiving one or more therapies.

Targets on cancer cells and/or cancer stem cells are also expressed on normal non-cancerous cells. Therefore, in some examples the identification of cancer cells and/or cancer stem cells can be made by comparing the relative amount of signal generated from target binding in a control sample and comparing it to the test sample for which the presence or absence of cancer cells and/or cancer stem cells is being determined. In such examples, the number, quantity, amount or relative amount of cancer cells and/or cancer stem cells in a sample can be expressed as the percentage of, e.g., overall cells, overall cancerous cells or overall stem cells in the sample.

The results from testing a sample for the presence of cancer cells and/or cancer stem cells and/or the amount of cancer cells and/or cancer stem cells present can be used to alter treatment regimes, including altering the variety of the oncolytic virus comprising an IL-4 receptor targeted cargo protein or the IL-4 or IL-13 mutein oncolytic virus combination used. For example, if testing before and after treatment reveals that the population of cancer cells and/or cancer stem cells increased and/or did not decrease treatment can be altered. For example, the dosage of the therapeutic can be altered and/or a IL-4 receptor targeted cargo protein designed to target distinct target can be substituted or added to the treatment regime.

The amount of cancer cells and/or cancer stem cells can be monitored/assessed using standard techniques known to one of ordinary skill in the art. Cancer cells and/or cancer stem cells can be monitored by obtaining a sample, and detecting cancer cells and/or cancer stem cells in the sample. The amount of cancer cells and/or cancer stem cells in a sample (which may be expressed as percentages of, e.g., overall cells or overall cancer cells) can be assessed by detecting the expression of antigens on cancer cells and/or cancer stem cells. Any technique known to those skilled in the art can be used for assessing the population of the cancer cells and/or cancer stem cells. Antigen expression can be assayed, for example, by immunoassays including, but not limited to, western blots, immunohistochemistry, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, immunofluorescence, protein A immunoassays, flow cytometry, and FACS analysis. In such circumstances, the amount of cancer cells and/or cancer stem cells in a test sample from a subject may be determined by comparing the results to the amount of stem cells in a reference sample (e.g., a sample from a subject who has no detectable cancer) or to a predetermined reference range, or to the patient him/herself at an earlier time point (e.g., prior to, or during therapy). For the purposes of immunoassays one or more of the targets displayed by the cancer stem cell can be used as the target for the immunoassay.

For example, brain cancer cells and/or cancer stem cells can be identified using a CD133+ target, as well as other targets known to be expressed on brain cancer cells and/or cancer stem cells. Additional exemplary markers can be found in Sakariassen et al., Neoplasia 9(11):882-92, 2007 and Vermeulen et al., Cell. Death Differ. 15(6):947-58, 2008 and U.S. patent application 2008/0118518, which is herein incorporated by reference.

F. Therapeutic Variations

One of ordinary skill in the art will appreciate that targets on cancer cells and/or cancer stem cells can also be expressed on normal healthy cells. For example, CD133 was initially shown to be expressed on primitive hematopoietic stem and progenitor cells and retinoblastoma and then subsequently shown to be expressed on cancer cells and/or cancer stem cells. Therefore, in some examples where a cancer stem cell target is expressed on a class of non-cancerous cells therapy can involve removal of a population of the non-cancerous cells followed by treatment directed to the cancer stem cell of interest and then reintroducing the non-cancerous cells expressing the target.

In another example, healthy populations of cells that express the same target as that of a cancer stem cell population are protected through the use of two or more IL-4 receptor targeted cargo proteins. A first IL-4 receptor targeted cargo protein is engineered to target a first cancer stem cell target (e.g., CD133). The cargo protein that is included in the first IL-4 receptor targeted cargo protein can be a toxin that is in an inactive form. A second IL-4 receptor targeted cargo protein is engineered to target a second target on the cancer stem cell (e.g., CD24). This second IL-4 receptor targeted cargo protein includes a protein sequence capable of activating the first IL-4 receptor targeted cargo protein. Thus, only a cancer stem cell that expresses the targets for both the first IL-4 receptor targeted cargo protein and the second cargo protein will receive the therapeutic activity of the cargo moiety.

In another therapeutic variation the subject is treated with an agonist to the target displayed on the cancer stem cell. The cancer cells and/or cancer stem cells then display an increased level of the target. The treatment with the agonist can then be administered before, during or after administration of the oncolytic virus comprising an IL-4 receptor targeted cargo protein or the IL-4 or IL-13 mutein oncolytic virus combination. One of ordinary skill in the art will appreciate that the exact timing of administration will depend upon the specific agonist chosen and the specific IL-4 receptor targeted cargo protein.

EXAMPLES

Example 1

This example describes an in vivo assay that can be used to test the anti-tumor activity of an oncolytic virus expressing a IL-4 targeted cargo protein when administered in a mouse xenograft tumor model.

Maraba DM strain (double mutation from Leu-123 to Trp in the M protein and Gln-242 to Arg in the G protein) and VSVΔ51 virus strain are engineered to express GFP or firefly luciferase and their targeting and replication in tumors following systemic administration can be examined using both bioluminescent imaging in whole animals, and fluorescent microscopy in tumor explants.

Various xenograft tumor mice models are established. For example, lung tumors are established by a single intravenous injection of $3\times10^5$ CT-26 colon cancer cells into 6-8 week old Balb/C animals. Ovarian cancer xenograft model is established by intraperitoneal injection of $1\times10^6$ human ovarian ES-2 cells into 6-8 week old athymic CD-I nude mice. Intratumoral or intravenous (tail vein) injection of PBS, Maraba DM virus engineered to express IL-13 mutein C11 (SEQ ID NO: 35), Maraba DM virus engineered to express IL-13 mutein DN (SEQ ID NO:38), VSVΔ51 virus engineered to express IL-13 mutein C11, or VSVΔ51 virus engineered to express IL-13 mutein DN is performed 1-2 times a week for 2 weeks with $1\times10^3$-$1\times10^{10}$ pfu of virus.

Targeting of the virus to tumor is observed by fluorescent microscopy, and it is observed that IL-4 targeted cargo proteins IL-13C11 and IL-13DN target the oncolytic virus to tumor and tumor microenvironment. Tumor regression is assessed 1, 2, 3, 4, 5, 6, 7, 8, 9, 10, 15, 20, and 25 days after the injection of the oncolytic virus, and thereafter weekly up to 6 months after treatment. Tumor biopsy samples are also assessed histopathologically. Mice are weighed to determine negative effects from the treatment. Oncloysis is also assessed after treatment.

Example 2

This example describes an in vivo assay that can be used to test the anti-tumor activity of an oncolytic virus expressing a IL-4 targeted cargo protein together a IL-2 mutein when administered in a mouse xenograft tumor model.

Maraba DM strain (double mutation from Leu-123 to Trp in the M protein and Gln-242 to Arg in the G protein) and VSVΔ51 virus strain are engineered to express GFP or firefly luciferase and their targeting and replication in tumors following systemic administration can be examined using both bioluminescent imaging in whole animals, and fluorescent microscopy in tumor explants. The Maraba DM virus and VSVΔ51 are engineered to express IL-13 mutein C11 together with IL-2 mutein H9-FEAA (SEQ ID NO:85) or IL-13 mutein DN together with IL-2 mutein H9-FEAA.

Various xenograft tumor mice models are established, such as lung tumors and ovarian tumors shown above. Intratumoral or intravenous (tail vein) injection of PBS, engineered Maraba DM virus or engineered VSVΔ51 virus is performed 1-2 times a week for 2 weeks with $1\times10^3$-$1\times10^{10}$ pfu of virus.

Targeting of the virus to tumor is observed by fluorescent microscopy, and it is observed that IL-4 targeted cargo proteins IL-13C11 and IL-13DN target the oncolytic virus to tumor and tumor microenvironment.

Tumor biopsy samples are collected 1, 2, 3, 4, 5, 6, 7, 8, 9, 10, 15, 20, and 25 days after the injection of the oncolytic virus, and total cell counts of CD8+ T cells and STAT5 phosphorylation are assessed by flow cytometry. Treatment with the oncolytic virus expressing the disclosed IL-2 mutein results in expansion/activation of CD8+ T cells and NK cells.

Tumor regression is assessed 1, 2, 3, 4, 5, 6, 7, 8, 9, 10, 15, 20, and 25 days after the injection of the oncolytic virus, and thereafter weekly up to 6 months after treatment. Oncloysis is also assessed after treatment.

The examples set forth above are provided to give those of ordinary skill in the art a complete disclosure and description of how to make and use the embodiments of the compositions, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only, and the application is to be limited only by the terms of the appended claims, along with the full scope of equivalents to which the claims are entitled.

What is claimed is:

1. A modified oncolytic virus vector comprising at least one nucleic acid sequence encoding an IL-4 receptor targeted cargo protein and an IL-2 mutein, wherein the oncolytic virus vector is a modified adenovirus vector.

2. The modified oncolytic virus vector of claim 1, wherein the IL-4 receptor targeted target cargo protein comprises a sequence including any of the amino acid sequences of SEQ ID NOs:2-69.

3. The modified oncolytic virus vector of claim 1, wherein the IL-2 mutein comprises amino acid substitutions L80F, R81D, L85V, I86V, and I92F in comparison to wild-type human IL-2 comprising the amino acid sequence of SEQ ID NO:81.

4. The modified oncolytic virus vector of claim 1, wherein the IL-2 mutein further comprises at least one amino acid substitution selected from the group consisting of F42A, E62A, and Y45A in comparison to wild-type human IL-2 comprising the amino acid sequence of SEQ ID NO:81.

5. The modified oncolytic virus vector of claim 1, wherein the IL-2 mutein comprises a sequence including any of the amino acid sequences of SEQ ID NOs:82-109.

6. The modified oncolytic virus vector according to claim 1, wherein the IL-4 receptor targeted cargo protein is an IL-4 mutein or an IL-13 mutein.

7. A modified oncolytic adenovirus vector comprising (i) an adenovirus genome, wherein optionally the nucleotides encoding amino acids 122-129 of E1A polypeptide are deleted, and (ii) at least one nucleic acid sequence encoding an IL-4 receptor targeted cargo protein and an IL-2 mutein.

8. The modified oncolytic virus vector of claim 7, wherein the IL-4 receptor targeted target protein comprises a sequence including any of the amino acid sequences of SEQ ID NOs:2-69.

9. The modified oncolytic virus vector of claim 7, wherein the IL-2 mutein comprises amino acid substitutions L80F, R81D, L85V, I86V, and I92F in comparison to wild-type human IL-2 comprising the amino acid sequence of SEQ ID NO:81.

10. The modified oncolytic virus vector of claim 9, wherein the IL-2 mutein further comprises at least one amino acid substitution selected from the group consisting of F42A, E62A, and Y45A in comparison to wild-type human IL-2 comprising the amino acid sequence of SEQ ID NO:81.

11. The modified oncolytic virus vector of claim 7, wherein the IL-2 mutein comprises a sequence including any of the amino acid sequences of SEQ ID NOs:82-109.

* * * * *